US012501829B2

(12) United States Patent
Lee et al.

(10) Patent No.: US 12,501,829 B2
(45) Date of Patent: Dec. 16, 2025

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE, AND DISPLAY DEVICE

(71) Applicant: SAMSUNG SDI CO., LTD., Yongin-si (KR)

(72) Inventors: Hanill Lee, Suwon-si (KR); Wook Kim, Suwon-si (KR); Hyung Sun Kim, Suwon-si (KR); Eunhye An, Suwon-si (KR); Jiah Yoon, Suwon-si (KR); Sung-Hyun Jung, Suwon-si (KR); Jongwoo Choi, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 786 days.

(21) Appl. No.: 17/515,850

(22) Filed: Nov. 1, 2021

(65) Prior Publication Data

US 2022/0140257 A1 May 5, 2022

(30) Foreign Application Priority Data

Nov. 4, 2020 (KR) ........................ 10-2020-0146197
Nov. 1, 2021 (KR) ........................ 10-2021-0148039

(51) Int. Cl.
*H10K 85/60* (2023.01)
*C07D 209/86* (2006.01)
(Continued)

(52) U.S. Cl.
CPC ....... *H10K 85/6572* (2023.01); *C07D 209/86* (2013.01); *C07D 487/04* (2013.01);
(Continued)

(58) Field of Classification Search
CPC ............. H10K 85/6572; H10K 85/654; H10K 2101/90; C07D 487/04; C09K 2211/1018
See application file for complete search history.

(56) References Cited

U.S. PATENT DOCUMENTS 5,061,569 A 10/1991 Vanslyke et al.
5,837,166 A 11/1998 Kawamura et al.
(Continued)

FOREIGN PATENT DOCUMENTS

CN 110746409 A 2/2020
CN 110785863 A 2/2020
(Continued)

OTHER PUBLICATIONS

Chinese Office Action and Search Report dated May 18, 2023.
(Continued)

*Primary Examiner* — Jenna N Chandhok
(74) *Attorney, Agent, or Firm* — Lee IP Law, P.C.

(57) ABSTRACT

A compound for an organic optoelectronic device, a composition for an organic optoelectronic device including the same, an organic optoelectronic device, and a display device, the compound being represented by a combination of Chemical Formula 1 and Chemical Formula 2,

[Chemical Formula 1]

(Continued)

-continued

[Chemical Formula 2]

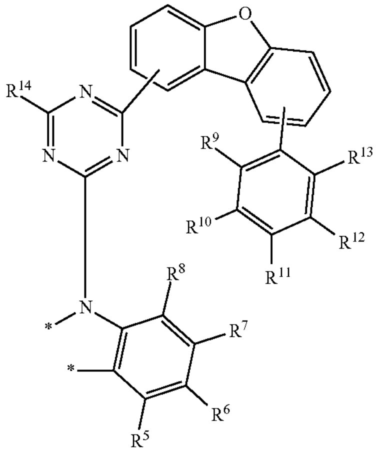

9 Claims, 2 Drawing Sheets

(51) Int. Cl.

| | |
|---|---|
| ***C07D 487/04*** | (2006.01) |
| ***C09K 11/06*** | (2006.01) |
| ***H10K 50/11*** | (2023.01) |
| ***H10K 101/10*** | (2023.01) |

(52) U.S. Cl.

CPC ............ *C09K 11/06* (2013.01); *H10K 85/654* (2023.02); *H10K 85/6574* (2023.02); *C09K 2211/1018* (2013.01); *H10K 50/11* (2023.02); *H10K 2101/10* (2023.02)

(56) References Cited

U.S. PATENT DOCUMENTS 10,897,016 B2 1/2021 Ma et al.
2015/0041785 A1 2/2015 Sannomiya et al.
2015/0115240 A1 4/2015 Fukumatsu et al.
2015/0171340 A1* 6/2015 Lee .................... H10K 85/6574 544/333
2017/0069849 A1* 3/2017 Lee ........................ C07F 9/6561
2017/0237017 A1* 8/2017 Parham ................ H10K 85/322 252/500
2017/0305854 A1 10/2017 Lee et al.
2019/0214571 A1 7/2019 Huh et al.
2020/0176688 A1* 6/2020 Cho ..................... C07D 487/04
2020/0203631 A1 6/2020 Gao et al.
2021/0104698 A1 4/2021 Kim et al.
2021/0122765 A1 4/2021 Wolohan et al.
2022/0006022 A1* 1/2022 Suh .................... H10K 85/6576
2022/0310936 A1* 9/2022 Suh ...................... C07D 405/14
2022/0416177 A1* 12/2022 Hayashi ............. H10K 85/6576
2023/0019297 A1 1/2023 Kim et al.
2023/0131577 A1* 4/2023 Hayashi ............... H10K 85/654 257/40
2023/0172065 A1 6/2023 Park et al.
2023/0247902 A1 8/2023 No et al.
2023/0263054 A1* 8/2023 Hwang ................ H10K 85/633 257/40

FOREIGN PATENT DOCUMENTS

| | | | |
|---|---|---|---|
| CN | 112996793 | A | 6/2021 |
| CN | 113004287 | A | 6/2021 |
| CN | 113004289 | A | 6/2021 |
| CN | 114105992 | A | 3/2022 |
| CN | 114163424 | A | 3/2022 |
| CN | 114456172 | A | 5/2022 |
| CN | 115669281 | A | 1/2023 |
| EP | 2947071 | A1 | 11/2015 |
| EP | 3034581 | A1 | 6/2016 |
| EP | 4254528 | A1 | 10/2023 |
| EP | 4349812 | A1 | 4/2024 |
| JP | 1993-009471 | A | 1/1993 |
| JP | 1995-126615 | A | 5/1995 |
| JP | 1998-095973 | A | 4/1998 |
| JP | 6091428 | B2 | 3/2017 |
| JP | 2022-189759 | A | 12/2022 |
| JP | 2023-534166 | A | 8/2023 |
| JP | 2023-537660 | A | 9/2023 |
| KR | 10-2014-0143397 | A | 12/2014 |
| KR | 10-2017-0107919 | A | 9/2017 |
| KR | 10-1818579 | B1 | 1/2018 |
| KR | 10-2018-0124766 | A | 11/2018 |
| KR | 10-2018-0137772 | A | 12/2018 |
| KR | 10-2019-0000597 | A | 1/2019 |
| KR | 10-2019-0001357 | A | 1/2019 |
| KR | 10-2019-0002206 | A | 1/2019 |
| KR | 10-1959821 | B1 | 3/2019 |
| KR | 10-2019-0090204 | A | 8/2019 |
| KR | 10-2031300 | B1 | 10/2019 |
| KR | 10-2045766 | B1 | 11/2019 |
| KR | 10-2054806 | B1 | 12/2019 |
| KR | 10-2069310 | B1 | 1/2020 |
| KR | 10-2020-0018760 | A | 2/2020 |
| KR | 10-2020-0046750 | A | 5/2020 |
| KR | 10-2193015 | B1 | 12/2020 |
| KR | 10-2021-0041166 | A | 4/2021 |
| KR | 10-2022-0017374 | A | 2/2022 |
| WO | WO 1995/009147 | A1 | 4/1995 |
| WO | WO 2013/088973 | A1 | 6/2013 |
| WO | WO 2013-133219 | A1 | 9/2013 |
| WO | WO 2013-133223 | A1 | 9/2013 |
| WO | WO 2016-064227 | A1 | 4/2016 |
| WO | WO 2016/194604 | A1 | 12/2016 |
| WO | WO 2018/095391 | A1 | 5/2018 |
| WO | WO 2018-182259 | A1 | 10/2018 |
| WO | WO-2018236092 | A1 * | 12/2018 ........... C07D 487/04 |

OTHER PUBLICATIONS

Korean Notice of Allowance dated Feb. 27, 2024.
International Search Report dated Oct. 18, 2022 received in co-pending related application, U.S. Appl. No. 18/561,095.
Japanese Office action dated Oct. 22, 2024.
Korean Office action dated Aug. 28, 2024, received in co-pending related application, U.S. Appl. No. 18/561,095.
European Search Report dated May 19, 2025.

* cited by examiner

COMPOUND FOR ORGANIC OPTOELECTRONIC DEVICE, COMPOSITION FOR ORGANIC OPTOELECTRONIC DEVICE, ORGANIC OPTOELECTRONIC DEVICE, AND DISPLAY DEVICE

CROSS-REFERENCE TO RELATED APPLICATION

This application claims priority to and the benefit of Korean Patent Application No. 10-2020-0146197 filed in the Korean Intellectual Property Office on Nov. 4, 2020 and Korean Patent Application No. 10-2021-0148039 filed in the Korean Intellectual Property Office on Nov. 1, 2021, the entire contents of which are incorporated herein by reference.

BACKGROUND

1. Field

Embodiments relate to a compound for an organic optoelectronic device, a composition for an organic optoelectronic device, an organic optoelectronic device, and a display device.

2. Description of the Related Art

An organic optoelectronic device (organic optoelectronic diode) is a device capable of converting electrical energy and optical energy to each other.

Organic optoelectronic devices may be divided into two types according to a principle of operation. One type is a photoelectric device that generates electrical energy by separating excitons formed by light energy into electrons and holes, and transferring the electrons and holes to different electrodes, respectively and another type is light emitting device that generates light energy from electrical energy by supplying voltage or current to the electrodes.

Examples of the organic optoelectronic device include an organic photoelectric device, an organic light emitting diode, an organic solar cell, and an organic photoconductor drum.

Among them, organic light emitting diodes (OLEDs) are attracting much attention in recent years due to increasing demands for flat panel display devices. The organic light emitting diode is a device that converts electrical energy into light, and the performance of the organic light emitting diode may be influenced by an organic material between electrodes.

SUMMARY

The embodiments may be realized by providing a compound for an organic optoelectronic device, the compound being represented by a combination of Chemical Formula 1 and Chemical Formula 2,

[Chemical Formula 1]

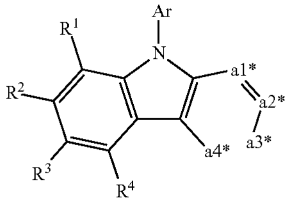

-continued

[Chemical Formula 2]

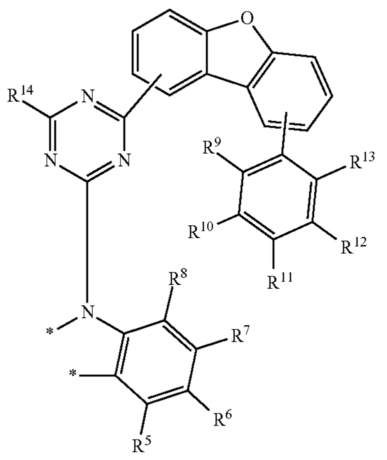

wherein, in Chemical Formulas 1 and 2, Ar is a substituted or unsubstituted C12 to C30 aryl group, two adjacent ones of a1* to a4* of Chemical Formula 1 are linking carbons linked at * of Chemical Formula 2, the remaining two of a1* to a4* of Chemical Formula 1, not linked at * of Chemical Formula 2, are C—$R^a$, $R^a$ and $R^1$ to $R^{13}$ are each independently hydrogen, deuterium, a cyano group, a halogen, a substituted or unsubstituted C1 to C20 alkyl group, or a substituted or unsubstituted C6 to C20 aryl group, and $R^{14}$ is a substituted or unsubstituted C6 to C20 aryl group.

The embodiments may be realized by providing a composition for an organic optoelectronic device, the composition comprising a first compound and a second compound, wherein the first compound is the compound according to an embodiment, and the second compound is represented by Chemical Formula 3; or a combination of Chemical Formula 4 and Chemical Formula 5,

[Chemical Formula 3]

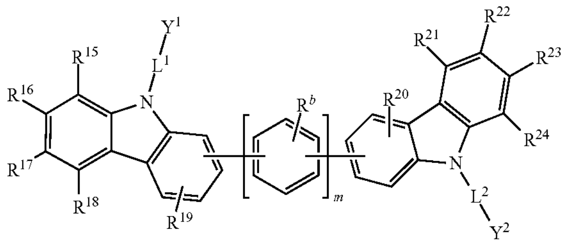

in Chemical Formula 3, $Y^1$ and $Y^2$ are each independently a substituted or unsubstituted C6 to C20 aryl group or a substituted or unsubstituted C2 to C30 heterocyclic group, $L^1$ and $L^2$ are each independently a single bond or a substituted or unsubstituted C6 to C20 arylene group, $R^b$ and $R^{15}$ to $R^{24}$ are each independently hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group, and m is an integer of 0 to 2;

[Chemical Formula 4]

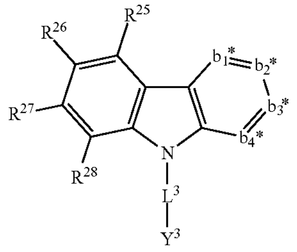

[Chemical Formula 5]

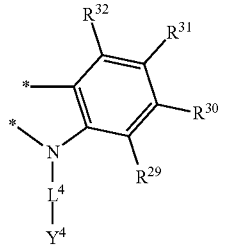

in Chemical Formula 4 and Chemical Formula 5, $Y^3$ and $Y^4$ are each independently a substituted or unsubstituted C6 to C20 aryl group or a substituted or unsubstituted C2 to C30 heterocyclic group, two adjacent ones of $b_1$* to $b_4$* of Chemical Formula 4 are linking carbons linked at * of Chemical Formula 5, the remaining two of $b_1$* to $b_4$* of Chemical Formula 4, not linked at * of Chemical Formula 5, are C-$L^a$-$R^c$, $L^a$, $L^3$, and $L^4$ are each independently a single bond or a substituted or unsubstituted C6 to C20 arylene group, and $R^c$ and $R^{25}$ to $R^{32}$ are each independently hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group.

The embodiments may be realized by providing an organic optoelectronic device including an anode and a cathode facing each other, and at least one organic layer between the anode and the cathode, wherein the at least one organic layer includes the compound according to an embodiment.

The embodiments may be realized by providing an organic optoelectronic device including an anode and a cathode facing each other, and at least one organic layer between the anode and the cathode, wherein the at least one organic layer includes the composition according to an embodiment.

The embodiments may be realized by providing a display device comprising the organic optoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
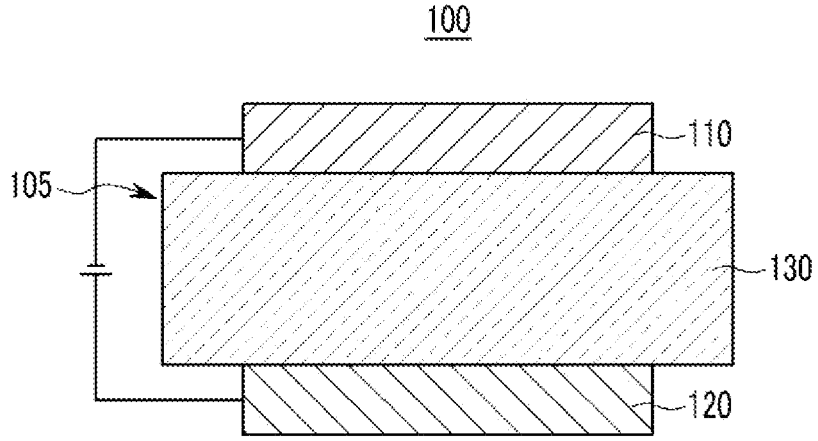
FIGS. 1 to 4 are cross-sectional views of organic light emitting diodes according to embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout. As used herein, the term "or" is not an exclusive term, e.g., "A or B" would include A, B, or A and B.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In a specific example, the "substituted" refers to replacement of at least one hydrogen of a substituent or a compound by deuterium, a C1 to C20 alkyl group, a C6 to C30 aryl group, or a cyano group. In a specific example, the "substituted" refers to replacement of at least one hydrogen of a substituent or a compound by deuterium, a C1 to C5 alkyl group, a C6 to C18 aryl group, or a cyano group. In a specific example, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, when a definition is not otherwise provided, "hetero" refers to one including one to three heteroatoms selected from N, O, S, P, and Si, and remaining carbons in one functional group.

As used herein, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic, or fused ring polycyclic (i.e., rings sharing adjacent pairs of carbon atoms) functional group.

As used herein, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or a combination thereof, but is not limited thereto.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, a substituted or unsubstituted dibenzothiophenyl group, or a combination thereof, but is not limited thereto.

As used herein, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device according to an embodiment is described.

The compound for an organic optoelectronic device according to an embodiment is represented by, e.g., a combination of Chemical Formula 1 and Chemical Formula 2.

[Chemical Formula 1]

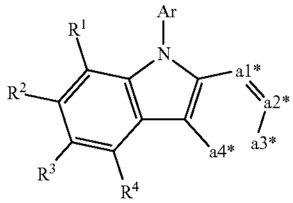

[Chemical Formula 2]

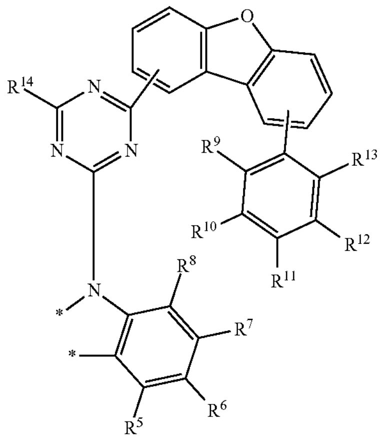

In Chemical Formulas 1 and 2, Ar may be or may include, e.g., a substituted or unsubstituted C12 to C30 aryl group.

Two adjacent ones of a1* to a4* of Chemical Formula 1 may be linking carbons linked at * of Chemical Formula 2, the remaining two of a1* to a4* of Chemical Formula 1, not linked at * of Chemical Formula 2, may be C—$R^a$. As used herein, the term "linking carbon" refers to a shared carbon at which fused rings are linked.

$R^a$ and $R^1$ to $R^{13}$ may each independently be or include, e.g., hydrogen, deuterium, a cyano group, a halogen, a substituted or unsubstituted C1 to C20 alkyl group, or a substituted or unsubstituted C6 to C20 aryl group.

$R^{14}$ may be or may include, e.g., a substituted or unsubstituted C6 to C20 aryl group.

The compound represented by the combination of Chemical Formula 1 and Chemical Formula 2 may include an indolocarbazole skeleton, and may have a structure in which it is directly substituted with a triazine moiety on one of the two N atoms of the indolocarbazole, and substituted with a substituted or unsubstituted C12 or higher aryl group on the other of the two N atoms of the indolocarbazole.

In addition, the triazine moiety may include a dibenzofuran group as a substituent thereon, and the dibenzofuran group may further include a substituted or unsubstituted phenyl group thereon.

As such, by designing a structure wrapped with or including indolocarbazole, triazine, and dibenzofuranyl groups, the interference of negative ions in the electron transport region may be minimized, and thus degradation of the device may be reduced or prevented.

In an implementation, the compound may be substituted with a triazine moiety on the N atom of indolocarbazole, and the it-bond may be broken by forming a C—N bond, thereby preventing the HOMO electron cloud from expanding. This may facilitate effective localization, which may help achieve a long life-span effect.

According to the substitution position of the substituted or unsubstituted phenyl group that further substitutes the dibenzofuran group, Chemical Formula 2 may be, e.g., represented by one of Chemical Formula 2-1 to Chemical Formula 2-4.

[Chemical Formula 2-1]

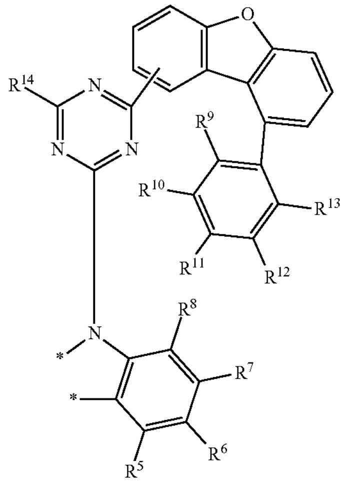

[Chemical Formula 2-2]

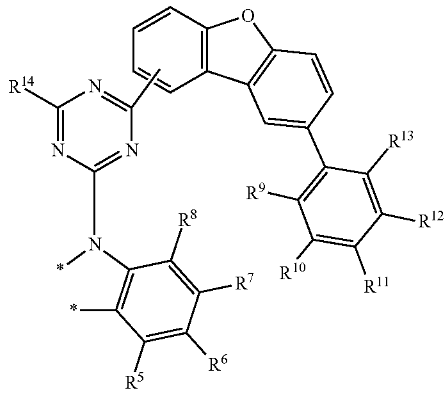

[Chemical Formula 2-3]

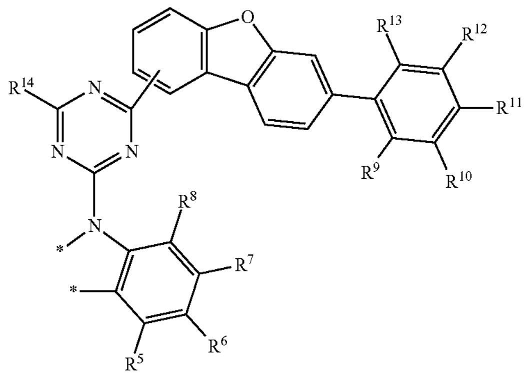

-continued

[Chemical Formula 2-4]

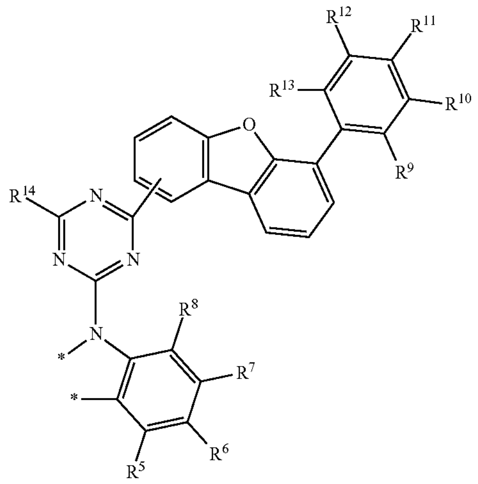

In Chemical Formula 2-1 to Chemical Formula 2-4, the definitions of $R^5$ to $R^{14}$, and * may be the same as described above.

In an implementation, Chemical Formula 2-1 may be, e.g., represented by one of Chemical Formula 2-1-i to Chemical Formula 2-1-iv.

[Chemical Formula 2-1-i]

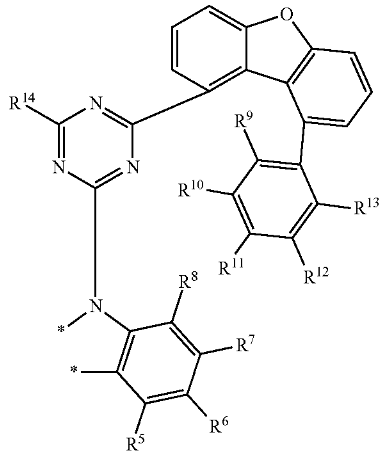

-continued
[Chemical Formula 2-1-ii]
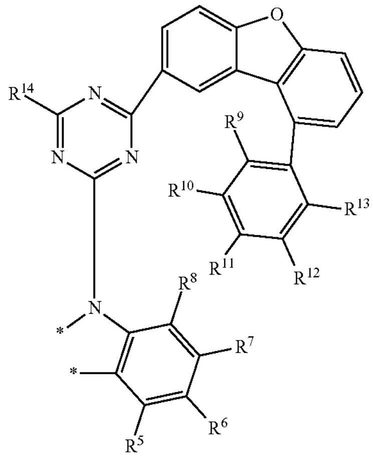
[Chemical Formula 2-1-iii]
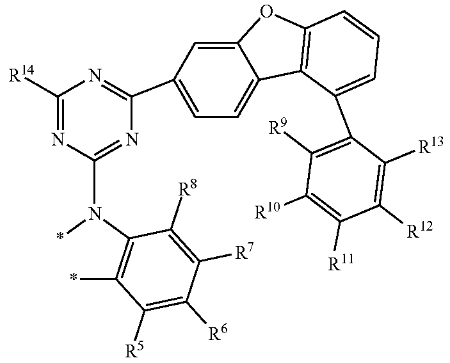
[Chemical Formula 2-1-iv]
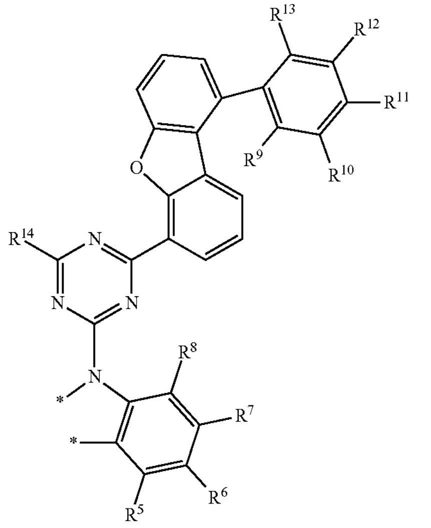
In Chemical Formula 2-1-i to Chemical Formula 2-1-iv, the definitions of $R^5$ to $R^{14}$, and * may be the same as described above.
In an implementation, Chemical Formula 2-2 may be, e.g., represented by one of Chemical Formula 2-2-i to Chemical Formula 2-2-iv.
[Chemical Formula 2-2-i]
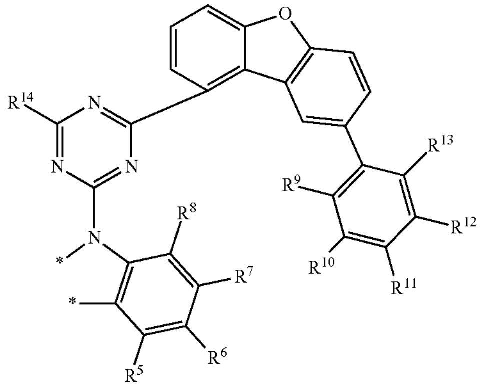
[Chemical Formula 2-2-ii]
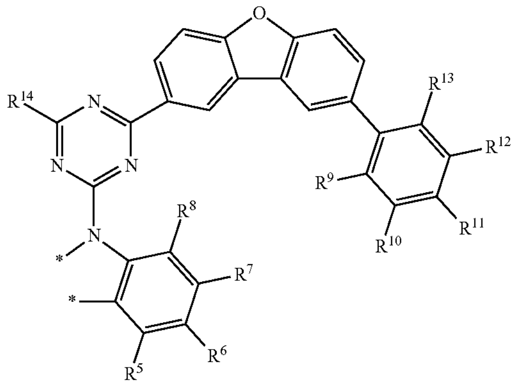
[Chemical Formula 2-2-iii]
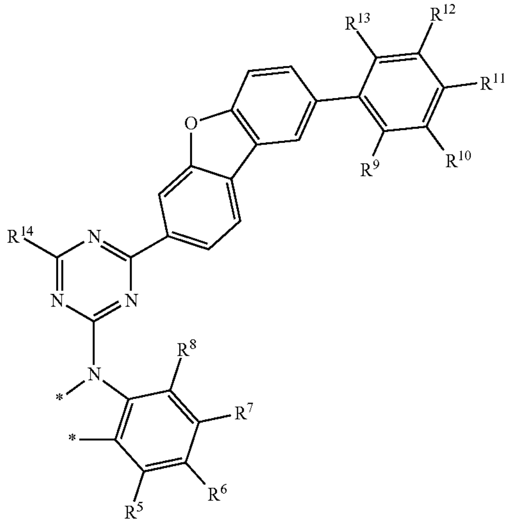

-continued
[Chemical Formula 2-2-iv]
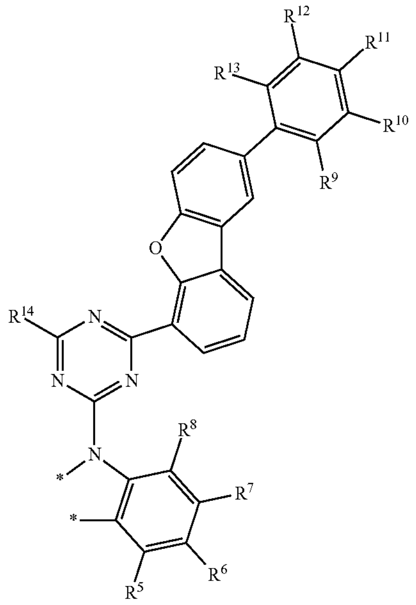
In Chemical Formula 2-2-i to Chemical Formula 2-2-iv, the definitions of $R^5$ to $R^{14}$, and * may be the same as described above.
In an implementation, Chemical Formula 2-3 may be, e.g., represented by one of Chemical Formula 2-3-i to Chemical Formula 2-3-iv.
[Chemical Formula 2-3-i]
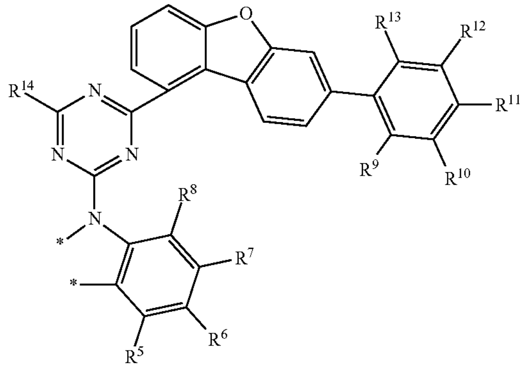
-continued
[Chemical Formula 2-3-ii]
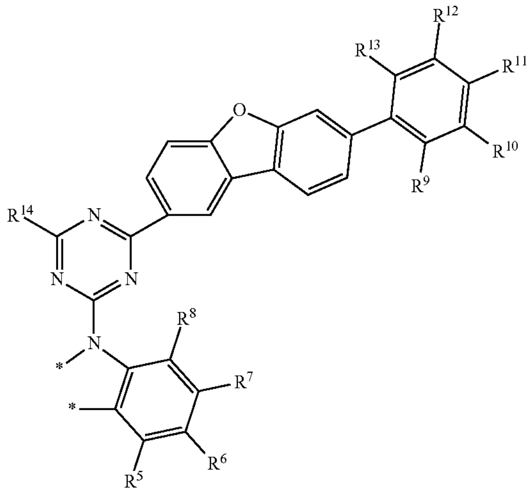
[Chemical Formula 2-3-iii]
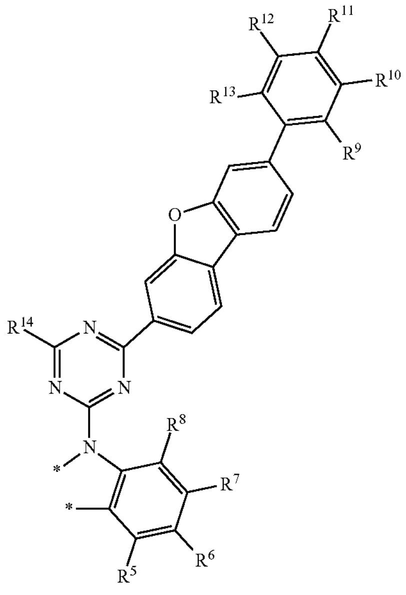

-continued
[Chemical Formula 2-3-iv]
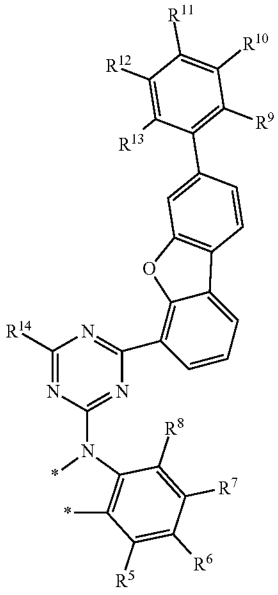
In Chemical Formula 2-3-i to Chemical Formula 2-3-iv, the definitions of $R^5$ to $R^{14}$, and * may be the same as described above.
In an implementation, Chemical Formula 2-4 may be, e.g., represented by one of Chemical Formula 2-4-i to Chemical Formula 2-4-iv.
[Chemical Formula 2-4-i]
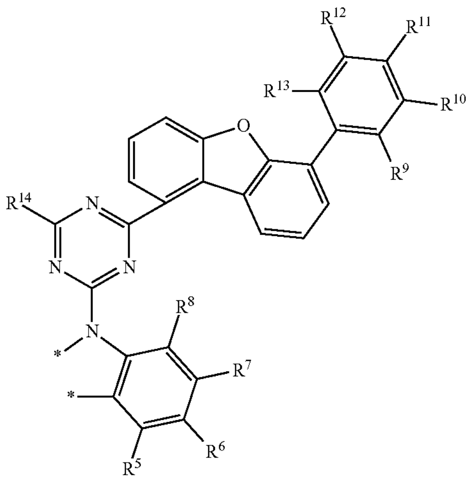
-continued
[Chemical Fomula 2-4-ii]
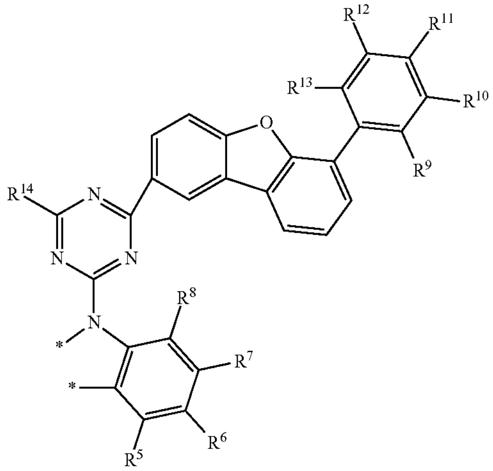
[Chemical Formula 2-4-iii]
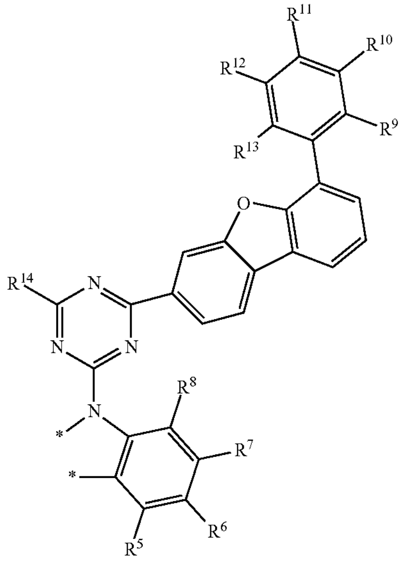
[Chemical Formula 2-4-iv]
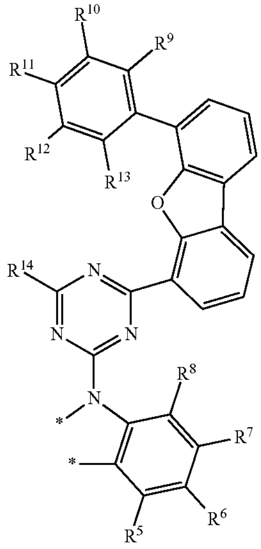

In Chemical Formula 2-4-i to Chemical Formula 2-4-iv, the definitions of $R^5$ to $R^{14}$, and * may be the same as described above.

In an implementation, the compound for an organic optoelectronic device according to an embodiment may be represented by a combination of Chemical Formula 1 and one of Chemical Formula 2-1-i to Chemical Formula 2-1-iv.

In an implementation, the compound for an organic optoelectronic device according to another embodiment may be represented by a combination of Chemical Formula 1 and Chemical Formula 2-2-ii.

In an implementation, the compound for an organic optoelectronic device according to another embodiment may be represented by a combination of Chemical Formula 1 and Chemical Formula 2-3-i.

In an implementation, the compound for an organic optoelectronic device according to another embodiment may be represented by a combination of Chemical Formula 1 and Chemical Formula 2-4-iv.

In the combination of Chemical Formula 1 and Chemical Formula 2-1-i, steric hindrance may occur as the dibenzofuranyl group is substituted on the triazine at the 1-position thereon and the dibenzofuranyl group is further substituted with the aryl group at the 8-position thereof, and thus a three-dimensional structure may be formed while having a non-planar angle with the triazine.

In an implementation, when the substituent is located at the 8-position of the dibenzofuran, it may have a larger angle. The larger the angle, the closer the shape of the molecule to a spherical shape, and the closer the molecule is to a spherical shape, the more densely it is arranged in the deposition process.

This structural feature may help reduce a gap between molecules to facilitate the flow of electrons/holes and may also facilitate formation of excitons, and thus low-driving, high-efficiency, and long life-span devices may be realized as a whole.

Therefore, it is possible to realize high-efficiency and long life-span characteristics of the organic light emitting diode to which it is applied.

In an implementation, the combination of Chemical Formula 1 and Chemical Formula 2 may be represented by, e.g., one of Chemical Formula 1A to Chemical Formula 1F, depending on the fusion form of indolocarbazole.

[Chemcial Formula 1A]

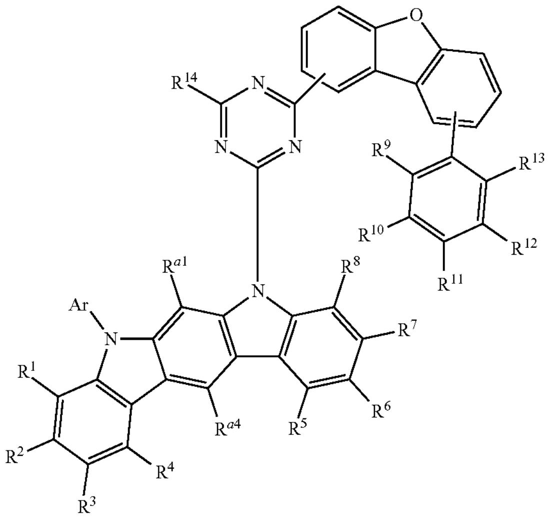

-continued

[Chemical Formula 1B]

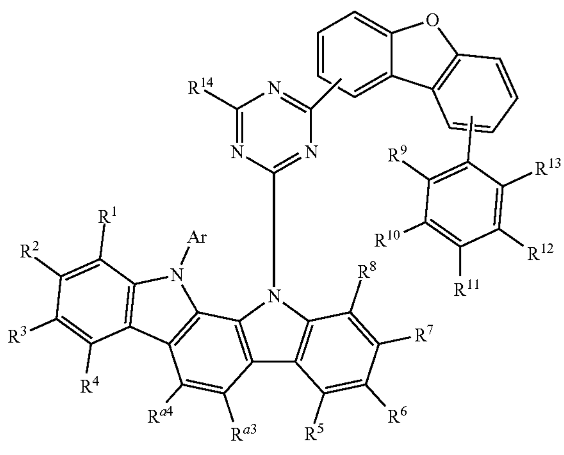

[Chemical Formula 1C]

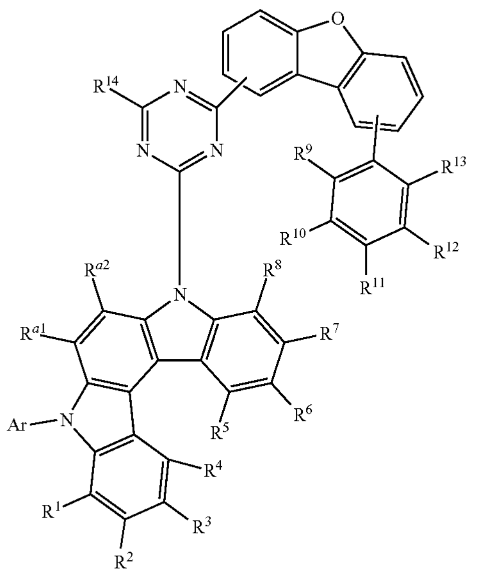

[Chemical Formula 1D]

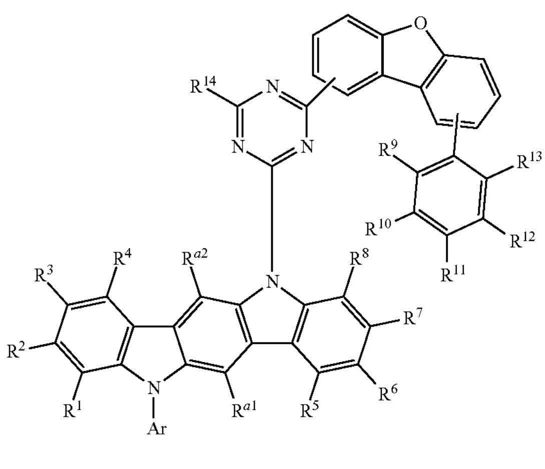

-continued

[Chemical Formula 1E]

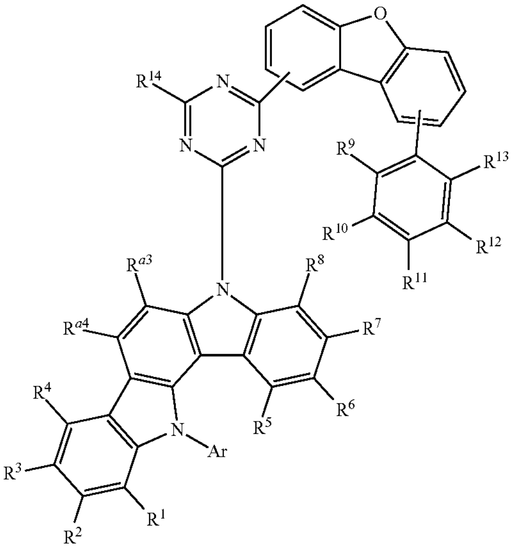

[Chemical Formula 1F]

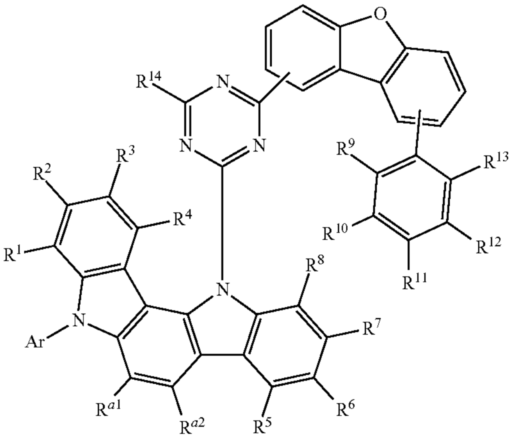

In Chemical Formula 1A to Chemical Formula 1F, Ar, and $R^1$ to $R^{14}$ may be defined the same as those described above.

$R^{a1}$ to $R^{a4}$ may each independently be defined the same as $R^a$.

In an implementation, the compound for an organic optoelectronic device according to an embodiment may be represented by, e.g., Chemical Formula 1B, Chemical Formula 1C, Chemical Formula 1E, or Chemical Formula 1F.

In an implementation, the compound for an organic optoelectronic device may be represented by, e.g., Chemical Formula 1B, Chemical Formula 1C, or Chemical Formula 1F.

In an implementation, the compound for an organic optoelectronic device may be represented by a combination of Chemical Formula 1 and Chemical Formula 2-1-i.

In an implementation, the combination of Chemical Formula 1 and Chemical Formula 2-1-i may be represented by, e.g., one of Chemical Formula 1A-1 to Chemical Formula 1F-1, depending on the fusion form of indolocarbazole.

[Chemical Formula 1A-1]

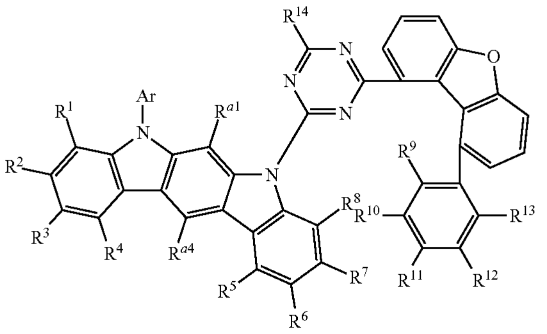

[Chemical Formula 1B-1]

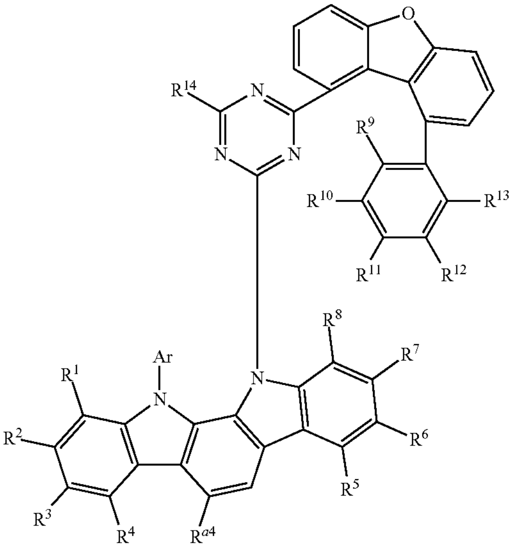

[Chemical Formula 1C-1]

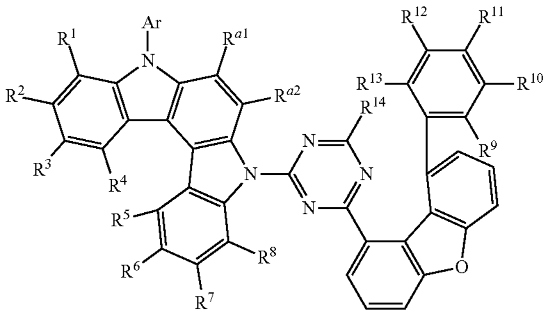

-continued

[Chemical Formula 1D-1]

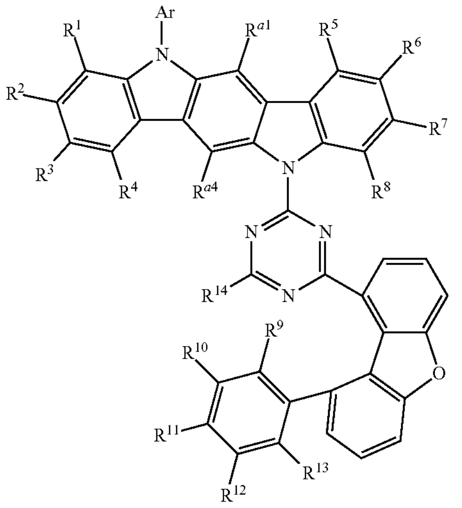

[Chemical Formula 1E-1]

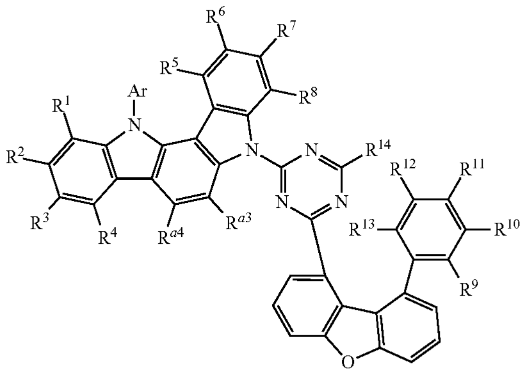

[Chemical Formula 1F-1]

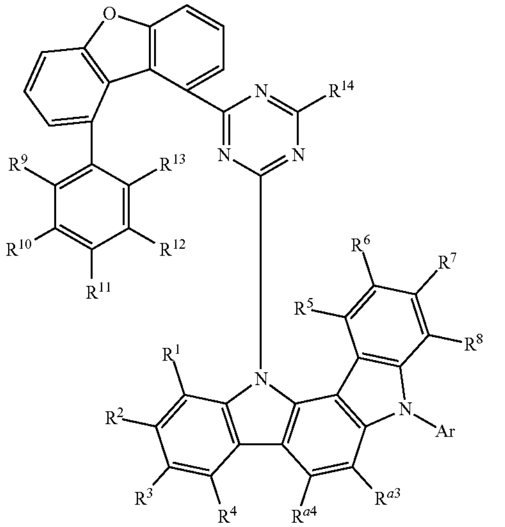

In Chemical Formula 1A-1 to Chemical Formula 1F-1, Ar, and $R^1$ to $R^{14}$ may be defined the same as those described above.

$R^{a1}$ to $R^{a4}$ may each independently be defined the same as $R^a$.

In an implementation, the compound for an organic optoelectronic device according to an embodiment may be represented by, e.g., Chemical Formula 1B-1, Chemical Formula 1C-1, Chemical Formula 1E-1, or Chemical Formula 1F-1.

In an implementation, the compound for an organic optoelectronic device may be represented by, e.g., Chemical Formula 1B-1, Chemical Formula 1C-1, or Chemical Formula 1F-1.

In an implementation, the compound for an organic optoelectronic device may be represented by, e.g., a combination of Chemical Formula 1 and Chemical Formula 2-2-ii.

In an implementation, the compound for an organic optoelectronic device may be represented by, e.g., Chemical Formula 1B-2.

[Chemical Formula 1B-2]

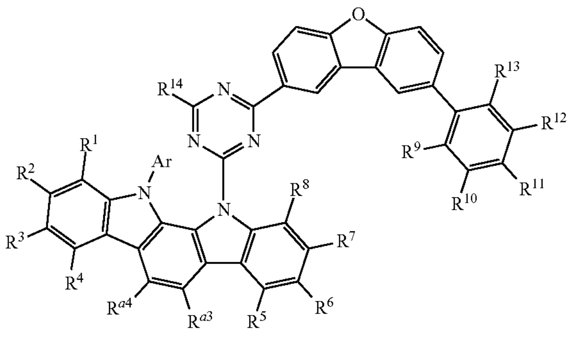

In Chemical Formula 1B-2, Ar, $R^1$ to $R^{14}$, $R^{a1}$ and $R^{a4}$ may be defined the same as those described above.

In an implementation, the compound for an organic optoelectronic device may be represented by, e.g., a combination of Chemical Formula 1 and Chemical Formula 2-3-i.

In an implementation, the compound for an organic optoelectronic device may be represented by, e.g., Chemical Formula 1B-3.

[Chemical Formula 1B-3]

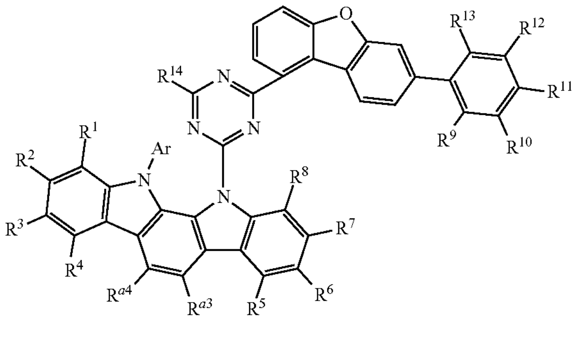

In Chemical Formula 1B-3, Ar, $R^1$ to $R^{14}$, $R^{a3}$ and $R^{a4}$ may be defined the same as those described above.

In an implementation, the compound for an organic optoelectronic device may be represented by, e.g., a combination of Chemical Formula 1 and Chemical Formula 2-4-iv.

In an implementation, the compound for an organic optoelectronic device may be represented by, e.g., Chemical Formula 1B-4.

[Chemical Formula 1B-4]

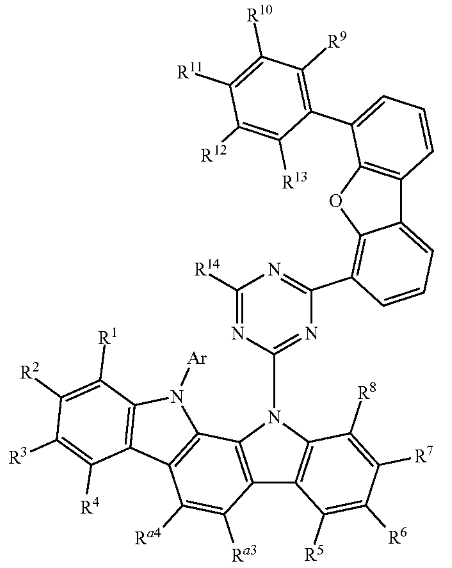

In Chemical Formula 1B-4, Ar, $R^1$ to $R^{14}$, $R^{a3}$ and $R^{a4}$ may be defined the same as those described above.

In an implementation, Ar may be, e.g., a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylene group.

In an implementation, Ar may be, e.g., a substituted or unsubstituted biphenyl group, or a substituted or unsubstituted terphenyl group.

In an implementation, Ar may be, e.g., a group of Group I.

[Group I]

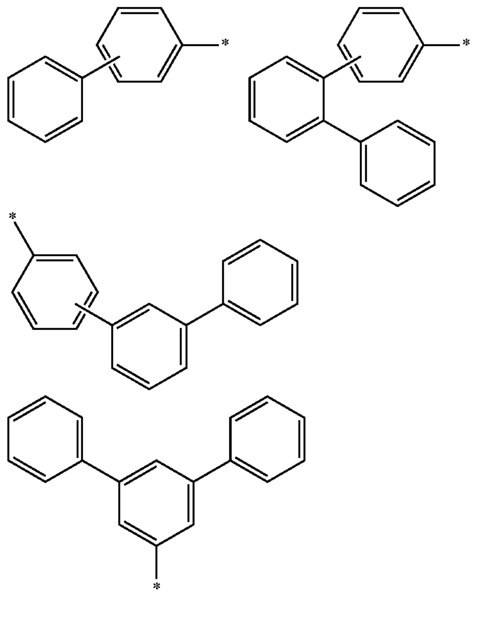

-continued

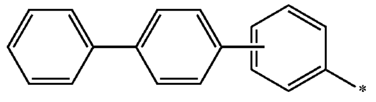

In Group I, * is a linking point (e.g., with N of Chemical Formula 1).

In an implementation, $R^{14}$ may be, e.g., a substituted or unsubstituted phenyl group, a substituted or unsubstituted biphenyl group, a substituted or unsubstituted terphenyl group, or a substituted or unsubstituted naphthyl group.

In an implementation, $R^{14}$ may be, e.g., a substituted or unsubstituted phenyl group, a substituted or unsubstituted biphenyl group, or a substituted or unsubstituted terphenyl group.

In an implementation, when $R^{14}$ is substituted, it may be substituted with, e.g., a cyano group or a phenyl group.

In an implementation, $R^9$ to $R^{13}$ may each independently be, e.g., hydrogen, deuterium, a substituted or unsubstituted phenyl group, or a substituted or unsubstituted biphenyl group.

In an implementation, $R^9$ to $R^{13}$ may each independently be, e.g., hydrogen, deuterium, a substituted or unsubstituted phenyl group, or a substituted or unsubstituted biphenyl group.

In an implementation, $R^1$ to $R^8$ may each independently be, e.g., hydrogen, deuterium, a substituted or unsubstituted phenyl group, or a substituted or unsubstituted biphenyl group.

In an implementation, $R^1$ to $R^8$ may each independently be, e.g., hydrogen, deuterium, or a substituted or unsubstituted phenyl group.

In an implementation, the compound for an organic optoelectronic device represented by the combination of Chemical Formula 1 and Chemical Formula 2 may be, e.g., a compound of Group 1.

[Group 1]

1

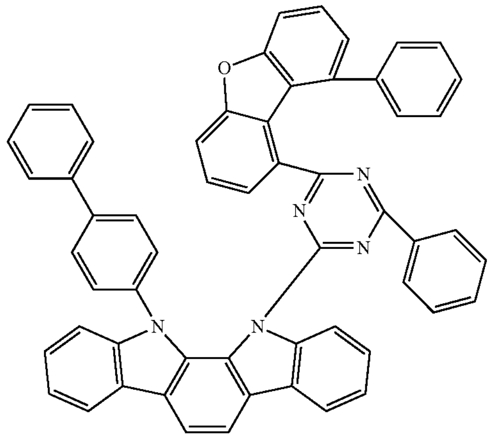

-continued
2
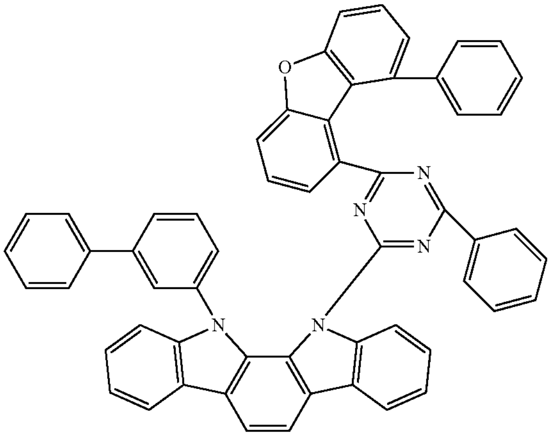
3
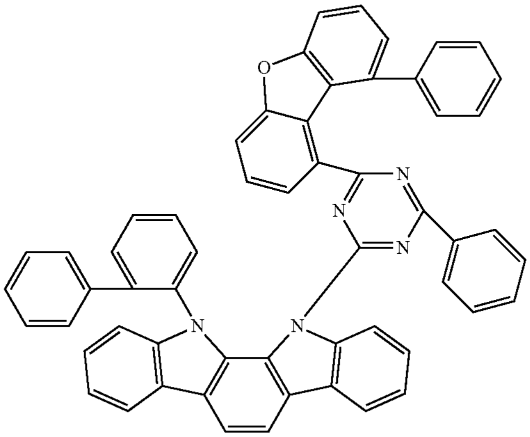
4
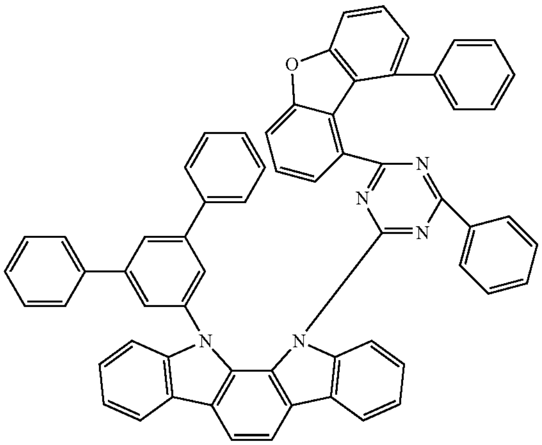
-continued
5
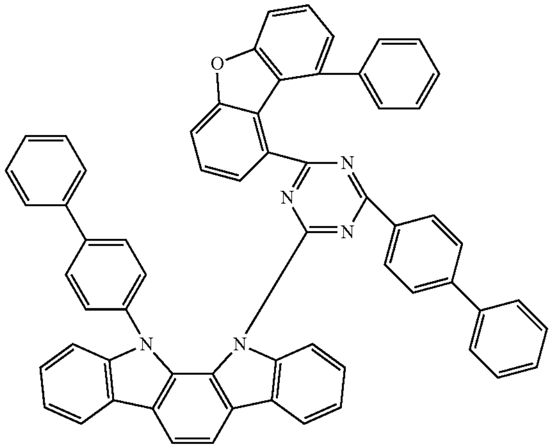
6
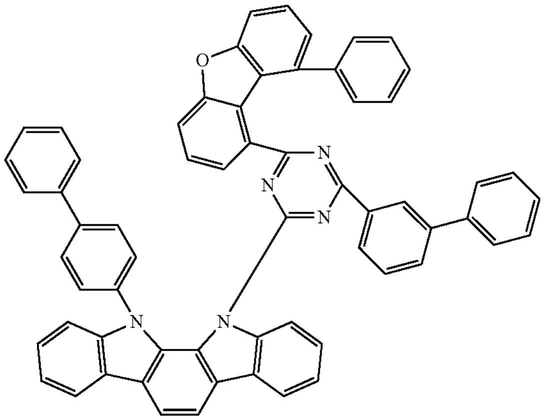
7
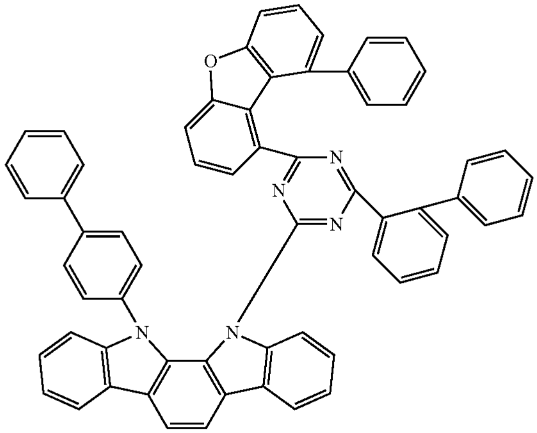

-continued
8
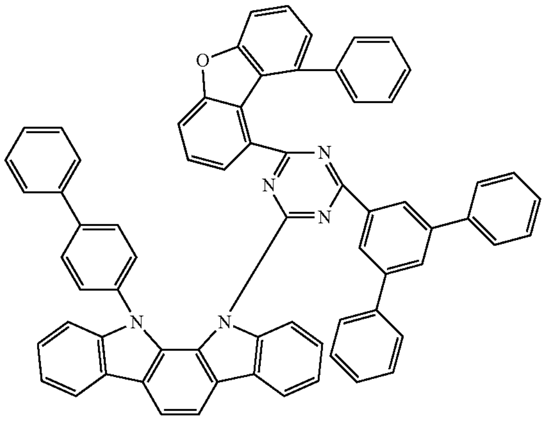
9
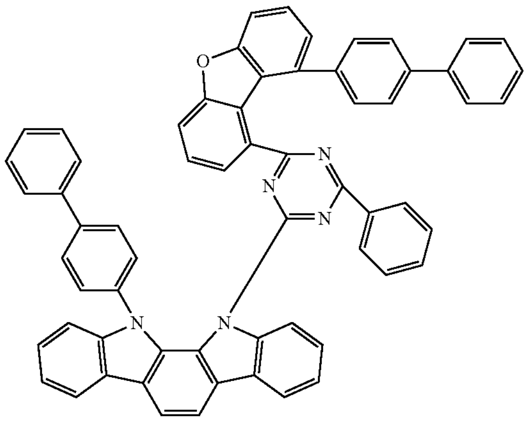
10
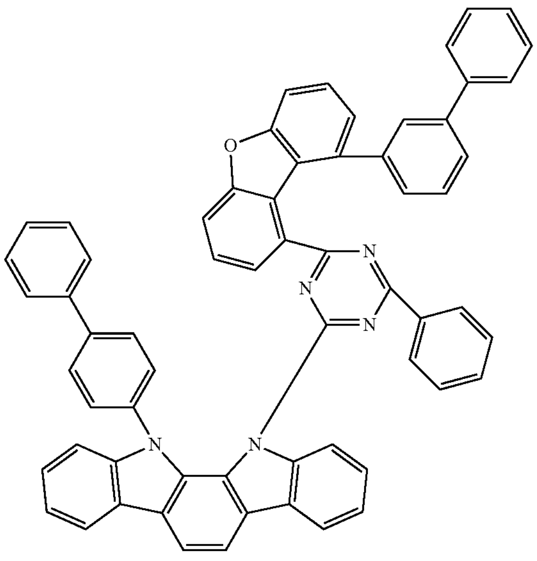
-continued
11
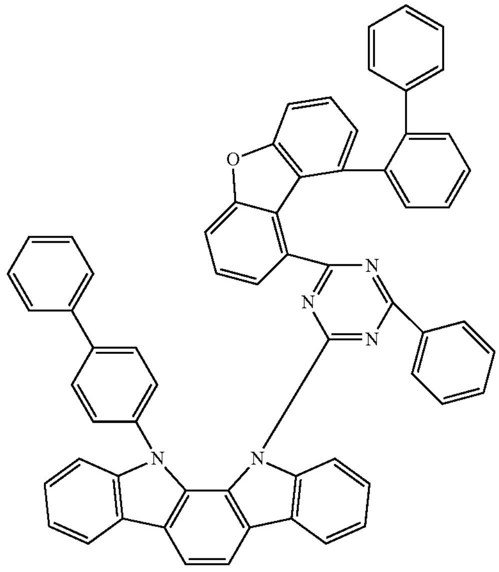
12
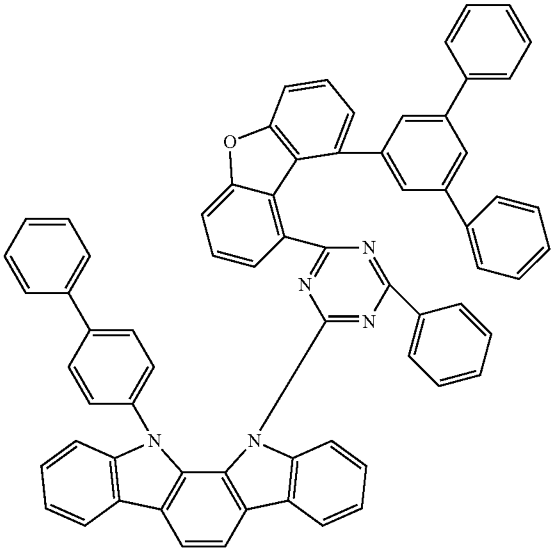

-continued
13
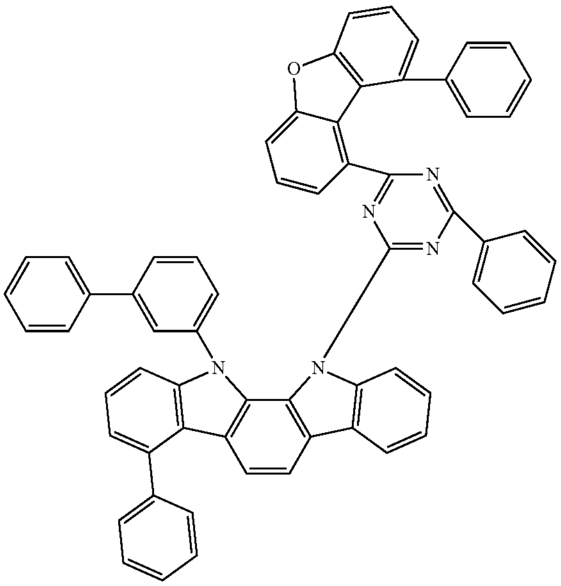
14
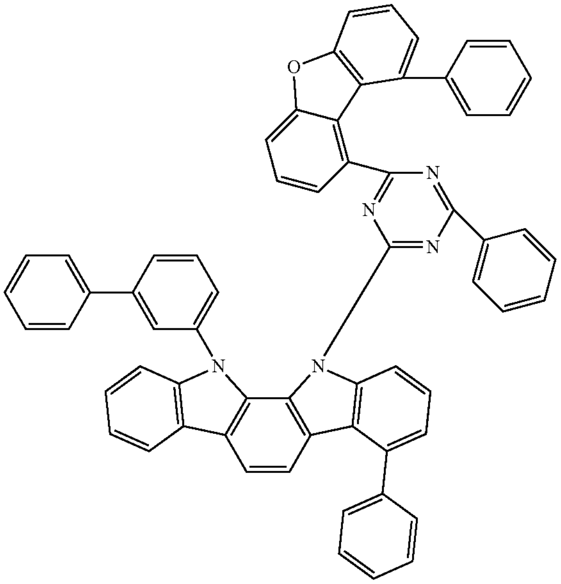
-continued
15
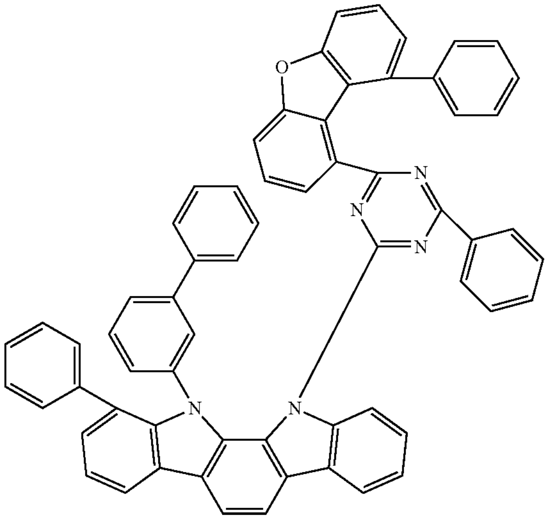
16
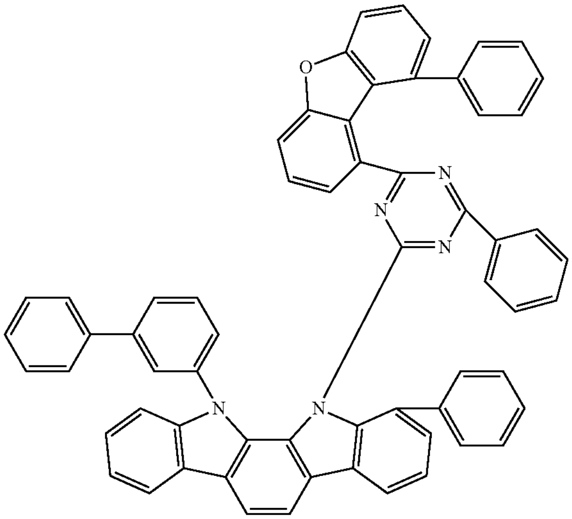
17
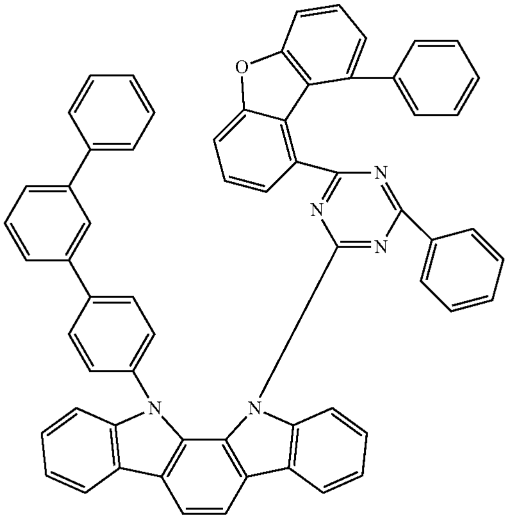

-continued
18
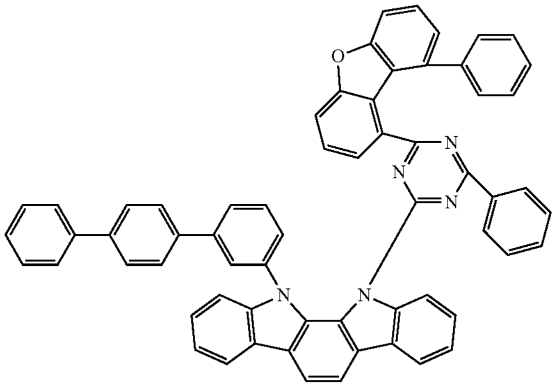
19
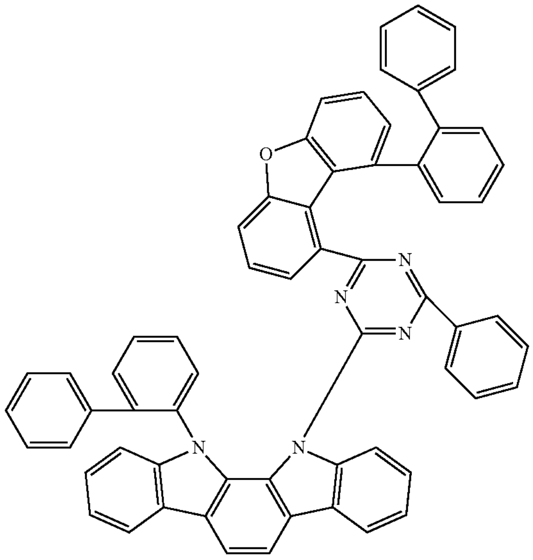
20
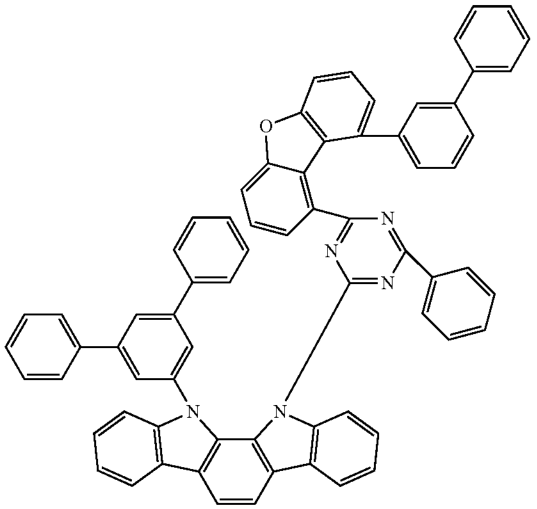
-continued
21
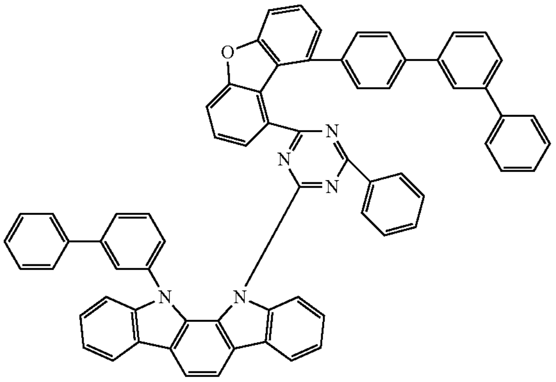
22
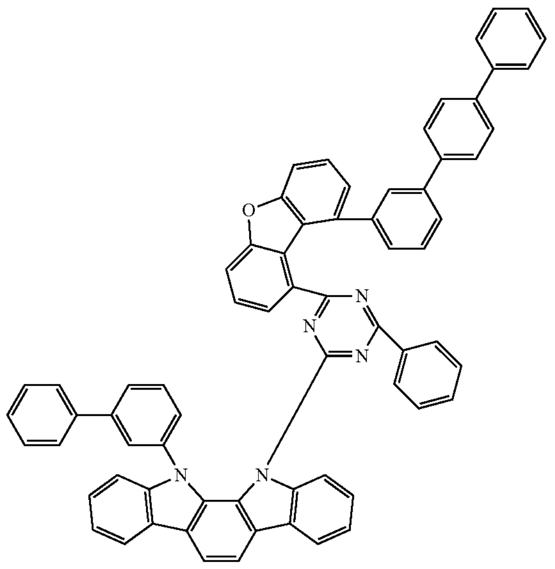
23
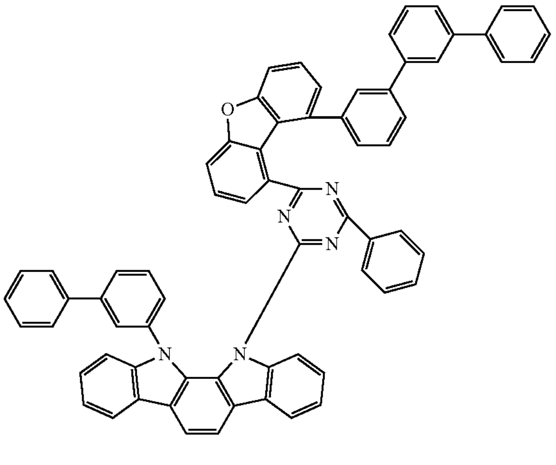

-continued
24
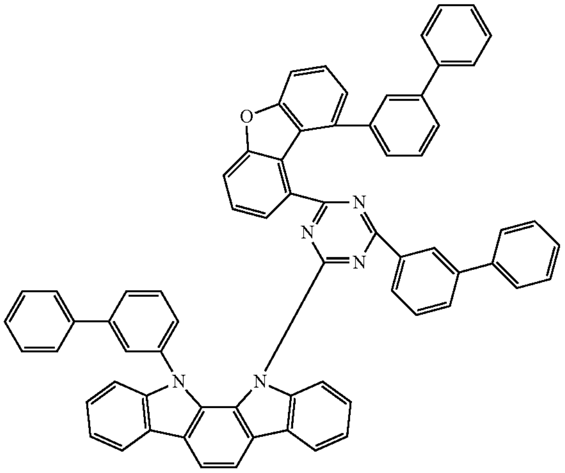
25
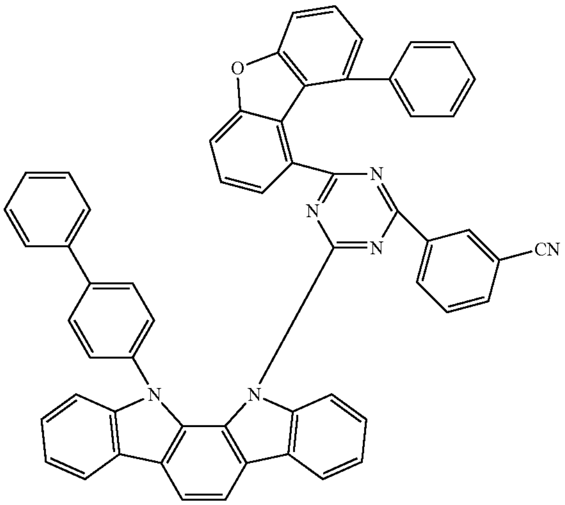
26
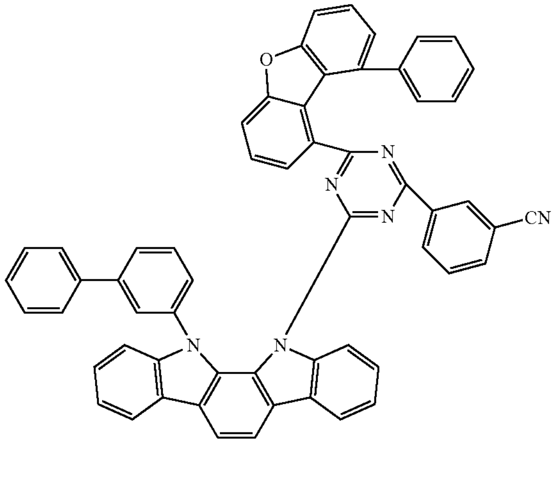
-continued
27
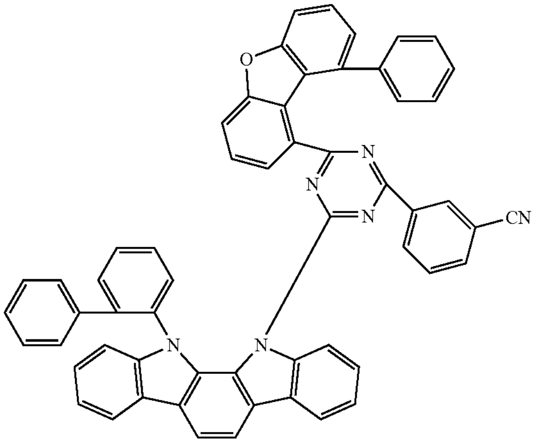
28
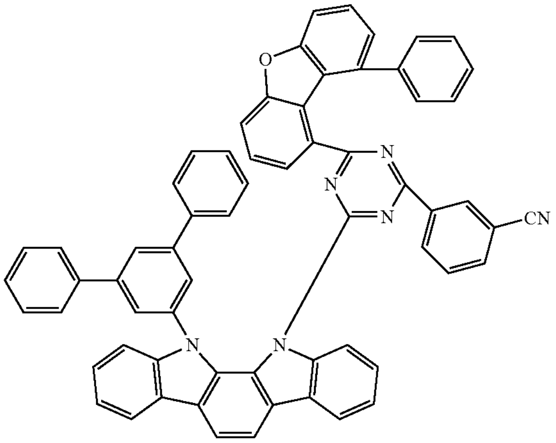
29
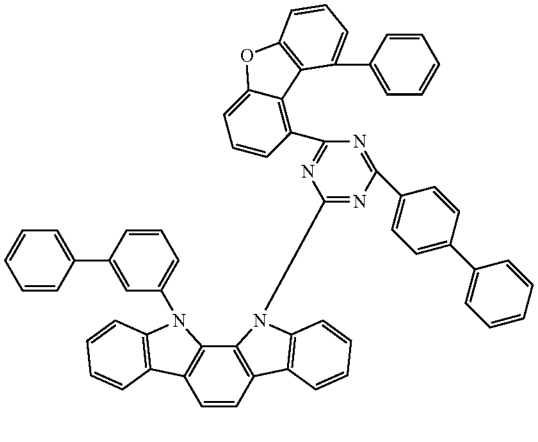

-continued
30
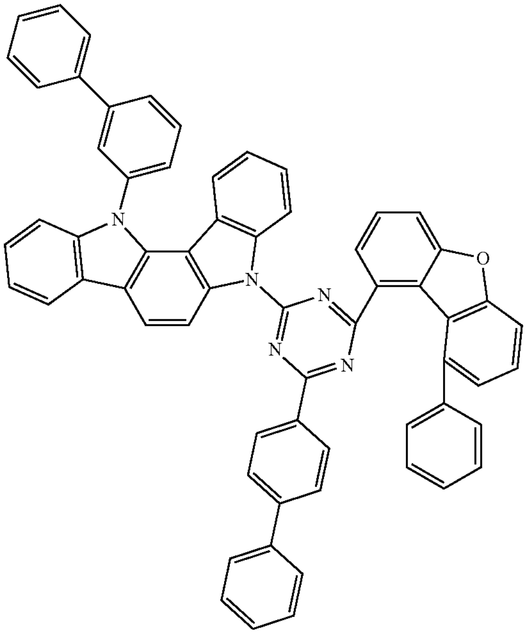
31
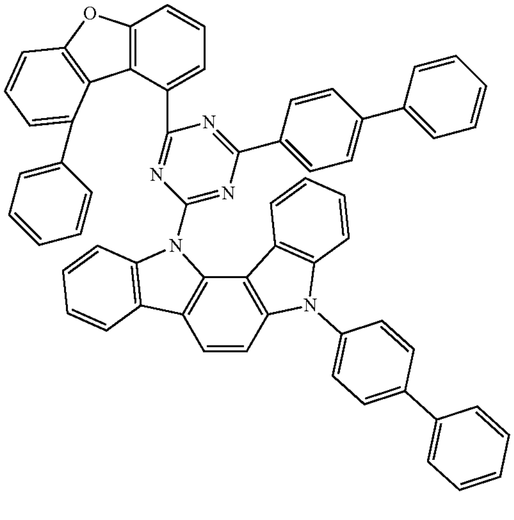
-continued
32
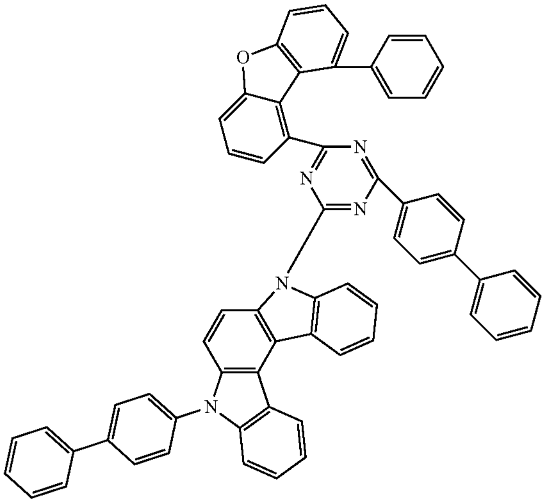
33
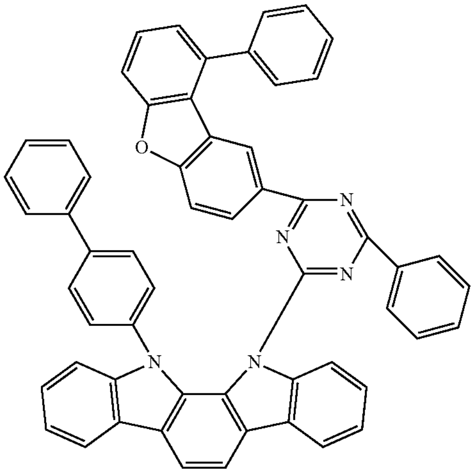
34
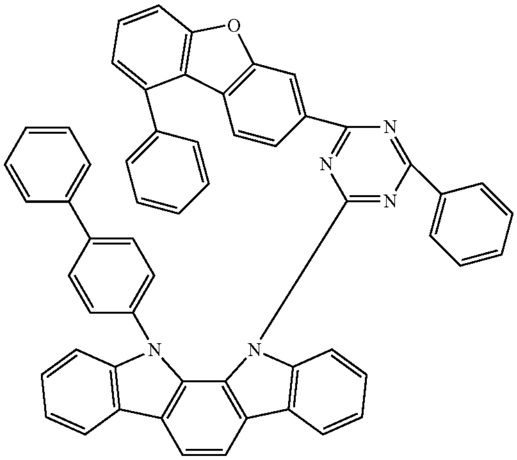

35
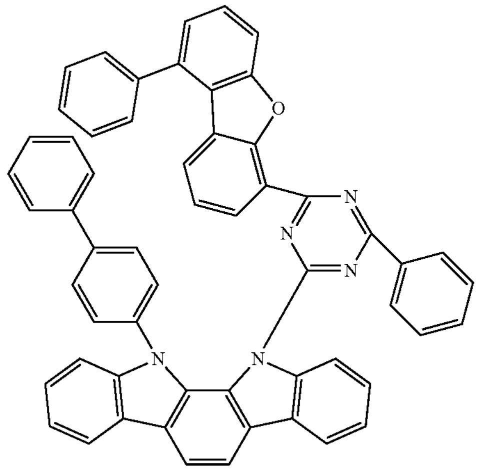
36
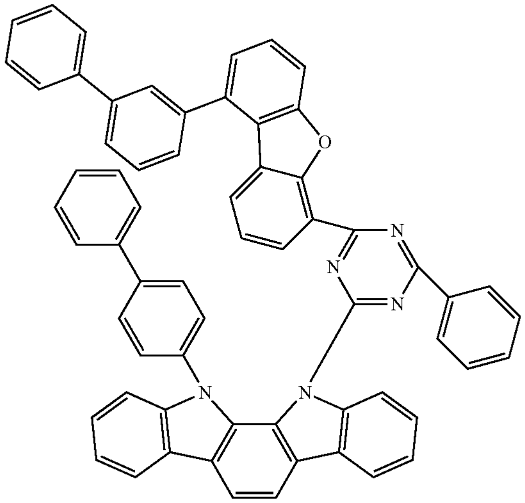
37
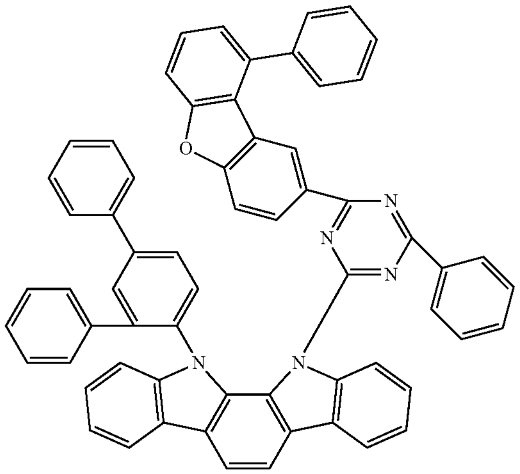
38
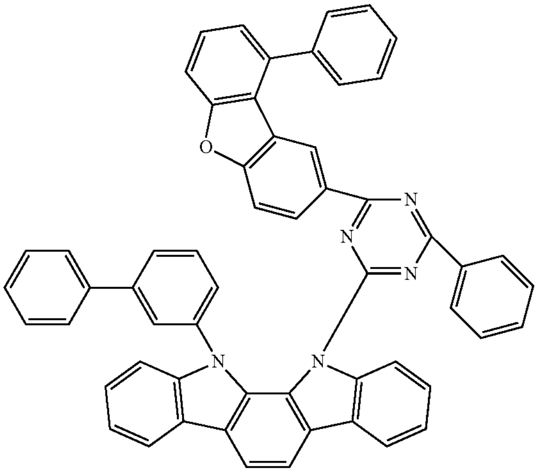
39
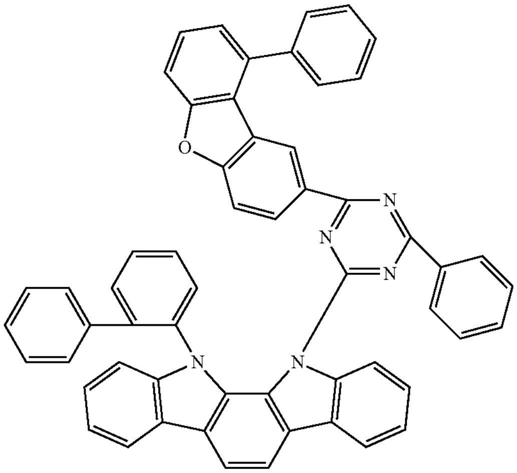
40
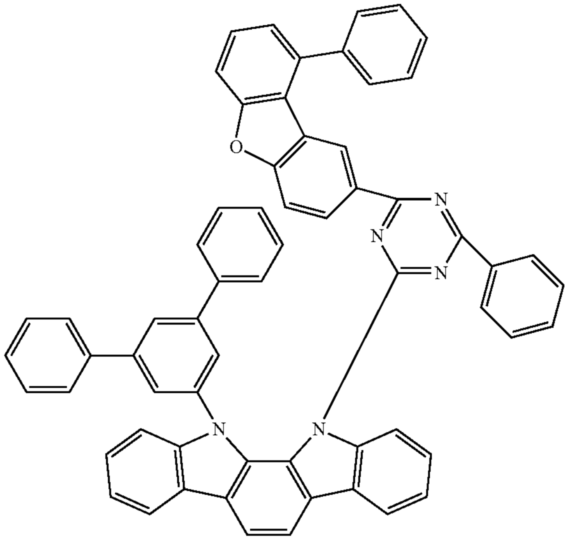

-continued
41
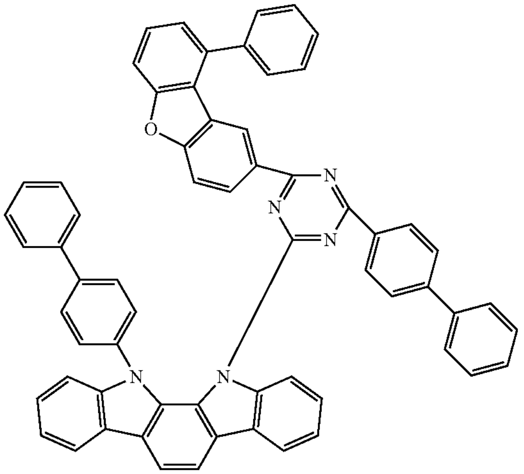
42
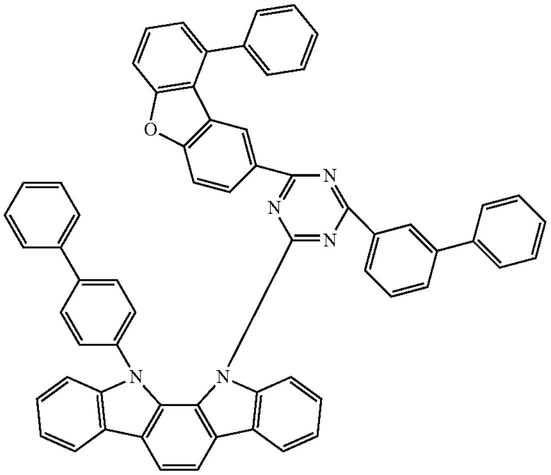
43
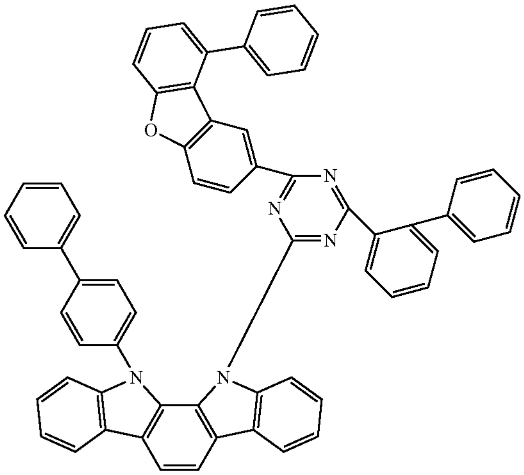
-continued
44
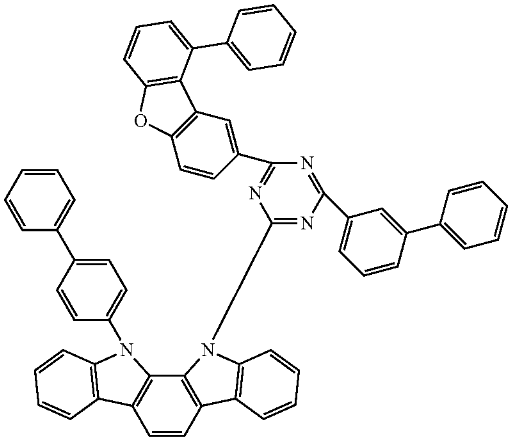
45
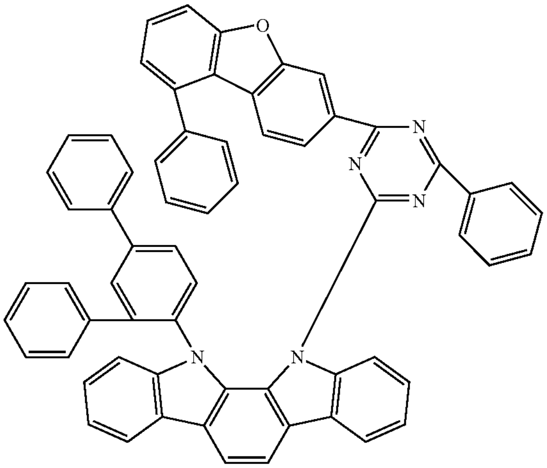
46
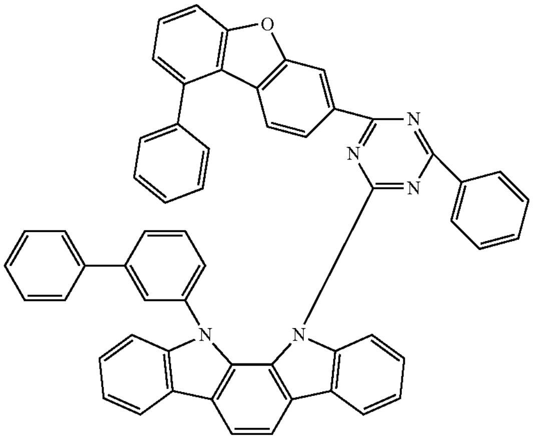

-continued
47
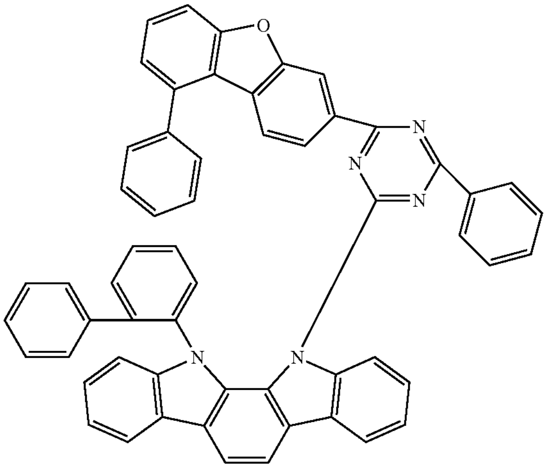
48
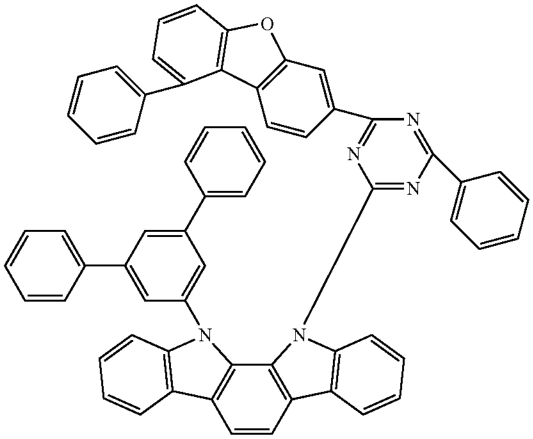
49
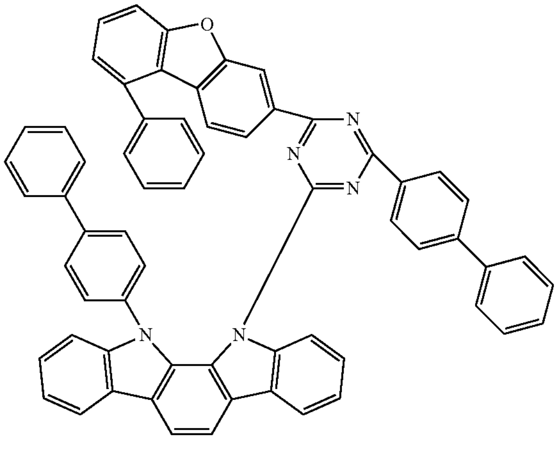
-continued
50
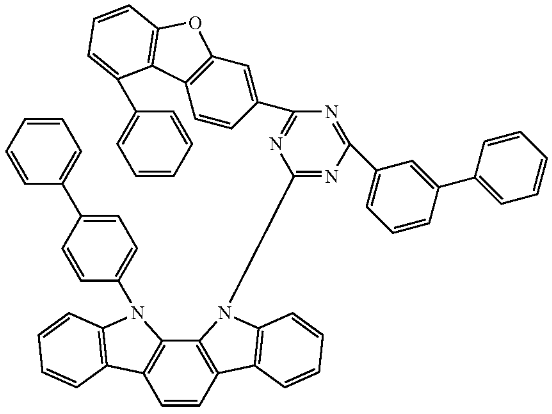
51
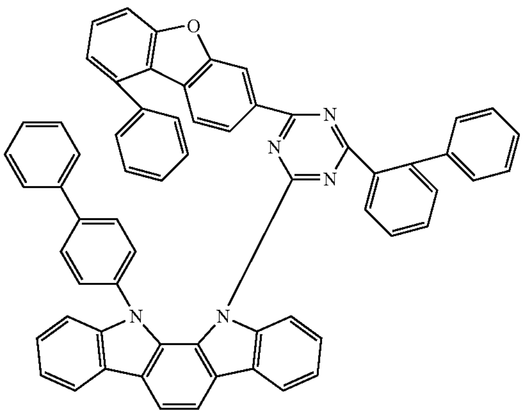
52
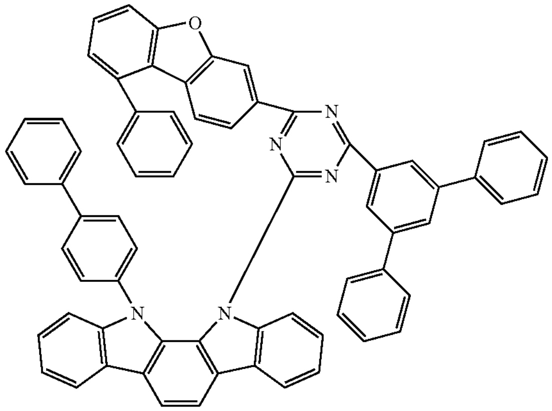

-continued
53
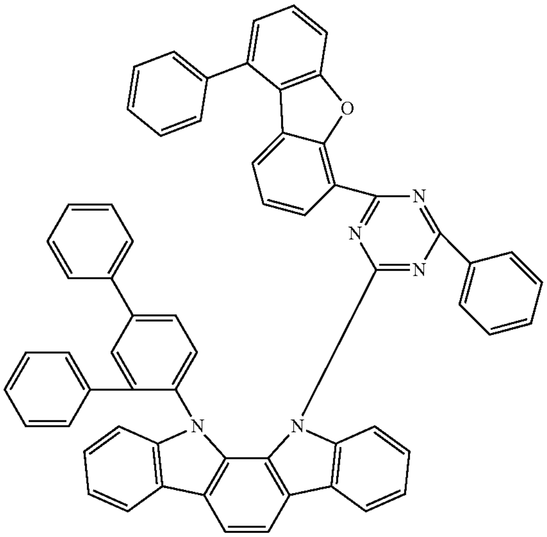
54
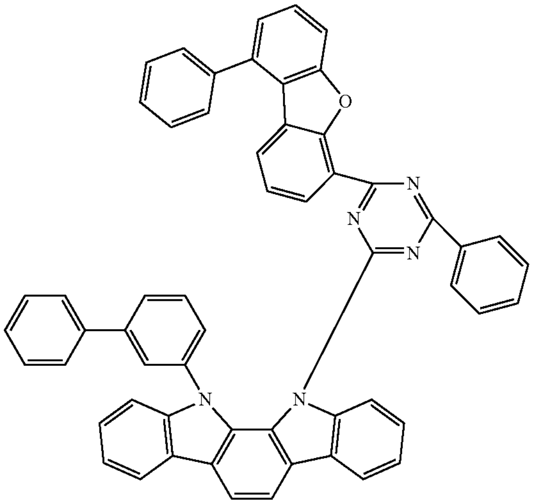
55
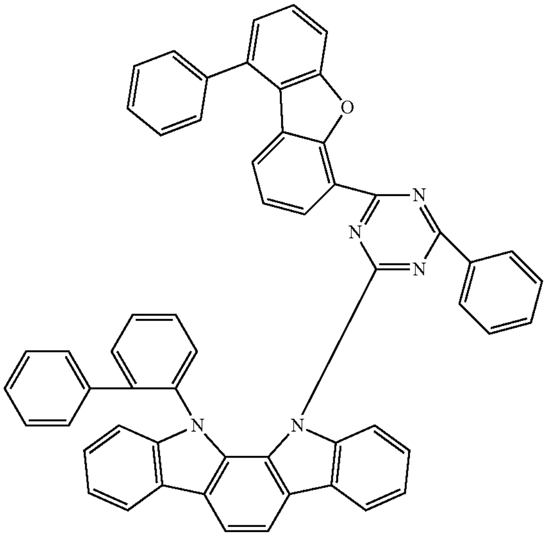
-continued
56
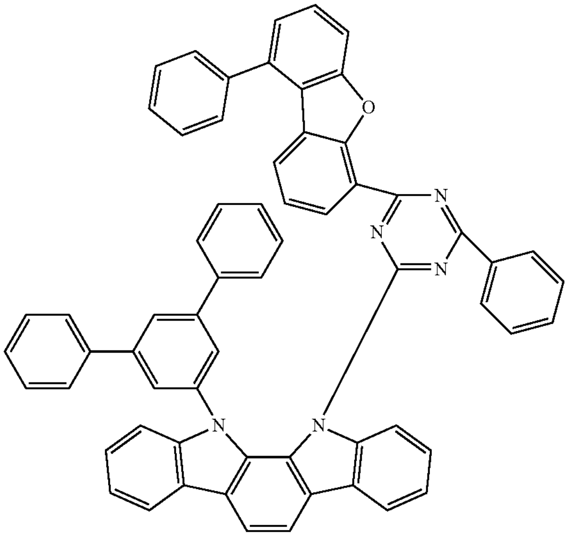
57
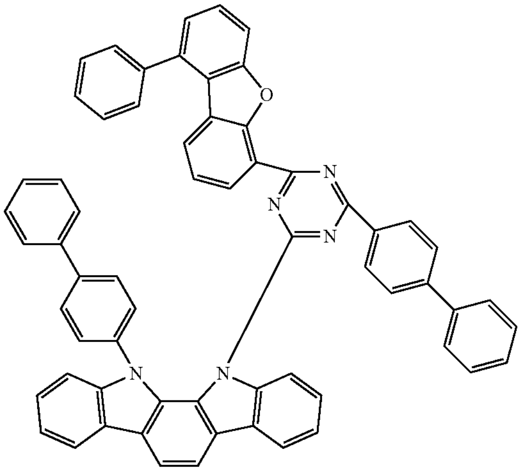
58
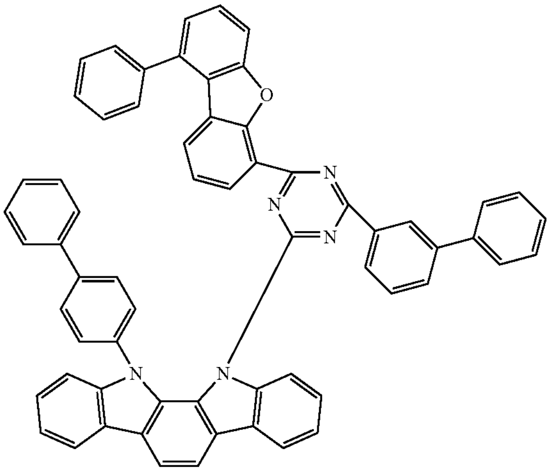

-continued
59
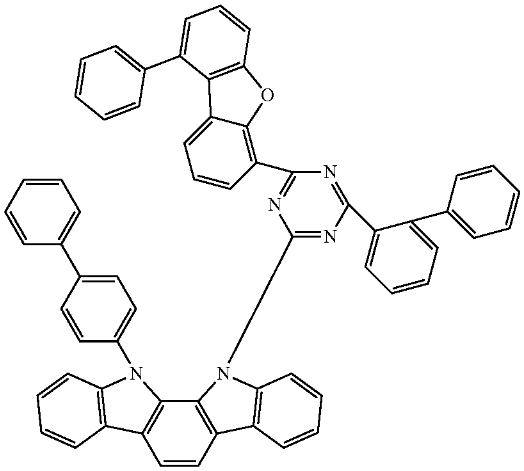
60
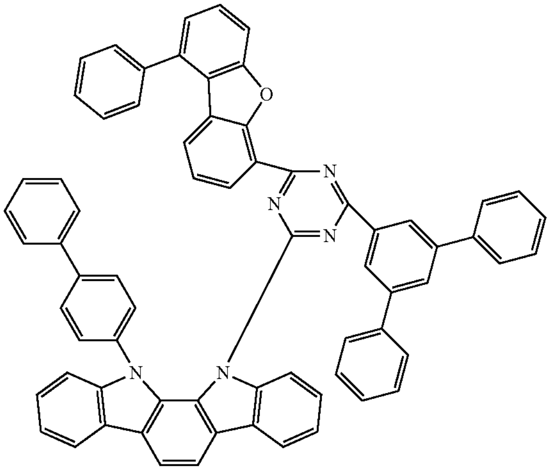
61
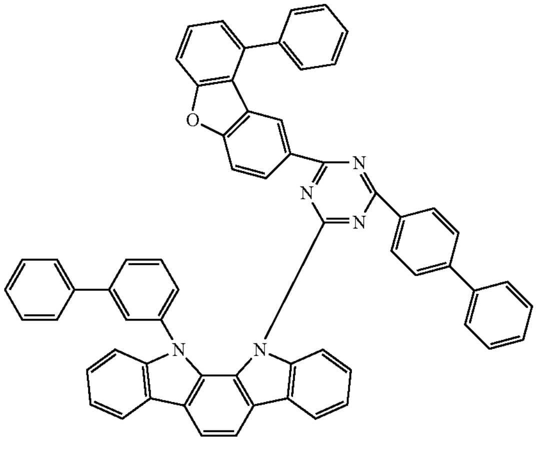
-continued
62
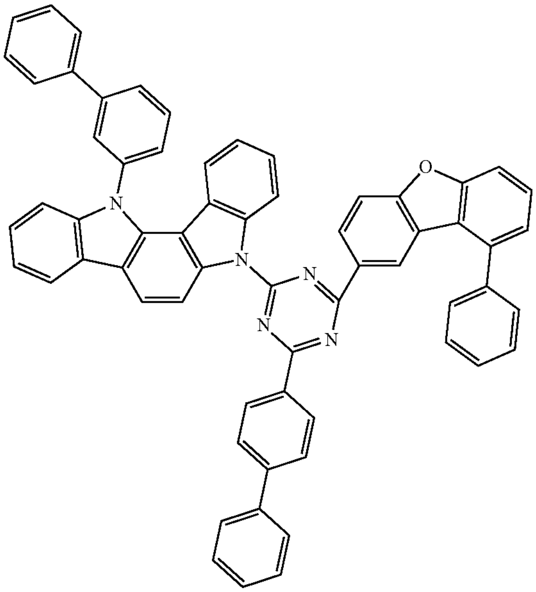
63
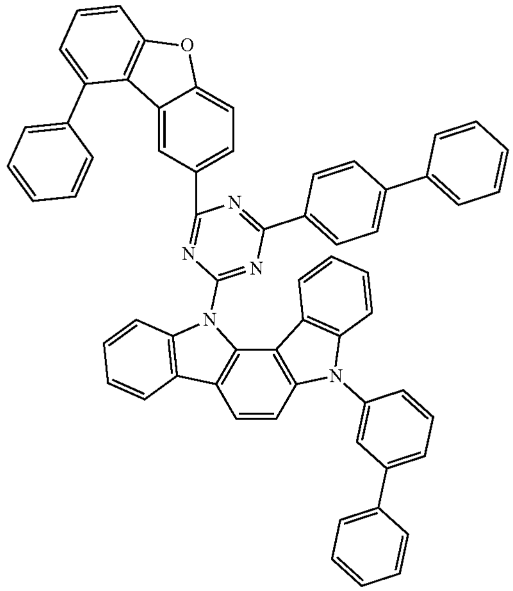

-continued
64
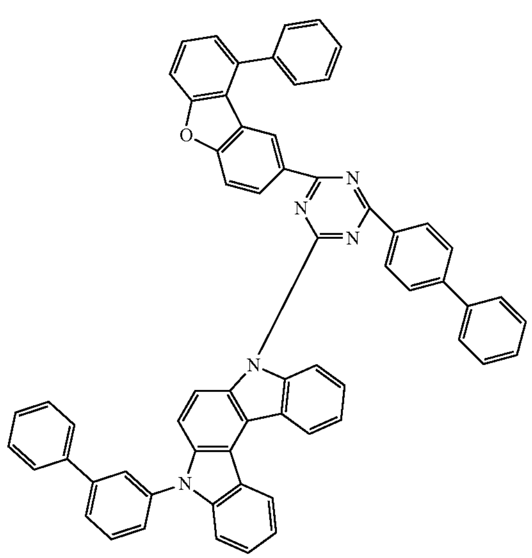
65
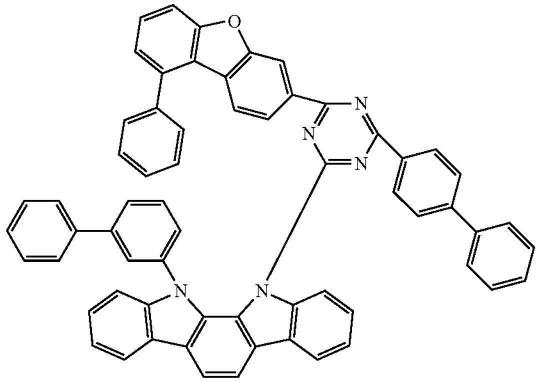
66
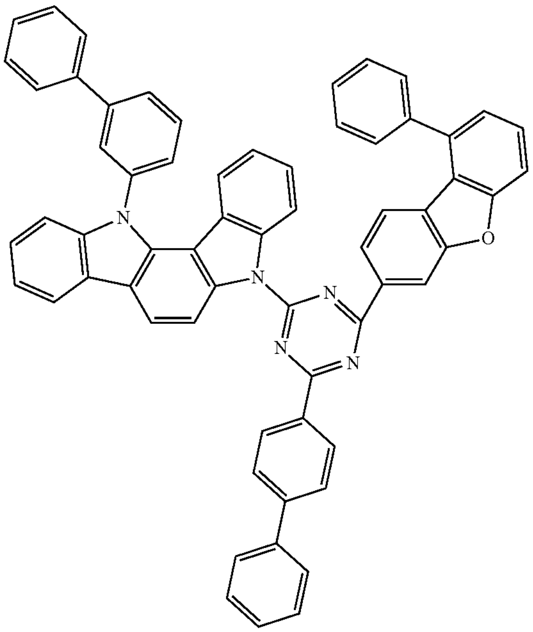
-continued
67
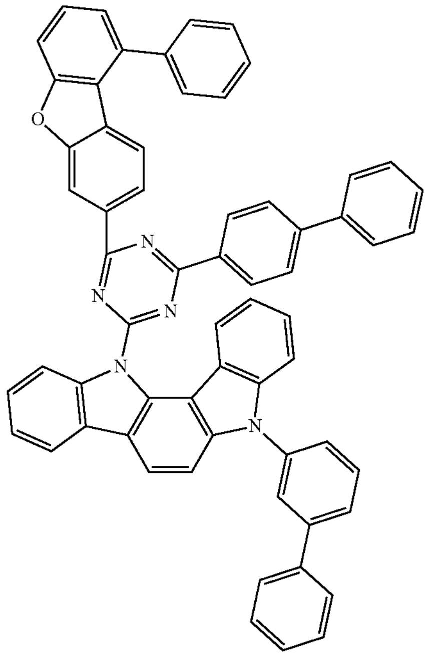
68
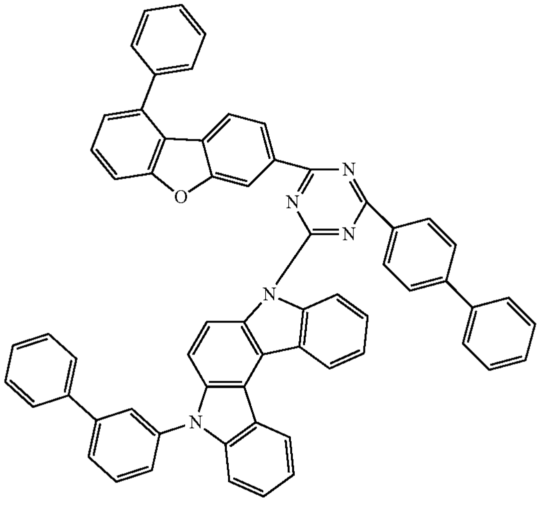
69
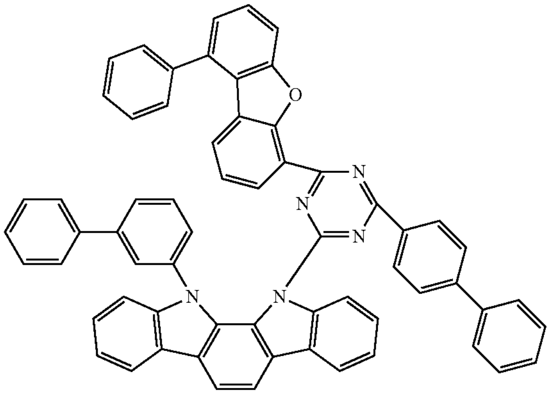

-continued
70
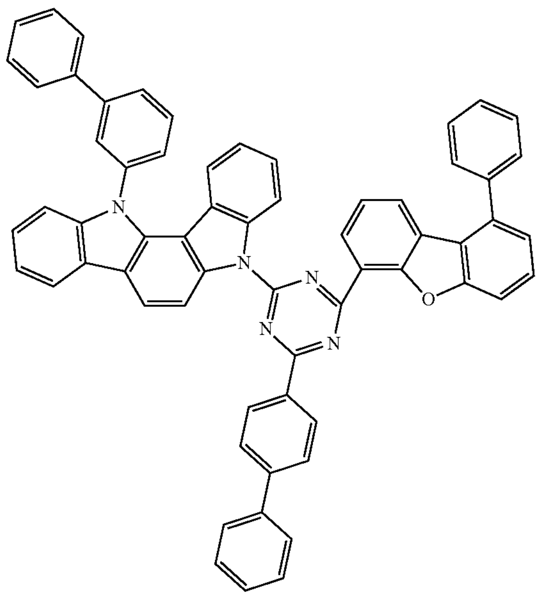
71
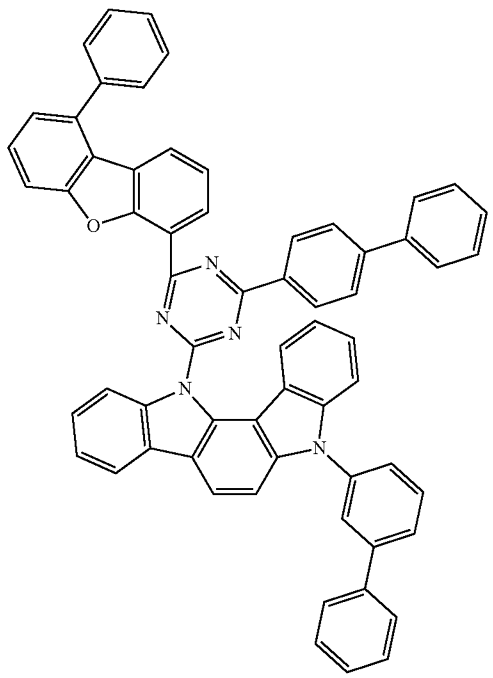
-continued
72
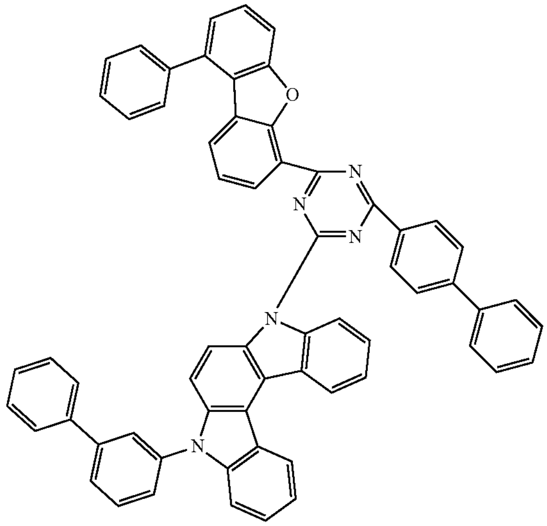
73
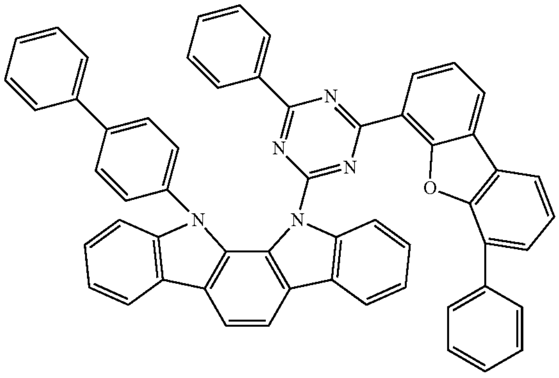
74
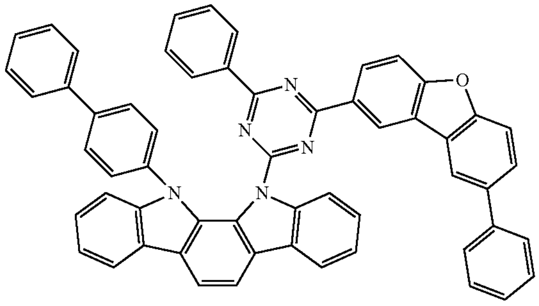
75
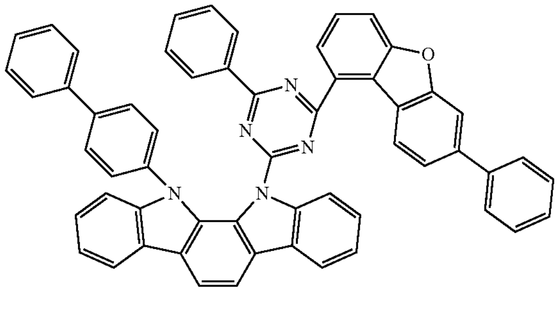

-continued
76
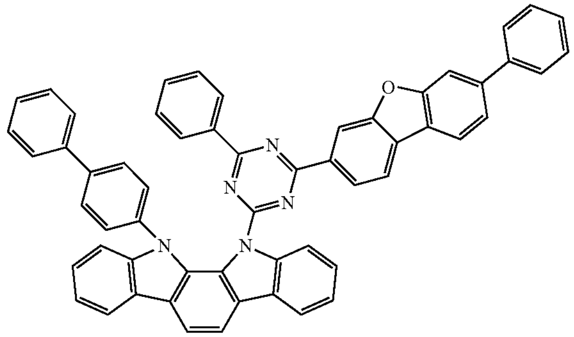
77
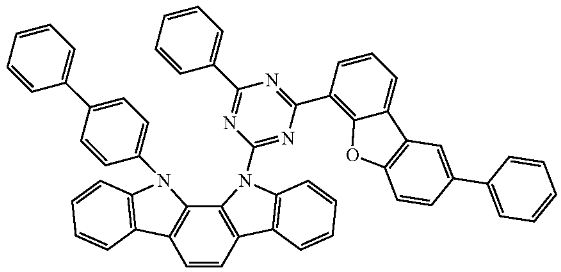
78
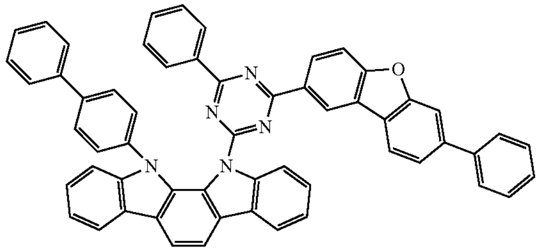
79
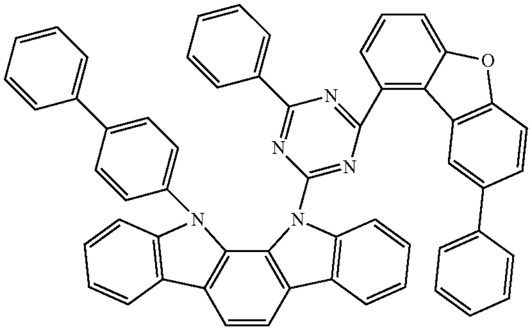
80
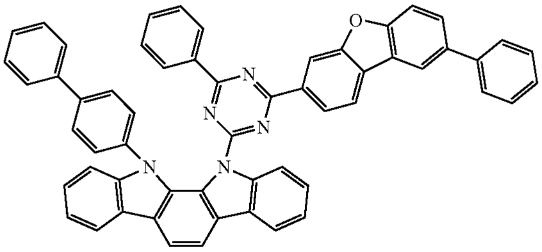
-continued
81
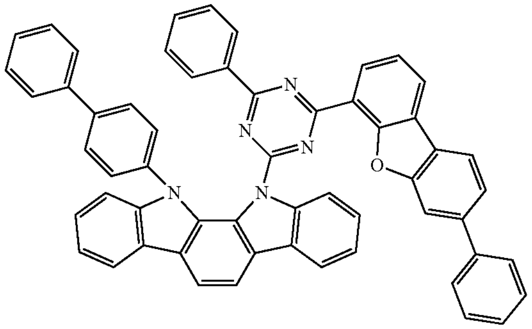
82
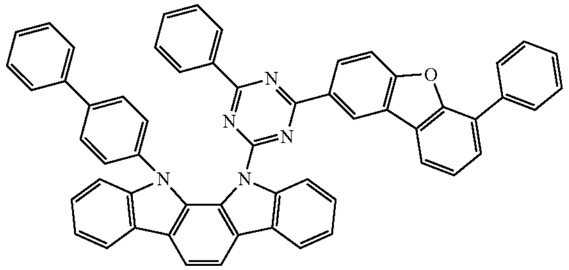
83
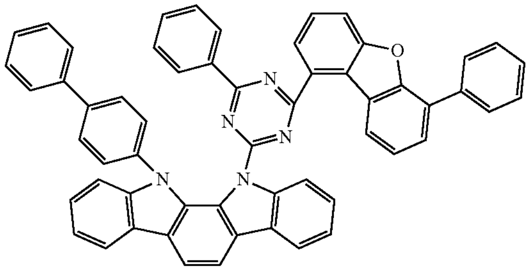
84
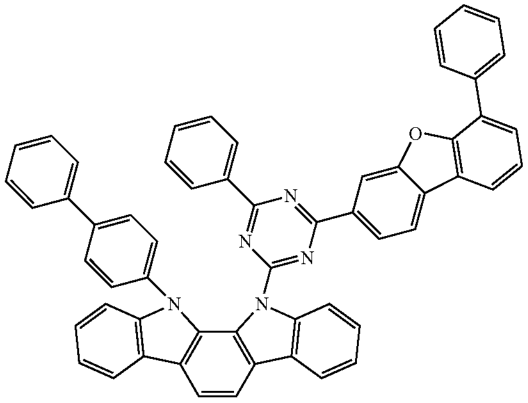

-continued
85
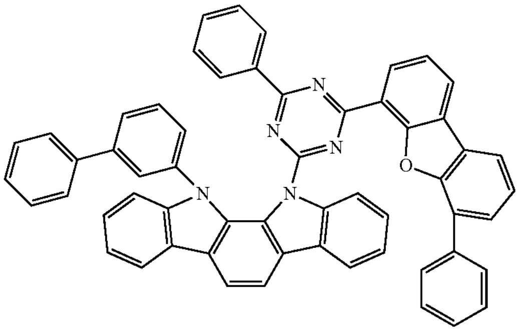
86
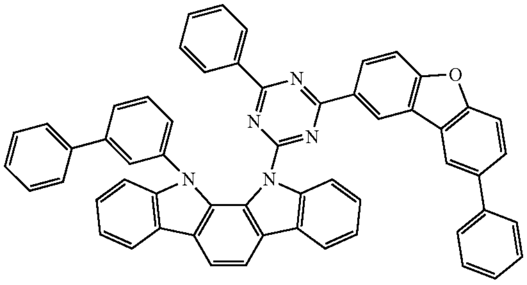
87
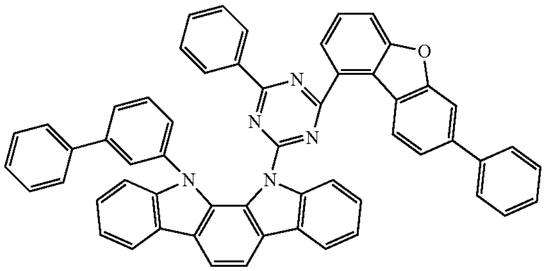
88
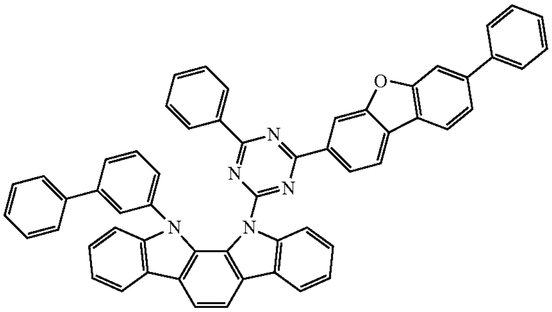
-continued
89
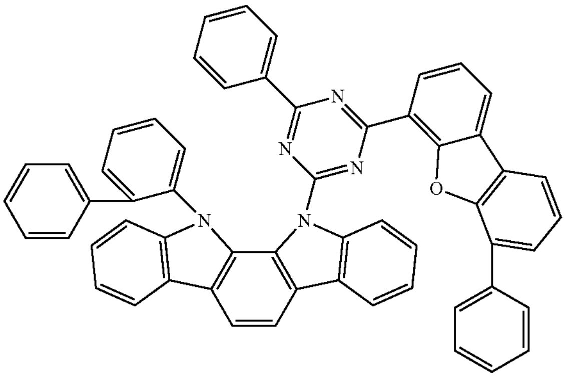
90
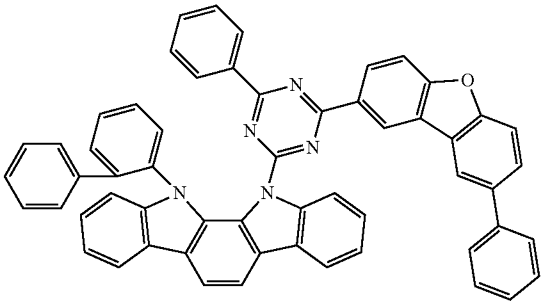
91
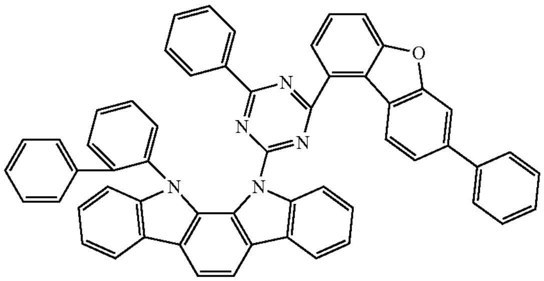
92
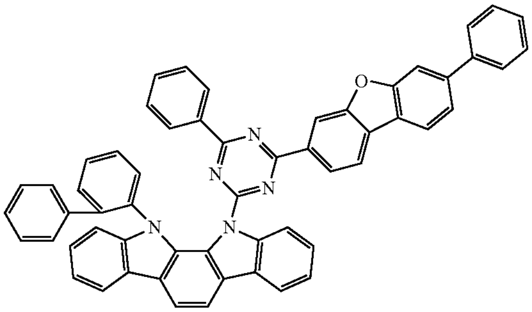

-continued
93
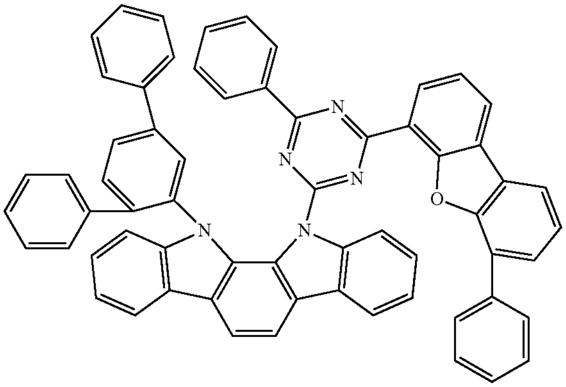
94
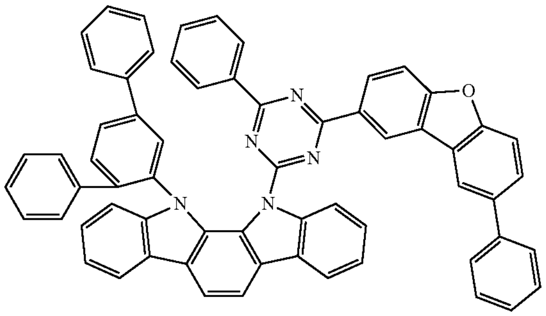
95
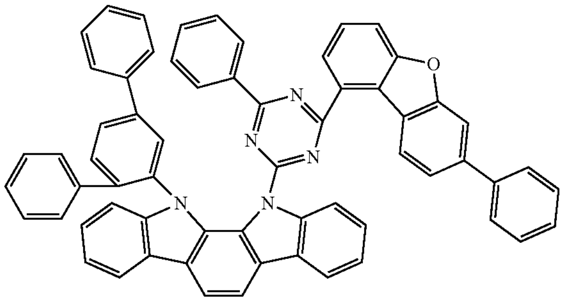
96
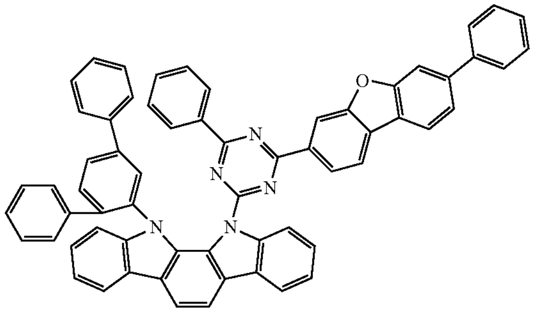
-continued
97
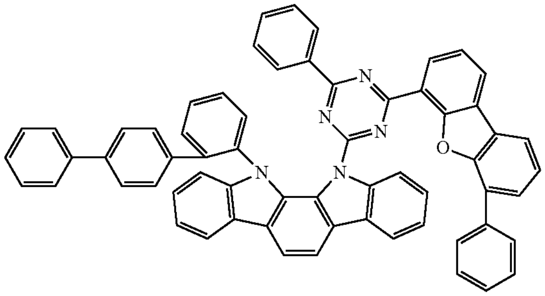
98
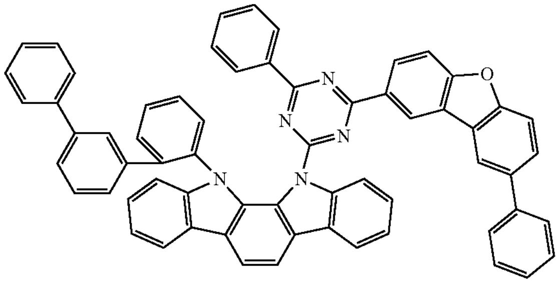
99
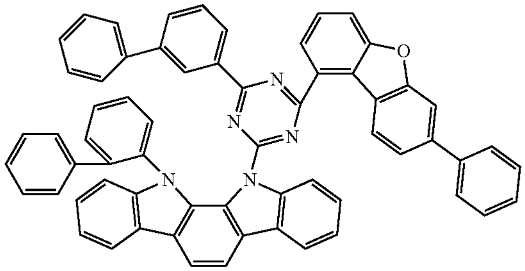
100
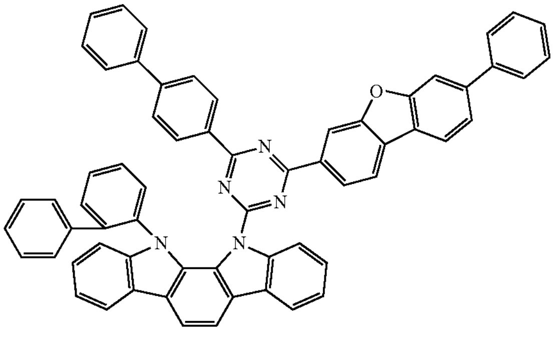

-continued
101
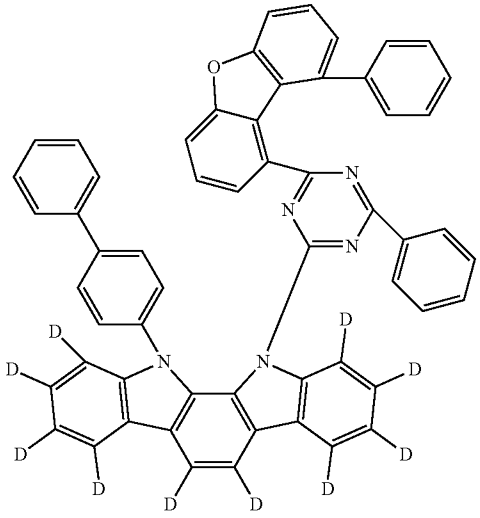
102
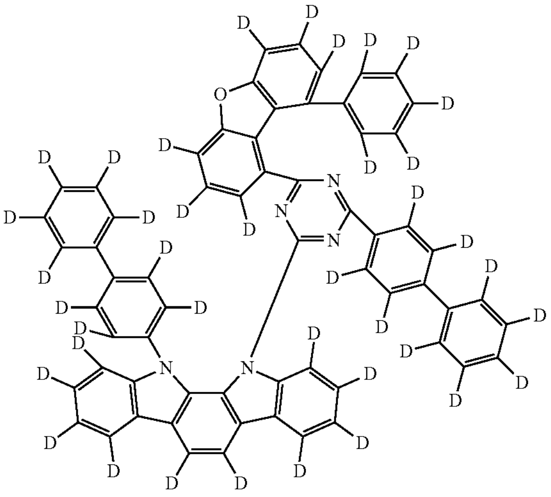
103
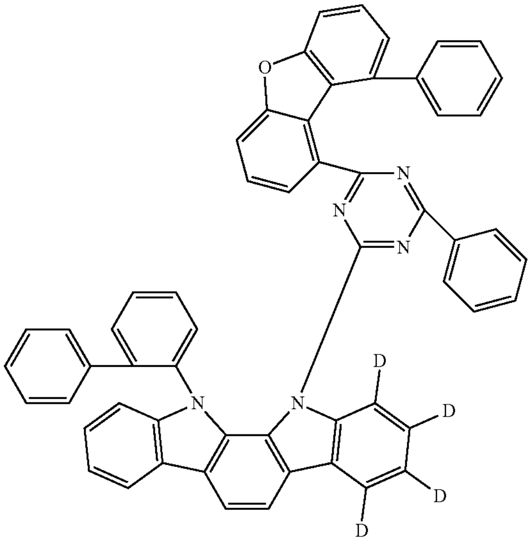
-continued
104
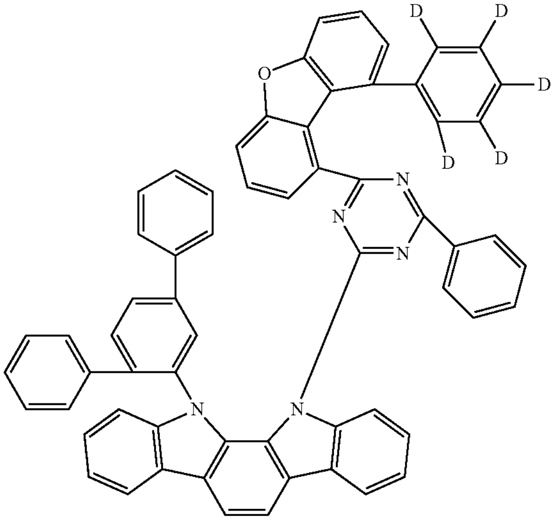
105
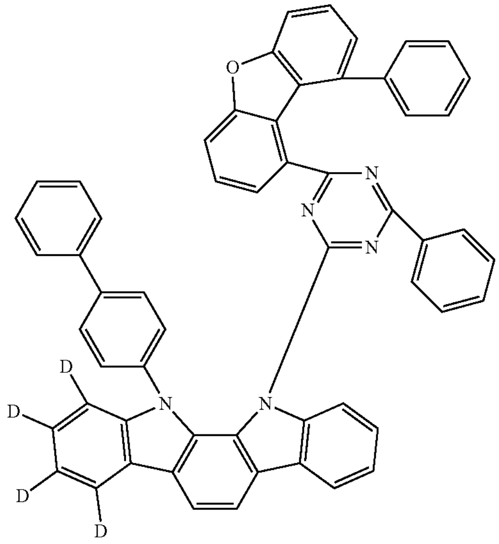
106
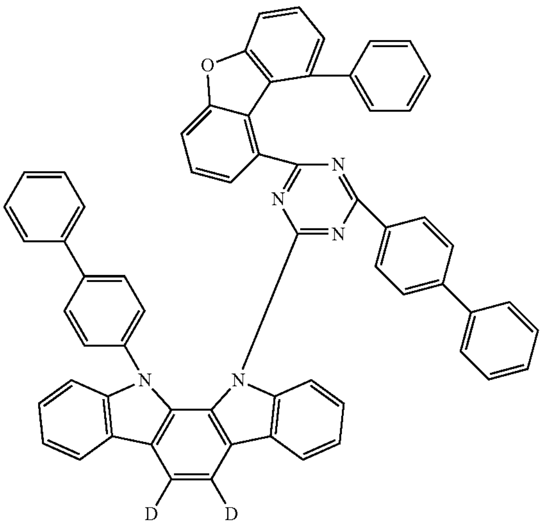

-continued

107

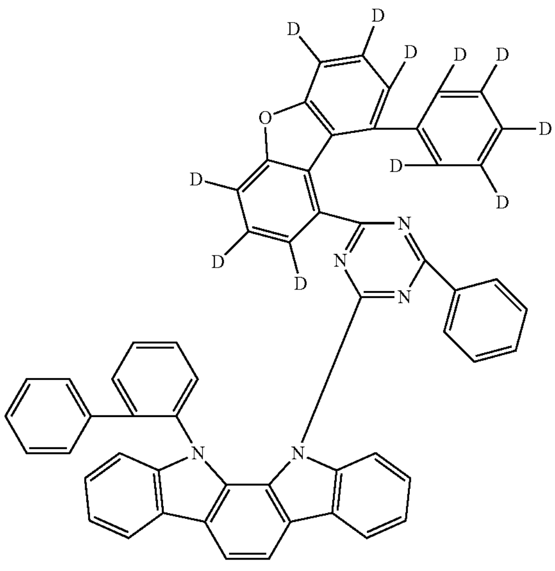

108

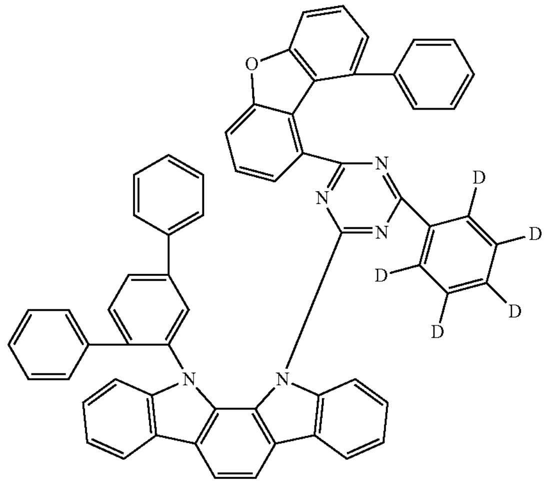

A composition for an organic optoelectronic device according to an embodiment may include, e.g., a first compound for an organic optoelectronic device, and a second compound for an organic optoelectronic device (e.g., as a mixture). The first compound for an organic optoelectronic device may be the aforementioned compound for an organic optoelectronic device (e.g., represented by the combination of Chemical Formulas 1 and 2) and the second compound for an organic optoelectronic device may be represented by, e.g., Chemical Formula 3; or a combination of Chemical Formula 4 and Chemical Formula 5.

[Chemical Formula 3]

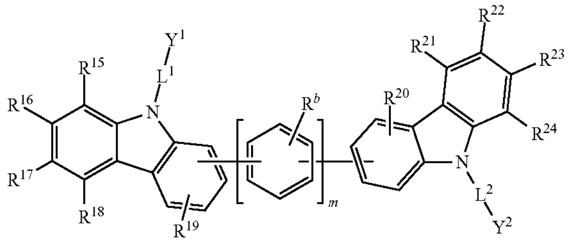

In Chemical Formula 3, $Y^1$ and $Y^2$ may each independently be or include, e.g., a substituted or unsubstituted C6 to C20 aryl group, or a substituted or unsubstituted C2 to C30 heterocyclic group.

$L^1$ and $L^2$ may each independently be or include, e.g., a single bond or a substituted or unsubstituted C6 to C20 arylene group.

$R^b$ and $R^{15}$ to $R^{24}$ may each independently be or include, e.g., hydrogen, deuterium, a cyano group, a halogen, a substituted or unsubstituted amino group, a substituted or unsubstituted C1 to C30 alkyl group, a substituted or unsubstituted C6 to C30 aryl group, a substituted or unsubstituted C2 to C30 heterocyclic group.

m may be, e.g., an integer of 0 to 2.

[Chemical Formula 4]

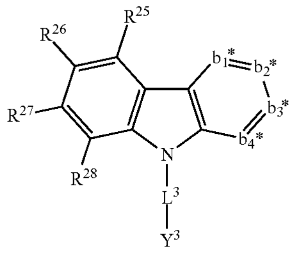

[Chemical Formula 5]

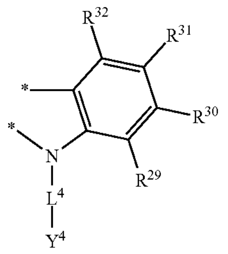

In Chemical Formula 4 and Chemical Formula 5, $Y^3$ and $Y^4$ may each independently be or include, e.g., a substituted or unsubstituted C6 to C20 aryl group, or a substituted or unsubstituted C2 to C30 heterocyclic group.

Two adjacent ones of $b_1$* to $b_4$* of Chemical Formula 4 may be linking carbons linked at * of Chemical Formula 5, the remaining two of $b_1$* to $b_4$* of Chemical Formula 4, not linked at * of Chemical Formula 5, may be C-$L^a$-$R^c$.

$L^a$, $L^3$, and $L^4$ may each independently be or include, e.g., a single bond or a substituted or unsubstituted C6 to C20 arylene group.

$R^c$ and $R^{25}$ to $R^{32}$ may each independently be or include, e.g., hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group.

The second compound for an organic optoelectronic device may be used in the light emitting layer together with the first compound for an organic optoelectronic device to help improve the mobility of charges and improve stability, thereby improving luminous efficiency and life-span characteristics.

In an implementation, $Y^1$ and $Y^2$ of Chemical Formula 3 may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted carbazolyl group, a substituted or unsubstituted dibenzothiophenyl group, a substituted or unsubstituted dibenzofuranyl group, a substituted or unsubstituted fluorenyl group, or a substituted or unsubstituted pyridinyl group.

In an implementation, $L^1$ and $L^2$ of Chemical Formula 3 may each independently be, e.g., a single bond, a substituted or unsubstituted phenylene group, or a substituted or unsubstituted biphenylene group.

In an implementation, $R^{15}$ to $R^{24}$ of Chemical Formula 3 may each independently be, e.g., hydrogen, deuterium, or a substituted or unsubstituted C6 to C12 aryl group.

m may be, e.g., 0 or 1.

In an implementation, "substituted" of Chemical Formula 3 refers to replacement of at least one hydrogen by deuterium, a C1 to C4 alkyl group, a C6 to C18 aryl group, or a C2 to C30 heteroaryl group.

In an implementation, Chemical Formula 3 may be represented by, e.g., one Chemical Formula 3-1 to Chemical Formula 3-15.

[Chemical Formula 3-1]

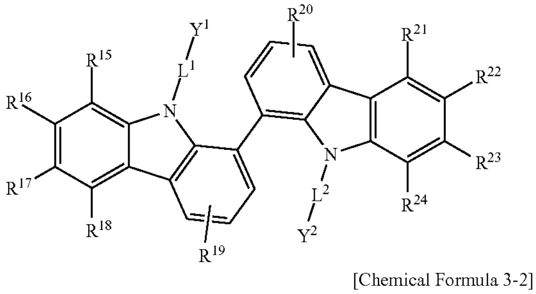

[Chemical Formula 3-2]

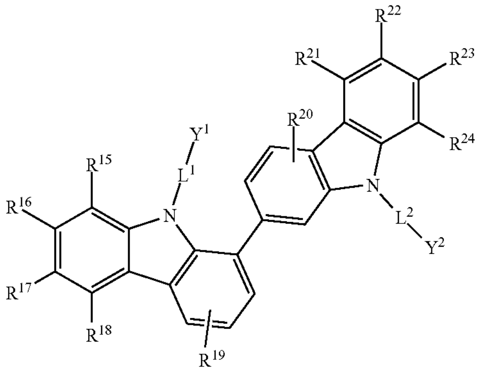

-continued

[Chemical Formula 3-3]

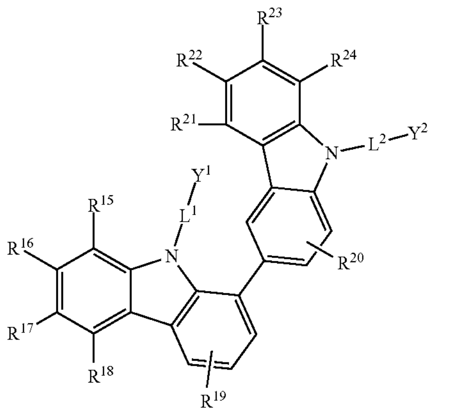

[Chemical Formula 3-4]

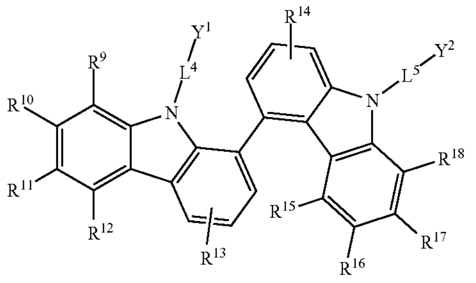

[Chemcal Formula 3-5]

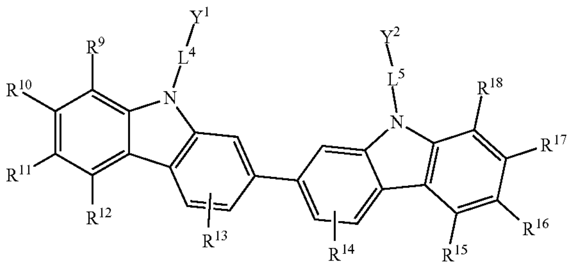

[Chemical Formula 3-6]

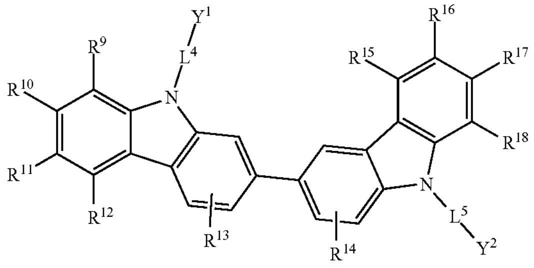

[Chemical Formula 3-7]

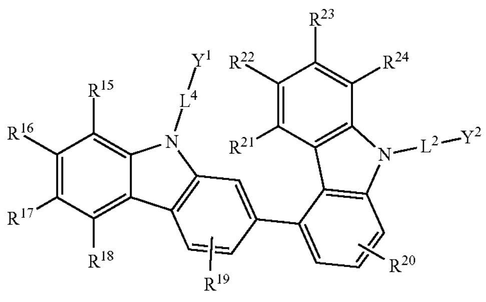

-continued
[Chemical Formula 3-8]
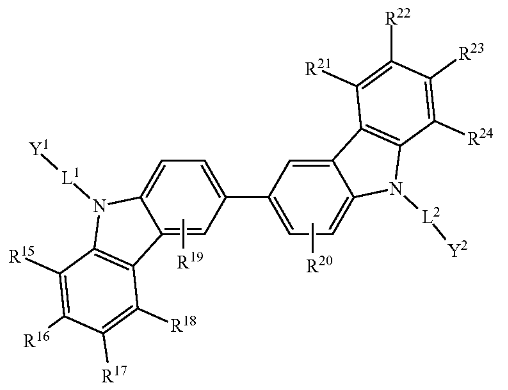
[Chemical Formula 3-9]
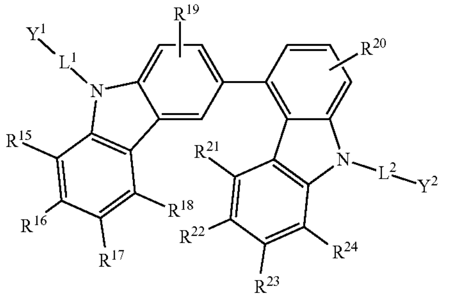
[Chemical Formula 3-10]
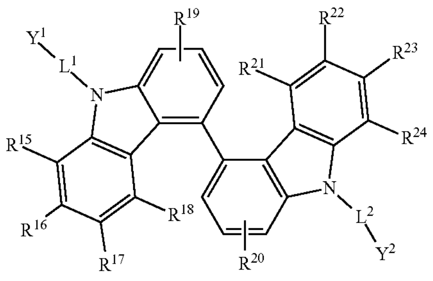
[Chemical Formula 3-11]
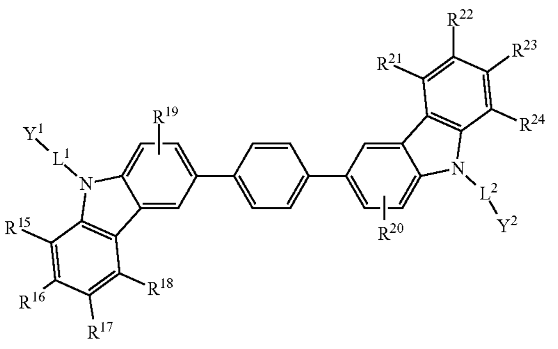
-continued
[Chemical Formula 3-12
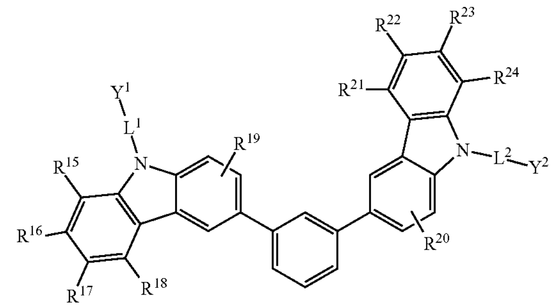
[Chemical Formula 3-13]
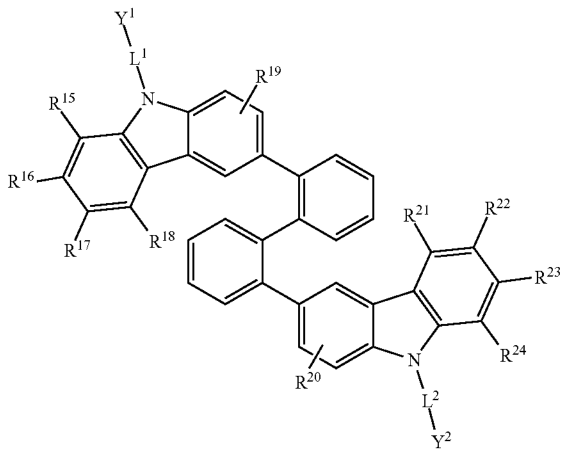
[Chemical Formula 3-14]
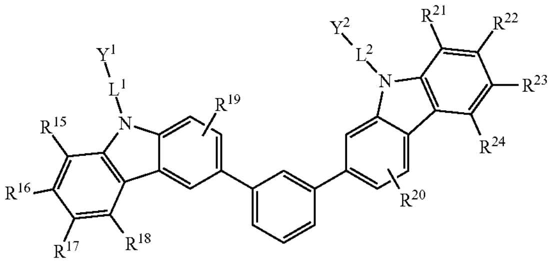
[Chemical Formula 3-15]
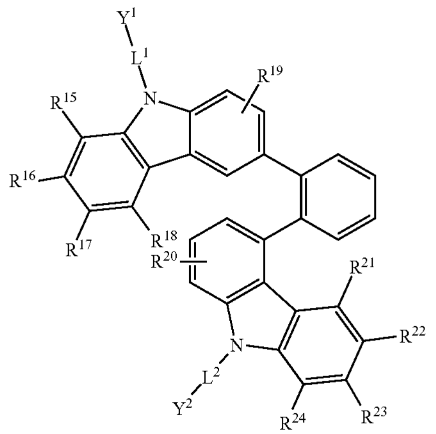
In Chemical Formula 3-1 to Chemical Formula 3-15, $R^{15}$ to $R^{24}$ may each independently be, e.g., hydrogen or a substituted or unsubstituted C6 to C12 aryl group. In an implementation, moieties *-$L^1$-$Y^1$ and *-$L^2$-$Y^2$ may each independently be, e.g., a moiety of Group II.
C-1
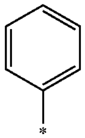
C-2
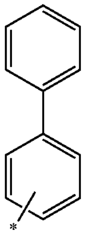
C-3
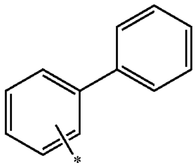
C-4
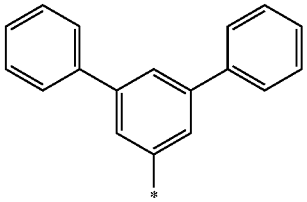
C-5
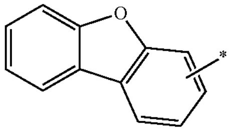
C-6
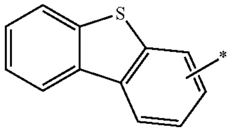
C-7
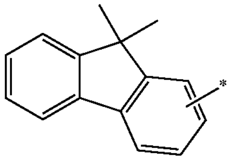
C-8
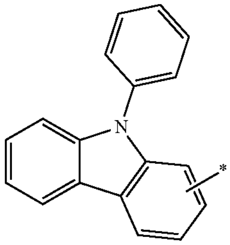
-continued
C-9
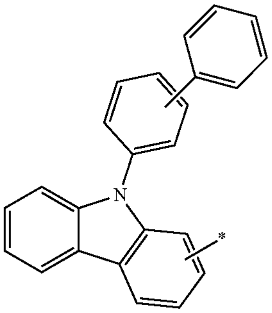
C-10
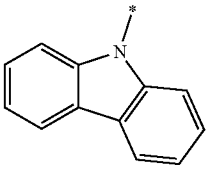
C-11
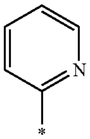
C-12
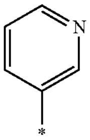
C-13
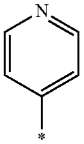
C-14
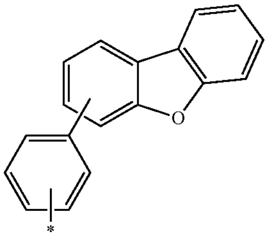
C-15
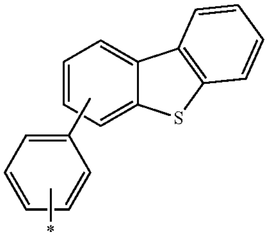

-continued

C-16

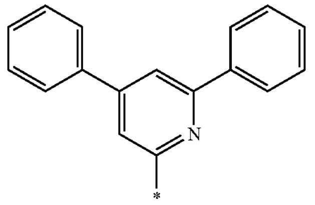

C-17

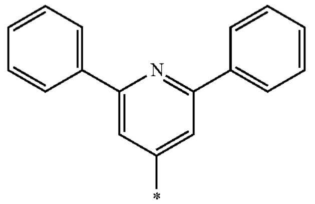

C-18

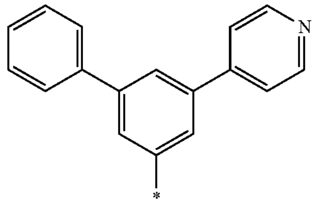

C-19

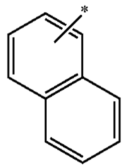

C-20

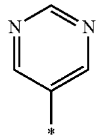

C-21

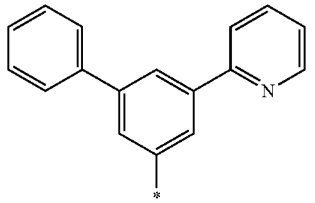

C-22

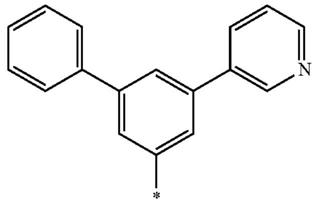

C-23

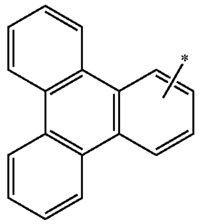

-continued

C-24

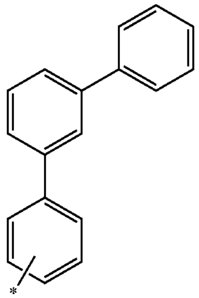

C-25

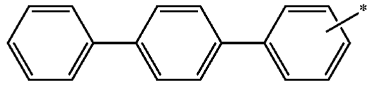

C-26

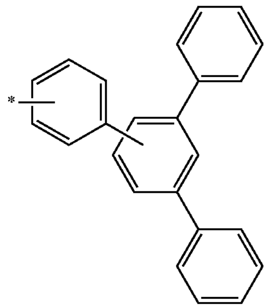

In Group II, * is a linking point (e.g., with N of the chemical formulae).

In an implementation, Chemical Formula 3 may be represented by, e.g., Chemical Formula 3-8.

In an implementation, moieties $*\text{-}L^1\text{-}Y^1$ and $*\text{-}L^2\text{-}Y^2$ of Chemical Formula 3-8 may each independently be a moiety of Group II, e.g., C-1, C-2, C-3, C-16, or C-23.

In an implementation, moieties $*\text{-}L^1\text{-}Y^1$ and $*\text{-}L^2\text{-}Y^2$ may be, e.g., C-1, C-2, or C-3 of Group II.

In an implementation, the second compound for an organic optoelectronic device represented by the combination of Chemical Formula 4 and Chemical Formula 5 may be represented by, e.g., Chemical Formula Chemical Formula 4A, Chemical Formula 4B, Chemical Formula 4C, Chemical Formula 4D, or Chemical Formula 4E.

[Chemical Formula 4A]

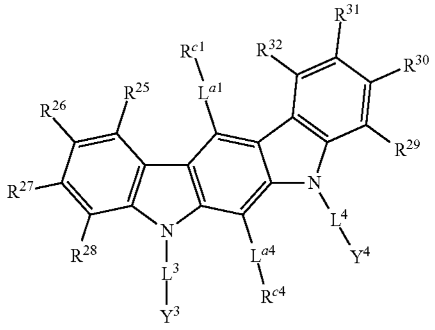

-continued

[Chemical Formula 4B]

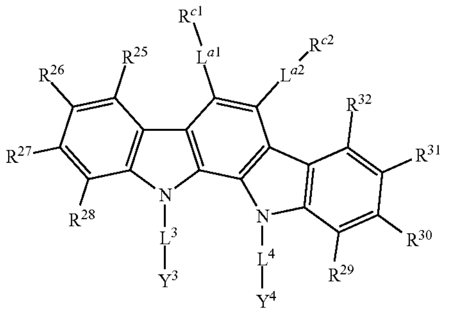

[Chemical Formula 4C]

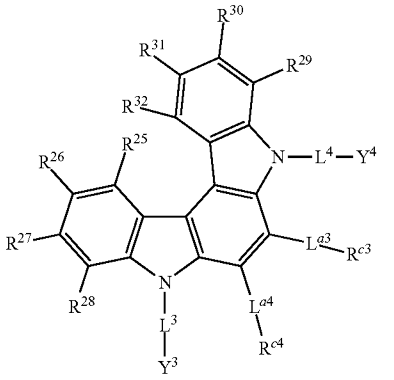

[Chemical Formula 4D]

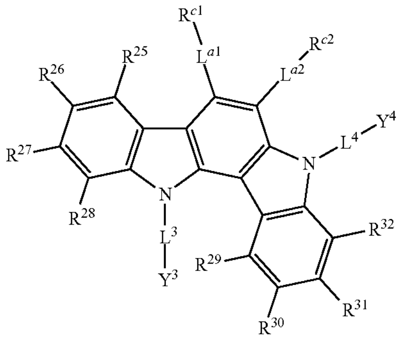

[Chemical Formula 4E]

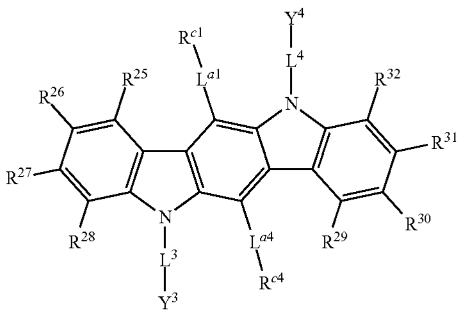

In Chemical Formula 4A to Chemical Formula 4E, $Y^3$, $Y^4$, $L^3$, $L^4$, and $R^{25}$ to $R^{32}$ may be defined the same as those described above.

$L^{a1}$ to $L^{a4}$ may be defined the same as $L^3$ and $L^4$.

$R^{c1}$ to $R^{c4}$ may be defined the same as $R^{19}$ to $R^{26}$.

In an implementation, $Y^3$ and $Y^4$ of Chemical Formulas 3 and 4 may each independently be, e.g., a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $R^{c1}$ to $R^{c4}$ and $R^{25}$ to $R^{32}$ may each independently be, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $Y^3$ and $Y^4$ in Chemical Formulas 4 and 5 may each independently be, e.g., a group of Group III.

[Group III]

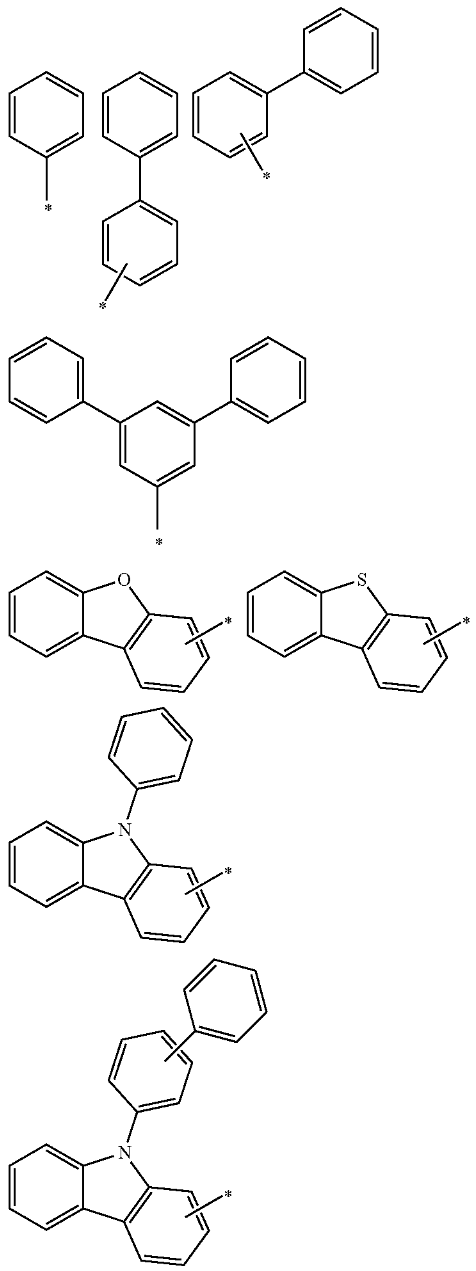

-continued

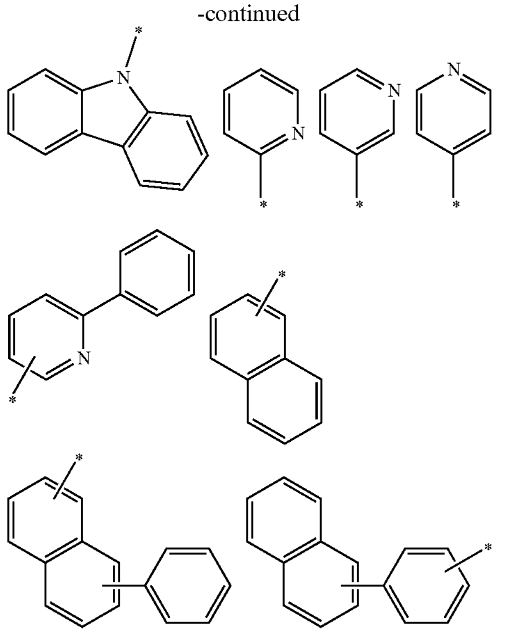

In Group III, * is a linking point with $L^3$ and $L^4$, respectively.

In an implementation, $R^{c1}$ to $R^{c4}$ and $R^{25}$ to $R^{32}$ may each independently be, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $R^{c1}$ to $R^{c4}$ and $R^{25}$ to $R^{32}$ may each independently be, e.g., hydrogen, deuterium, a cyano group, or a substituted or unsubstituted phenyl group.

In an implementation, each of $R^{c1}$ to $R^{c4}$ may be, e.g., hydrogen, and $R^{25}$ to $R^{32}$ may each independently be, e.g., hydrogen or a phenyl group.

In an implementation, the second compound for an organic optoelectronic device may be represented by, e.g., Chemical Formula 3-8, wherein in Chemical Formula 3-8, $Y^1$ and $Y^2$ may each independently be, e.g., a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, $L^3$ and $L^4$ may each independently be, e.g., a single bond or a substituted or unsubstituted C6 to C20 arylene group, and $R^{15}$ to $R^{24}$ may each independently be, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, the second compound for an organic optoelectronic device may be represented by, e.g., Chemical Formula 4C or Chemical Formula 4D, wherein in Chemical Formula 4C and Chemical Formula 4D, $L^{a1}$ to $L^{a4}$ may be, e.g., a single bond, $L^3$ and $L^4$ may each independently be, e.g., a single bond or a substituted or unsubstituted C6 to C12 arylene group, $R^{25}$ to $R^{32}$, and $R^{c1}$ to $R^{c4}$ may each be, e.g., hydrogen, and $Y^3$ and $Y^4$ may each independently be, e.g., a substituted or unsubstituted phenyl group, a substituted or unsubstituted biphenyl group, or a substituted or unsubstituted terphenyl group.

In an implementation, the second compound for an organic optoelectronic device may be, e.g., a compound of Group 2.

[Group 2]

[A-1]

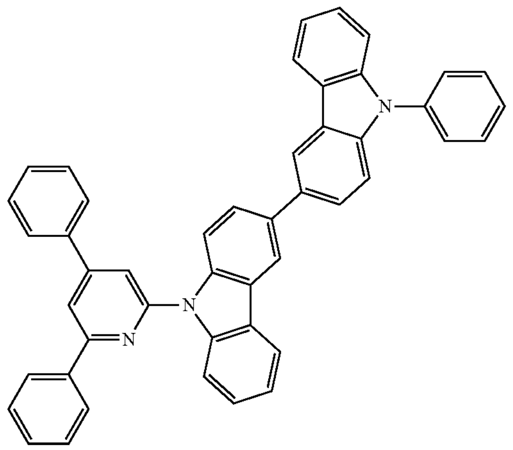

[A-2]

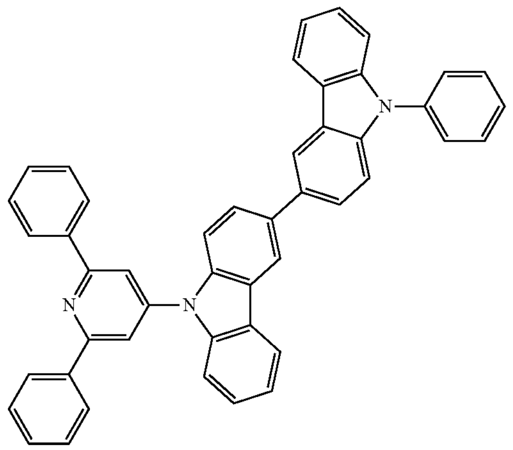

-continued
[A-3]
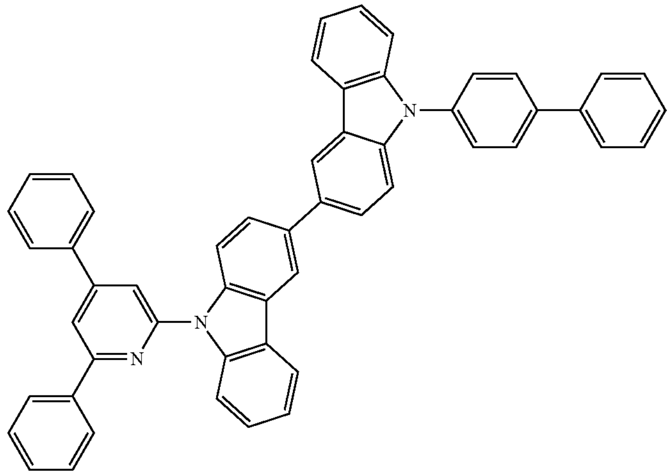
[A-4]
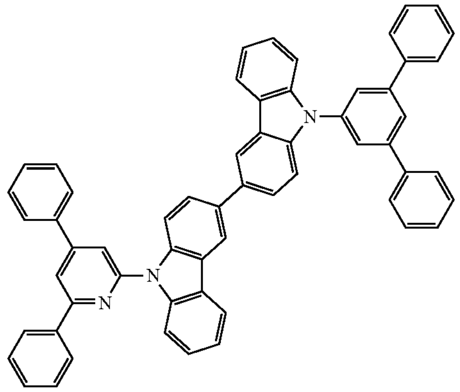
[A-5]
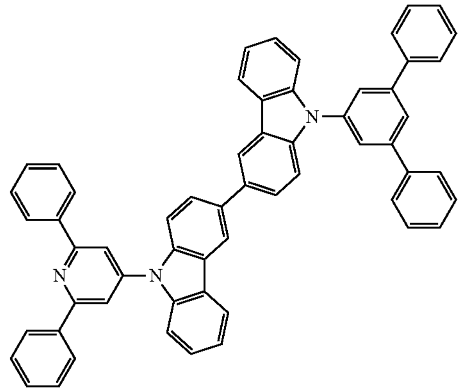
[A-6]
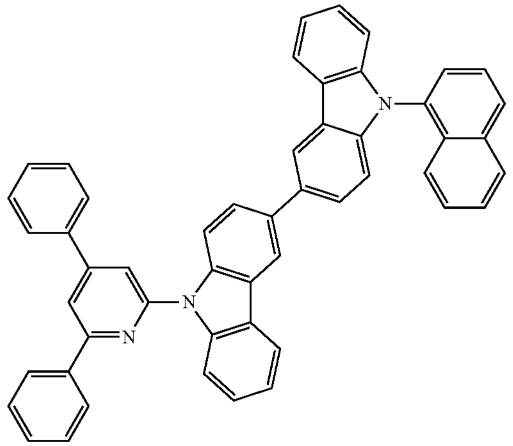
[A-7]
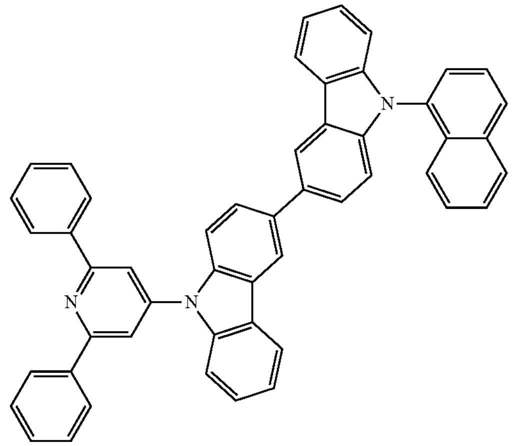

-continued
[A-8]
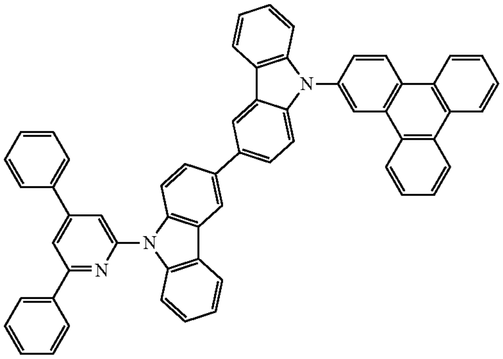
[A-9]
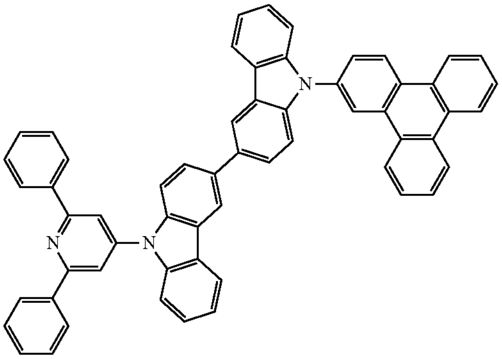
[A-10]
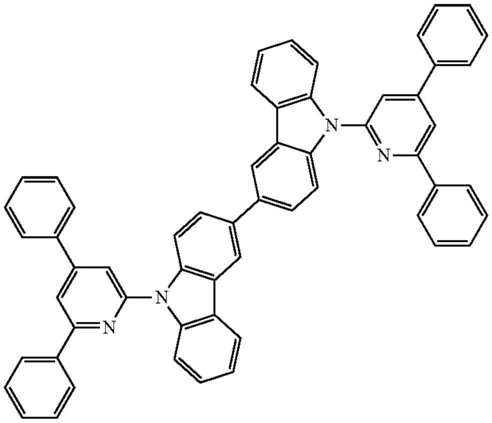
[A-11]
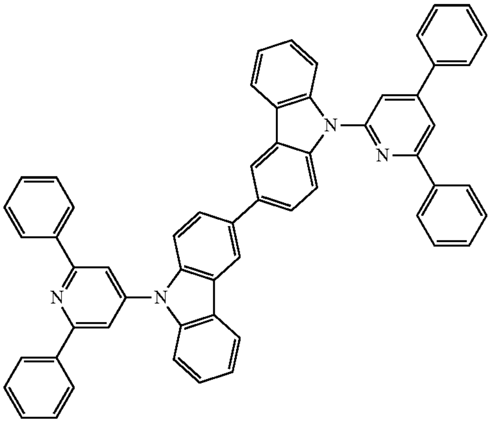
[A-12]
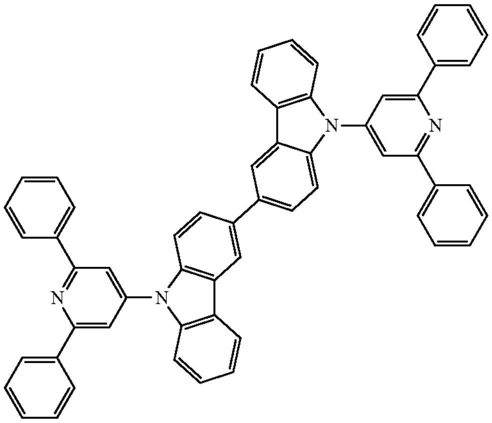
[A-13]
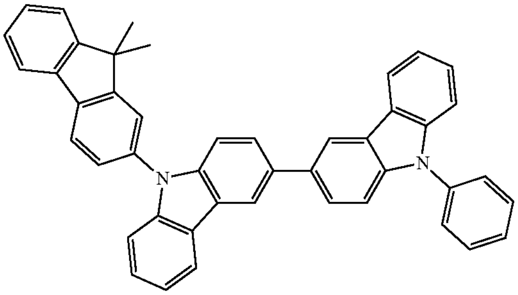
[A-14]
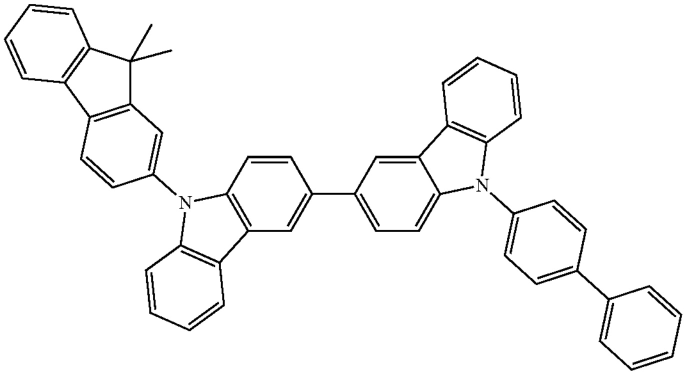

-continued
[A-15]
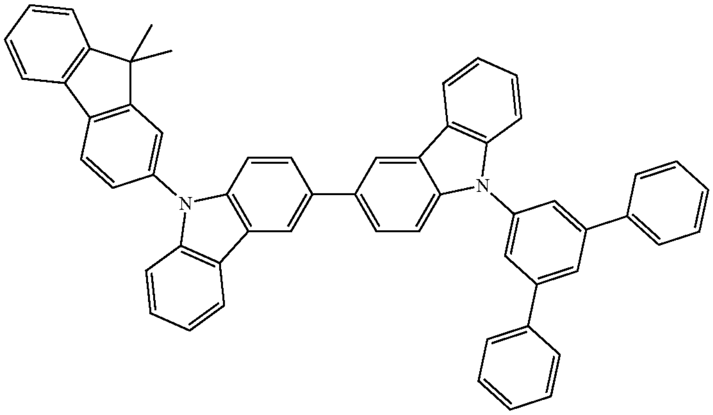
[A-16]
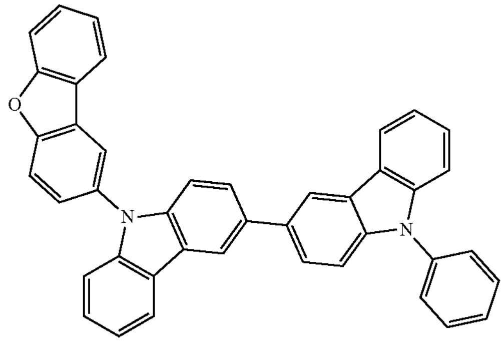
[A-17]
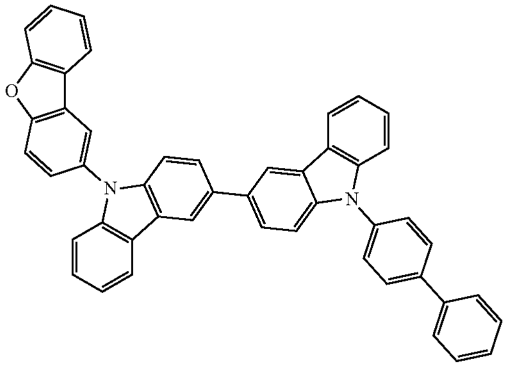
[A-18]
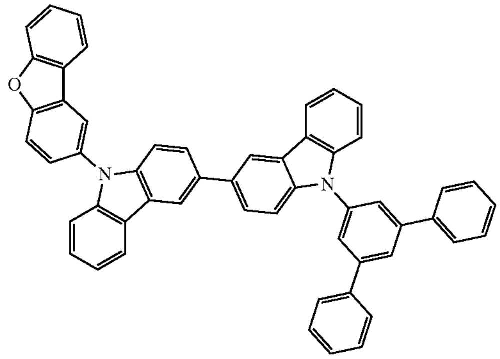
[A-19]
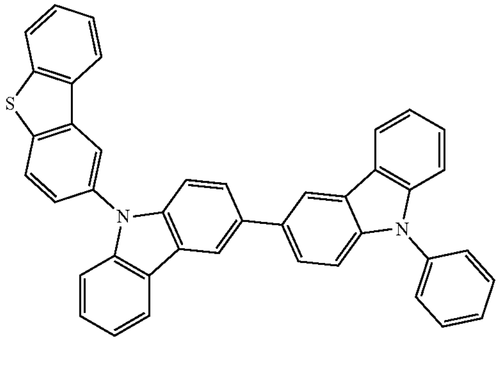
[A-20]
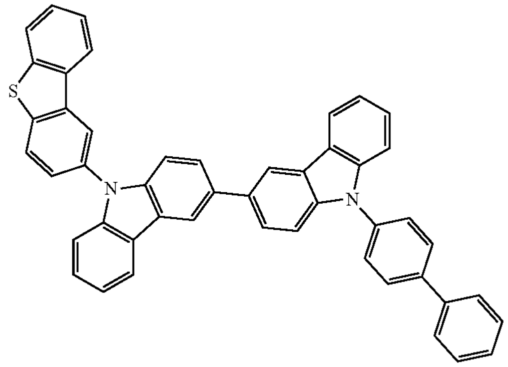
[A-21]
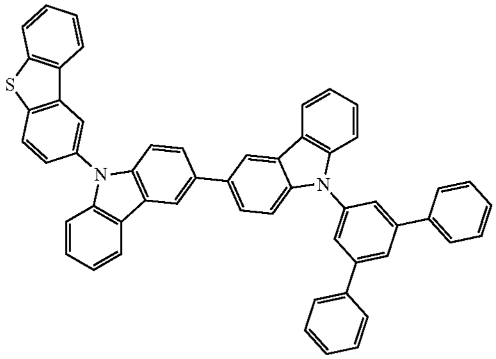

-continued
[A-22]
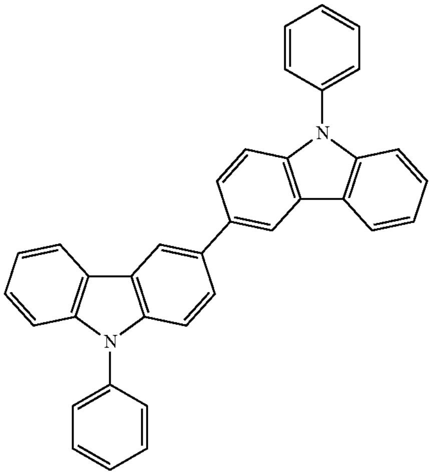
[A-23]
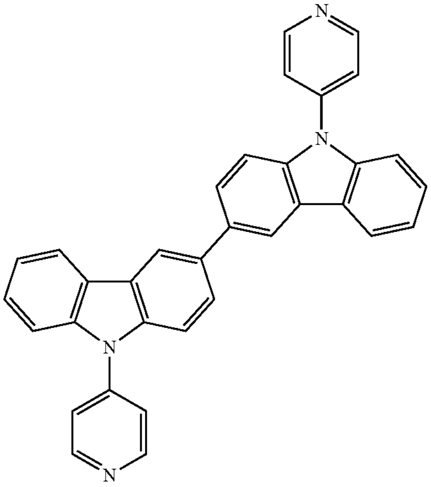
[A-24]
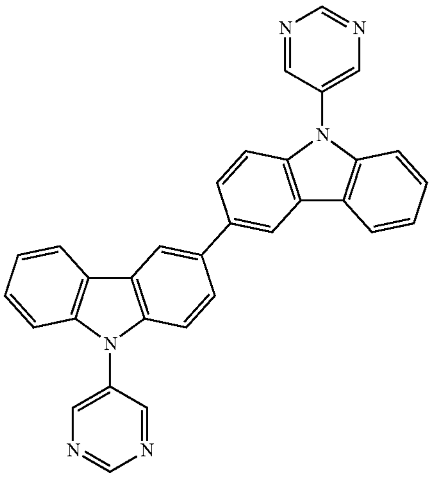
[A-25]
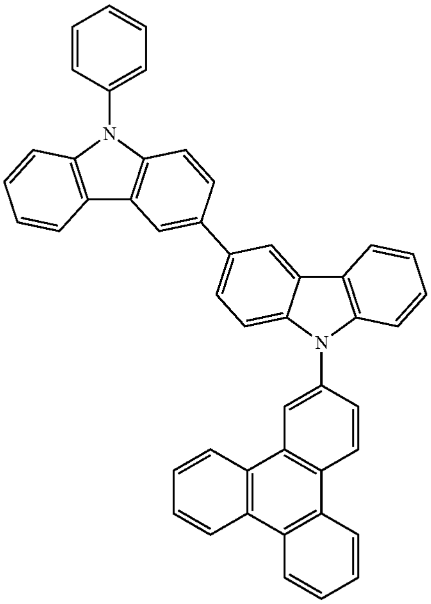

-continued
[A-26]
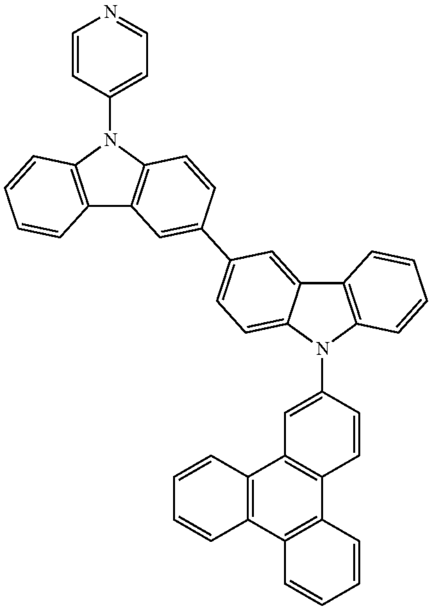
[A-27]
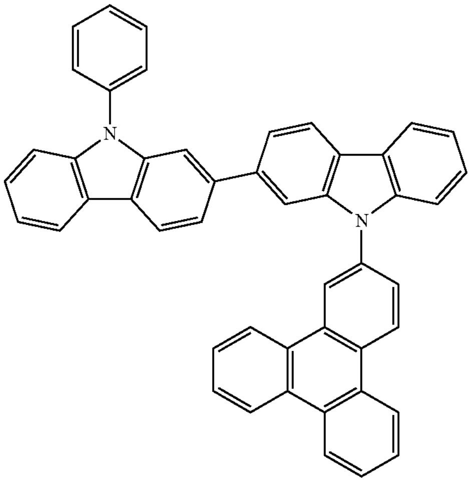
[A-28]
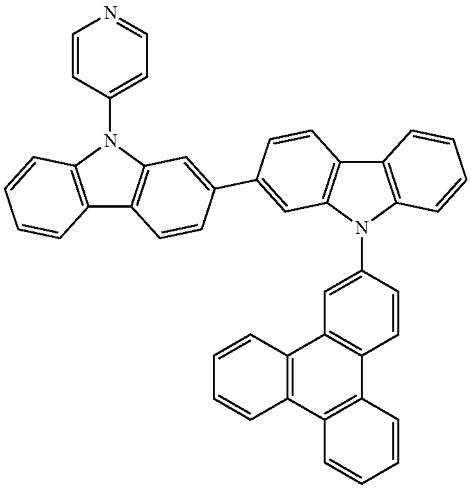
[A-29]
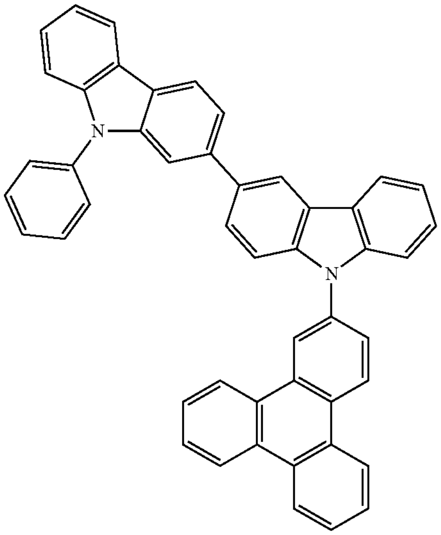

-continued
[A-30]
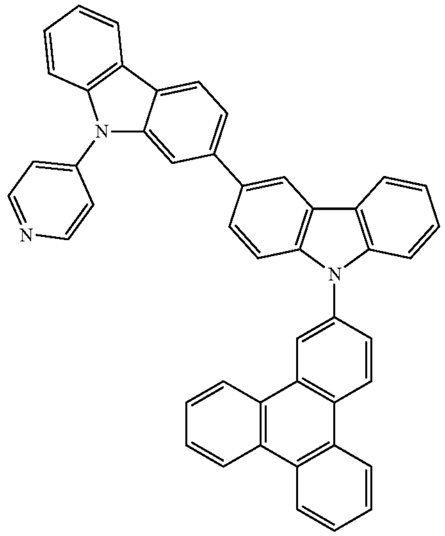
[A-31]
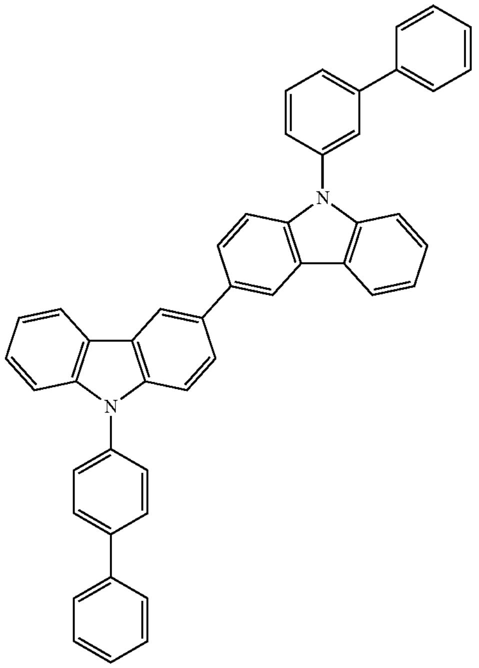
[A-32]
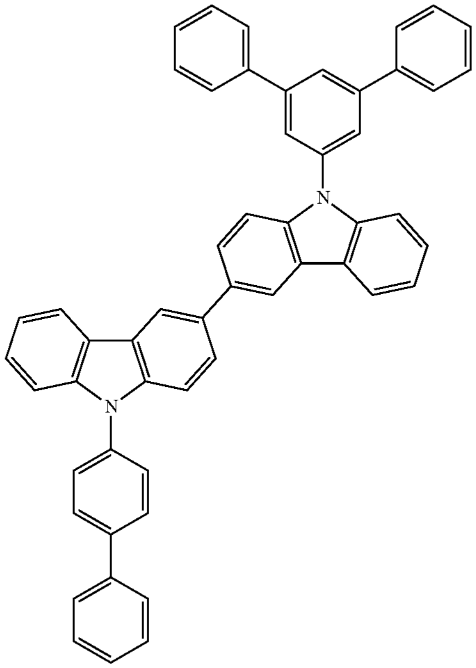
[A-33]
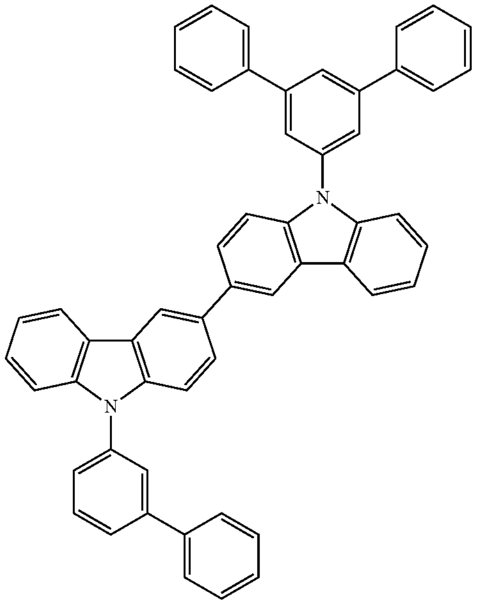

-continued
[A-34]
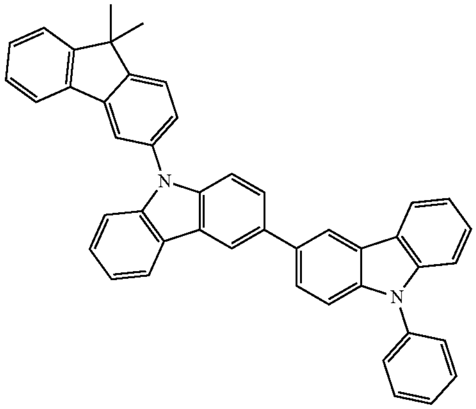
[A-35]
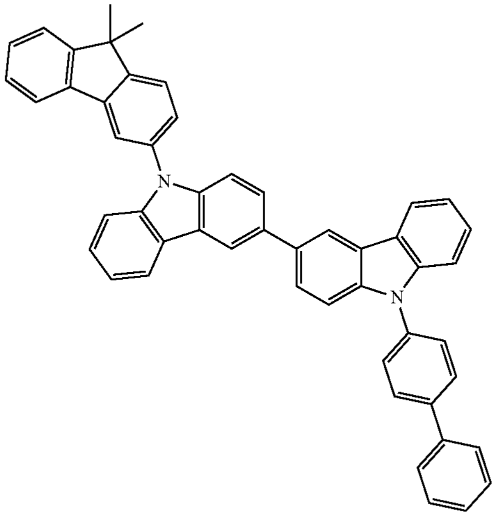
[A-36]
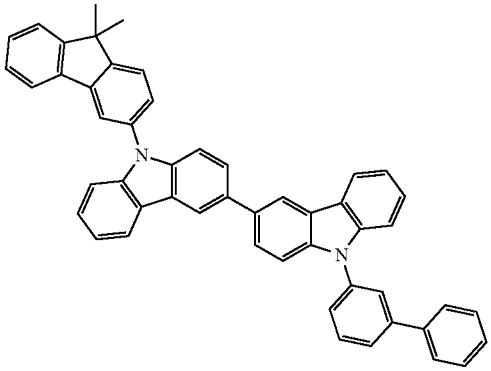
[A-37]
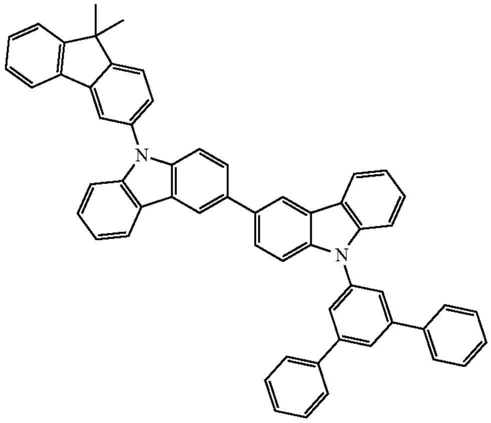
[A-38]
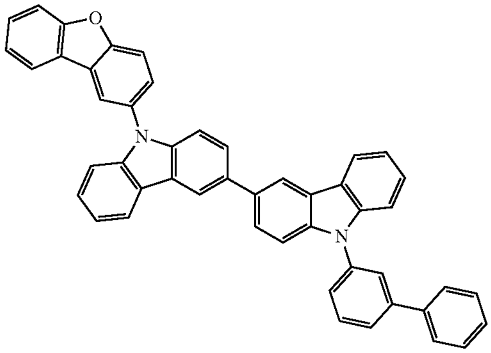
[A-39]
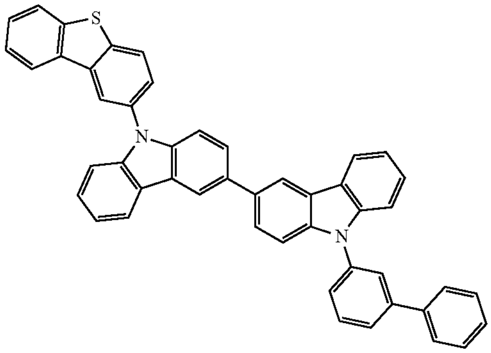

-continued
(A-40)
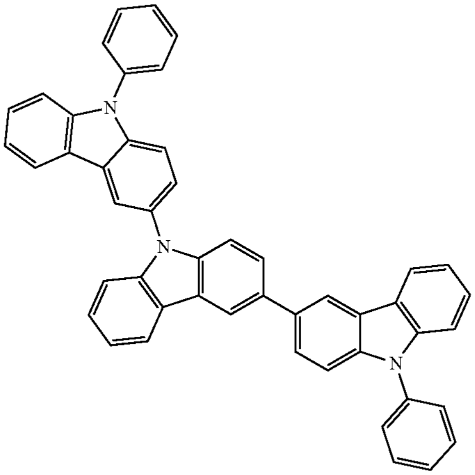
(A-41)
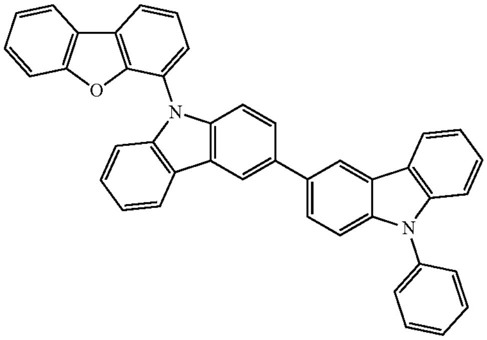
[A-42]
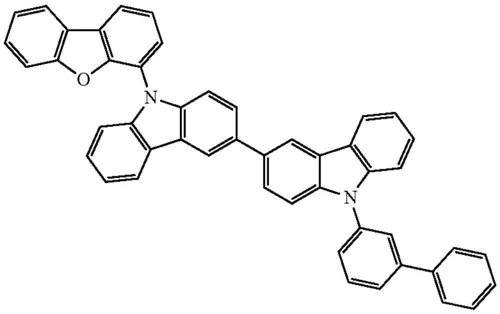
[A-43]
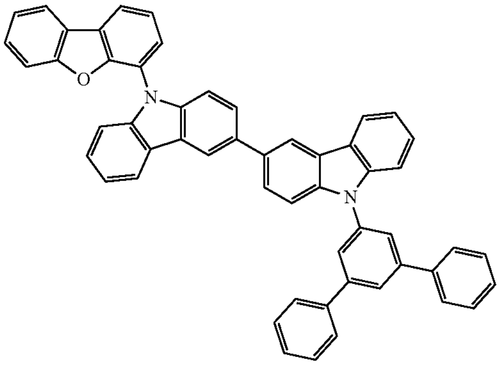
[A-44]
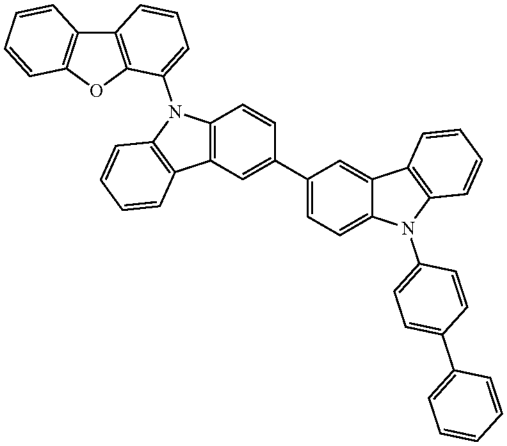
[A-45]
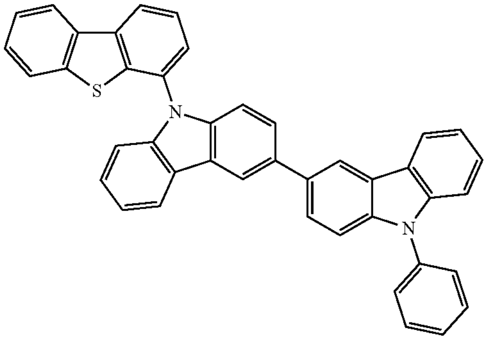

-continued
[A-46]
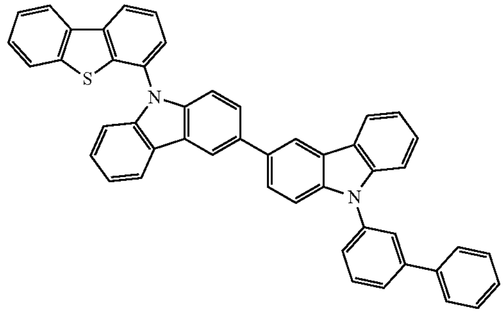
[A-47]
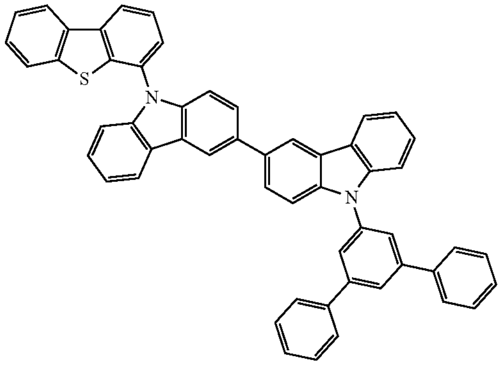
[A-48]
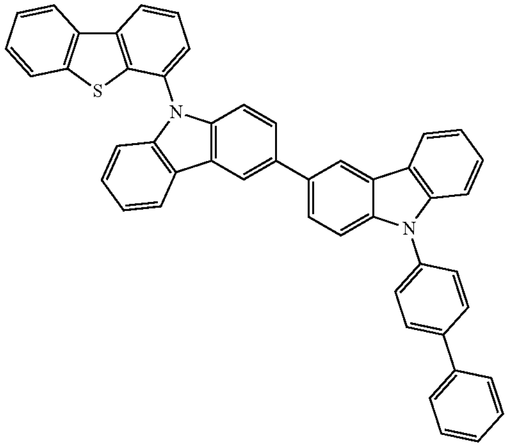
[A-49]
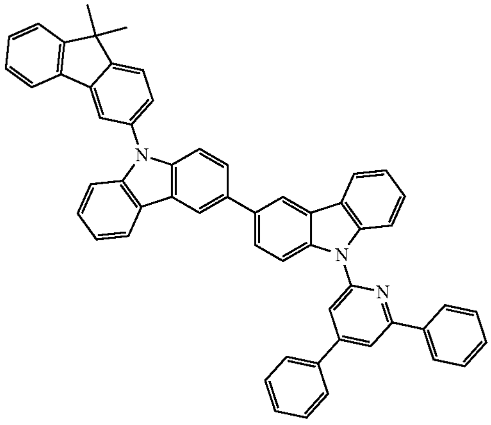
[A-50]
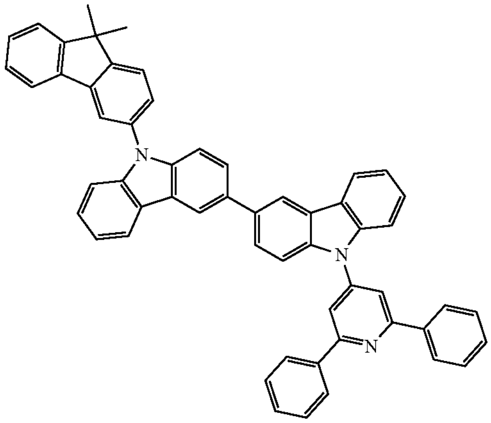
[A-51]
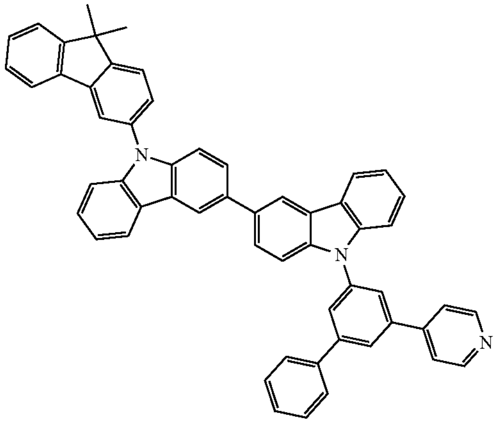

-continued
[A-52]
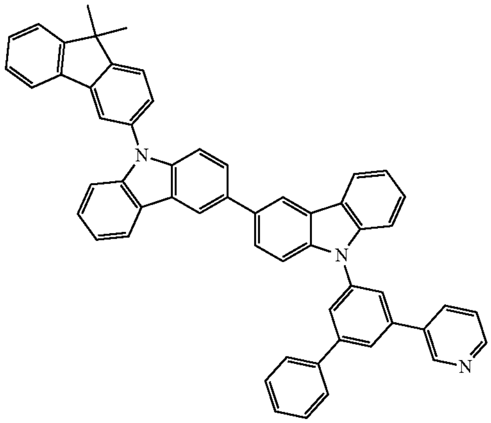
[A-53]
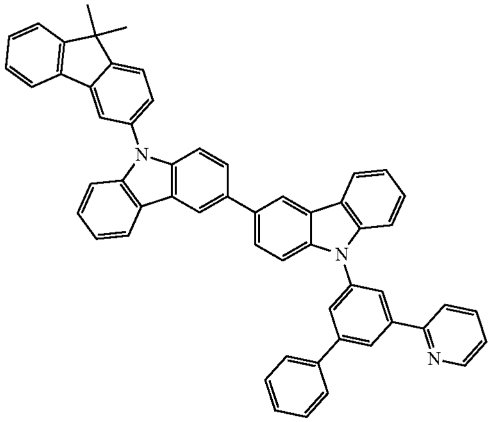
[A-54]
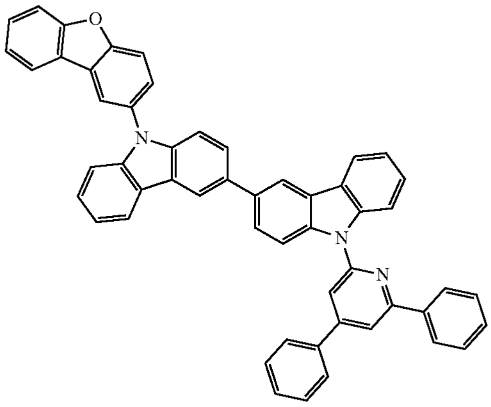
[A-55]
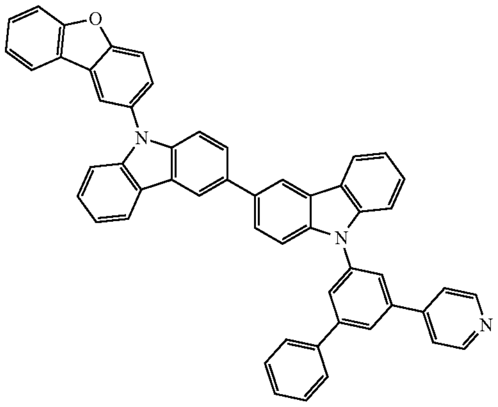
[A-56]
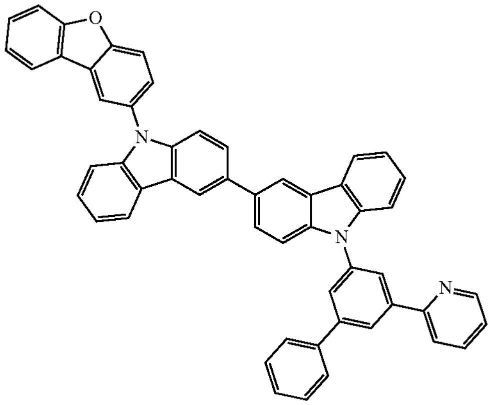
[A-57]
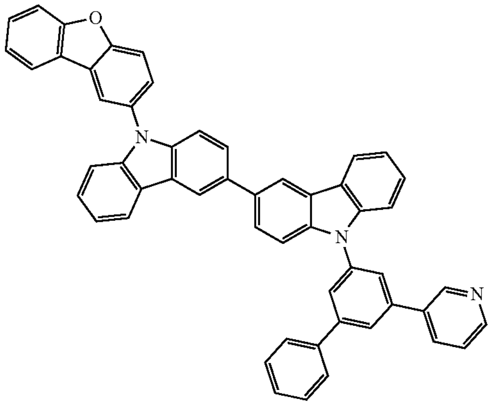
[A-58]
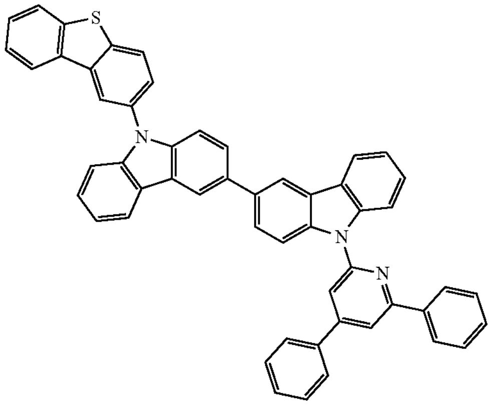
[A-59]
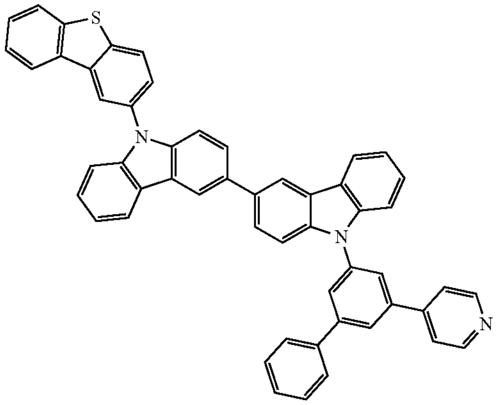

-continued
[A-60]
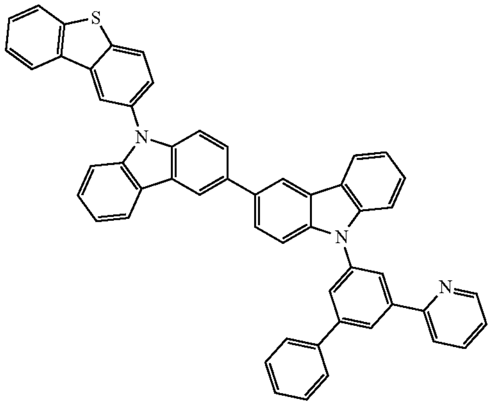
[A-61]
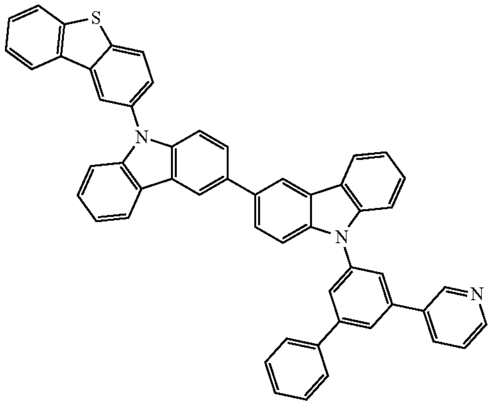
[A-62]
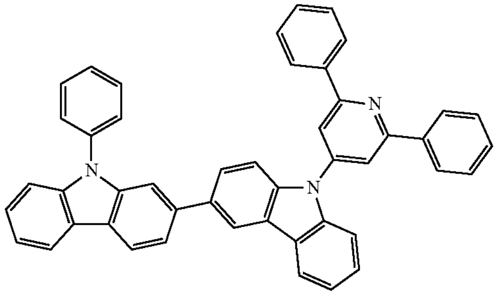
[A-63]
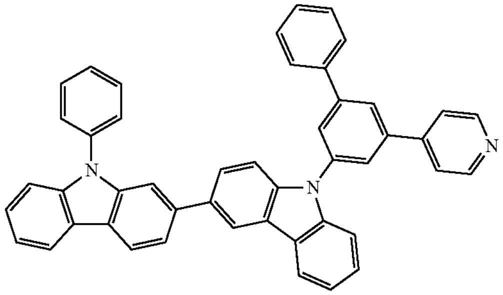
[A-64]
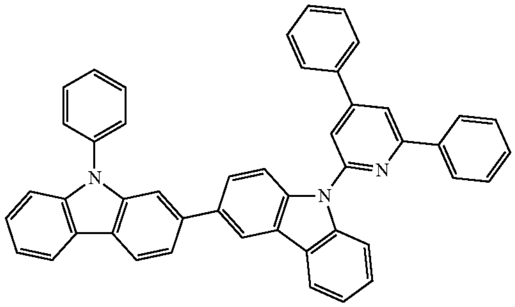
[A-65]
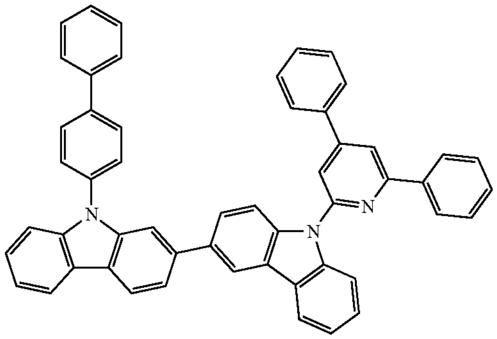
[A-66]
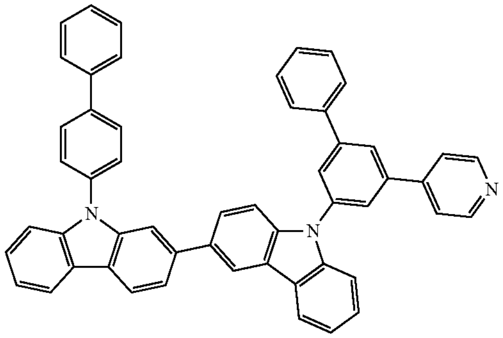
[A-67]
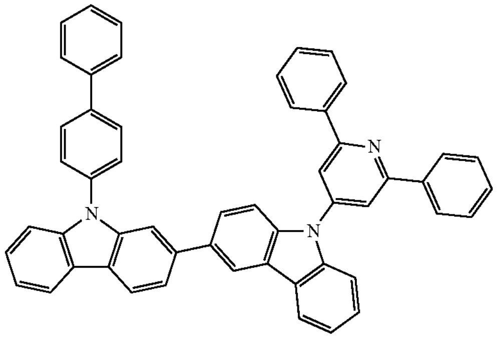

-continued
[A-68]
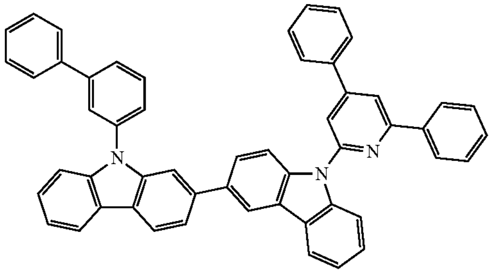
[A-69]
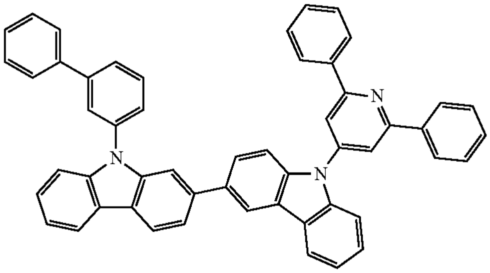
[A-70]
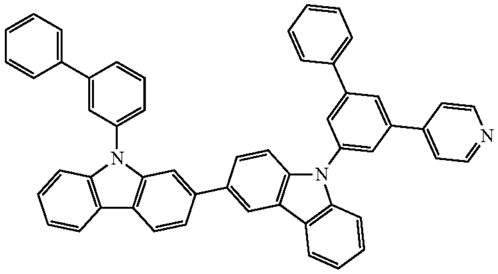
[A-71]
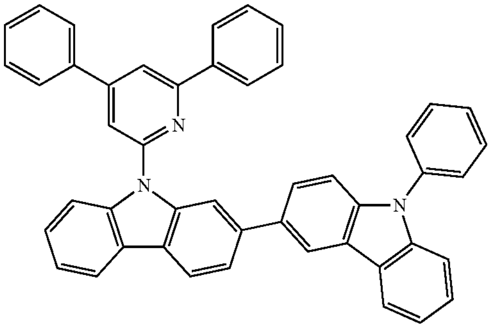
[A-72]
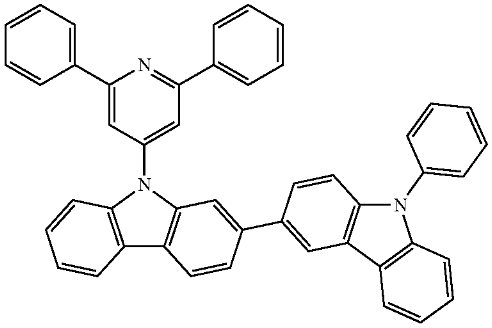
[A-73]
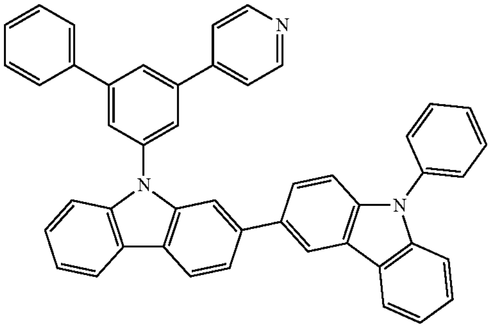
[A-74]
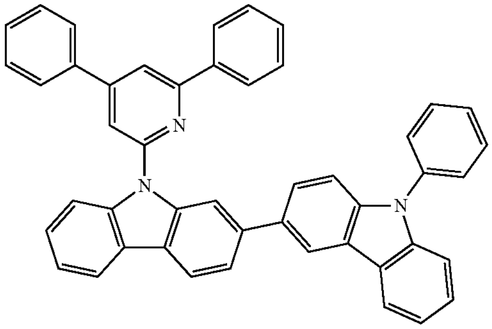
[A-75]
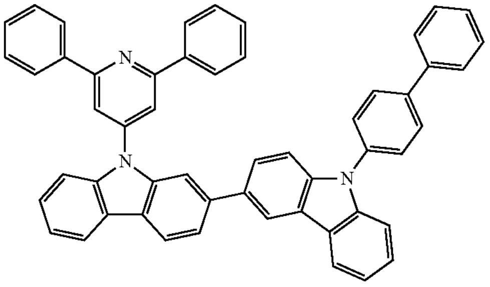
[A-76]
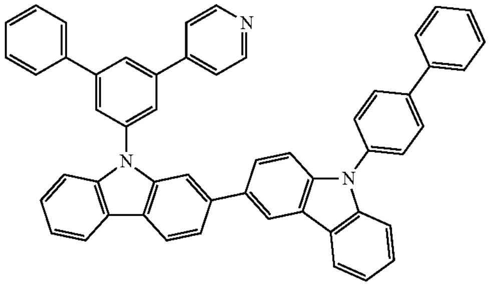
[A-77]
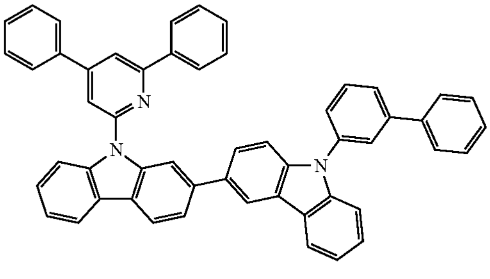

-continued
[A-78]
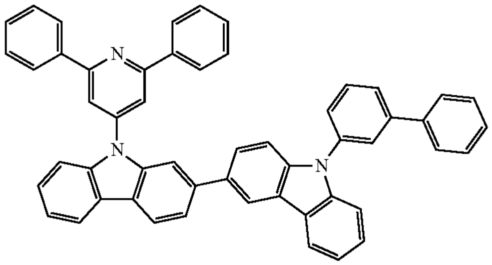
[A-79]
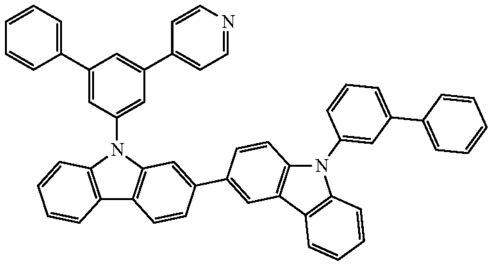
[A-80]
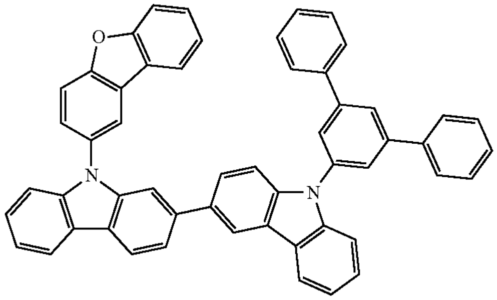
[A-81]
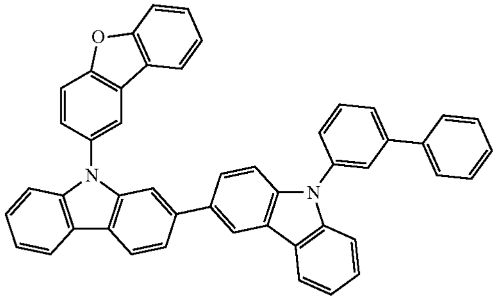
[A-82]
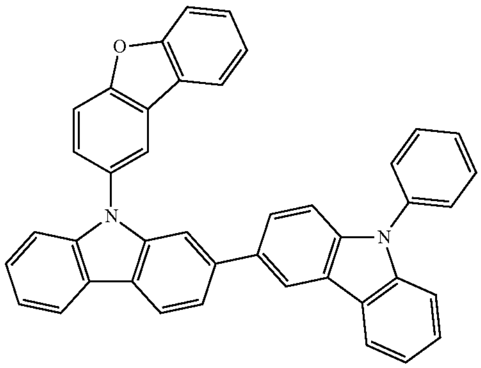
[A-83]
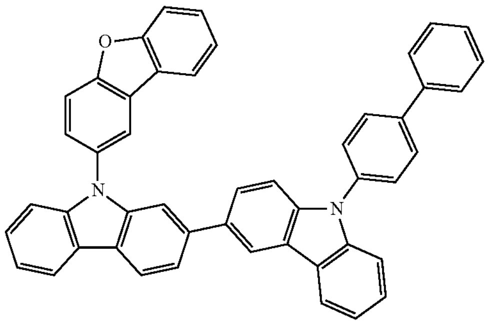
[A-84]
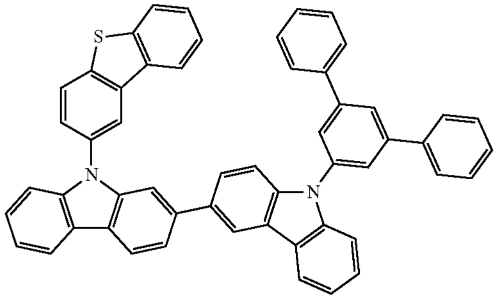
[A-85]
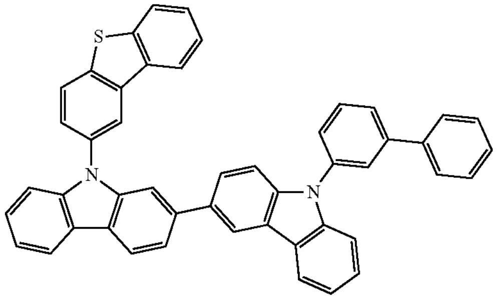
[A-86]
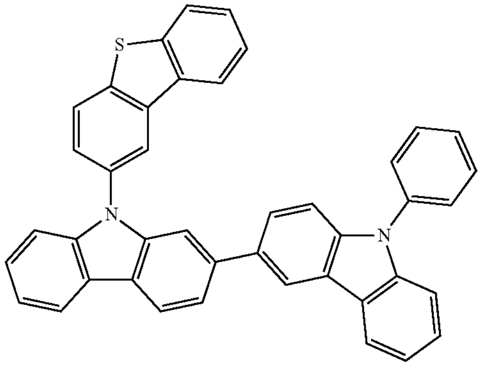
[A-87]
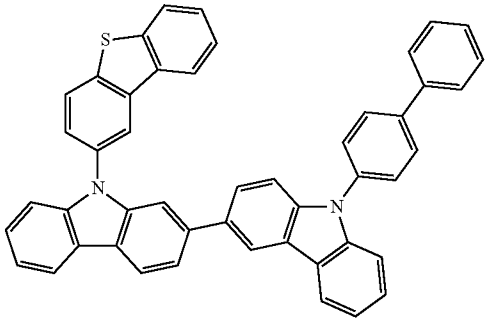

-continued
[A-88]
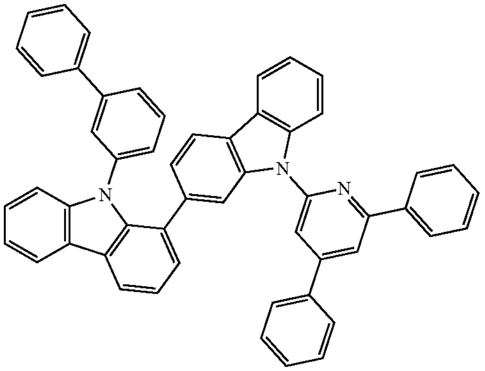
[A-89]
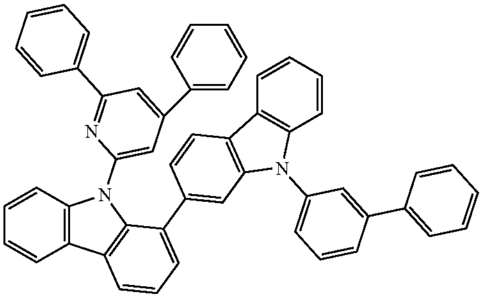
[A-90]
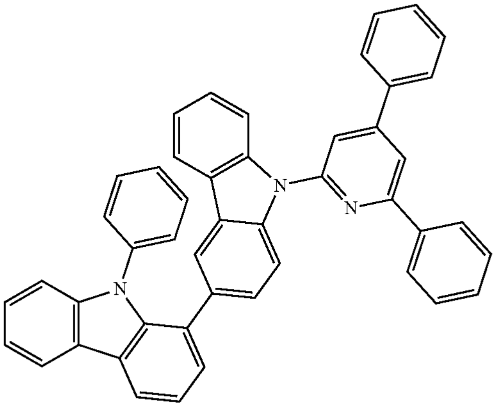
[A-91]
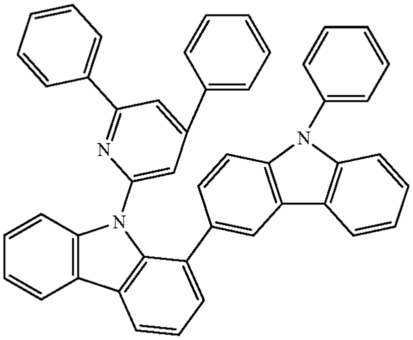
[A-92]
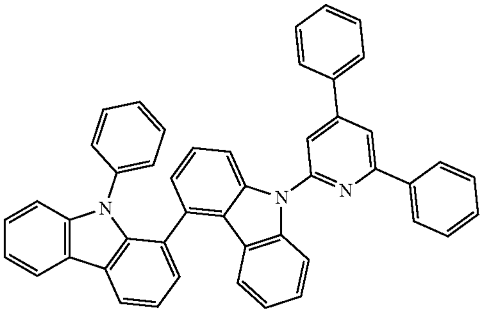
[A-93]
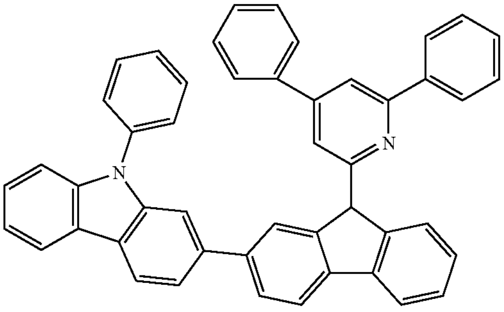
[A-94]
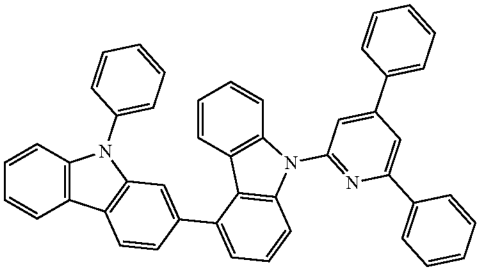
[A-95]
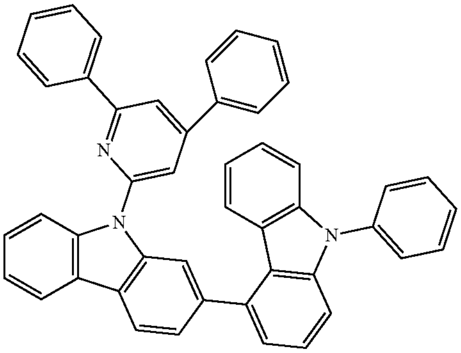

-continued
[A-96]
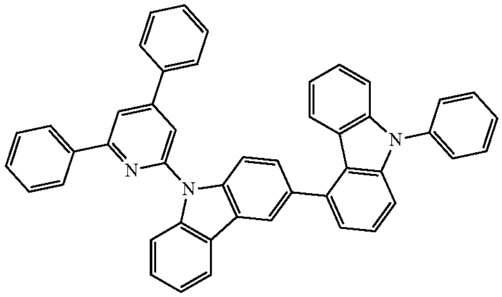
[A-97]
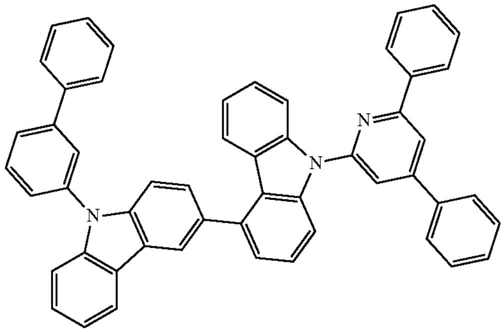
[A-98]
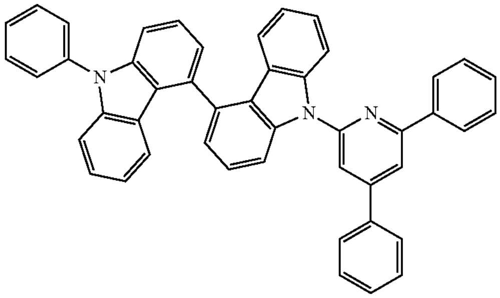
[A-99]
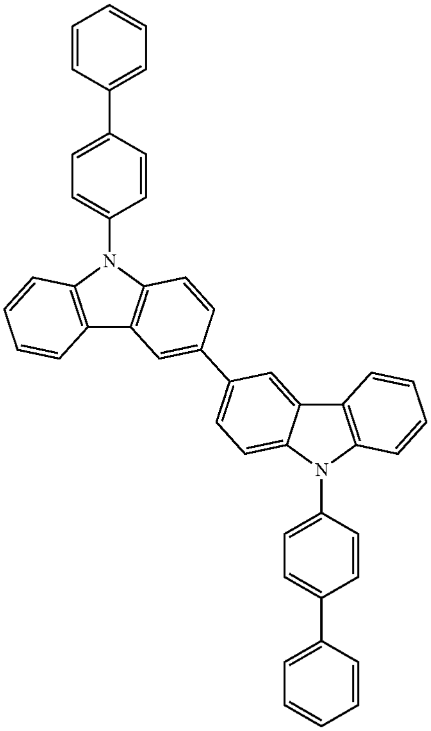

-continued
[A-100]
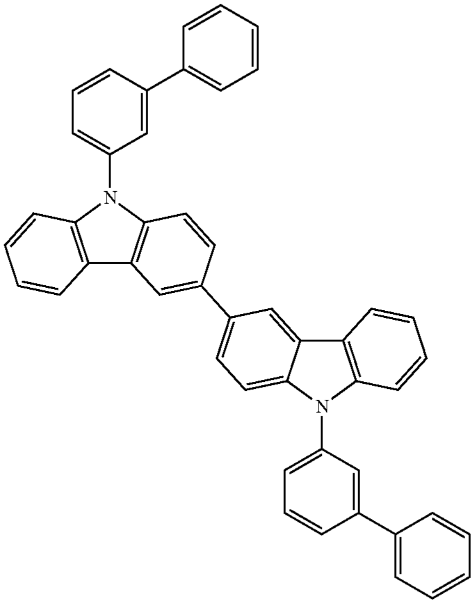
[A-101]
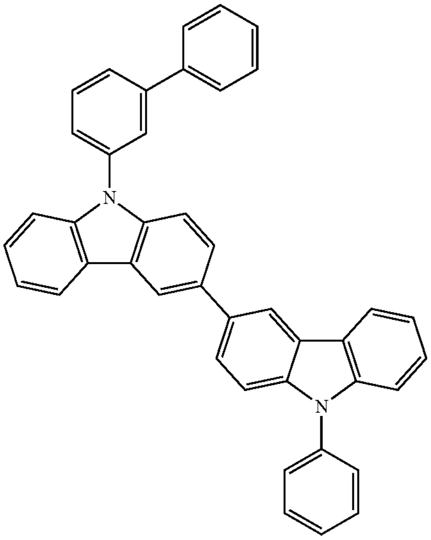
[A-102]
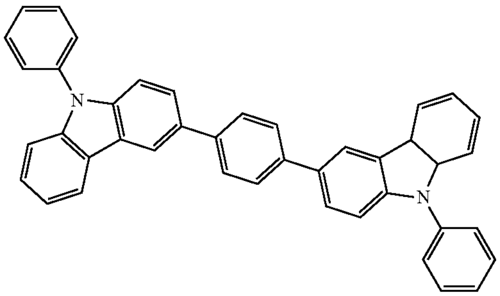
[A-103]
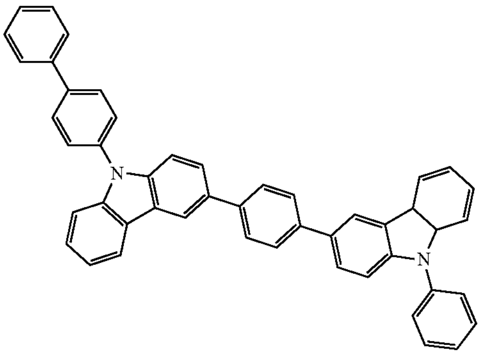
[A-104]
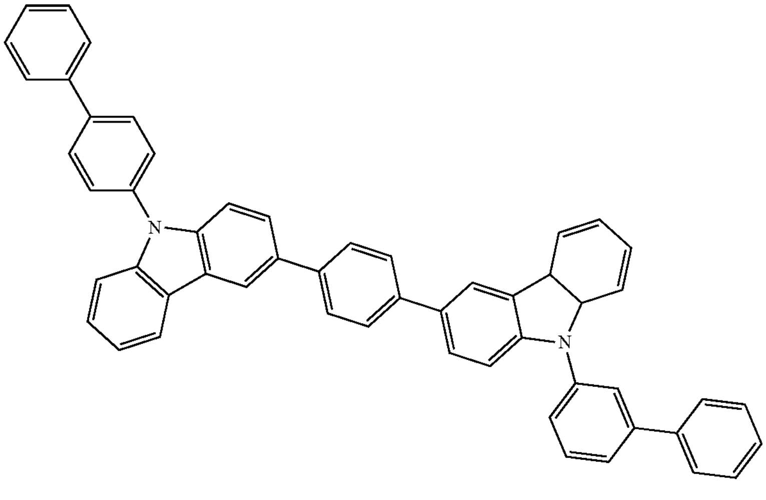

-continued
[A-105]
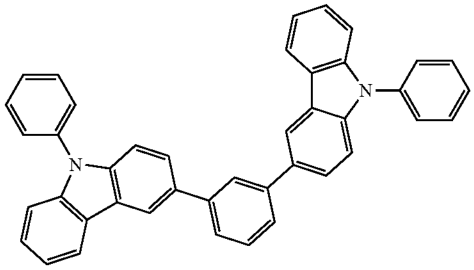
[A-106]
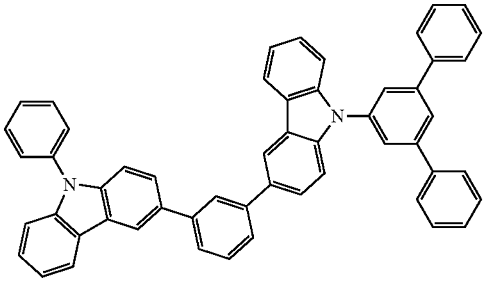
[A-107]
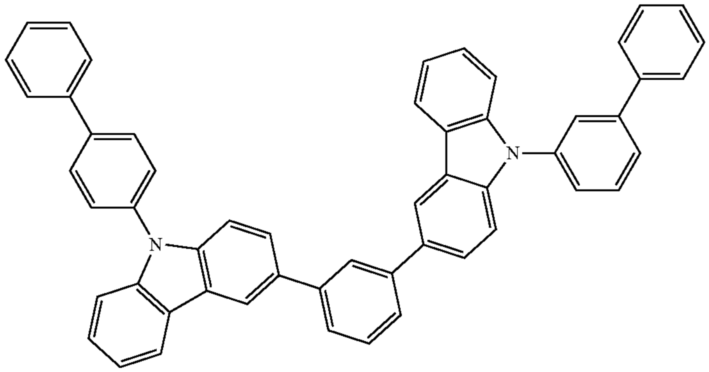
[A-108]
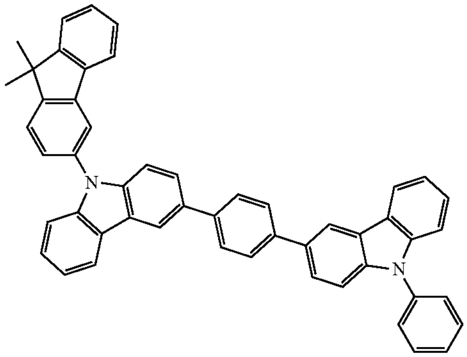
[A-109]
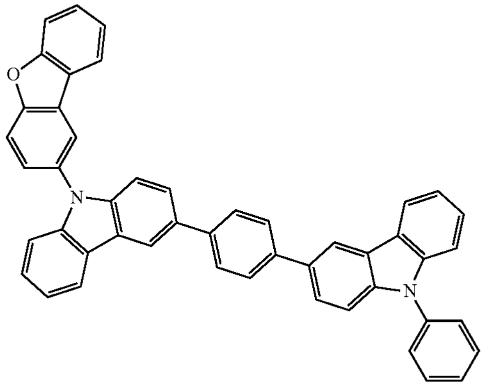
[A-110]
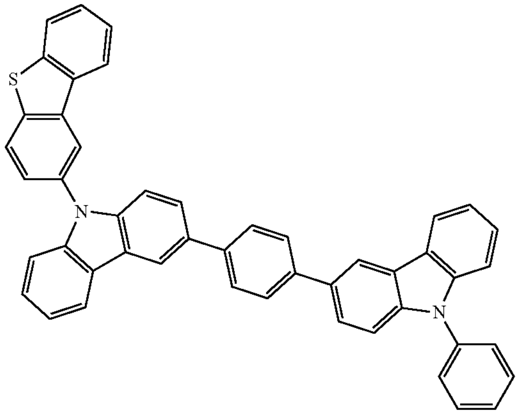

-continued
[A-111]
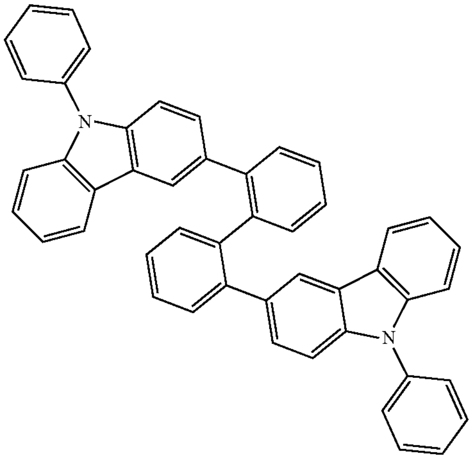
[A-112]
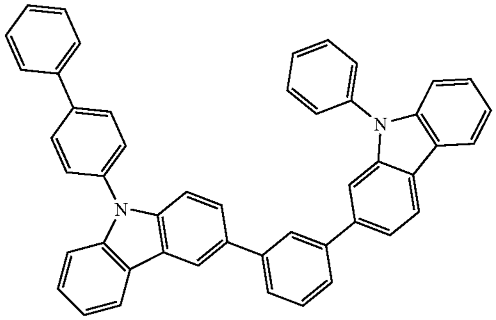
[A-113]
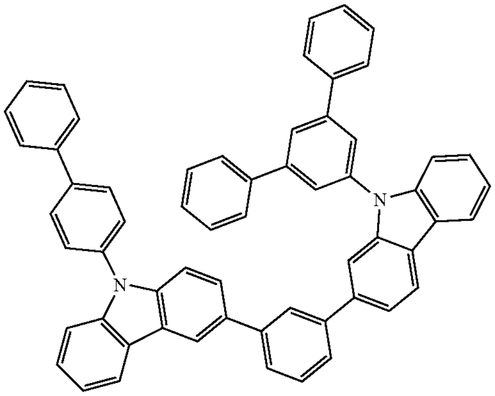
[A-114]
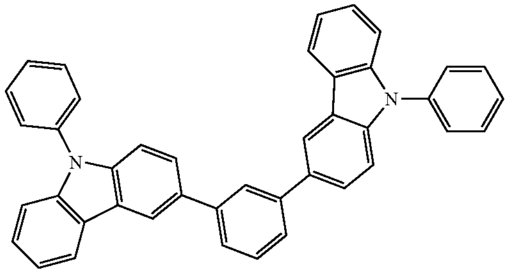
[A-115]
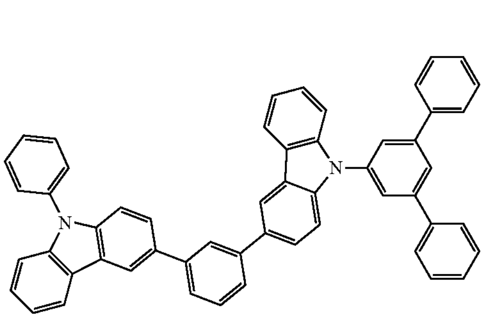
[A-116]
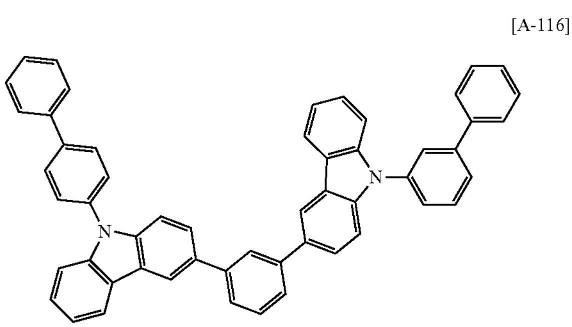

-continued
[A-117]
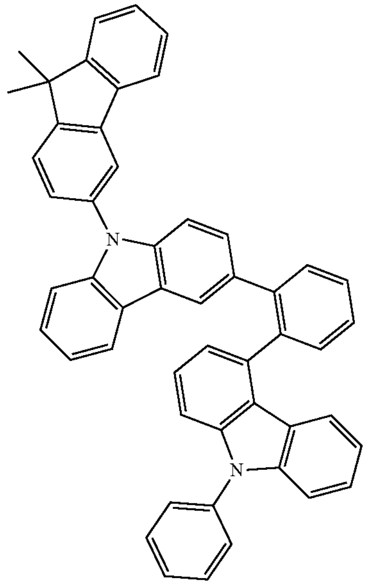
[A-118]
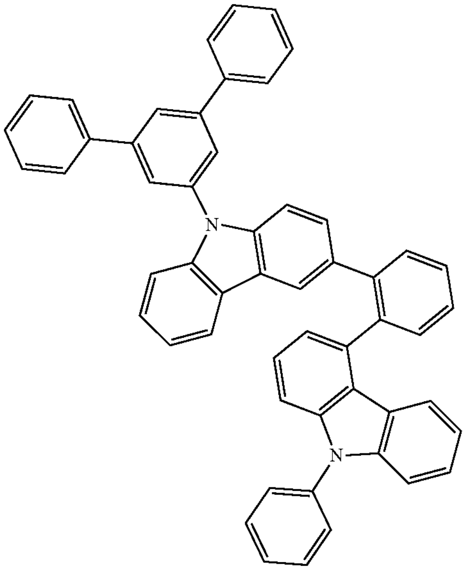
[A-119]
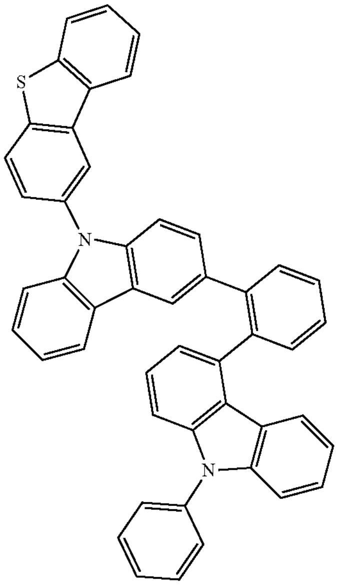
[A-120]
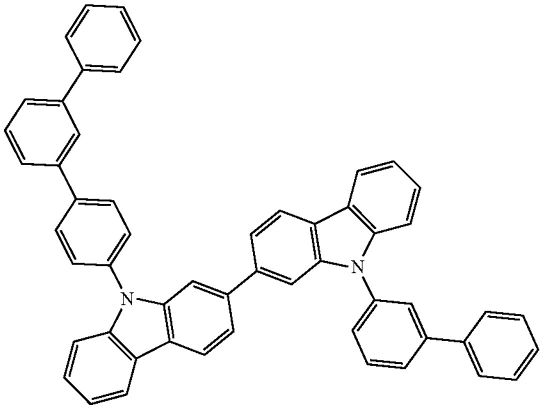
[A-121]
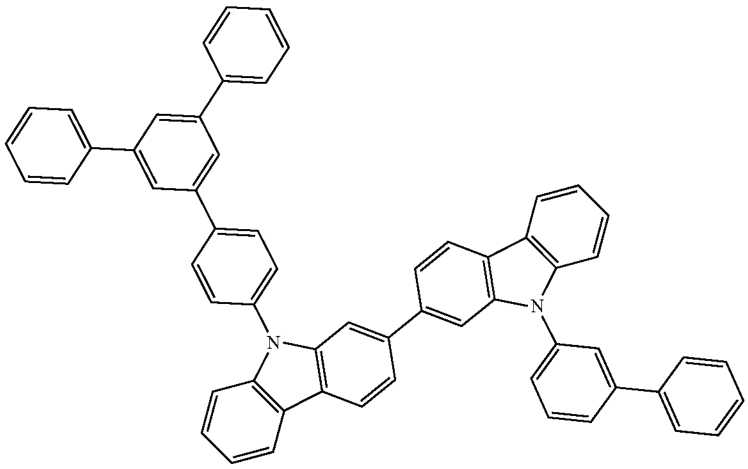

-continued
[A-122]
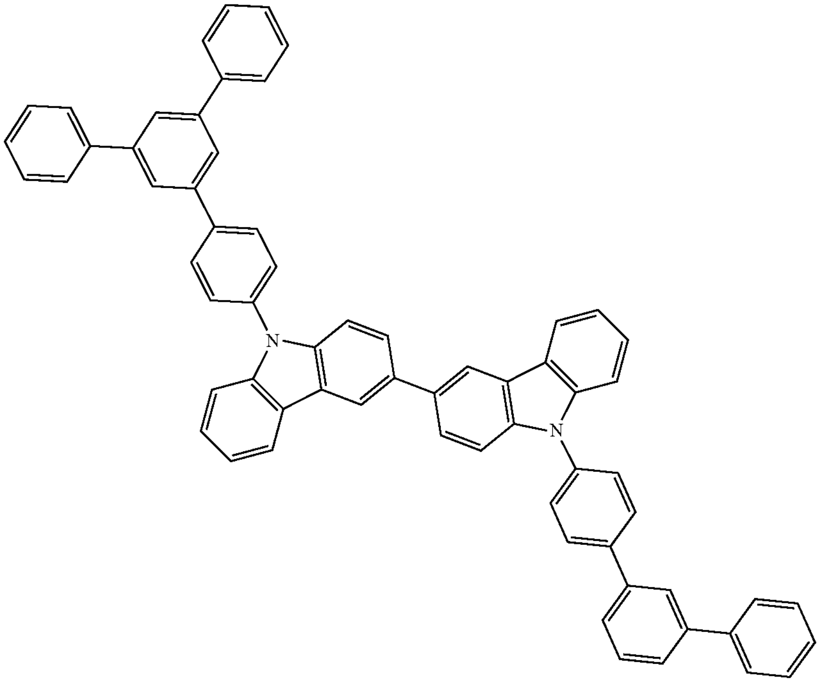
[A-123]
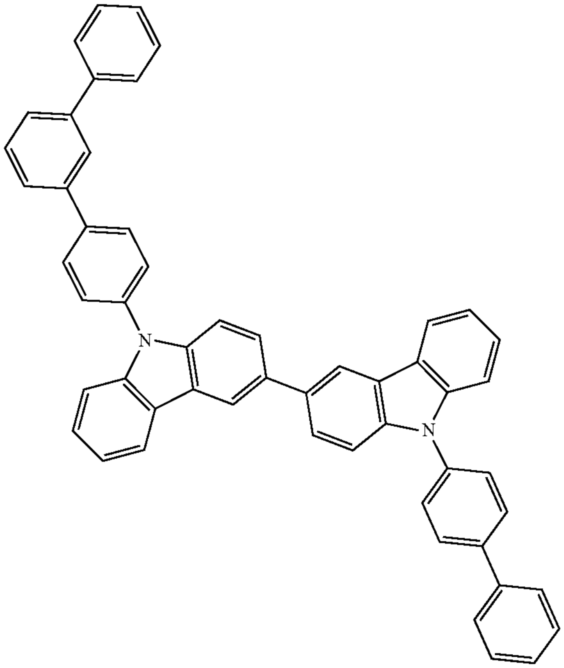

-continued
[A-124]
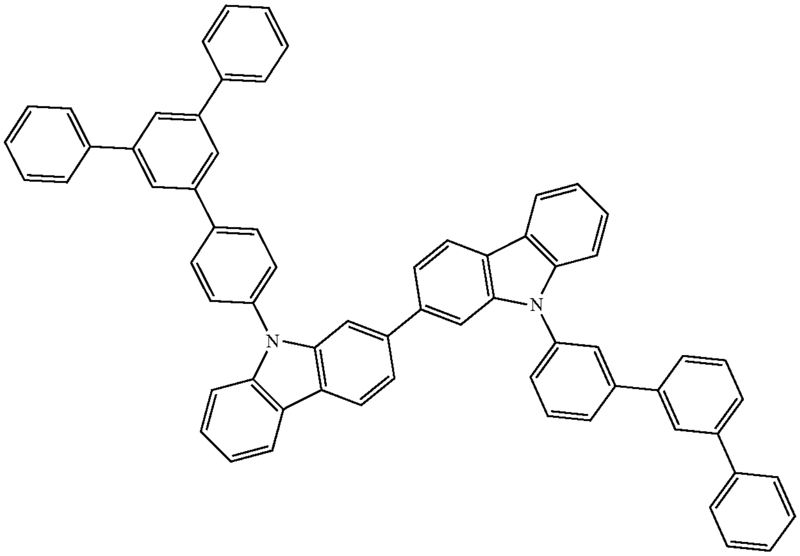
[A-125]
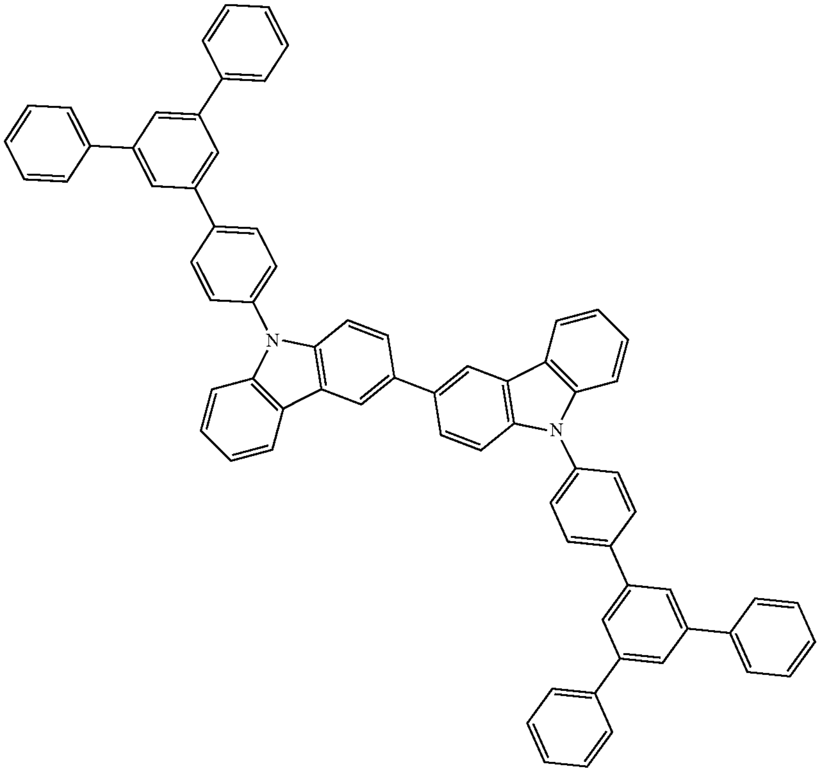

-continued
[A-126]
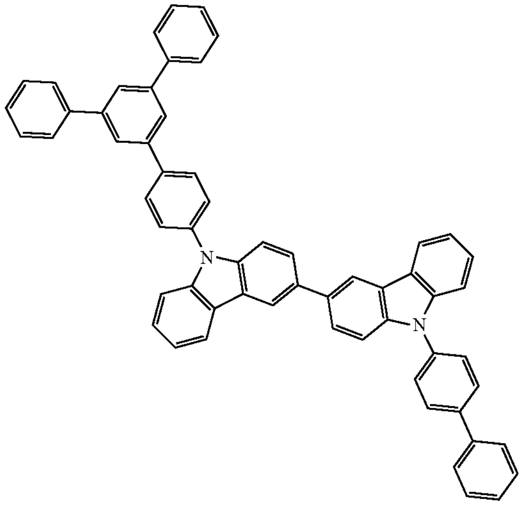
[A-127]
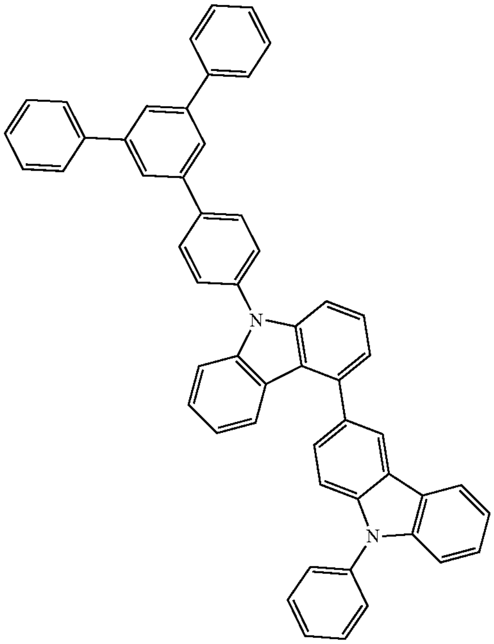
[A-128]
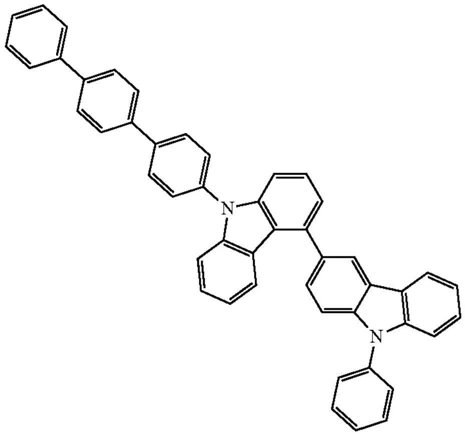
[A-129]
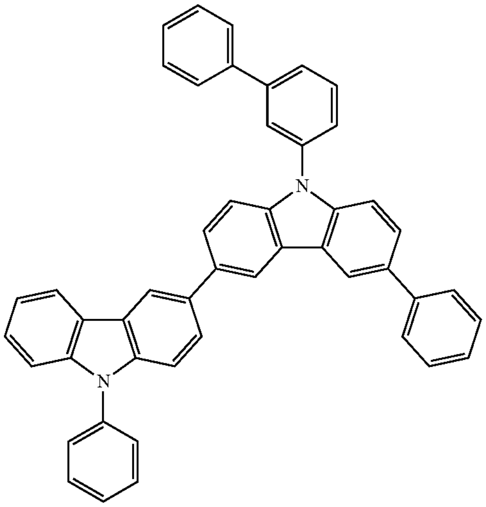

-continued
[A-130]
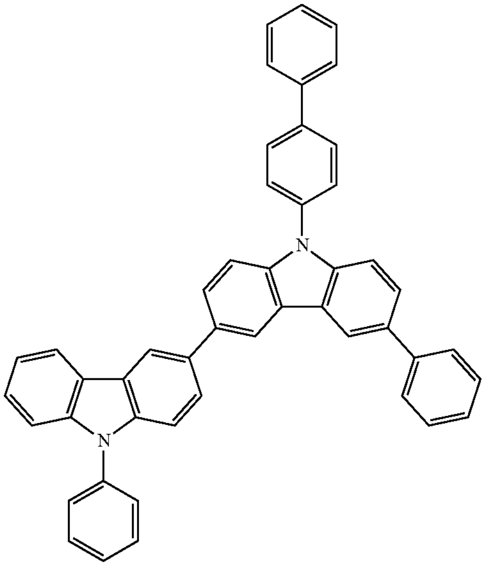
[A-131]
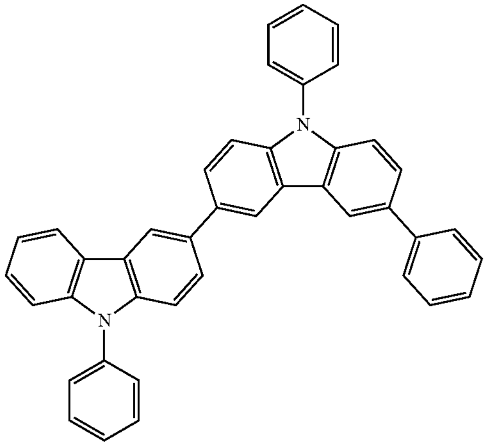
[A-132]
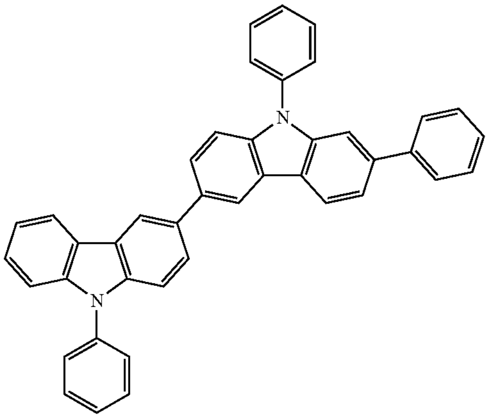
[A-133]
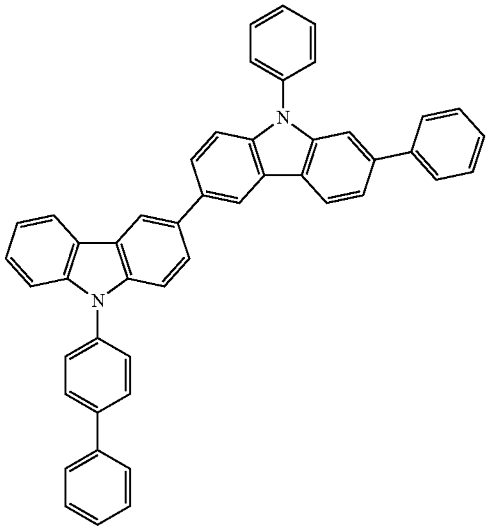
[A-134]
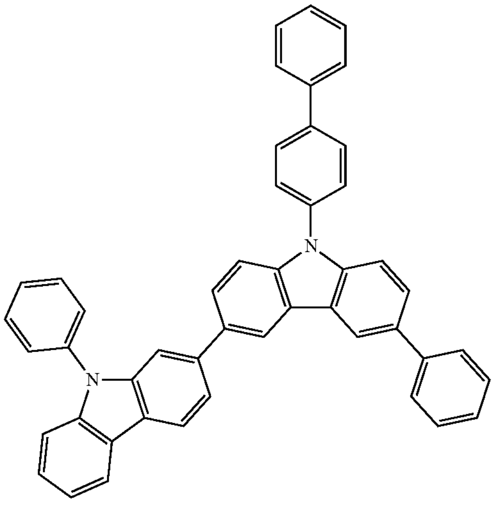
[A-135]
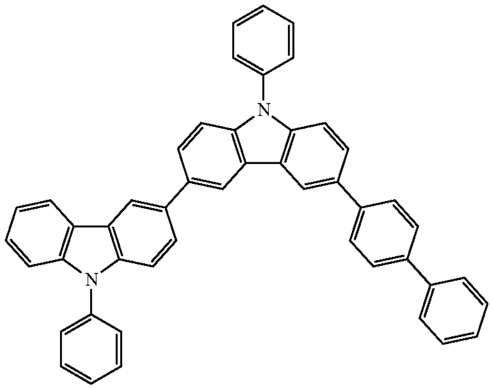

-continued
[A-136]
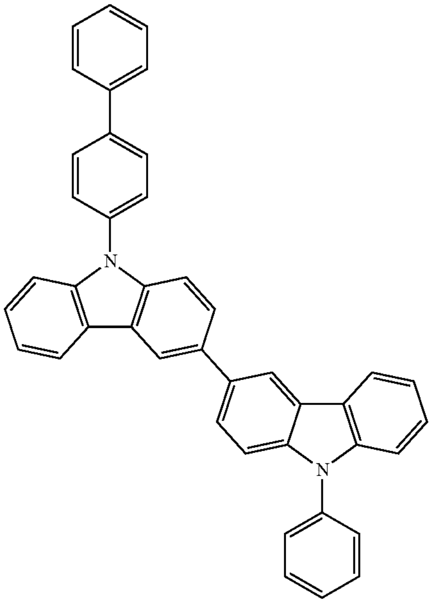
[A-137]
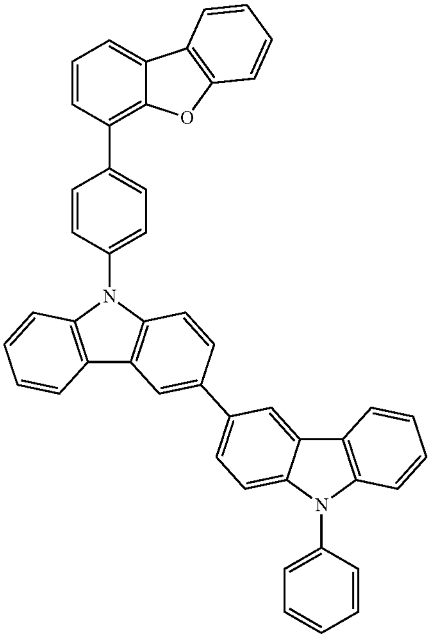
[A-138]
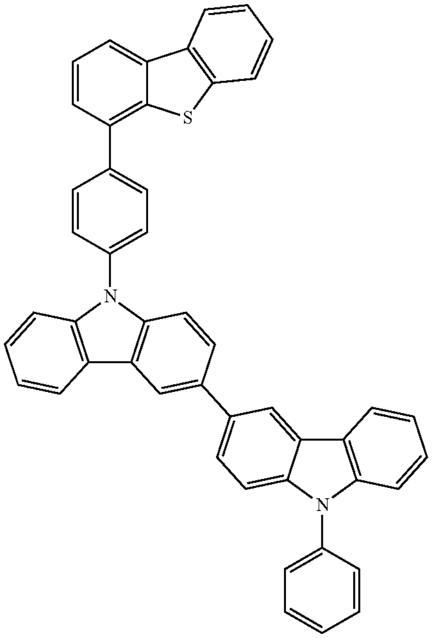
[B-1]
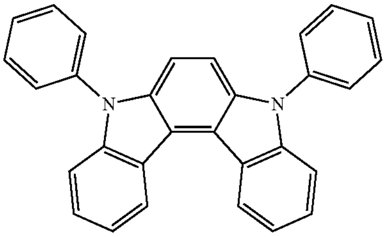
[B-2]
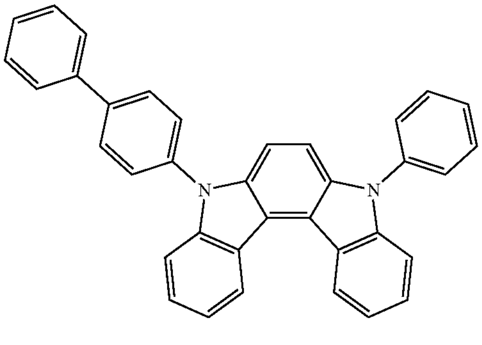
[B-3]
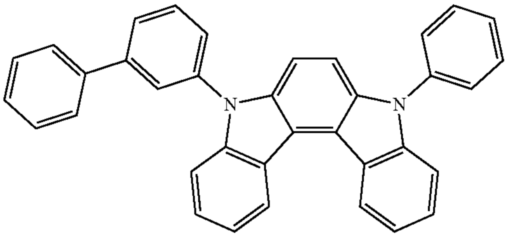

-continued
[B-4]
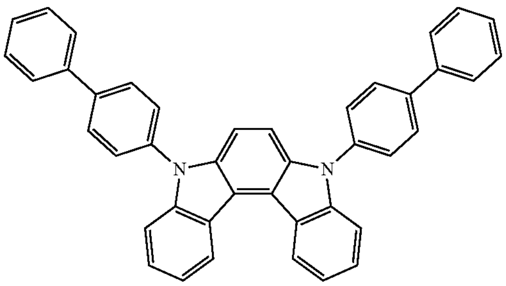
[B-5]
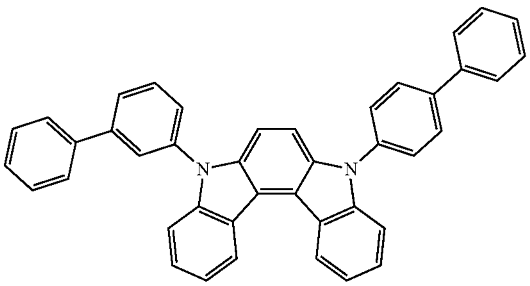
[B-6]
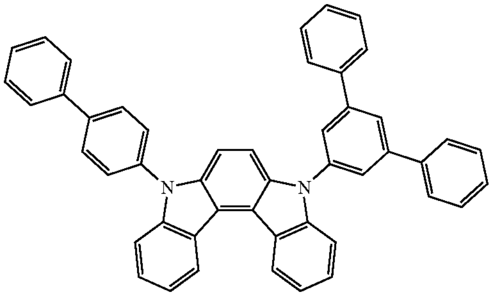
[B-7]
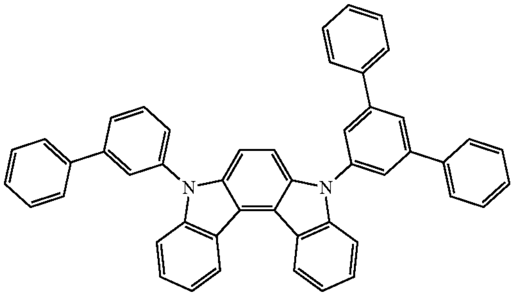
[B-8]
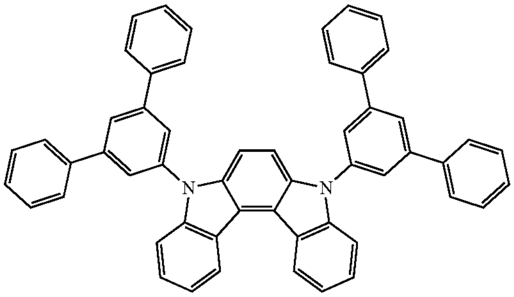
[B-9]
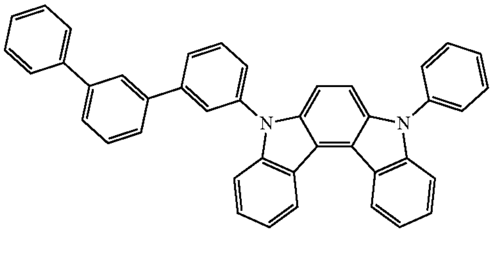
[B-10]
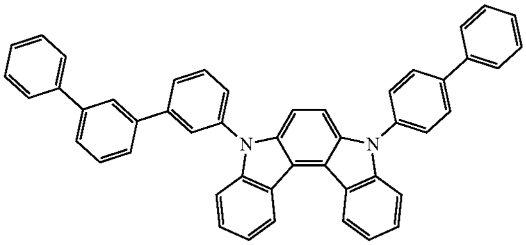
[B-11]
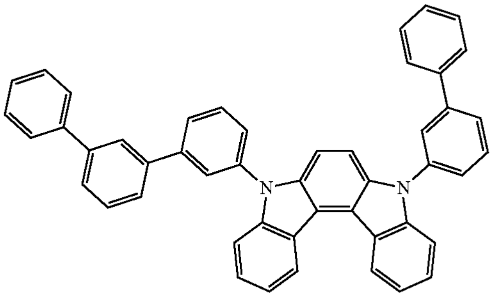
[B-12]
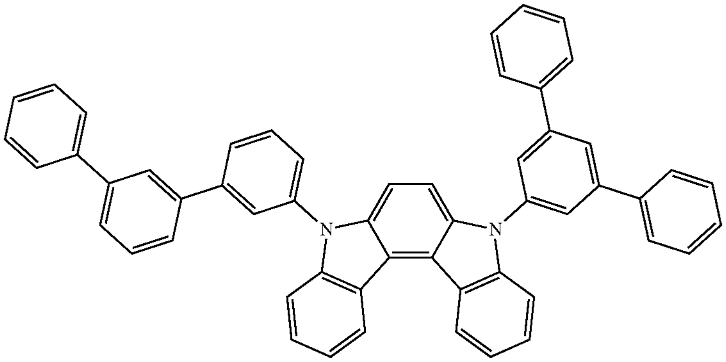

-continued
[B-13]
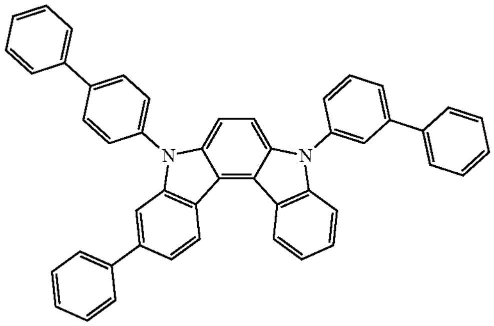
[B-14]
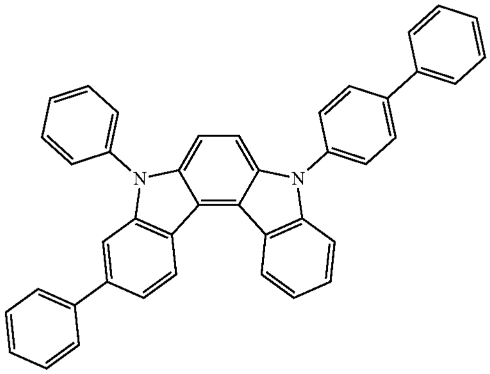
[B-15]
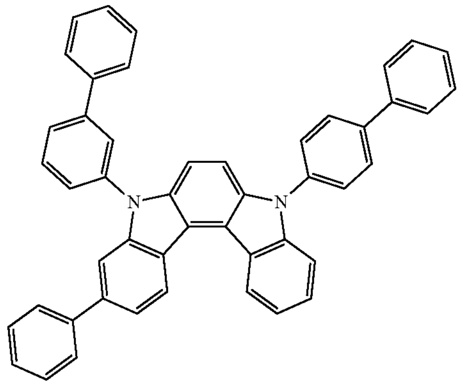
[B-16]
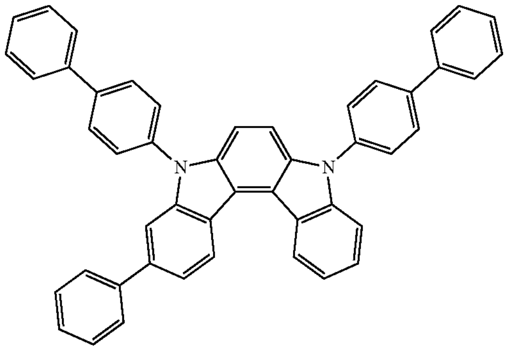
[B-17]
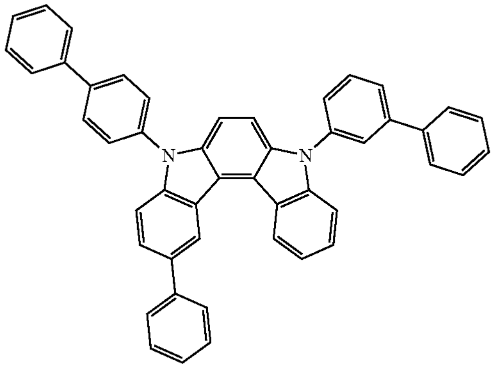
[B-18]
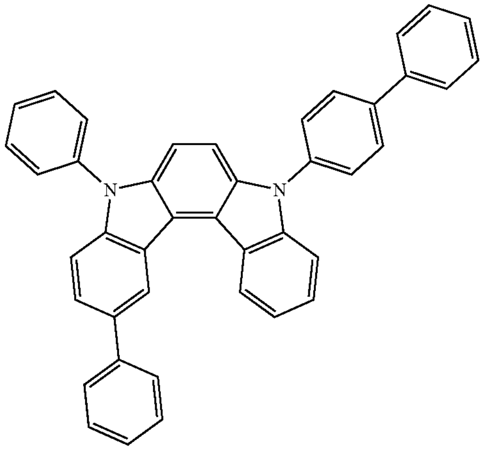

-continued
[B-19]
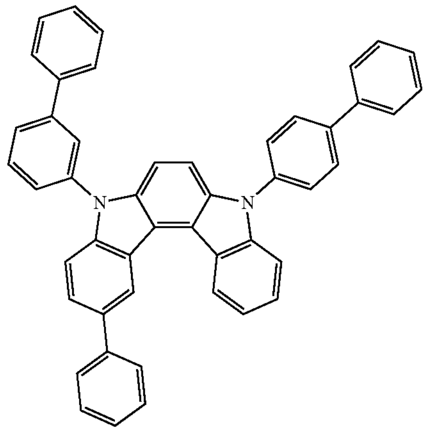
[B-20]
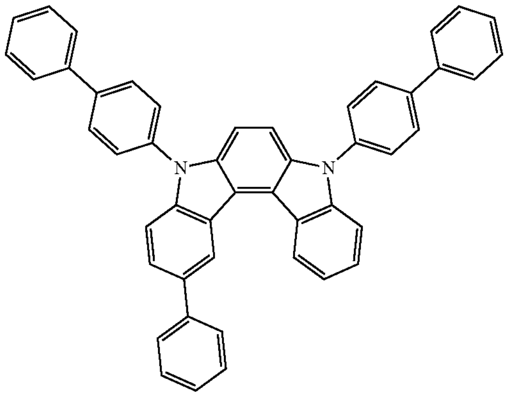
[B-21]
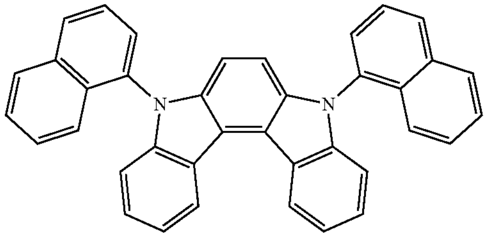
[B-22]
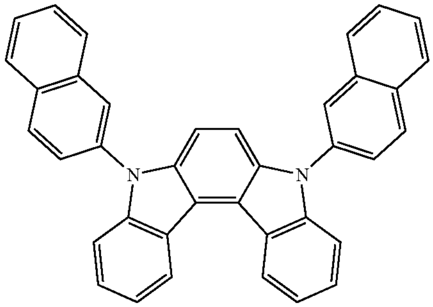
[B-23]
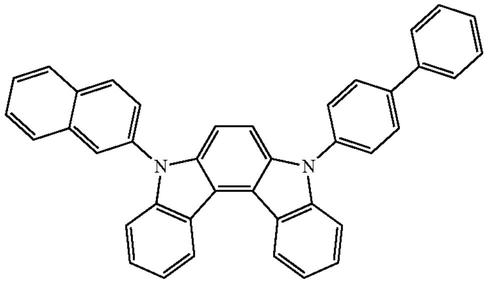
[B-24]
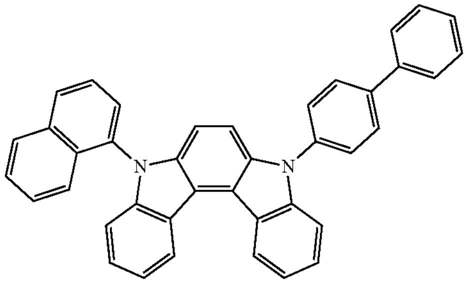
[B-25]
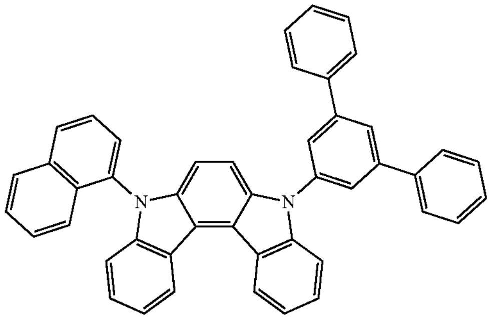
[B-26]
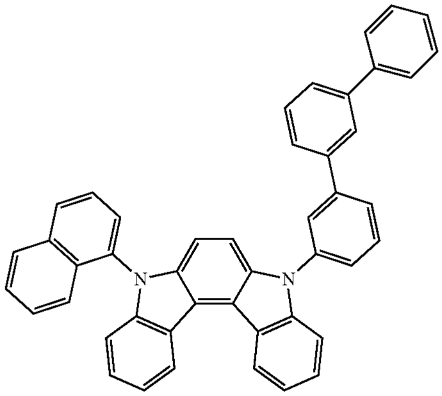

-continued
[B-27]
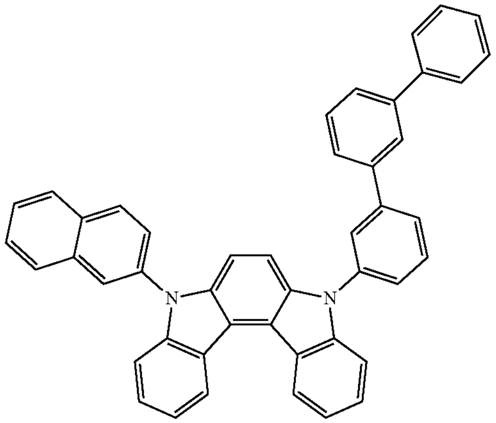
[B-28]
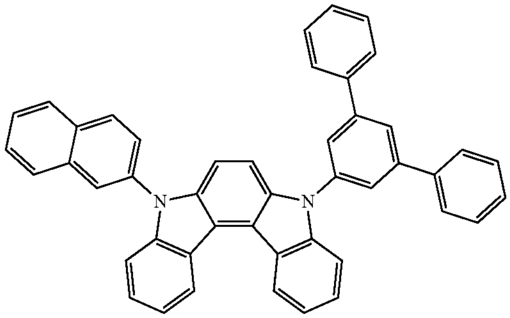
[B-29]
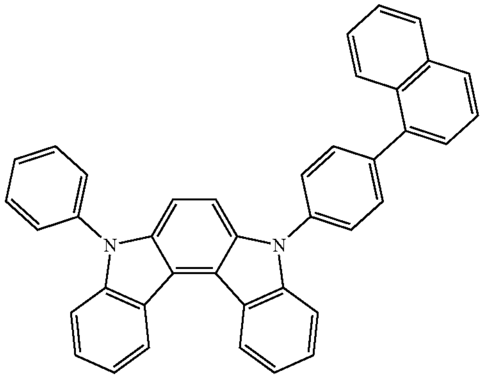
[B-30]
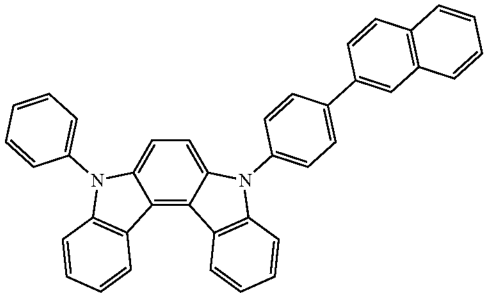
[B-31]
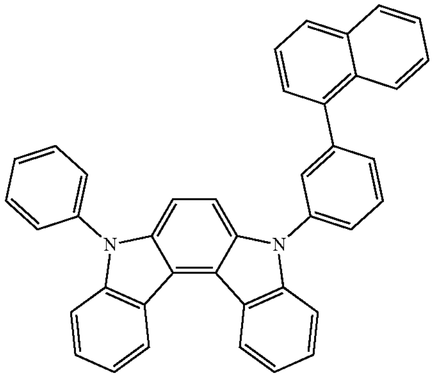
[B-32]
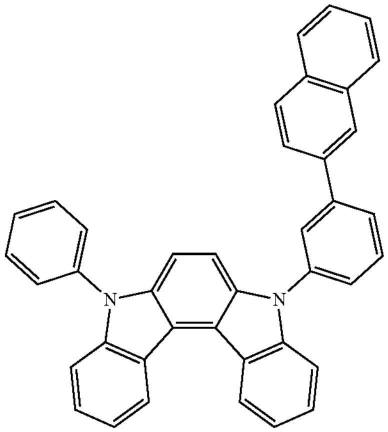
[B-33]
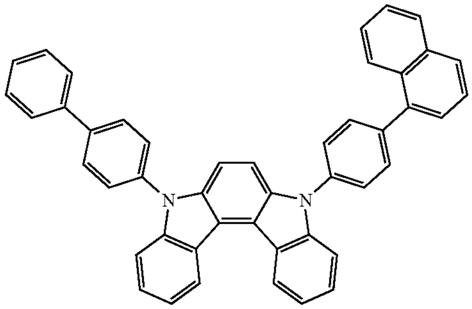
[B-34]
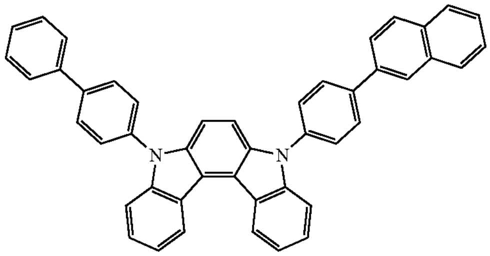

-continued
[B-35]
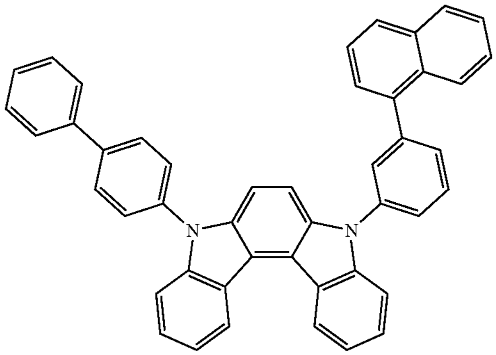
[B-36]
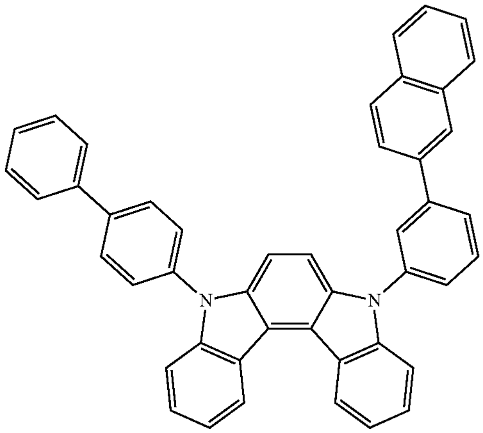
[B-37]
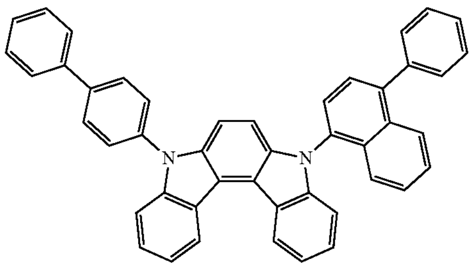
[B-38]
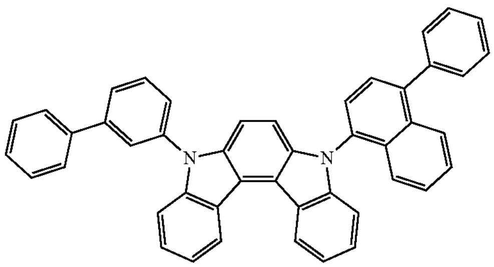
[B-39]
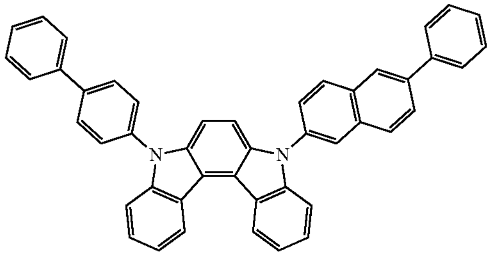
[B-40]
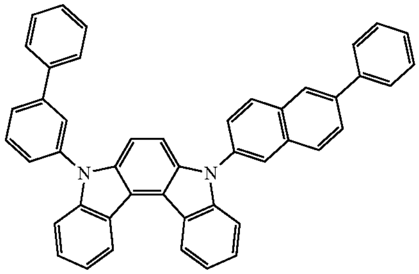
[B-41]
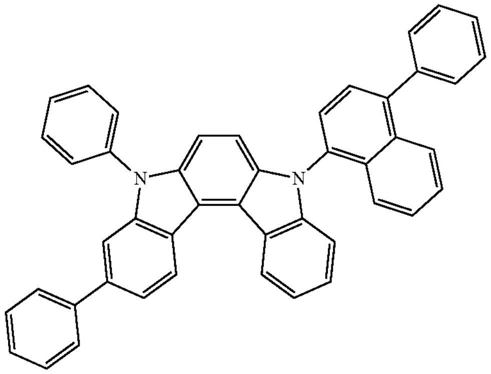
[B-42]
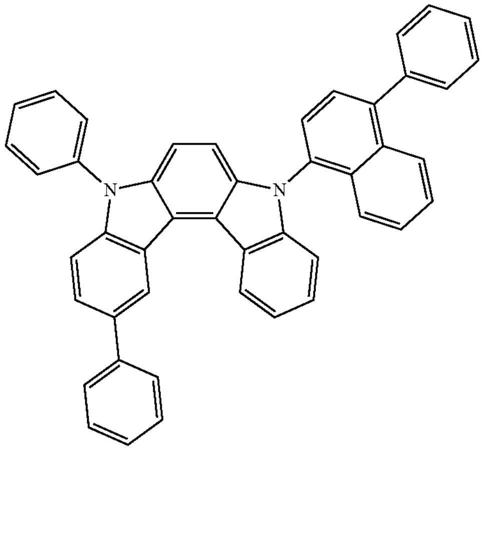

-continued
[B-43]
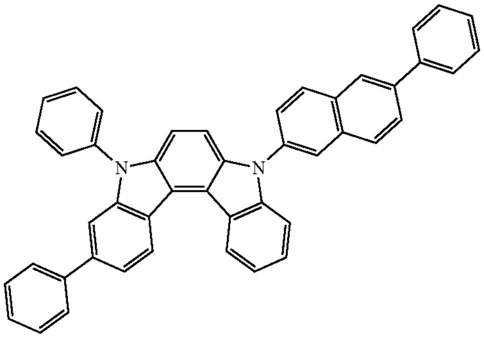
[B-44]
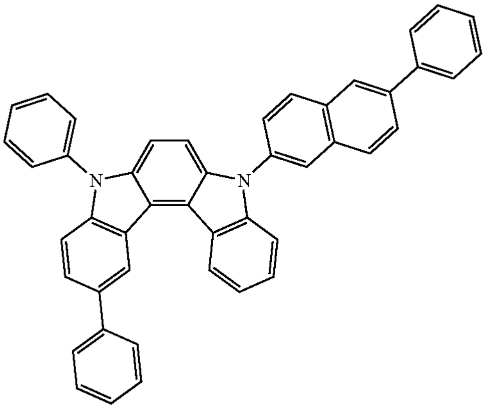
[B-45]
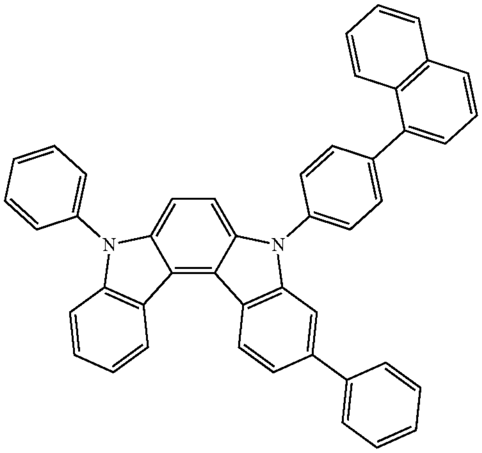
[B-46]
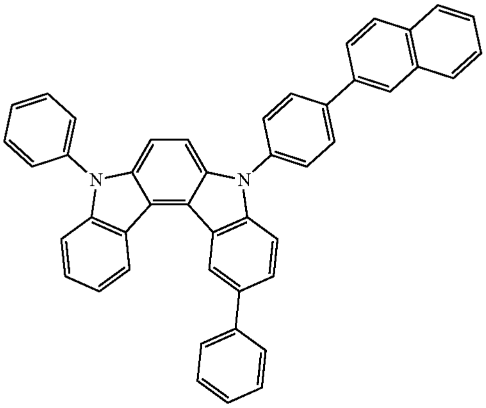
[B-47]
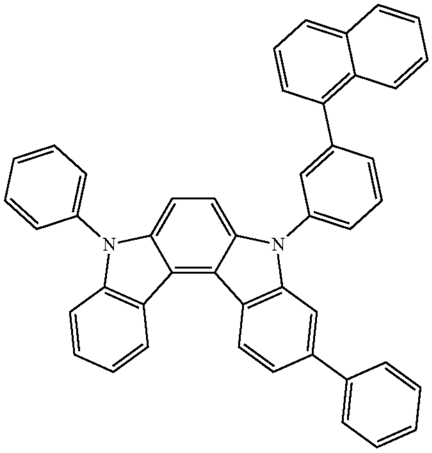
[B-48]
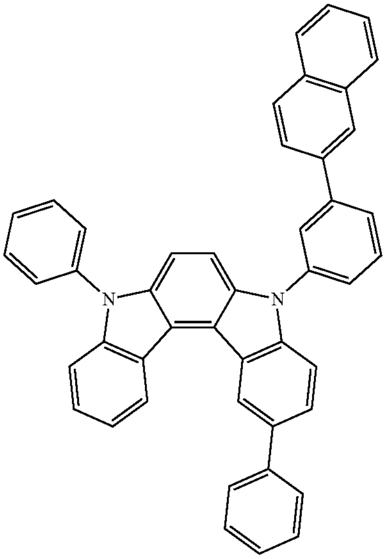

-continued
[B-49]
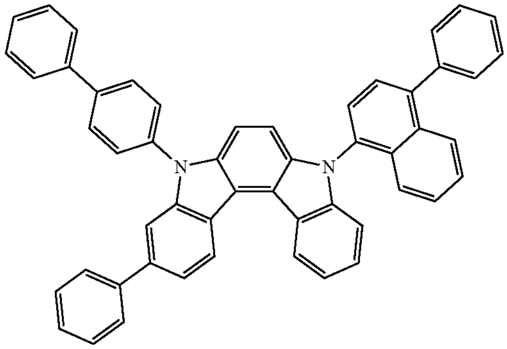
[B-50]
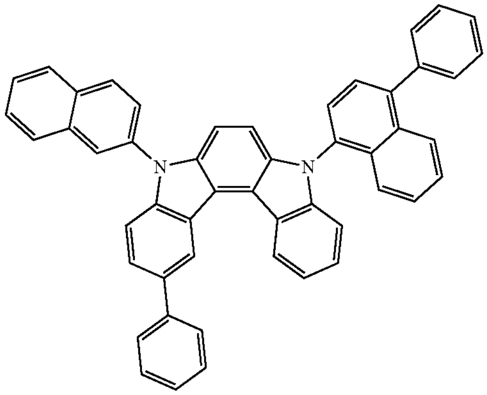
[B-51]
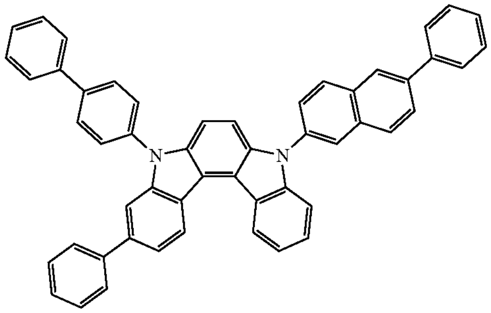
[B-52]
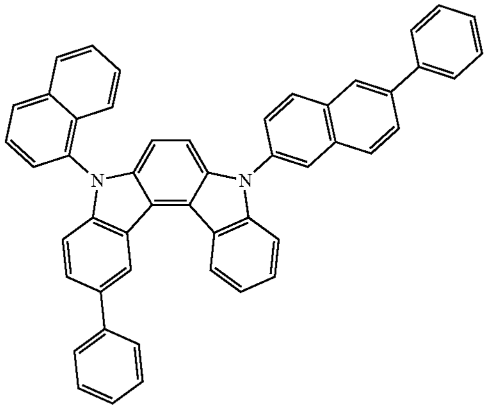
[B-53]
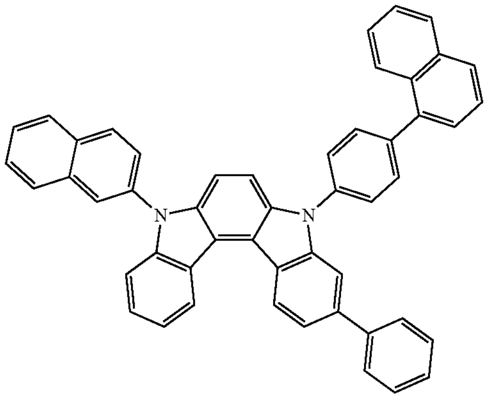
[B-54]
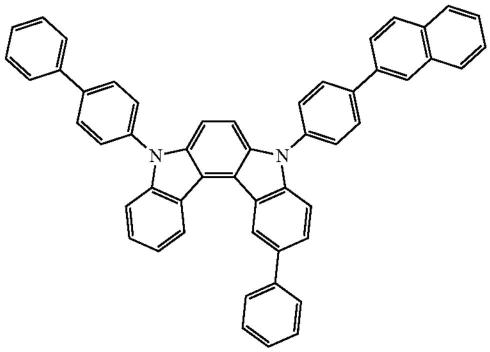

-continued

[B-55]

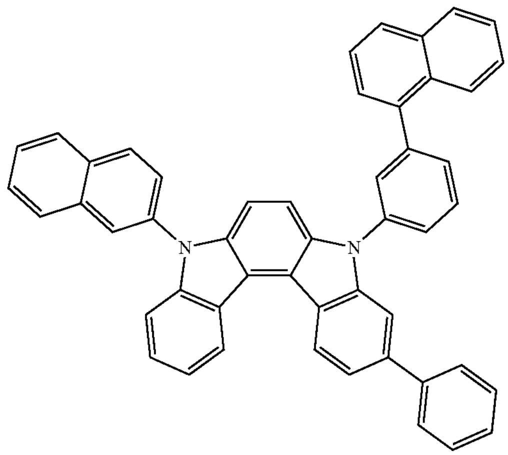

[B-56]

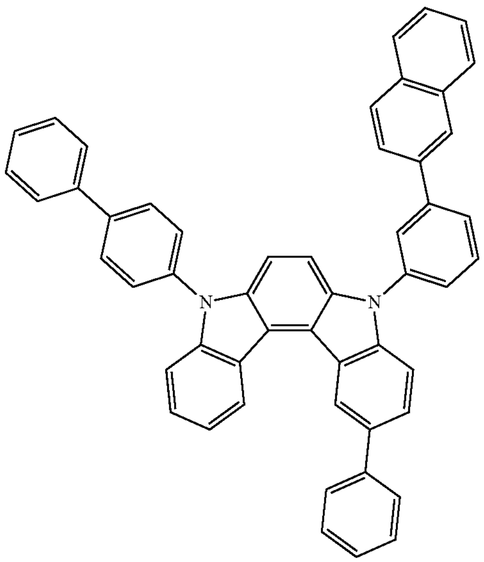

[B-57]

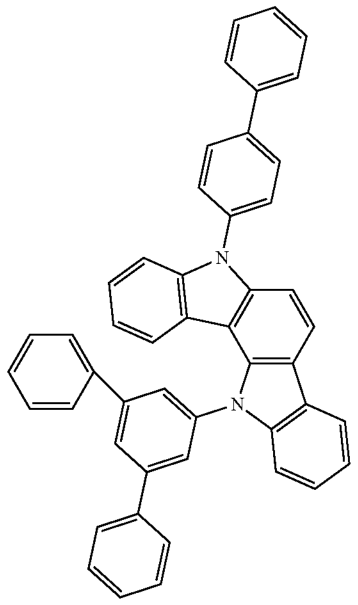

The first compound for an organic optoelectronic device and the second compound for an organic optoelectronic device may be included, e.g., in a weight ratio of about 1:99 to about 99:1. Within the above range, an appropriate weight ratio may be adjusted using the electron transport capability of the first compound for the organic optoelectronic device and the hole transport capability of the second compound for an organic optoelectronic device to implement bipolar characteristics and to improve the efficiency and life-span. Within the above range, e.g., they may be included in a weight ratio of about 10:90 to about 90:10, about 10:90 to about 80:20, e.g., about 10:90 to about 70:30, or about 20:80 to about 70:30. In an implementation, they may be included in a weight ratio of about 20:80, about 30:70, or about 40:60.

In addition to the aforementioned first compound for an organic optoelectronic device and second compound for an organic optoelectronic device, one or more additional compounds may be further included.

The aforementioned compound for an organic optoelectronic device or composition for an organic optoelectronic device may be a composition further including a dopant.

The dopant may be, e.g., a phosphorescent dopant and may be, for example a red, green or blue phosphorescent dopant, for example a red or green phosphorescent dopant.

The dopant is a material mixed with the compound or composition for an organic optoelectronic device in a trace amount to cause light emission, and may be generally a material such as a metal complex that emits light by multiple excitation into a triplet or more. The dopant may be, e.g., an inorganic, organic, or organic-inorganic compound, and one or more types thereof may be used.

Examples of the dopant may be a phosphorescent dopant and examples of the phosphorescent dopant may be an organic metal compound including Ir, Pt, Os, Ti, Zr, Hf, Eu, Tb, Tm, Fe, Co, Ni, Ru, Rh, Pd, or a combination thereof.

In an implementation, the phosphorescent dopant may be, e.g., a compound represented by Chemical Formula Z.

$L^5MX$ [Chemical Formula Z]

In Chemical Formula Z, M may be, e.g., a metal, and $L^5$ and X may each independently be, e.g., ligands forming a complex with M.

M may be, e.g., Ir, Pt, Os, Ti, Zr, Hf, Eu, Tb, Tm, Fe, Co, Ni, Ru, Rh, Pd, or a combination thereof, and $L^5$ and X may be, e.g., a bidentate ligand.

Hereinafter, an organic optoelectronic device including the aforementioned compound for an organic optoelectronic device or composition for an organic optoelectronic device is described.

The organic optoelectronic device may be a suitable device to convert electrical energy into photoenergy and vice versa, and may be, e.g., an organic photoelectric device, an organic light emitting diode, an organic solar cell, or an organic photoconductor drum.

Herein, an organic light emitting diode as one example of an organic optoelectronic device is described referring to drawings.

FIGS. 1 to 4 are cross-sectional views of organic light emitting diodes according to embodiments.

Referring to FIG. 1, an organic light emitting diode 100 according to an embodiment includes an anode 120 and a cathode 110 facing each other and an organic layer 105 disposed between the anode 120 and cathode 110.

The anode 120 may be made of a conductor having a large work function to help hole injection, and may be, e.g., a metal, a metal oxide or a conductive polymer. The anode 120 may be, e.g., a metal such as nickel, platinum, vanadium, chromium, copper, zinc, gold, or the like or an alloy thereof; a metal oxide such as zinc oxide, indium oxide, indium tin oxide (ITO), indium zinc oxide (IZO), or the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, or polyaniline.

The cathode 110 may be made of a conductor having a small work function to help electron injection, and may be, e.g., a metal, a metal oxide, or a conductive polymer. The cathode 110 may be, e.g., a metal such as magnesium, calcium, sodium, potassium, titanium, indium, yttrium, lithium, gadolinium, aluminum silver, tin, lead, cesium, barium, or the like, or an alloy thereof; or a multi-layer structure material such as LiF/Al, $LiO_2$/Al, LiF/Ca, or $BaF_2$/Ca.

The organic layer 105 may include the aforementioned compound for an organic optoelectronic device or composition for an organic optoelectronic device.

The organic layer 105 may include the light emitting layer 130, and the light emitting layer 130 may include the aforementioned compound for an organic optoelectronic device or composition for an organic optoelectronic device.

The composition for an organic optoelectronic device further including the dopant may be, e.g., a red light emitting composition.

The light emitting layer 130 may include, e.g., the aforementioned first compound for an organic optoelectronic device and second compound for an organic optoelectronic device, respectively, as a phosphorescent host.

The organic layer may further include a charge transport region in addition to the light emitting layer.

The auxiliary layer may be, e.g., the hole auxiliary layer 140.

Figure 2:
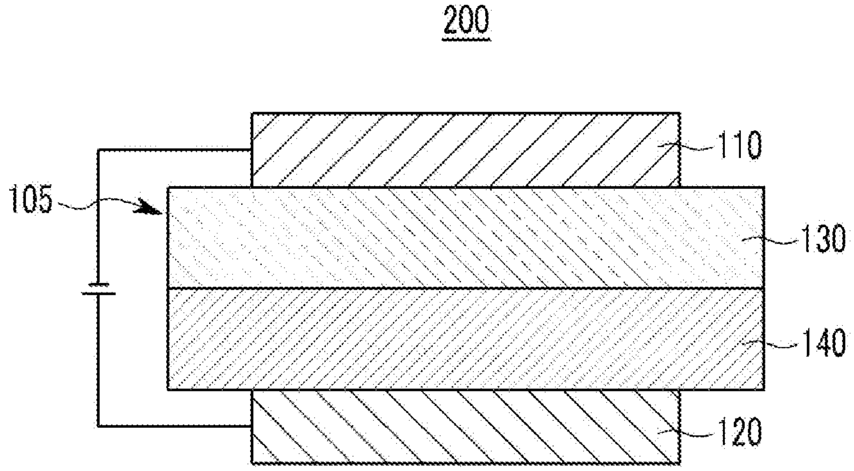

Referring to FIG. 2, an organic light emitting diode 200 may further include a hole transport region 140 in addition to the light emitting layer 130. The hole transport region 140 may help further increase hole injection and/or hole mobility and block electrons between the anode 120 and the light emitting layer 130. In an implementation, the hole transport region 140 may include a hole transport layer between the anode 120 and the light emitting layer 130, and a hole transport auxiliary layer between the light emitting layer 130 and the hole transport layer. In an implementation, at least one of the compounds of Group E may be included in at least one of the hole transport layer and the hole transport auxiliary layer.

[Group E]

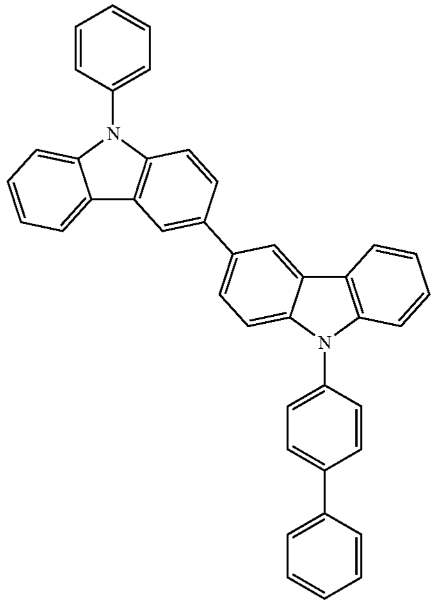

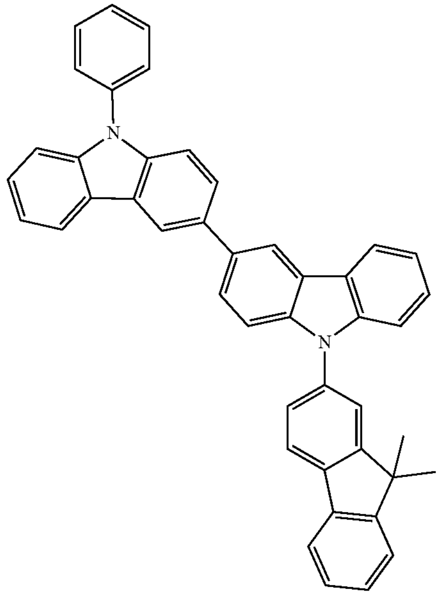

-continued
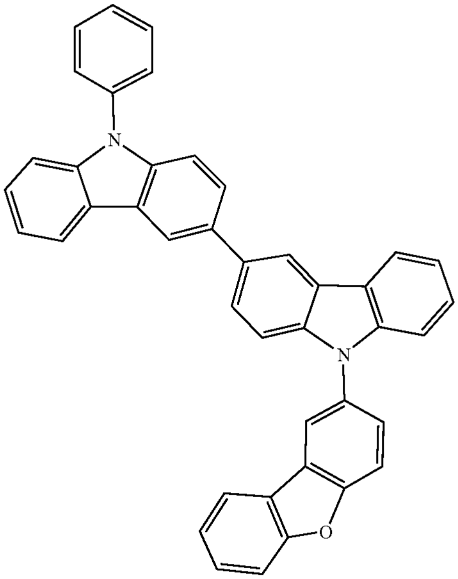
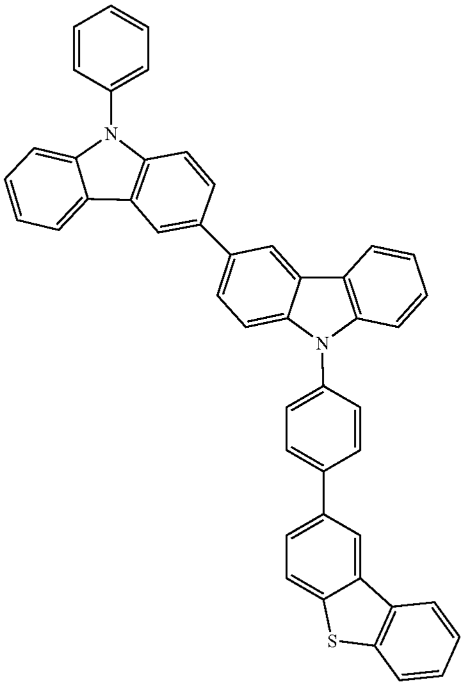
-continued
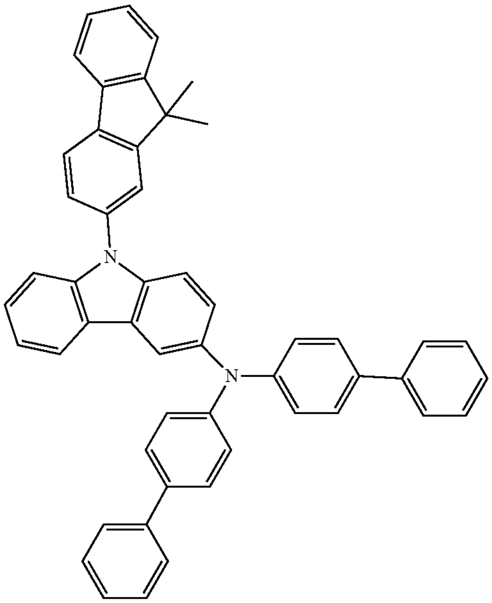
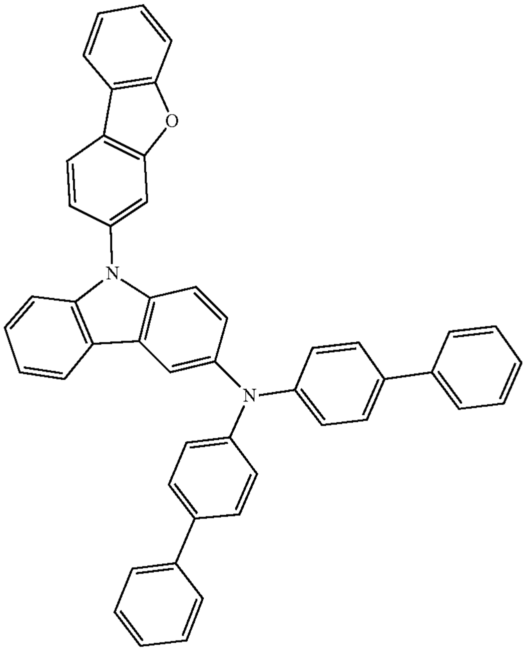
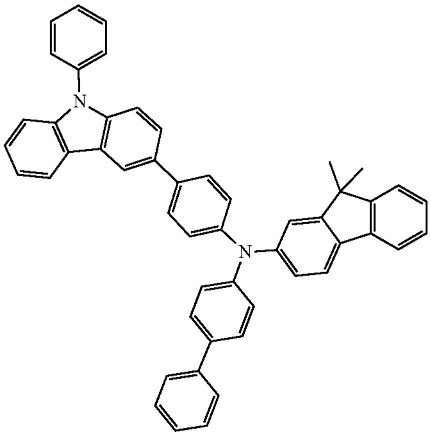

-continued
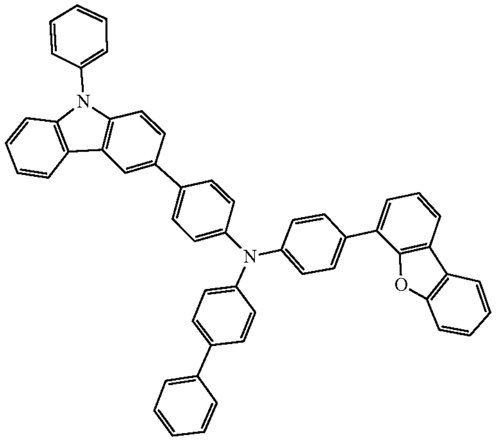
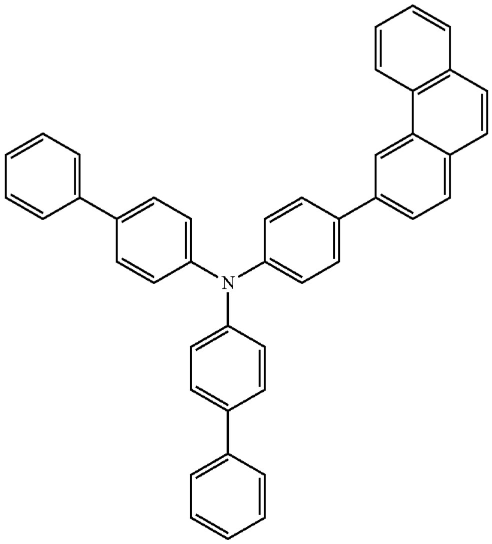
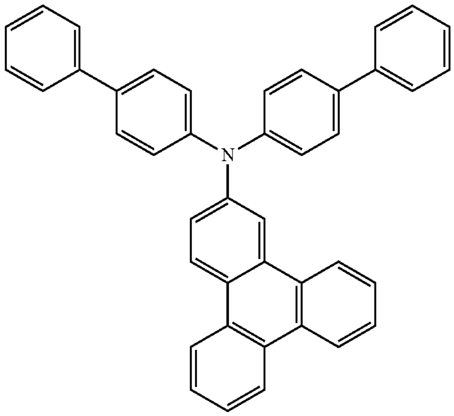
-continued
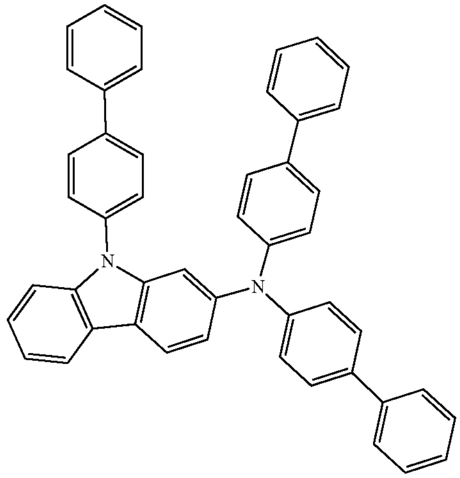
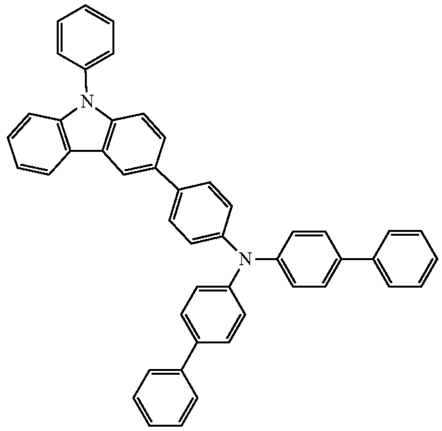
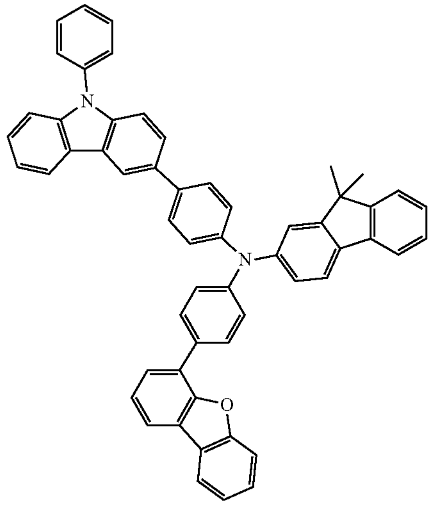

-continued
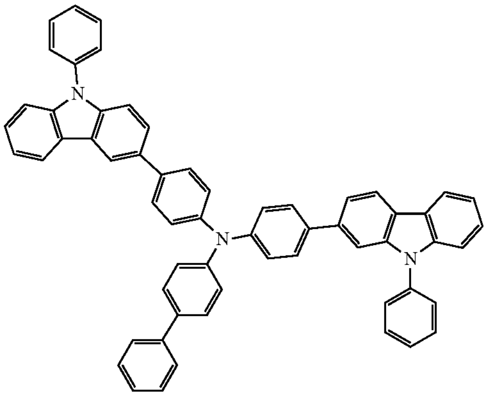
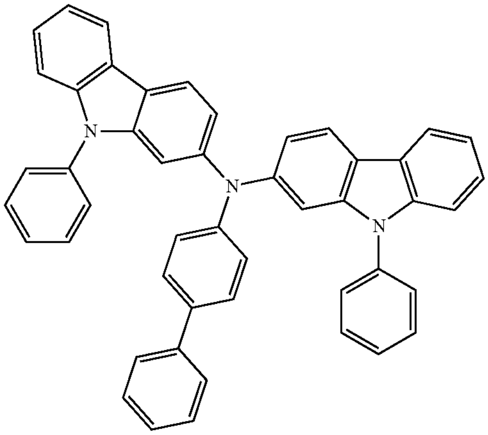
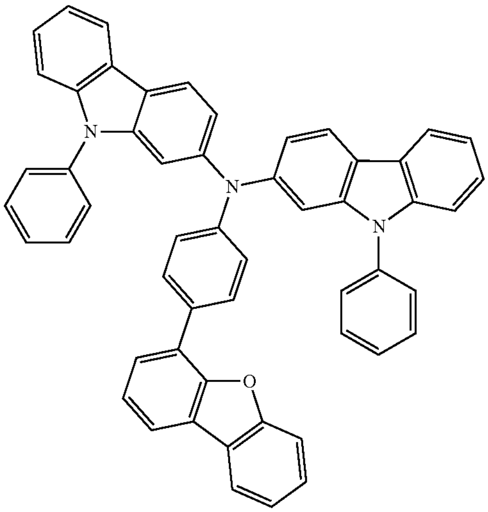
-continued
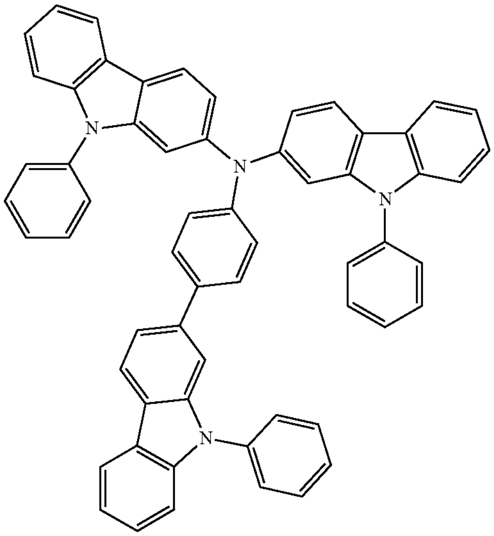
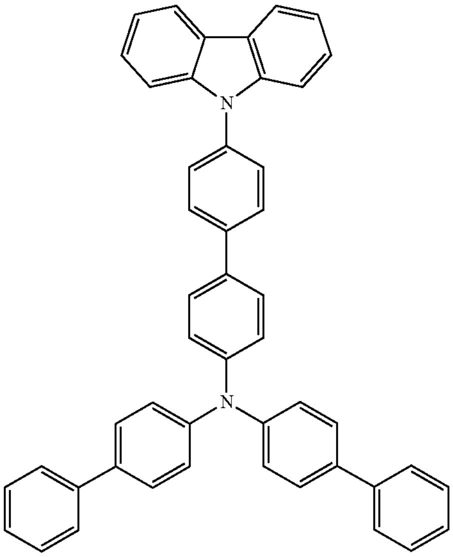
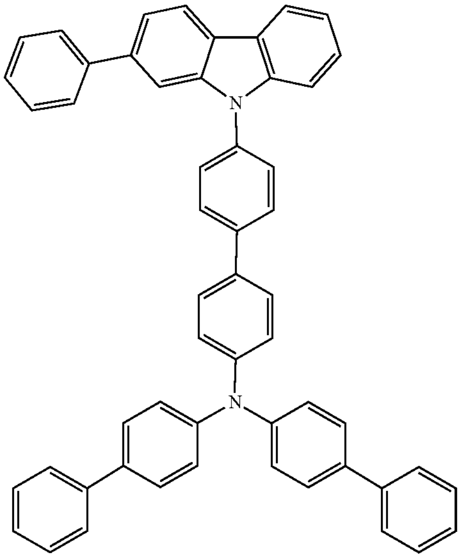

-continued
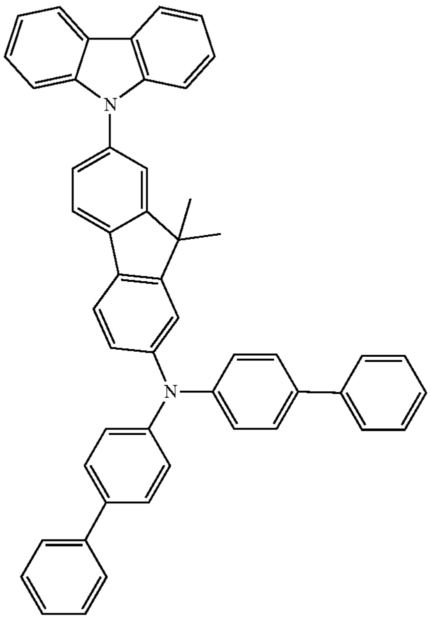
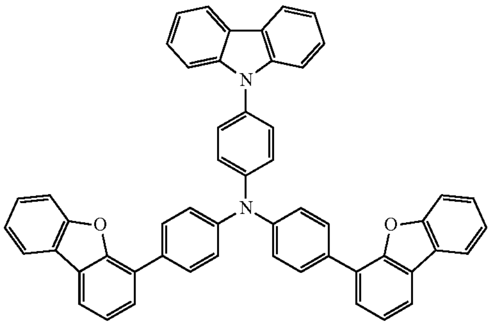
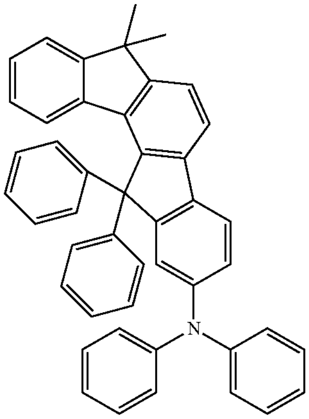
-continued
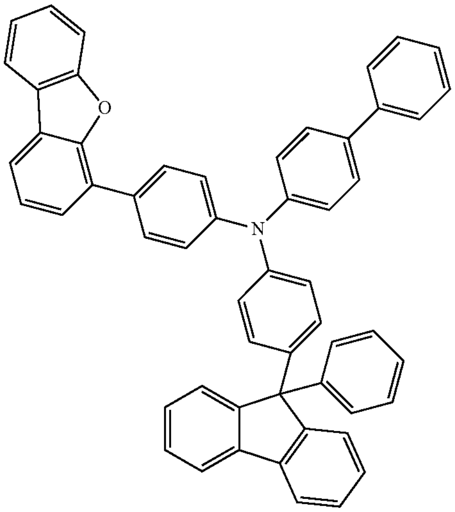
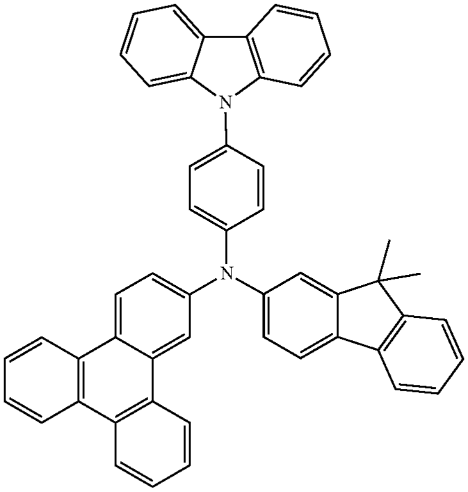
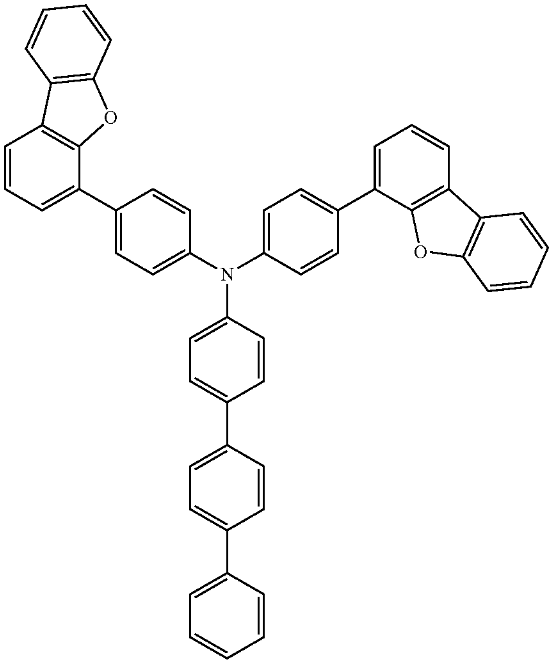

-continued
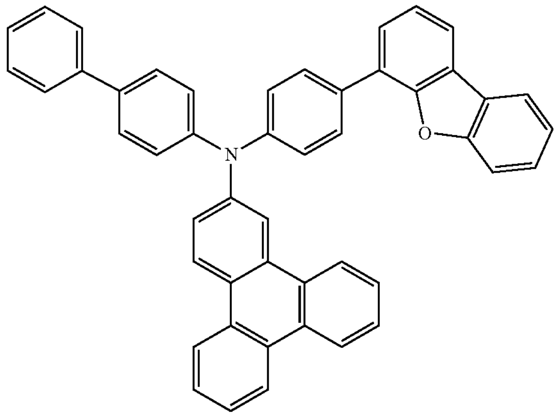
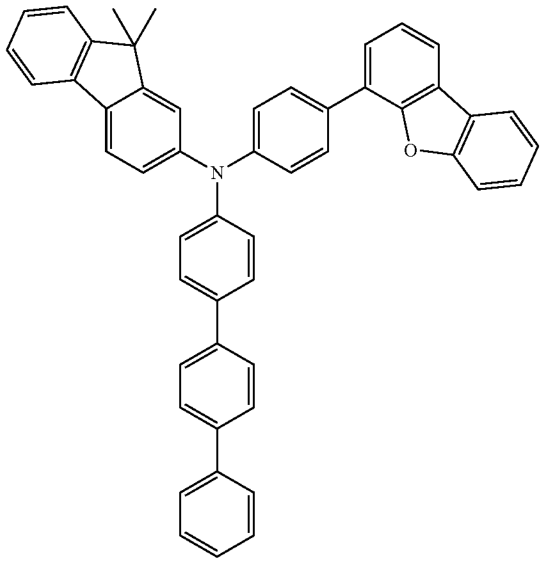
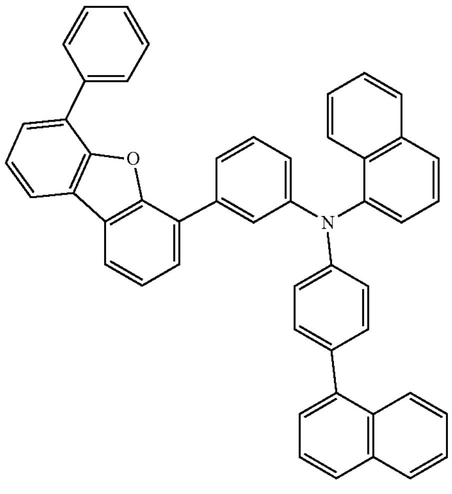
-continued
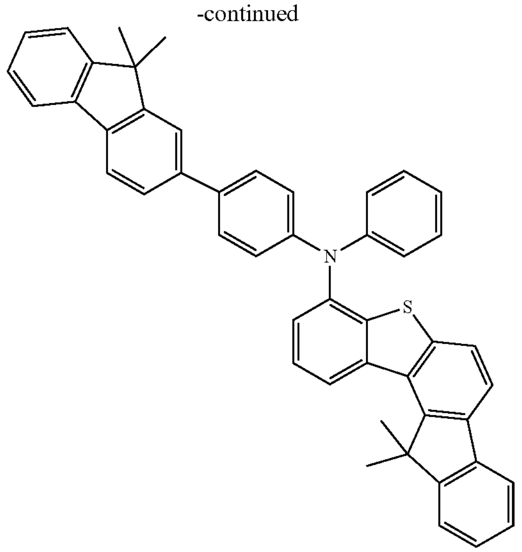
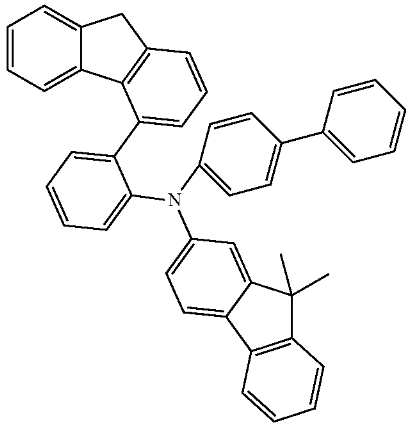
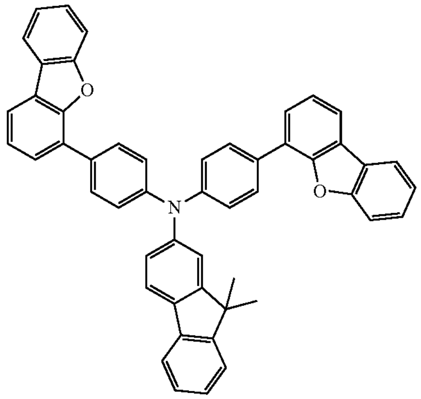
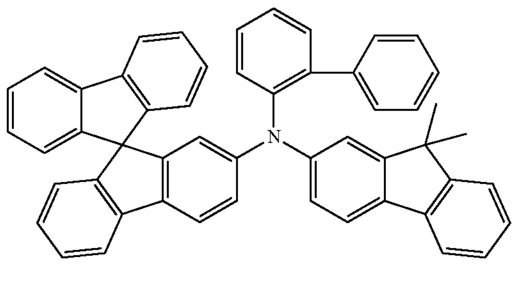

-continued
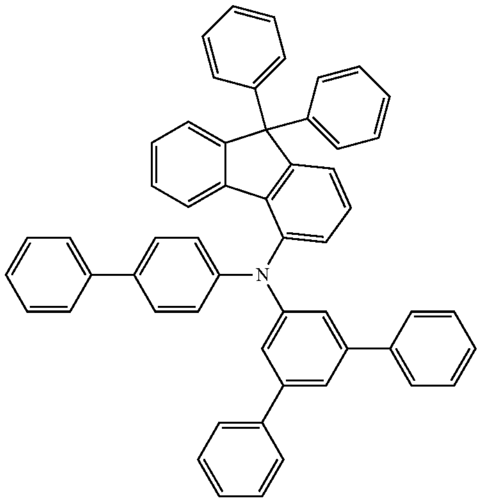
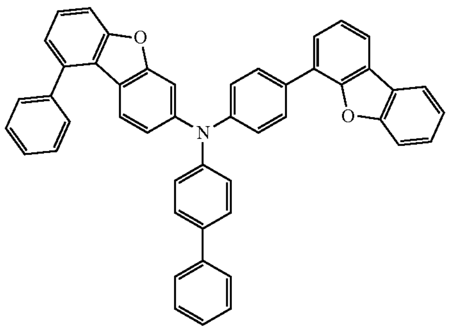
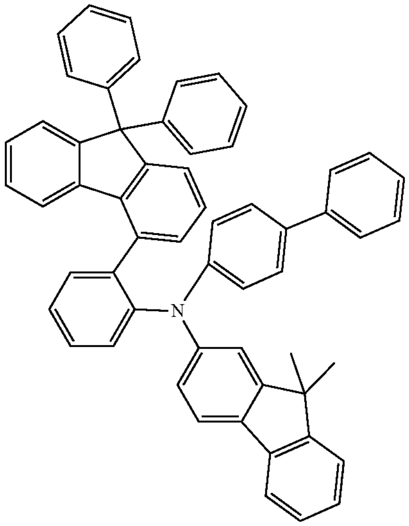
-continued
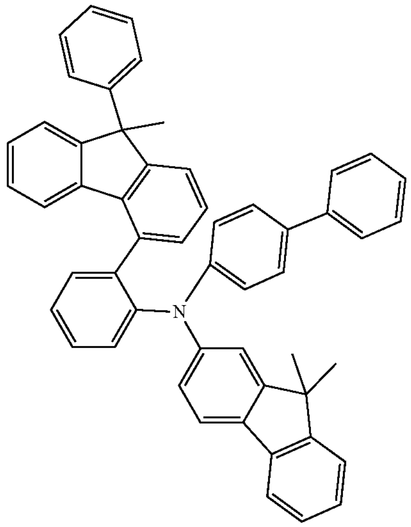
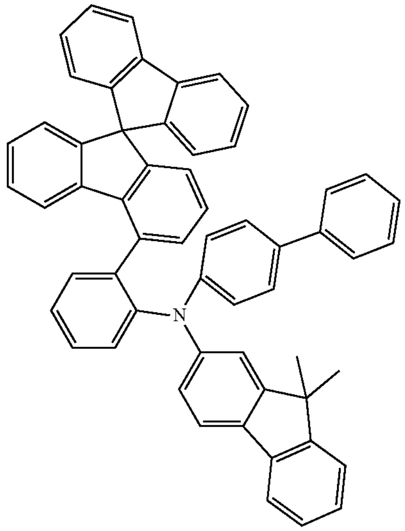
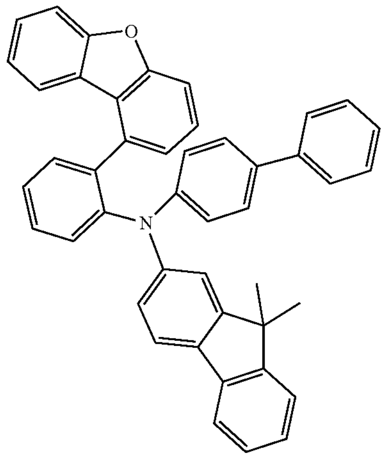

-continued
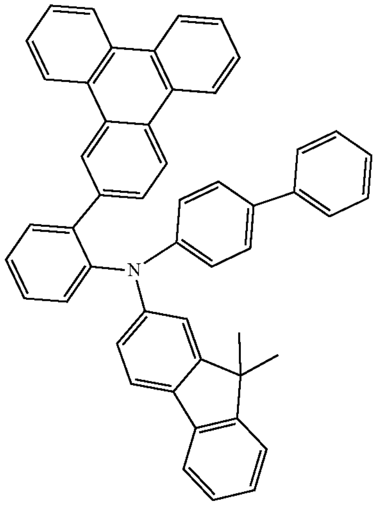
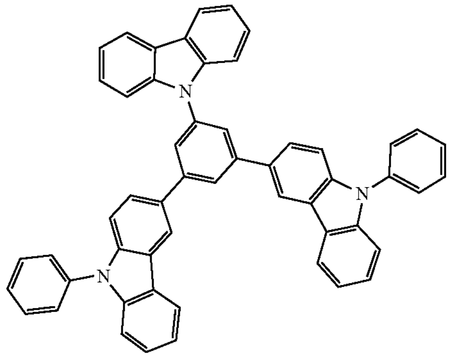
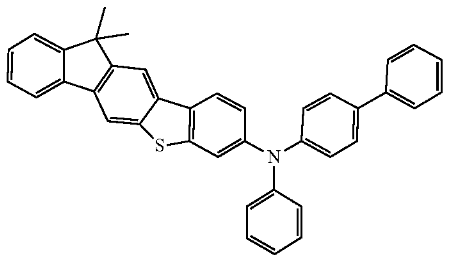
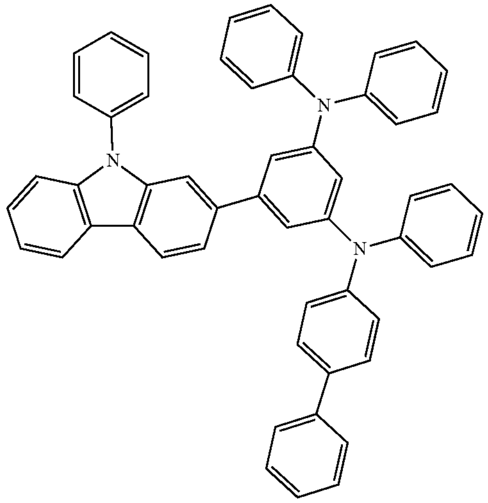
-continued
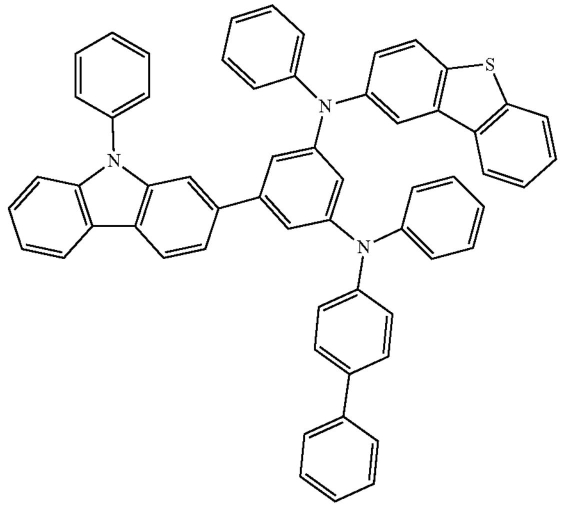
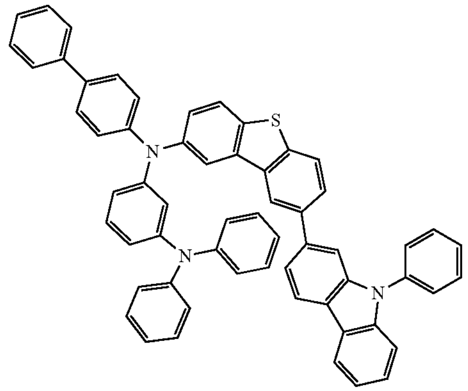
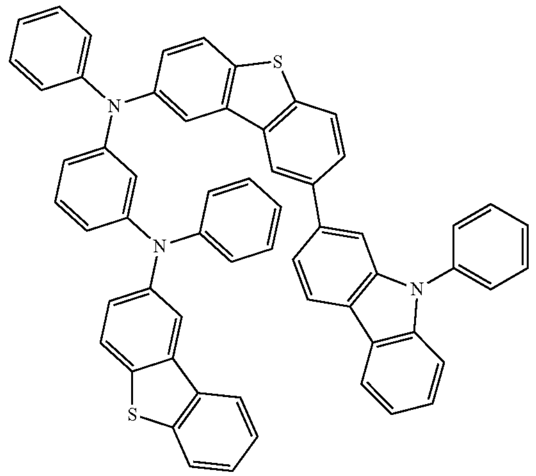
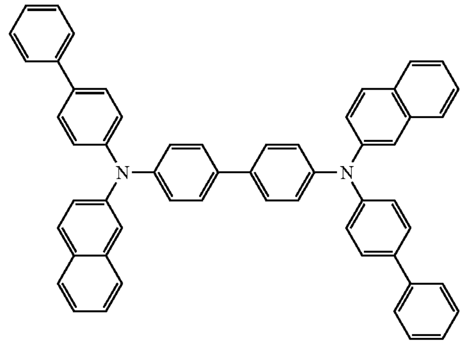

-continued
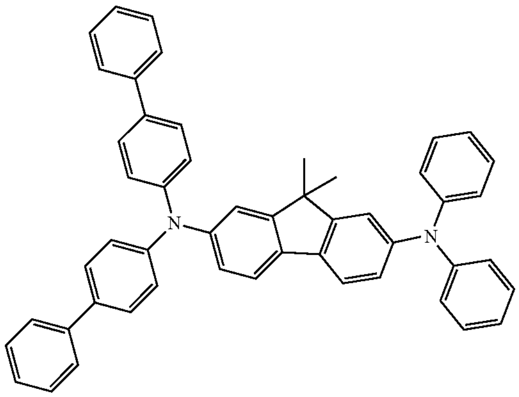
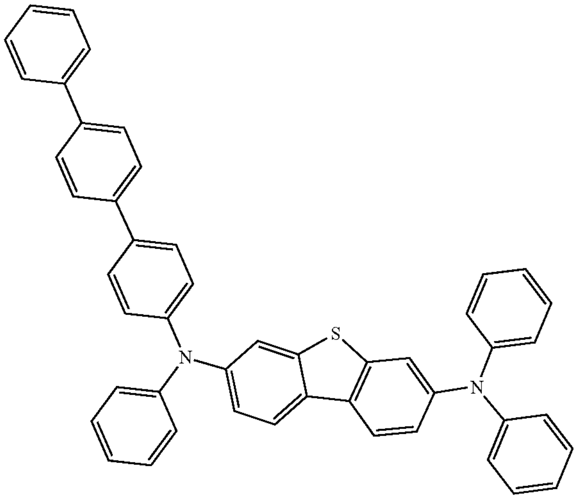
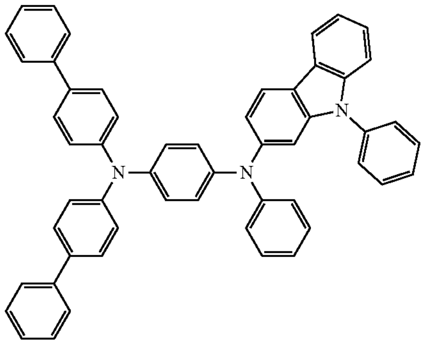
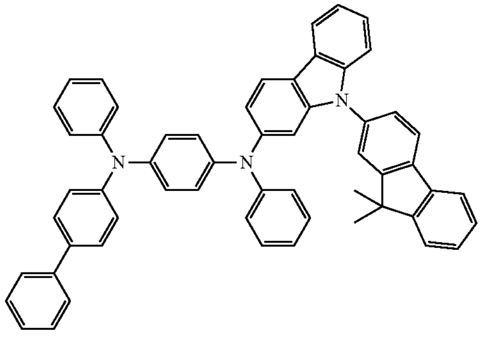
-continued
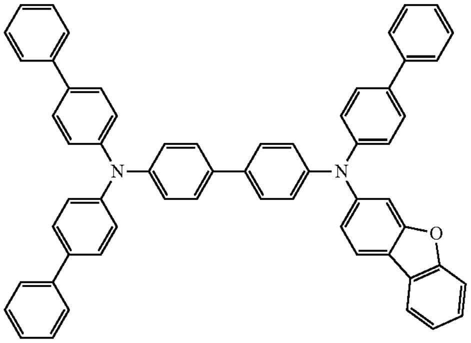
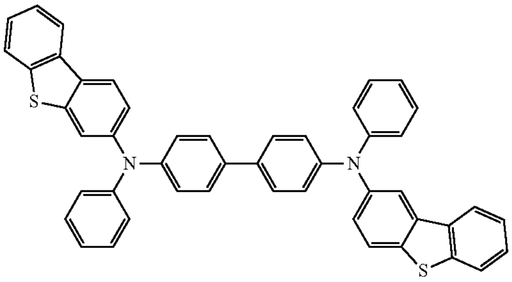
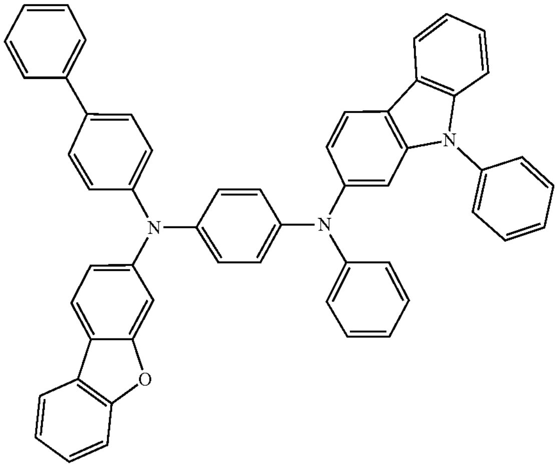
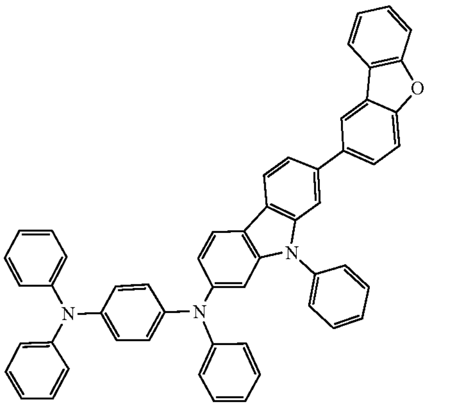

-continued
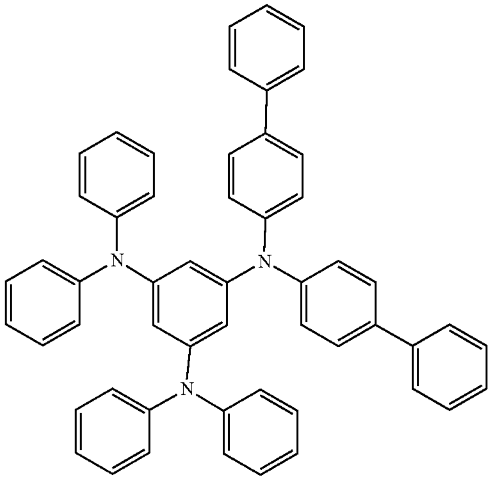
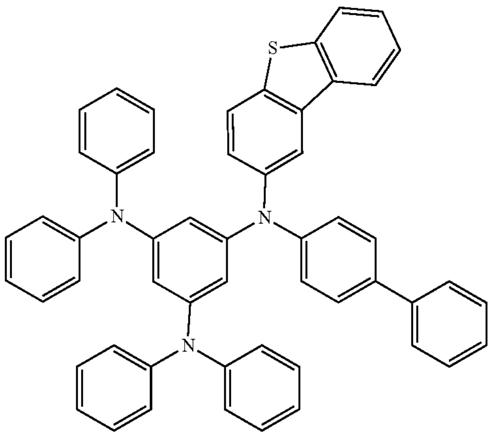
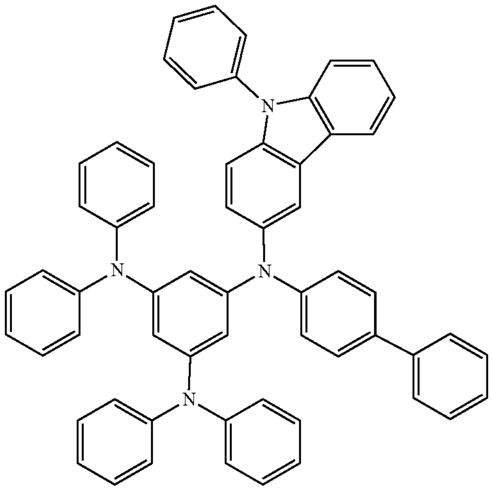
-continued
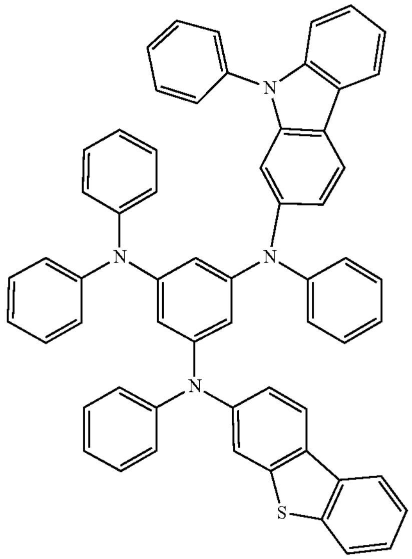
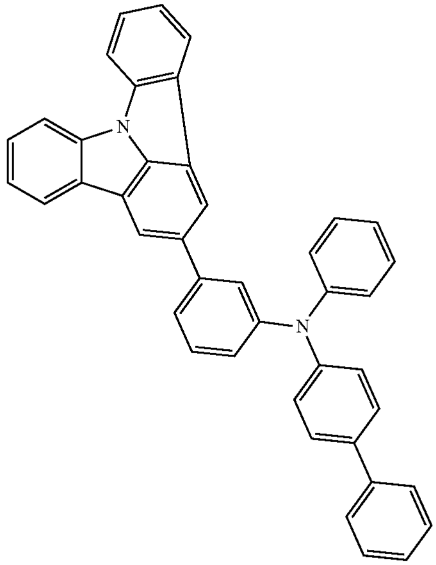
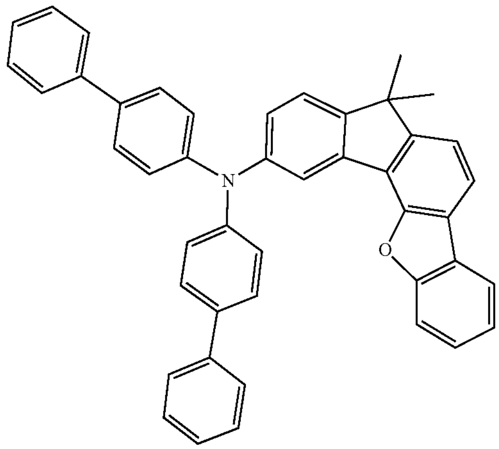

-continued
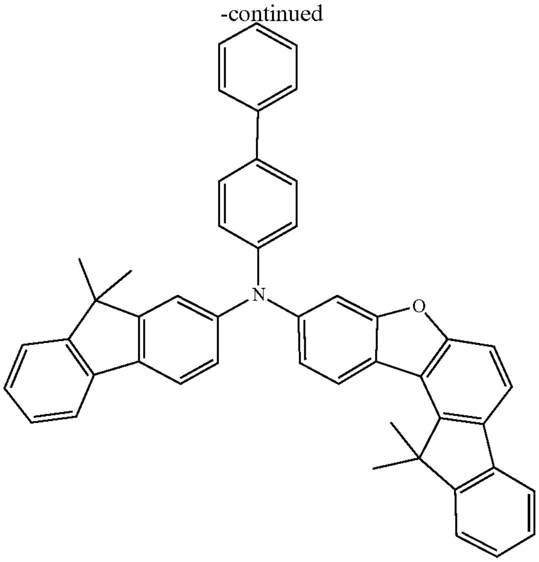
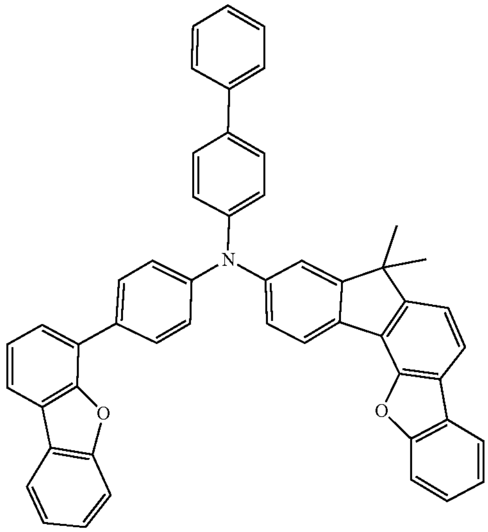
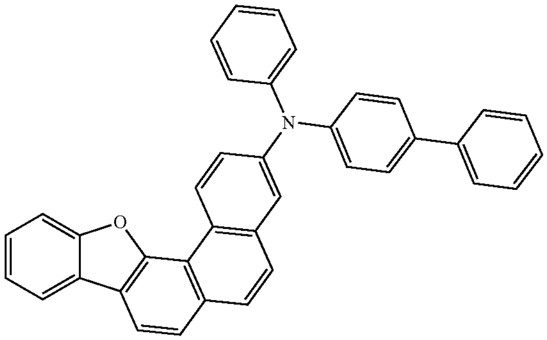
-continued
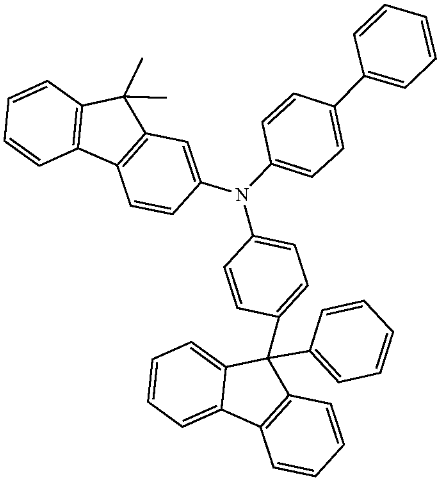
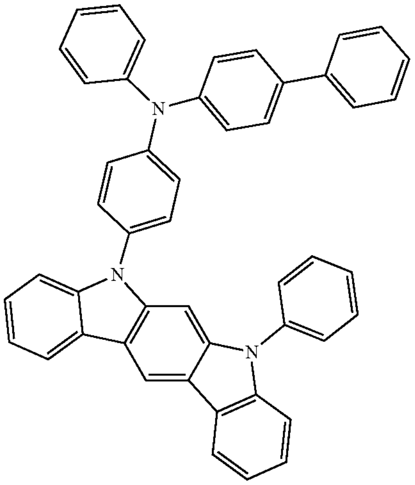
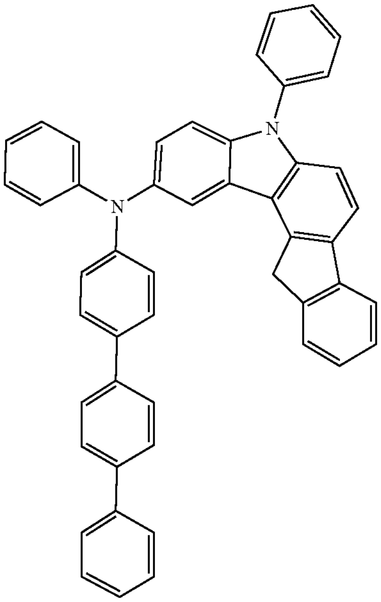

-continued
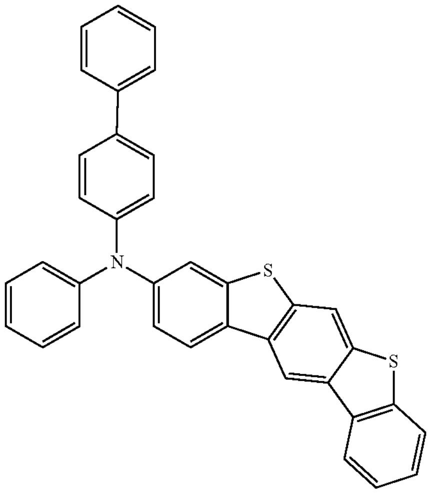
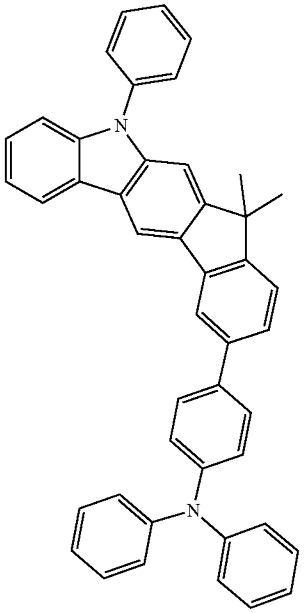
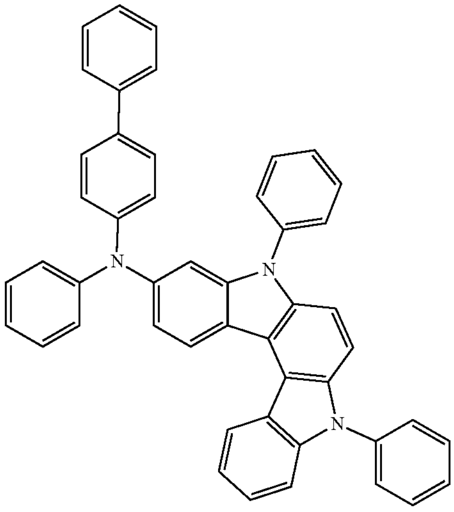
-continued
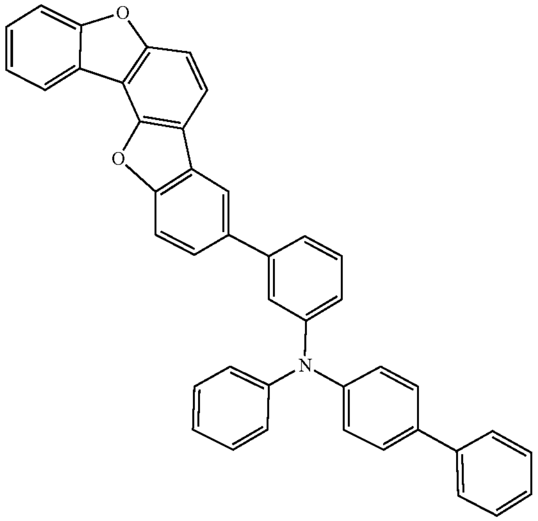
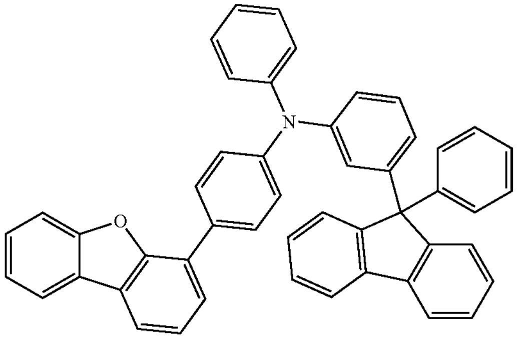
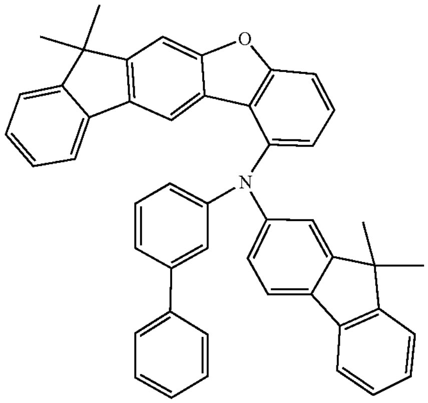
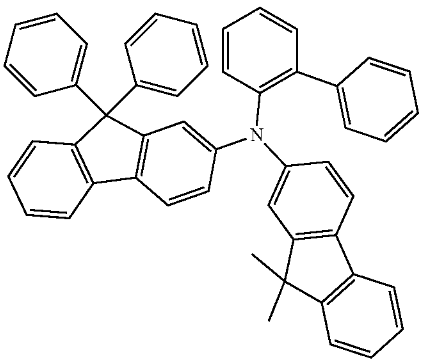

-continued
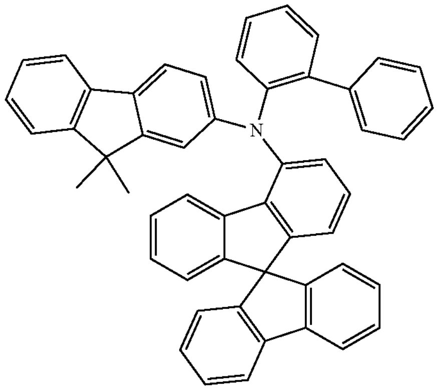
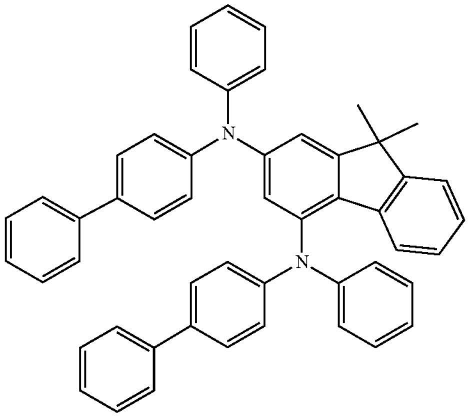
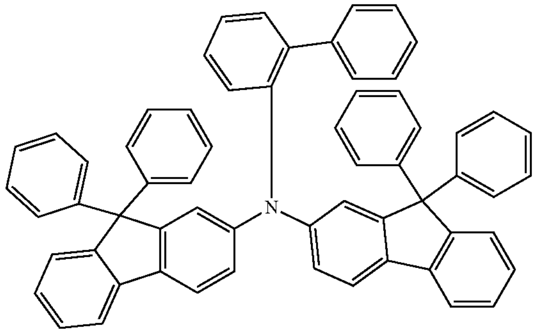
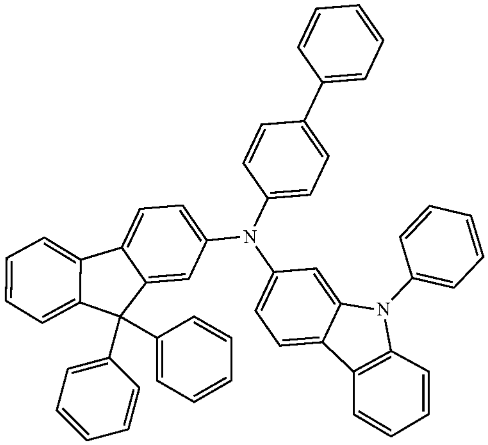
-continued
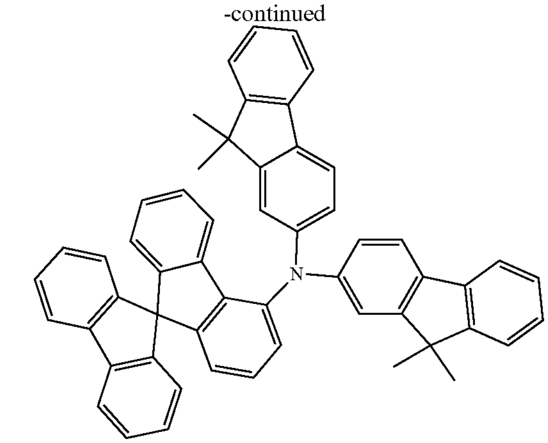
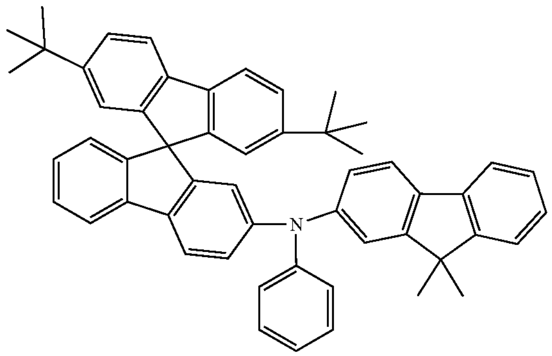
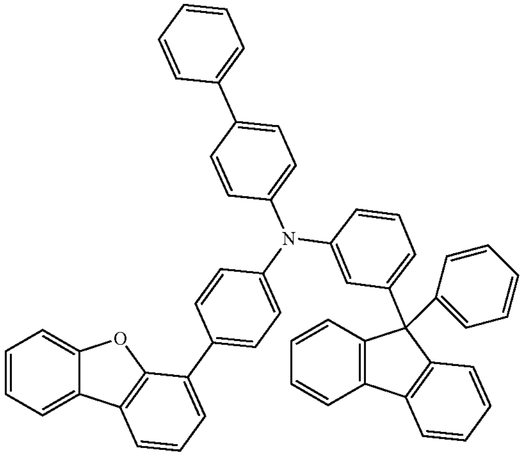
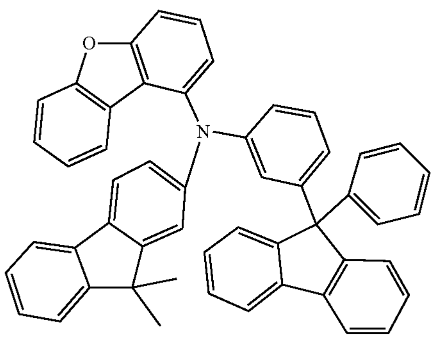

-continued
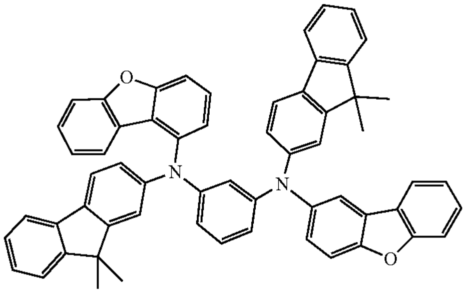
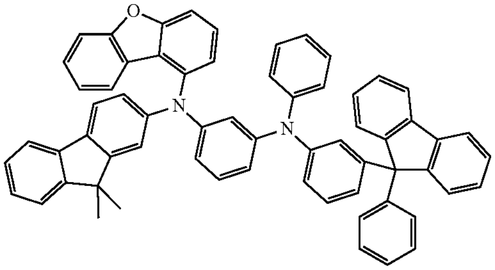
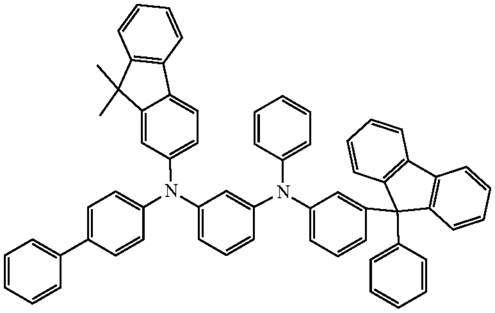
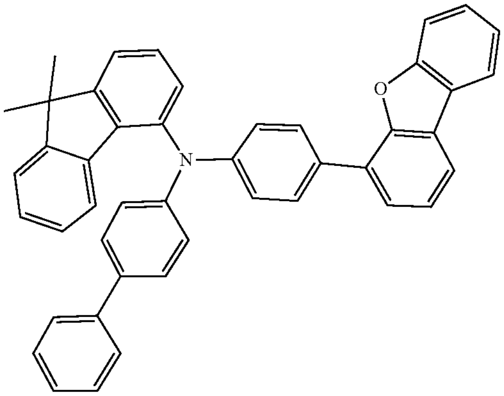
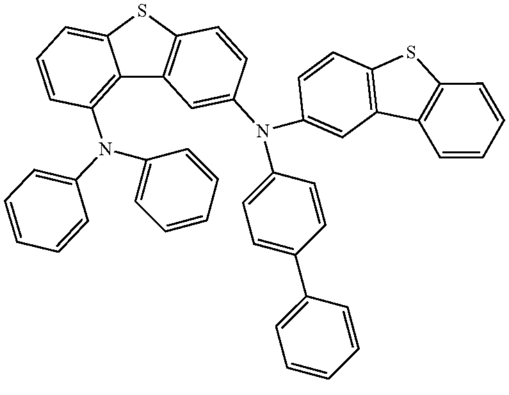
-continued
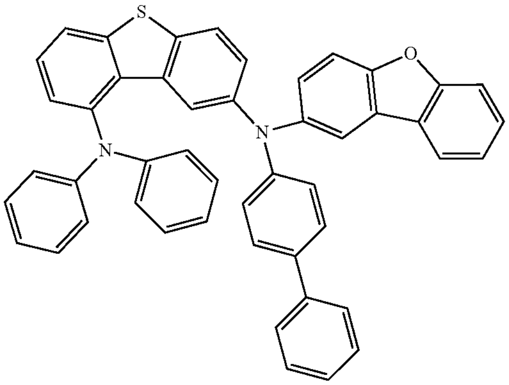
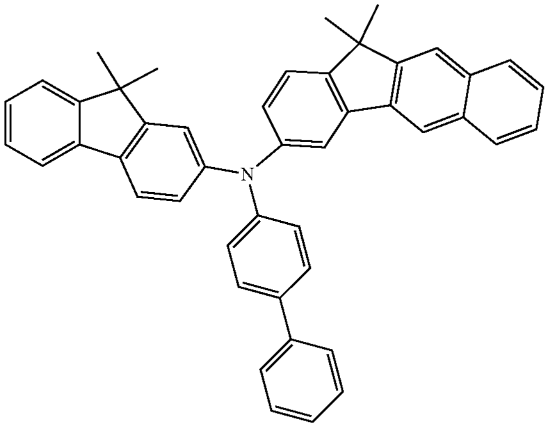
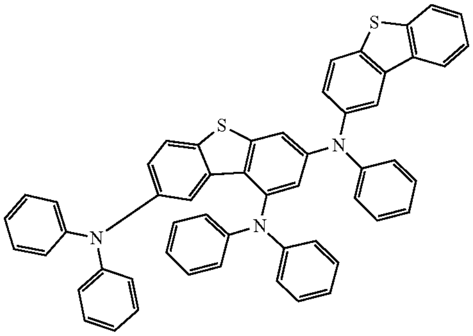
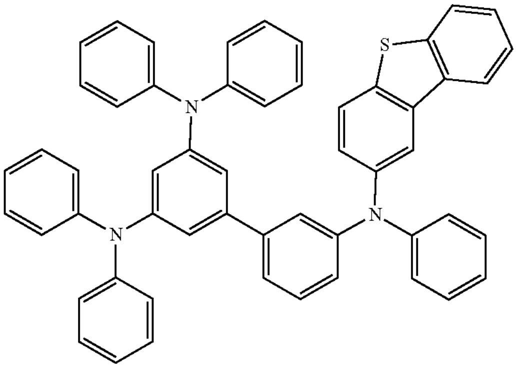

-continued

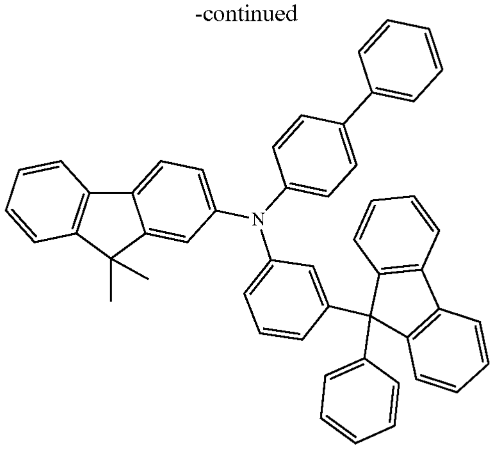

In the hole transport region, in addition to the compounds described above, other suitable compounds may also be used.

In an implementation, the charge transport region may be, e.g., the electron transport region 150.

Figure 3:
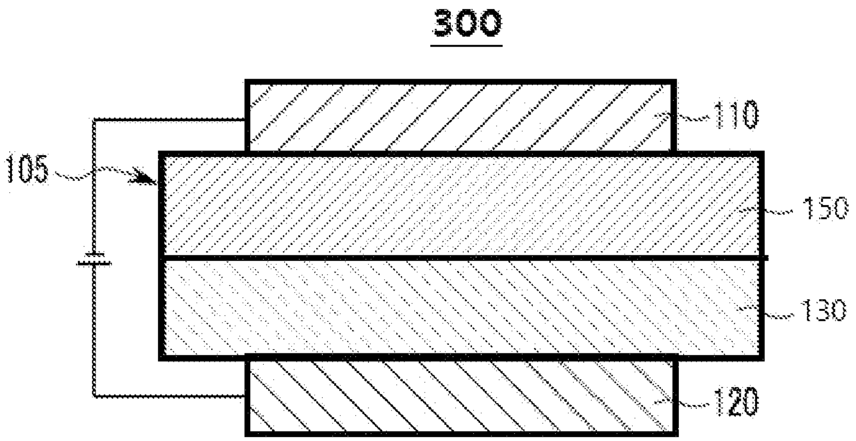

Referring to FIG. 3, the organic light emitting diode 300 may further include an electron transport region 150 in addition to the light emitting layer 130. The electron transport region 150 may help further increase electron injection and/or electron mobility and block holes between the cathode 110 and the light emitting layer 130.

In an implementation, the electron transport region 150 may include an electron transport layer between the cathode 110 and the light emitting layer 130, and an electron transport auxiliary layer between the light emitting layer 130 and the electron transport layer. In an implementation, at least one of the compounds of Group F may be included in at least one of the electron transport layer and the electron transport auxiliary layer.

[Group F]

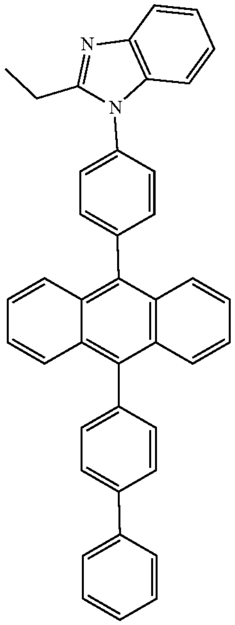

-continued

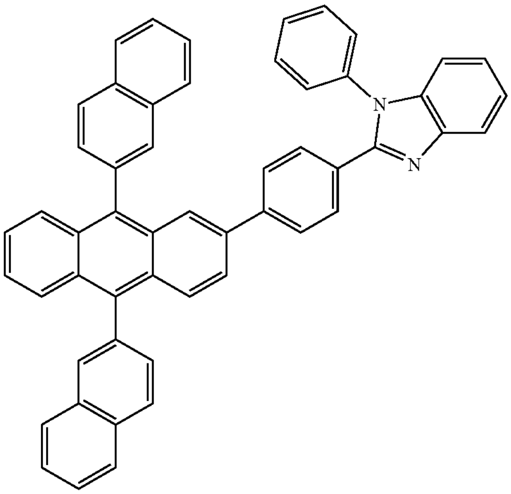

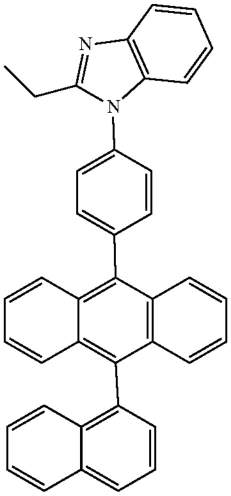

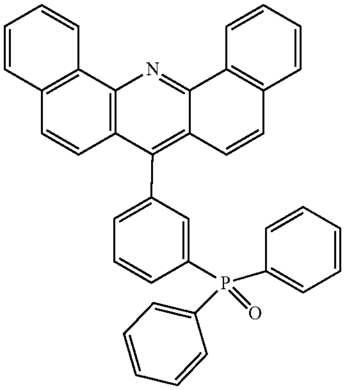

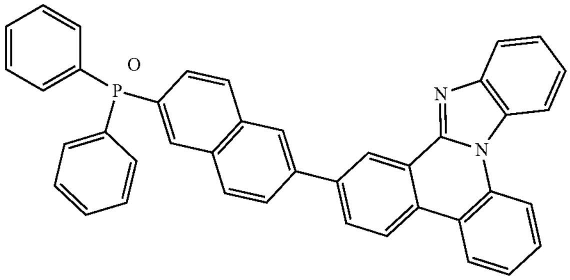

-continued
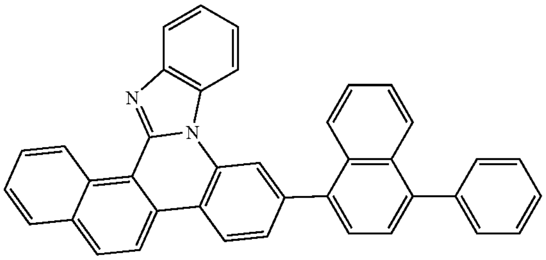
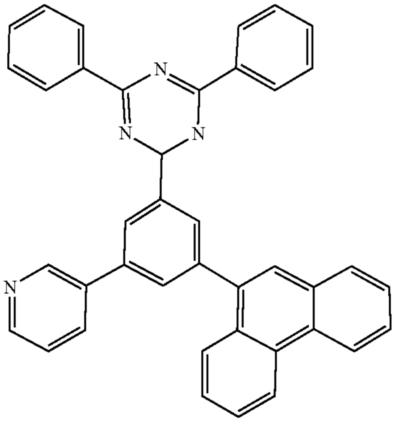
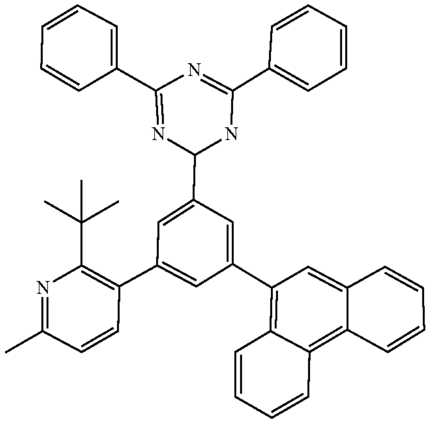
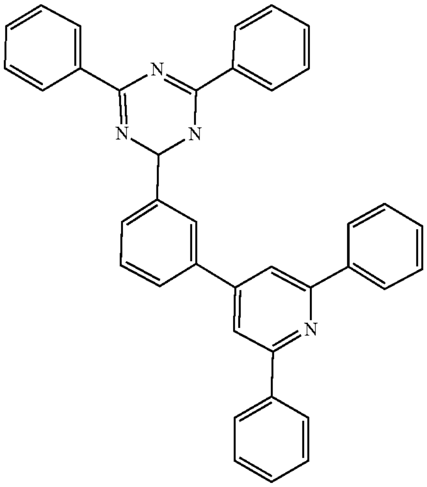
-continued
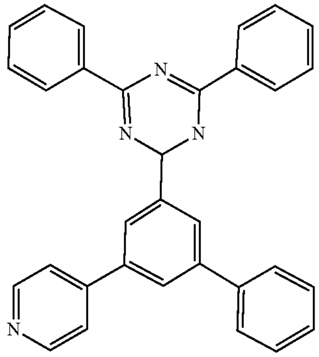
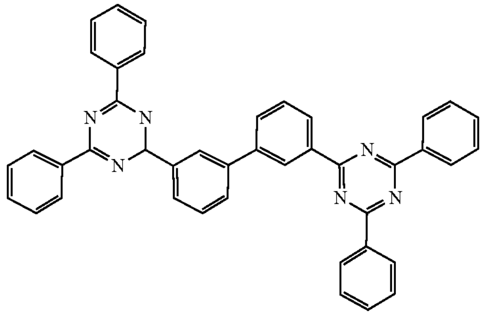
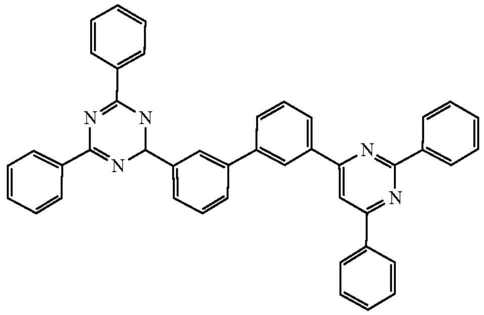
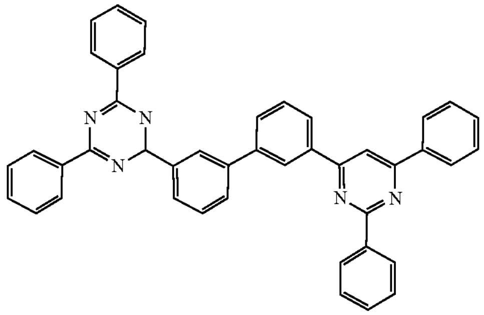
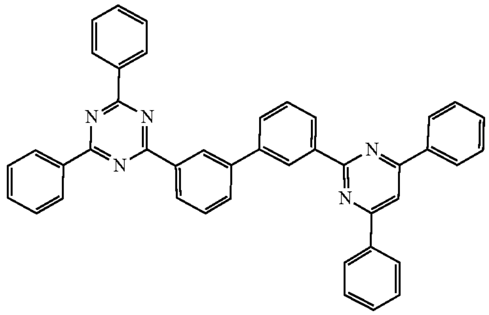

-continued
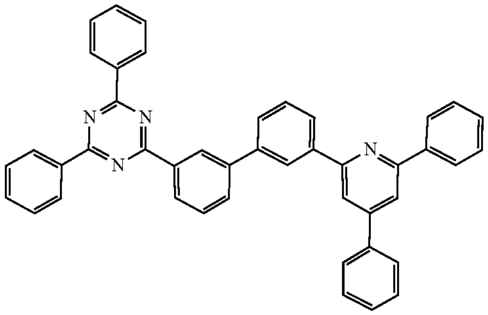
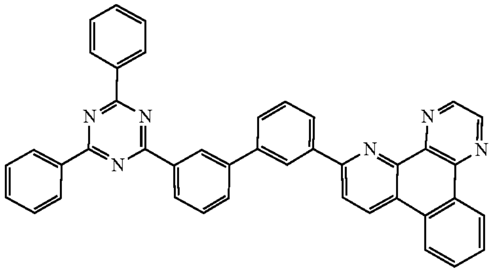
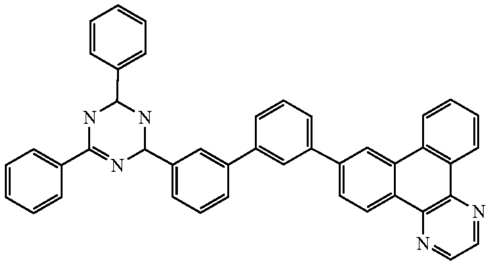
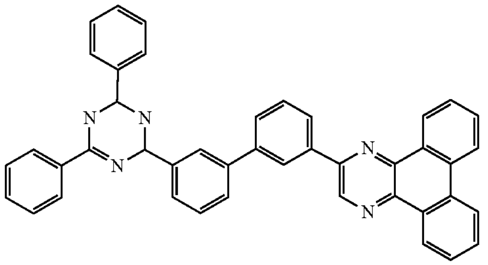
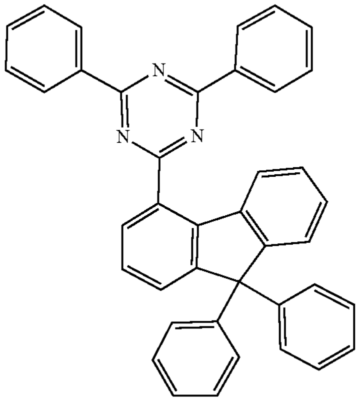
-continued
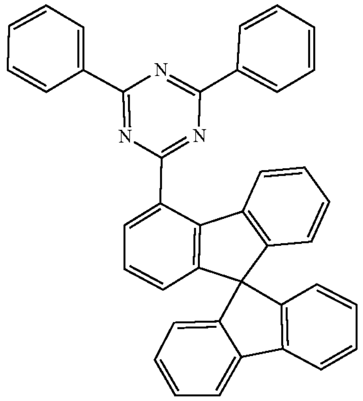
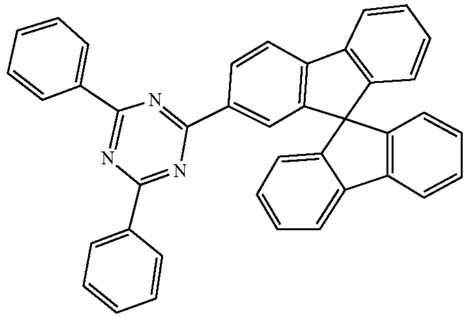
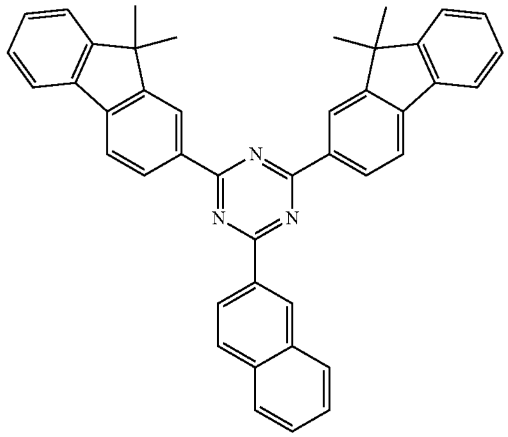
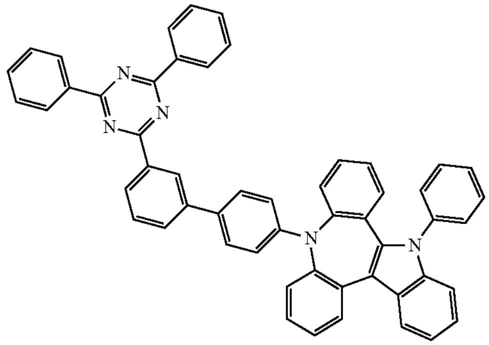

-continued
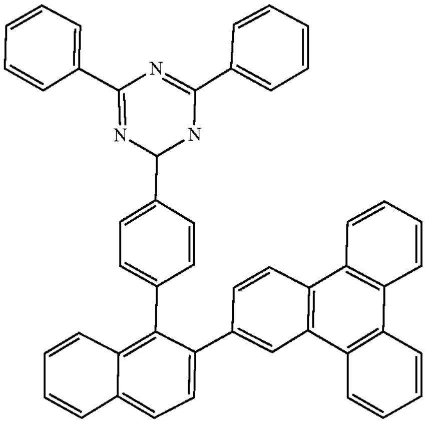
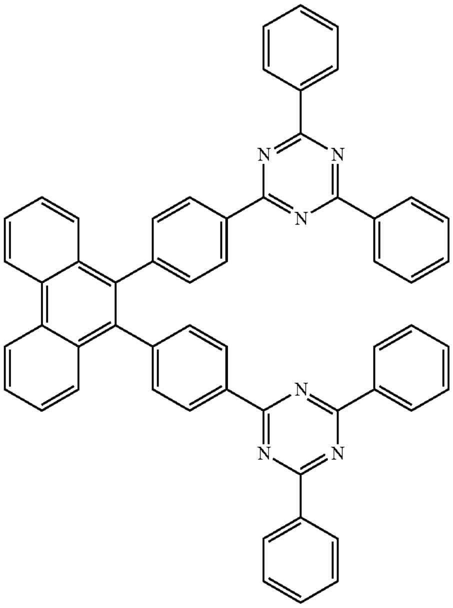
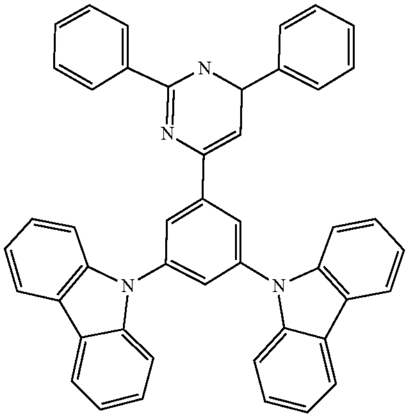
-continued
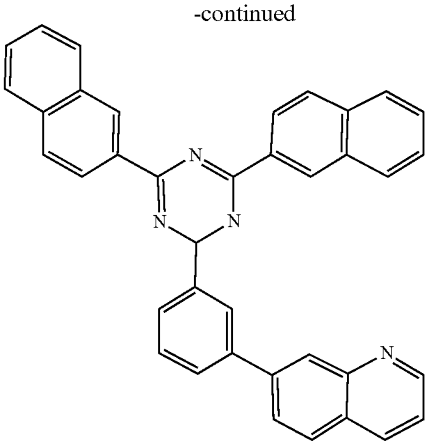
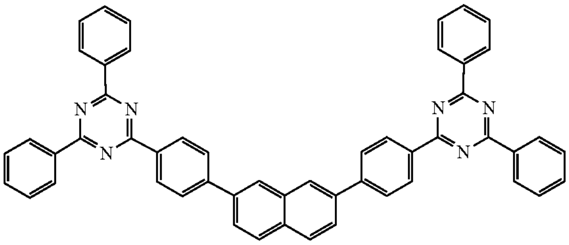
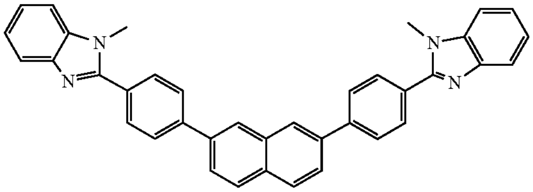
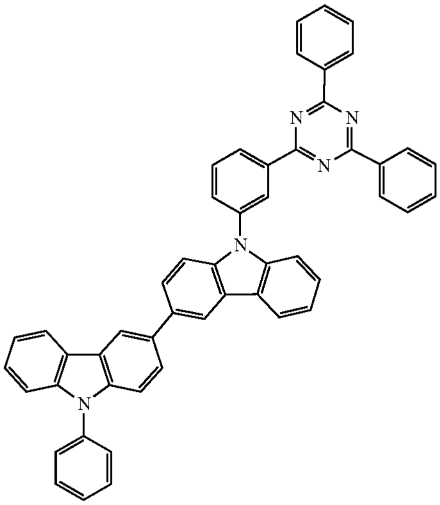
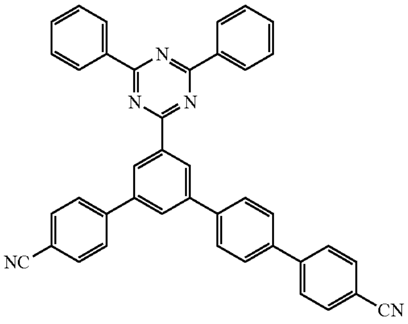

-continued
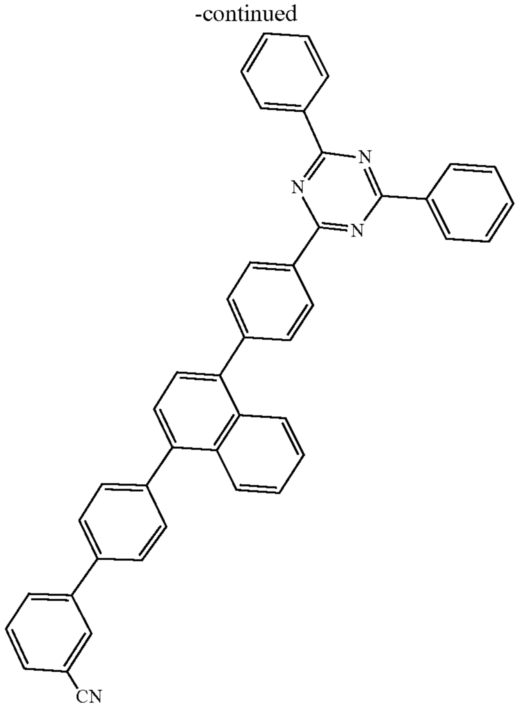
-continued
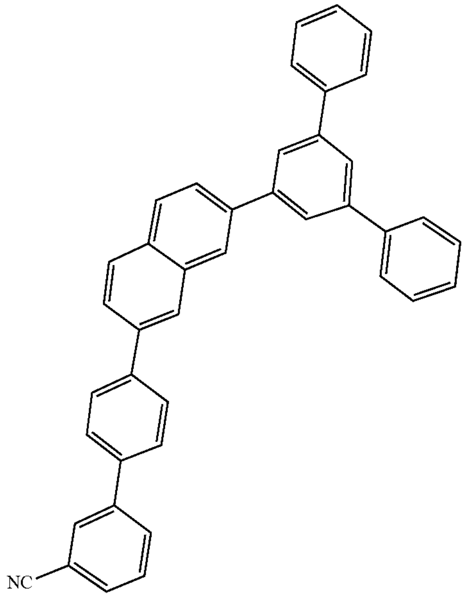
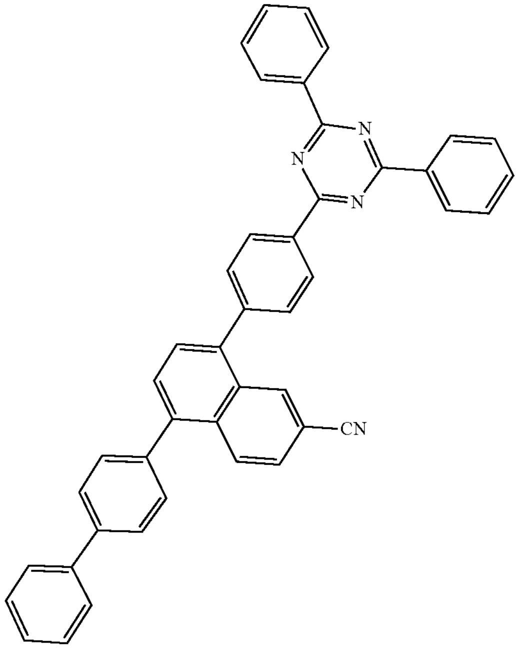
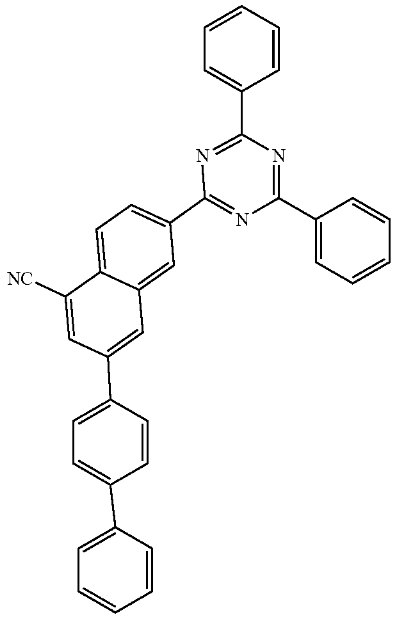

-continued
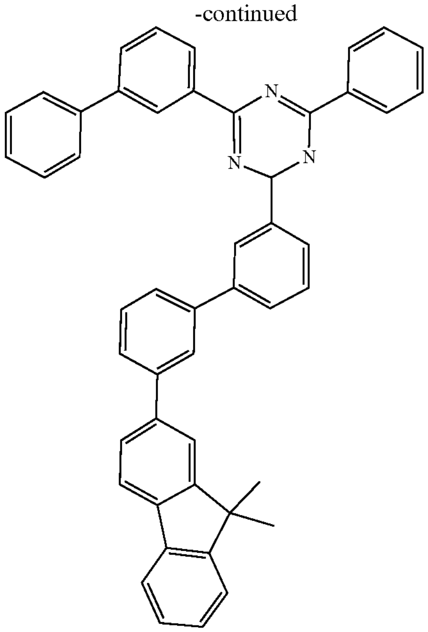
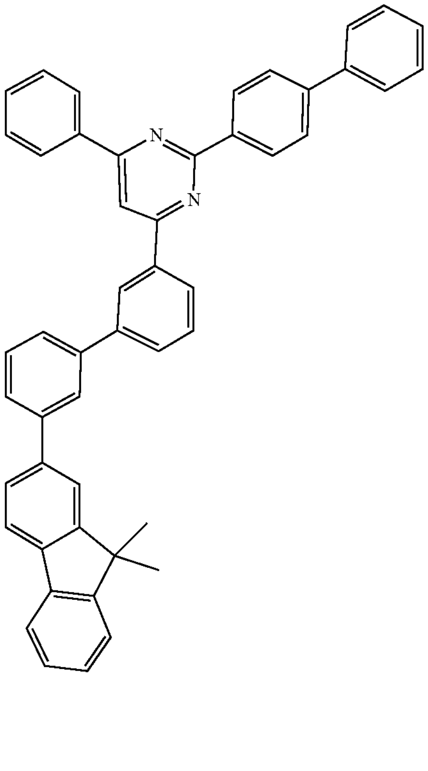
-continued
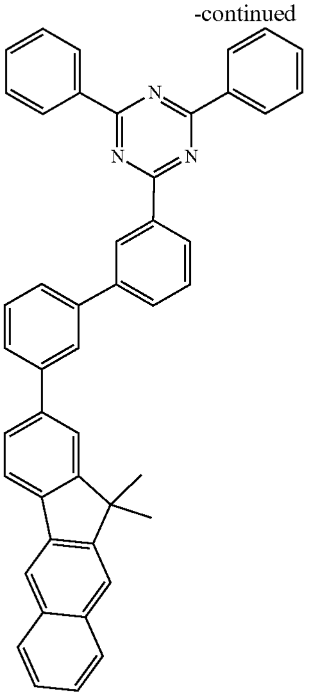
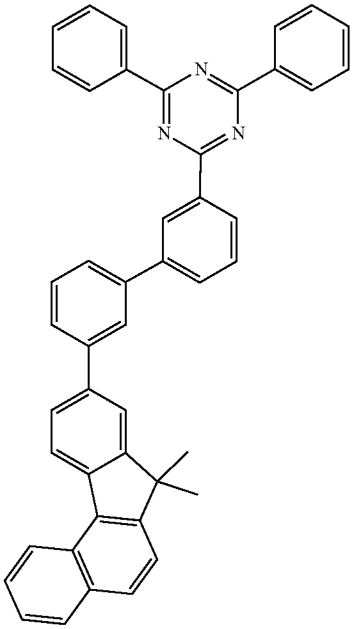

-continued
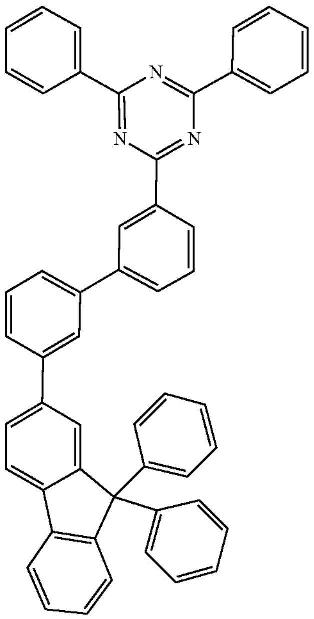
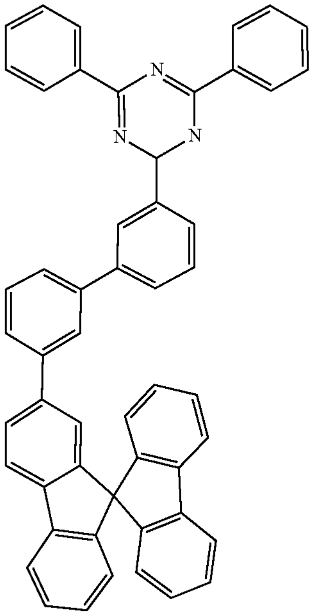
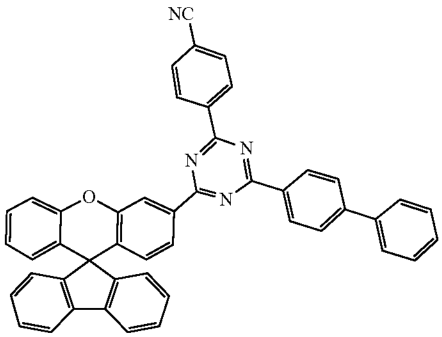
-continued
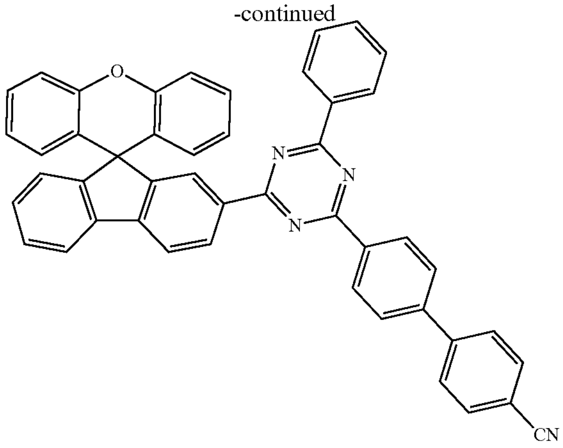
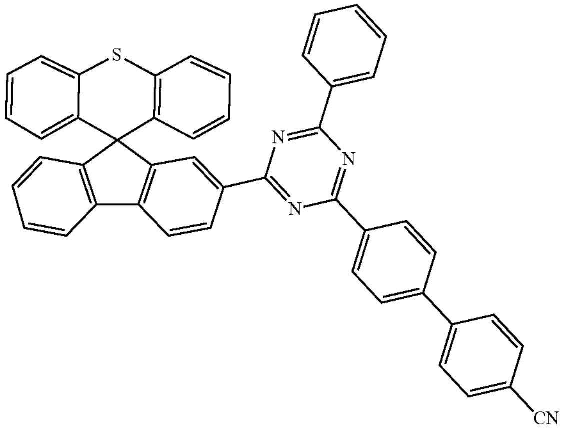
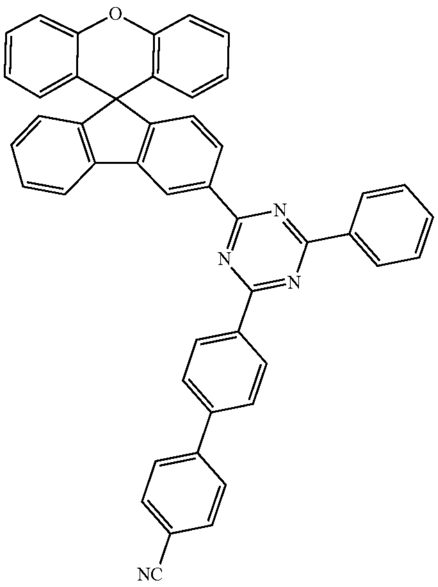

-continued

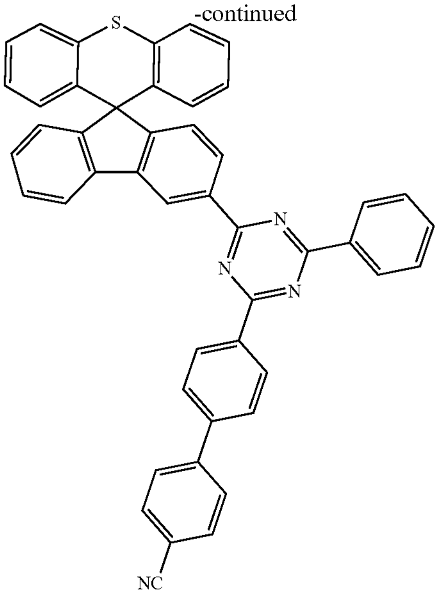

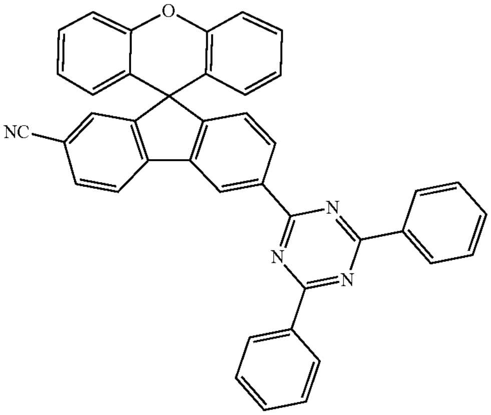

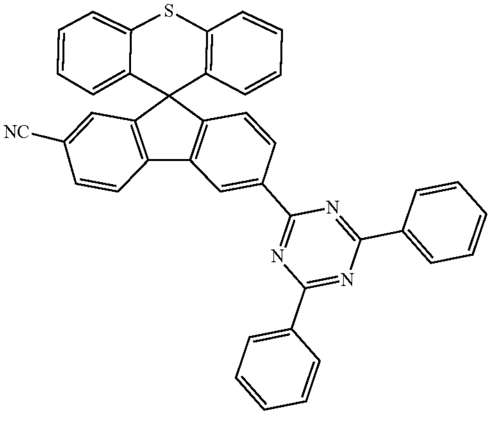

An embodiment may provide an organic light emitting diode including the light emitting layer 130 as the organic layer 105 as shown in FIG. 1.

Another embodiment may provide an organic light emitting diode including a hole transport region 140 in addition to the light emitting layer 130 as the organic layer 105, as shown in FIG. 2.

Another embodiment may provide an organic light emitting diode including an electron transport region 150 in addition to the light emitting layer 130 as the organic layer 105 as shown in FIG. 3.

Figure 4:
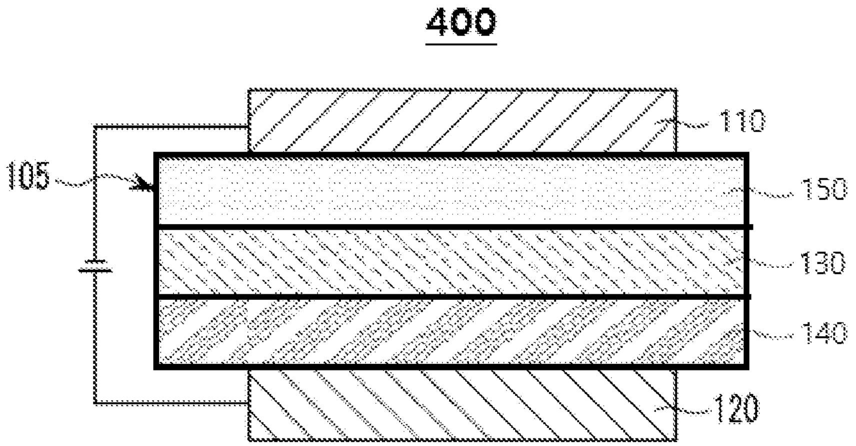

Another embodiment may provide an organic light emitting diode including a hole transport region 140 and an electron transport region 150 in addition to the light emitting layer 130 as the organic layer 105, as shown in FIG. 4.

In another embodiment, an organic light emitting diode may further include an electron injection layer, a hole injection layer, or the like, in addition to the light emitting layer 130 as the organic layer 105 in each of FIGS. 1 to 4.

The organic light emitting diodes 100, 200, 300, and 400 may be manufactured by forming an anode or a cathode on a substrate, and then forming an organic layer by a dry film method such as vacuum deposition, sputtering, plasma plating and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in examples and synthesis examples were purchased from Sigma-Aldrich Co. Ltd., TCI Inc., Tokyo Chemical Industry Co., Ltd., or P&H Tech Co., Ltd., as far as there is no particular comment or were synthesized by suitable methods.

(Preparation of Compound for Organic Optoelectronic Device)

Synthesis Example 1: Synthesis of Intermediate I-1

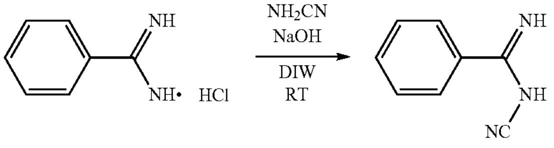

I-1

Under a nitrogen atmosphere, cyanamide (50 g, 1,189 mmol) was dissolved in 0.2 L of deionized water, and sodium hydroxide (90.6 g, 2,264 mmol) and benzamidine hydrochloride (117 g, 1,132 mmol) were sequentially slowly added thereto and then, stirred at room temperature for 12 hours. When a reaction was completed, a solid produced therein was filtered and dried at room temperature to obtain Intermediate I-1 (148 g, 90%).

HRMS (70 eV, EI+): m/z calcd for C8H7N3: 145.0640, found: 145.

Elemental Analysis: C, 66%; H, 5%

Synthesis Example 2: Synthesis of Intermediate I-2

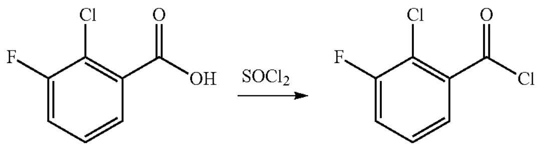

I-2

Under a nitrogen atmosphere, 2-chloro-3-fluorobenzoic acid (50 g, 286 mmol) purchased from Tokyo Chemical Industry Co., Ltd. (http://www.tcichemicals.com/) was dissolved in 0.5 L of thionyl chloride and then, heated under reflux at 80° C. for 1 hour. When a reaction was completed, 0.1 L of toluene was added thereto, and the solvent was all removed by using a rotary decompression concentrator. The residue was vacuum-dried at room temperature to obtain Intermediate I-2 (54.3 g, 99%).

HRMS (70 eV, EI+): m/z calcd for C7H3Cl2FO: 191.9545, found: 191.

Elemental Analysis: C, 44%; H, 2%

Synthesis Example 3: Synthesis of Intermediate I-3

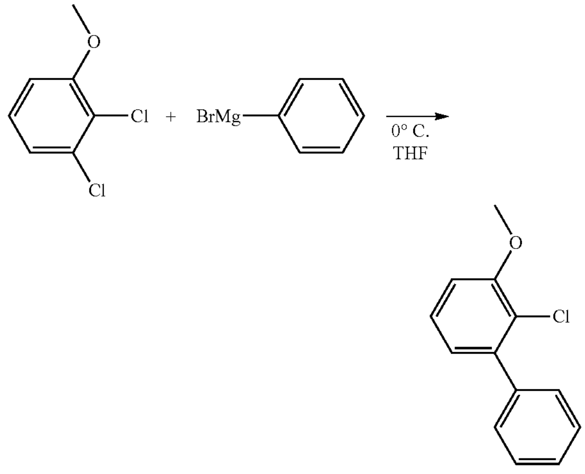

I-3

Under a nitrogen atmosphere, 2,3-dichloroanisole (200 g, 1,130 mmol) purchased from Tokyo Chemical Industry Co., Ltd. was dissolved in 1 L of tetrahydrofuran, and then, 0.31 L of a phenyl magnesium bromide solution (3.0 M in diethyl ether) purchased from Sigma Aldrich Co., Ltd. (http://www.sigmaaldrich.com/) was slowly added thereto in a dropwise fashion at 0° C. When a reaction was completed, ammonium chloride (75.6 g, 1,413 mmol) saturated in water was added to the reaction solution and then, extracted with dichloromethane (DCM), treated with anhydrous magnesium sulfate to remove moisture, filtered, and then, concentrated under a reduced pressure. The obtained residue was purified through flash column chromatography, obtaining Intermediate I-3 (471 g, 50%).

HRMS (70 eV, EI+): m/z calcd for C13H11ClO: 218.0498, found: 218.

Elemental Analysis: C, 71%; H, 5%

Synthesis Example 4: Synthesis of Intermediate I-4

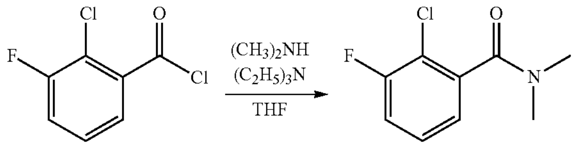

I-2 I-4

Under a nitrogen atmosphere, 0.15 L of a dimethylamine solution (2.0 M in THF) and triethylamine (60.5 g, 598 mmol) were dissolved in 0.5 L of tetrahydofuran (THF), and Intermediate I-2 (57.8 g, 299 mmol) dissolved in 0.5 L of THF was slowly added thereto in a dropwise fashion at 0° C. After stirring the mixture for 1 hour, water was added to the reaction solution and then, extracted with dichloromethane (DCM), treated with anhydrous magnesium sulfate to remove moisture, filtered, and concentrated under a reduced pressure. The obtained residue was separated and purified through flash column chromatography, obtaining Intermediate I-4 (57.7 g, 96%).

HRMS (70 eV, EI+): m/z calcd for C9H9ClFNO: 201.0357, found: 201.

Elemental Analysis: C, 54%; H, 5%

Synthesis Example 5: Synthesis of Intermediate I-5

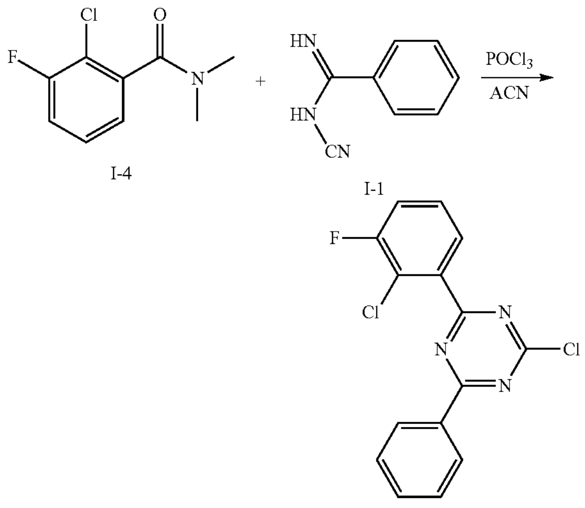

I-4 I-1

I-5

Under a nitrogen atmosphere, Intermediate I-4 (57.7 g, 286 mmol) was dissolved in 1 L of acetonitrile (ACN), and Intermediate I-1 (41.5 g, 286 mmol) and phosphorus oxychloride (48.2 g, 315 mmol) were added thereto and then, heated under reflux at 90° C. for 2 days. When a reaction was completed, a solid produced therein was filtered, washed with distilled water and ethanol, and dried, obtaining Intermediate I-5 (46.7 g, 51%).

HRMS (70 eV, EI+): m/z calcd for C15H8Cl2FN3: 319.0079, found: 319.

Elemental Analysis: C, 56%; H, 3%

Synthesis Example 6: Synthesis of Intermediate I-6

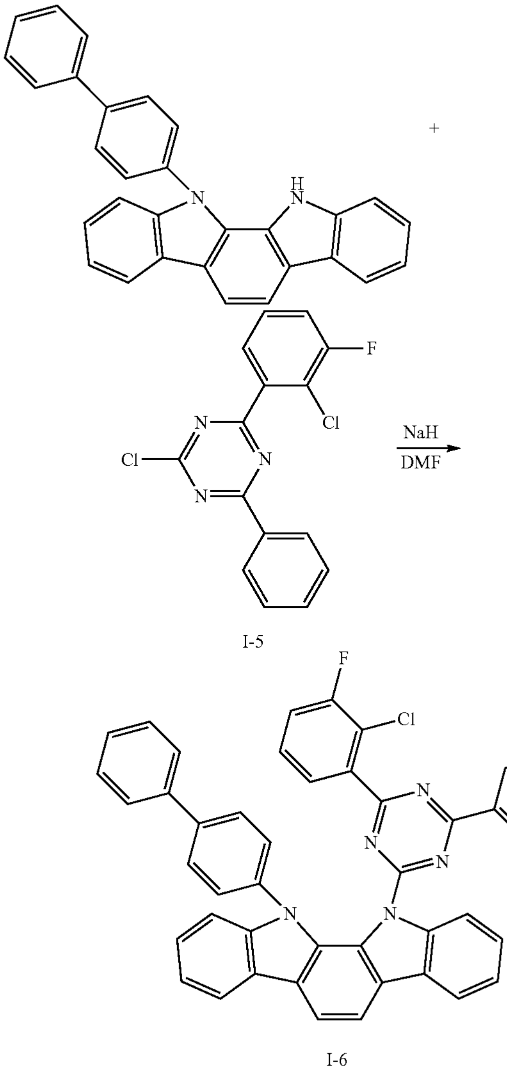

I-5

I-6

Under a nitrogen atmosphere, 11-(biphenyl-4-yl)-11,12-dihydroindolo[2,3-a]carbazole (100 g, 245 mmol) purchased from Ukseung Chemical Co., Ltd. (http://www.ukseung-.co.kr/) was dissolved in 1 L of dimethylformamide (DMF), and sodium hydride (7.05 g, 294 mmol) was added thereto at 0° C. and then, stirred. After 1 hour, Intermediate I-5 (94.1 g, 294 mmol) was added thereto and then, stirred for 1 hour. When a reaction was completed, water was added to the reaction solution at 0° C. and then, extracted with dichloromethane (DCM), treated with anhydrous magnesium sulfate to remove moisture, filtered, and concentrated under a reduced pressure. The obtained residue was separated and purified through flash column chromatography, obtaining Intermediate I-6 (142 g, 84%).

HRMS (70 eV, EI+): m/z calcd for C45H27ClFN5: 691.1939, found: 691.

Elemental Analysis: C, 84%; H, 4%

Synthesis Example 7: Synthesis of Intermediate I-7

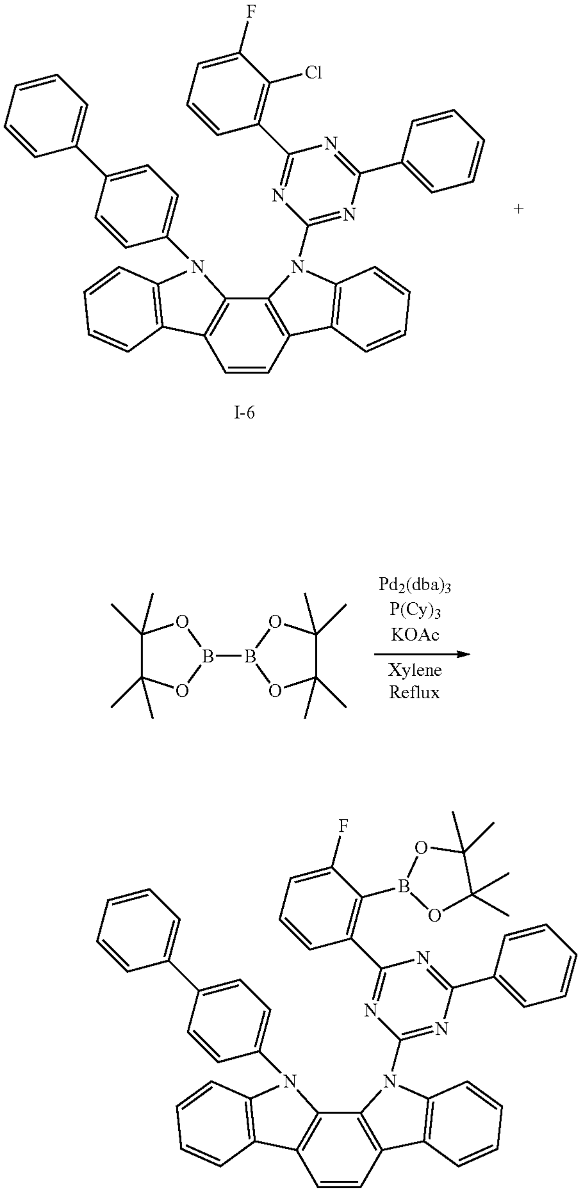

I-6

I-7

Under a nitrogen atmosphere, Intermediate I-6 (140 g, 202 mmol) was dissolved in 1 L of xylene, and then, bis(pinacolato)diboron (61.6 g, 243 mmol), tris(dibenzylideneacetone)dipalladium(0) (1.85 g, 2.02 mmol), tricyclohexylphosphine (2.27 g, 8.08 mmol), and potassium acetate (59.5 g, 606 mmol) were added thereto and then, heated under reflux for 13 hours. When a reaction was completed, water was added to the reaction solution and then, extracted with dichloromethane (DCM), treated with anhydrous magnesium sulfate to remove moisture, filtered, and concentrated under a reduced pressure. The obtained residue was separated and purified through flash column chromatography, obtaining Intermediate I-7 (39.6 g, 25%).

HRMS (70 eV, EI+): m/z calcd for C51H39BFN5O2: 783.3181, found: 783.

Elemental Analysis: C, 78%; H, 5%

Synthesis Example 8: Synthesis of Intermediate I-8

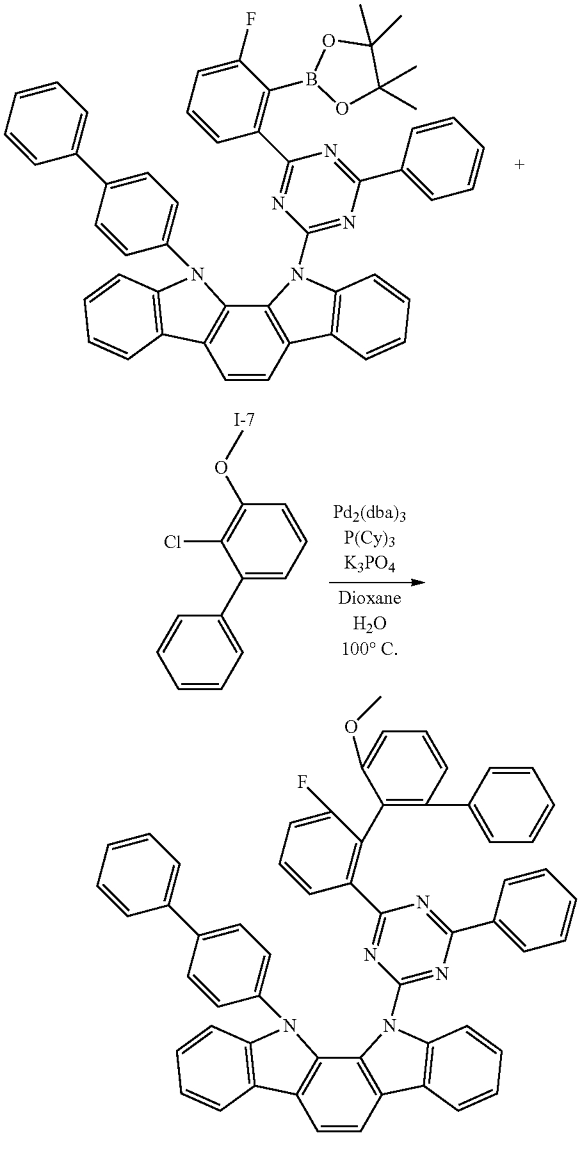

I-7

I-8

Under a nitrogen atmosphere, Intermediate I-7 (38 g, 48.5 mmol) was dissolved in 0.3 L of dioxane, and then, Intermediate I-3 (15.9 g, 72.7 mmol), tris(dibenzylideneacetone) dipalladium(0) (1.33 g, 1.46 mmol), tricyclohexylphosphine (2.04 g, 7.28 mmol), and potassium phosphate tribasic (30.9 g, 146 mmol) were added thereto and then, heated under reflux for 15 hours. When a reaction was completed, water was added to the reaction solution and then, extracted with dichloromethane (DCM), treated with anhydrous magnesium sulfate to remove moisture, filtered, and concentrated under a reduced pressure. The obtained residue was separated and purified through flash column chromatography, obtaining Intermediate I-8 (22.4 g, 55%).

HRMS (70 eV, EI+): m/z calcd for C58H38FN5O: 839.3060, found: 839.

Elemental Analysis: C, 83%; H, 5%

Synthesis Example 9: Synthesis of Intermediate I-9

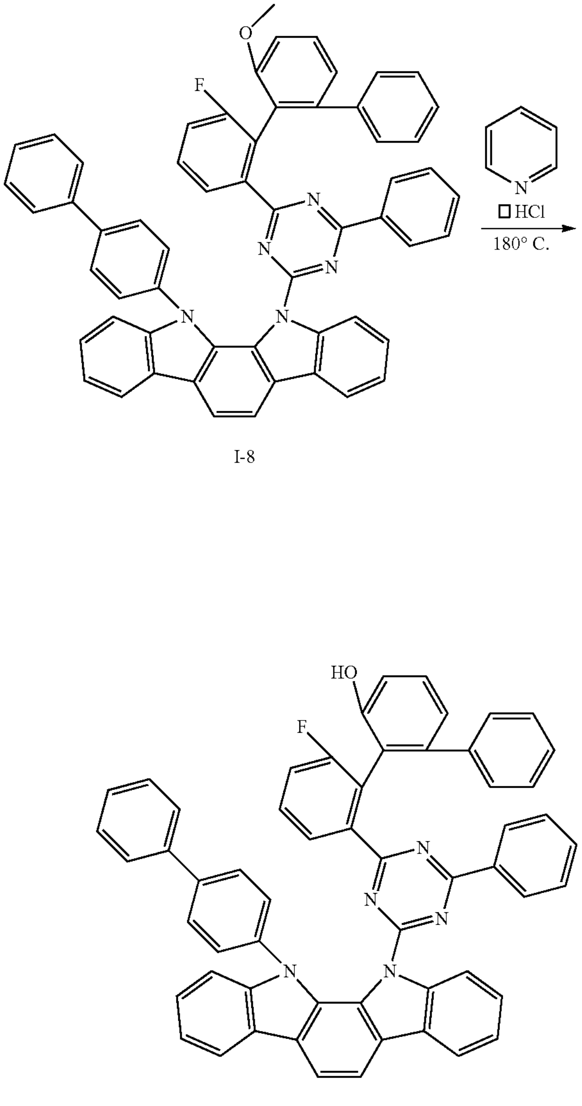

I-8

I-9

Under a nitrogen atmosphere, Intermediate I-8 (22 g, 26.2 mmol) and pyridine hydrochloride (15.1 g, 131 mmol) were heated under reflux at 180° C. for 12 hours. When a reaction was completed, water was added to the reaction solution and then, extracted with ethyl acetate (EA), treated with anhydrous magnesium sulfate to remove moisture, filtered, and concentrated under a reduced pressure. The obtained residue was separated and purified through flash column chromatography, obtaining Intermediate I-9 (17.3 g, 80%).

HRMS (70 eV, EI+): m/z calcd for C57H36FN5O: 825.2904, found: 825.

Elemental Analysis: C, 83%; H, 4%

Synthesis Example 10: Synthesis of Compound 1

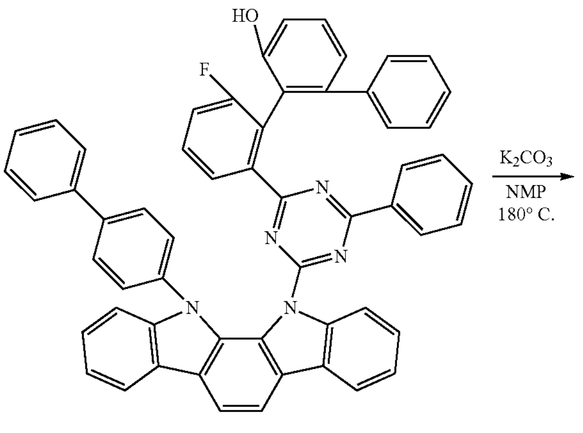

I-9

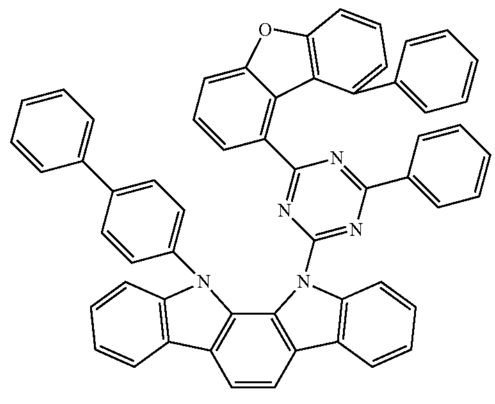

1

Under a nitrogen atmosphere, Intermediate I-9 (10 g, 12.1 mmol) was dissolved in 0.1 L of N-methyl-2-pyrrolidone (NMP) and then, potassium carbonate (3.35 g, 24.2 mmol) was added thereto and then, heated under reflux for 3 hours. When a reaction was completed, water was added to the reaction solution and then, extracted with dichloromethane (DCM), treated with anhydrous magnesium sulfate to remove moisture, filtered, and concentrated under a reduced pressure. The obtained residue was separated and purified through flash column chromatography, obtaining Compound 1 (7.51 g, 77%).

HRMS (70 eV, EI+): m/z calcd for C57H35N5O: 805.2842, found: 805.

Elemental Analysis: C, 85%; H, 4%

Synthesis Example 11: Synthesis of Intermediate I-10

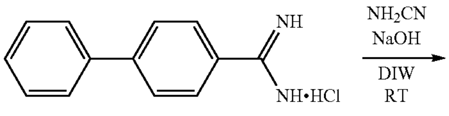

-continued

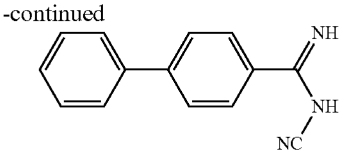

I-10

Intermediate I-10 (111 g, 98%) was obtained according to the same method as in Synthesis Example 1 except that biphenyl-4-carboximidamide hydrochloride (100 g, 512 mmol) was used.

HRMS (70 eV, EI+): m/z calcd for C14H11N3: 221.0953, found: 221.

Elemental Analysis: C, 76%; H, 5%

Synthesis Example 12: Synthesis of Intermediate I-11

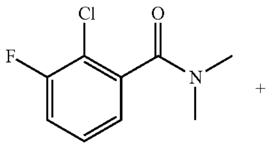

I-4

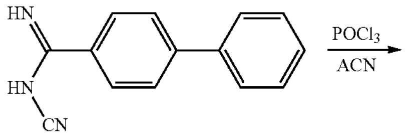

I-10

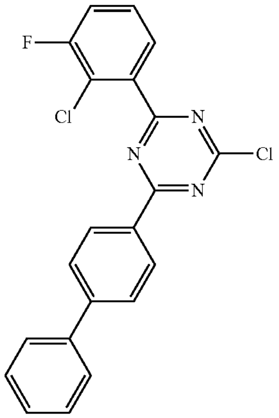

I-11

Intermediate I-11 (93.4 g, 95%) was obtained according to the same method as in Synthesis Example 5 except that Intermediate I-4 (50 g, 248 mmol) and Intermediate I-10 (54.9 g, 248 mmol) were used.

HRMS (70 eV, EI+): m/z calcd for C21H12C12FN3: 395.0392, found: 395.

Elemental Analysis: C, 64%; H, 3%

Synthesis Example 13: Synthesis of Intermediate I-12

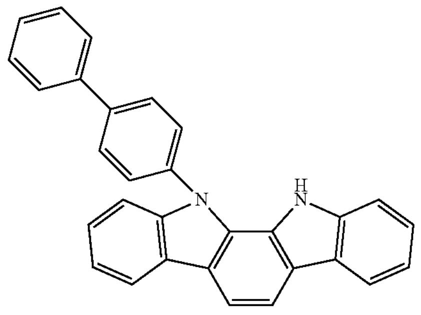

+

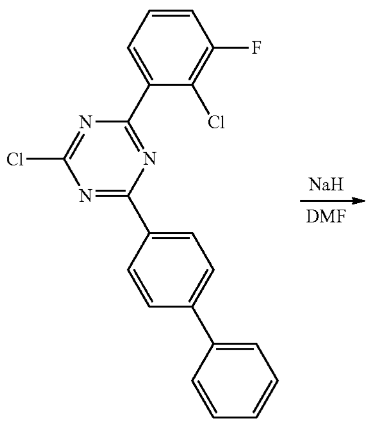

I-11

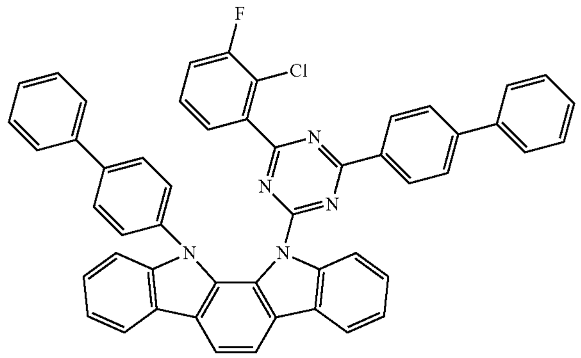

I-12

Intermediate I-12 (173 g, 91%) was obtained according to the same method as in Synthesis Example 6 except that 11-(biphenyl-4-yl)-11,12-dihydroindolo[2,3-a]carbazole (100 g, 248 mmol) purchased from Ukseung Chemical Co., Ltd. and Intermediate I-11 (118 g, 298 mmol) were used.

HRMS (70 eV, EI+): m/z calcd for C51H31ClFN5: 767.2252, found: 767.

Elemental Analysis: C, 80%; H, 4%

Synthesis Example 14: Synthesis of Intermediate I-13

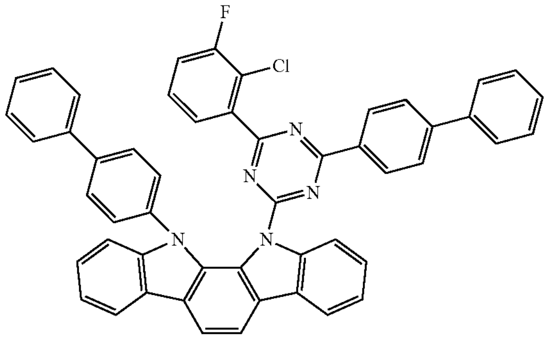

I-12

+

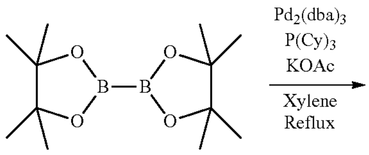

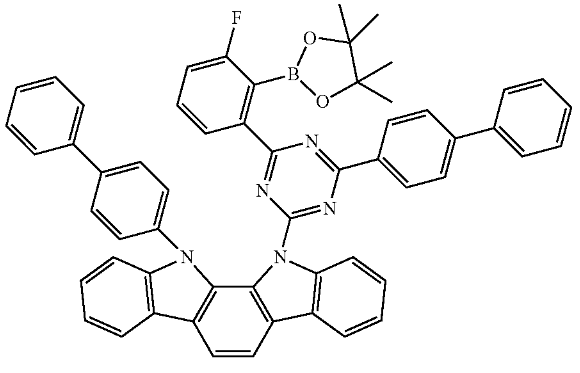

I-13

Intermediate I-13 (36.9 g, 30%) was obtained according to the same method as Synthesis Example 7 except that Intermediate I-12 (110 g, 143 mmol) was used.

HRMS (70 eV, EI+): m/z calcd for C57H43BFN5O2: 859.3494, found: 859.

Elemental Analysis: C, 80%; H, 5%

Synthesis Example 15: Synthesis of Intermediate I-14

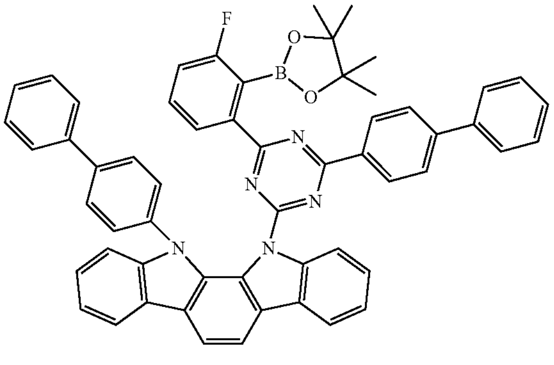

I-13

+

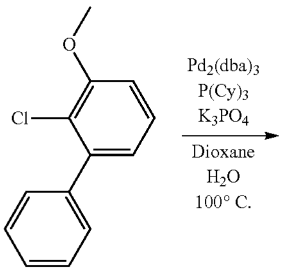

I-3

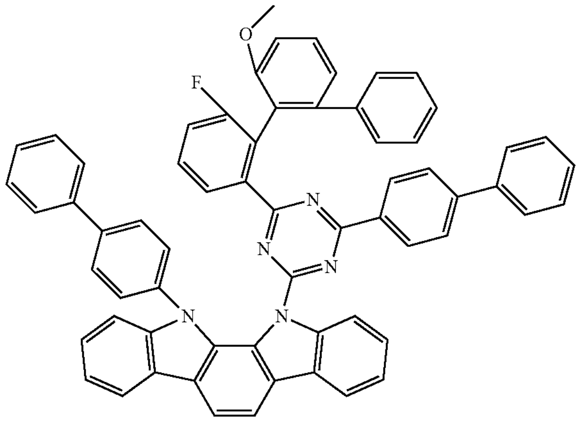

I-14

Intermediate I-14 (17.9 g, 48%) was obtained according to the same method as Synthesis Example 8 except that Intermediate I-13 (35 g, 40.7 mmol) and Intermediate I-3 (13.4 g, 61.1 mmol) were used.

HRMS (70 eV, EI+): m/z calcd for C64H42FN5O: 915.3373, found: 915.

Elemental Analysis: C, 84%; H, 5%

Synthesis Example 16: Synthesis of Intermediate I-15

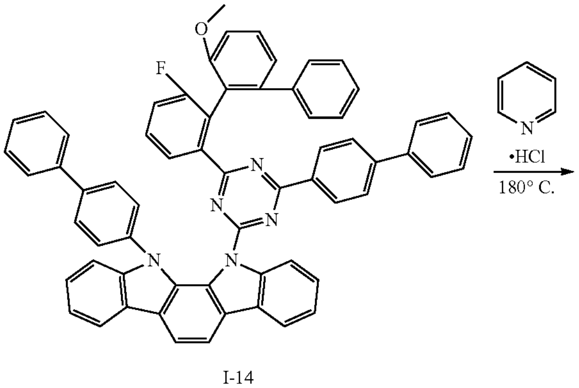

I-14

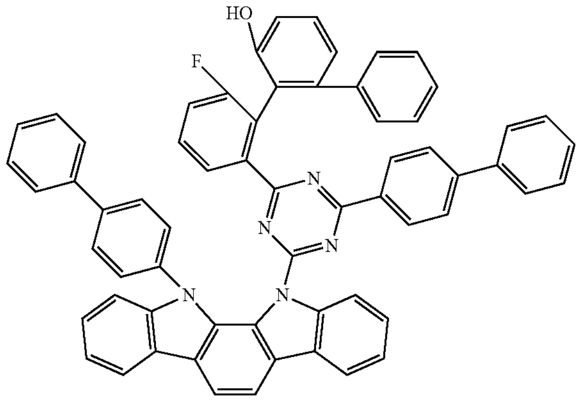

I-15

Intermediate I-15 (13.3 g, 90%) was obtained according to the same method as Synthesis Example 9 except that Intermediate I-14 (15 g, 16.4 mmol) was used.

HRMS (70 eV, EI+): m/z calcd for C63H40FN5O: 901.3217, found: 901.

Elemental Analysis: C, 84%; H, 4%

Synthesis Example 17: Synthesis of Compound 5

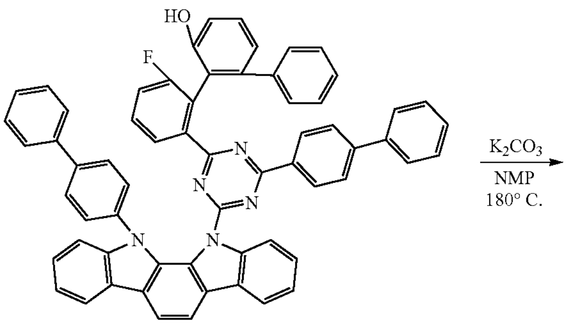

I-15

-continued

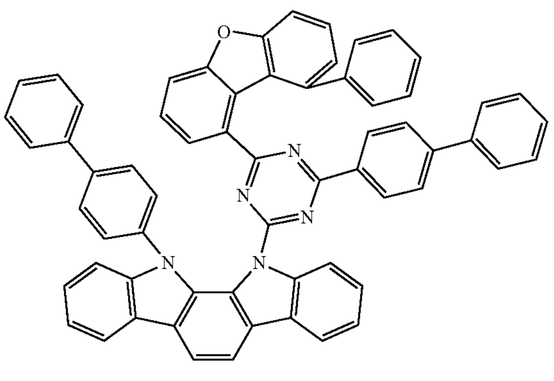

5

Compound 5 (7.34 g, 75%) was obtained according to the same method as Synthesis Example 10 except that Intermediate I-15 (10 g, 11.1 mmol) was used.

HRMS (70 eV, EI+): m/z calcd for C63H39N5O: 881.3155, found: 881.

Elemental Analysis: C, 86%; H, 4%

Synthesis Example 18: Synthesis of Intermediate I-16

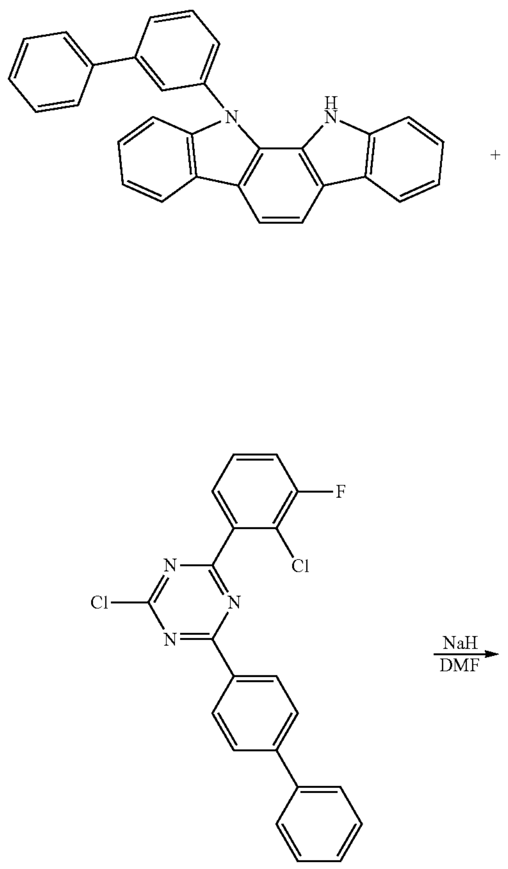

I-11

-continued

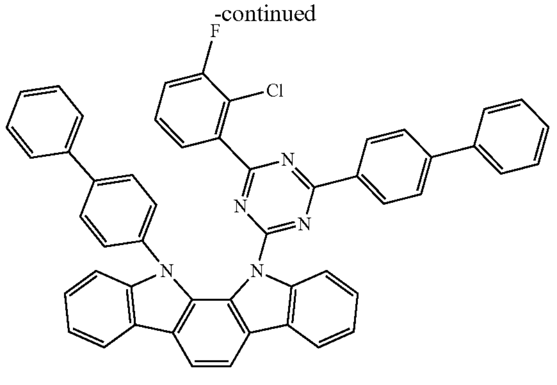

I-16

Intermediate I-16 (171 g, 90%) was obtained according to the same method as Synthesis Example 6 except that 11-(biphenyl-3-yl)-11,12-dihydroindolo[2,3-a]carbazole (100 g, 248 mmol) purchased from Ukseung Chemical Co., Ltd. and Intermediate I-11 (118 g, 298 mmol) were used.

HRMS (70 eV, EI+): m/z calcd for C51H31ClFN5: 767.2252, found: 767.

Elemental Analysis: C, 80%; H, 4%

Synthesis Example 19: Synthesis of Intermediate I-17

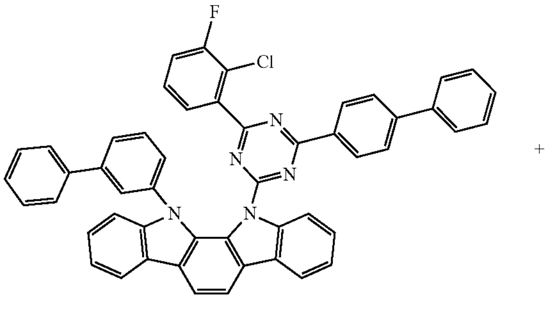

I-16

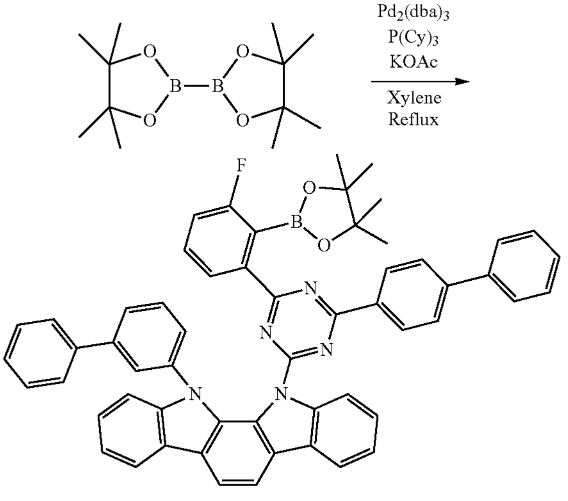

I-17

Intermediate I-17 (26.5 g, 23%) was obtained according to the same method as Synthesis Example 7 except that Intermediate I-16 (150 g, 195 mmol) was used.

HRMS (70 eV, EI+): m/z calcd for C57H43BFN5O2: 859.3494, found: 859.

Elemental Analysis: C, 80%; H, 5%

Synthesis Example 20: Synthesis of Intermediate I-18

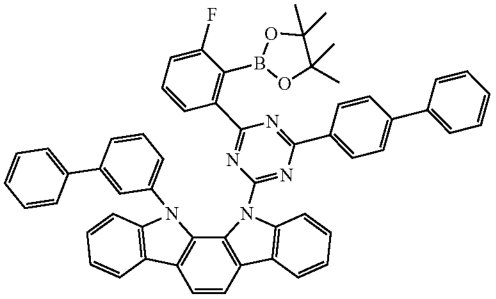

I-17

+

-continued

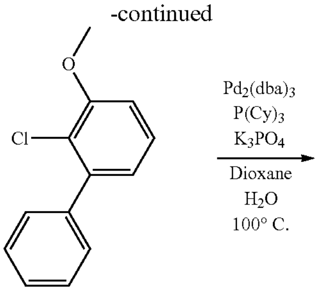

I-3

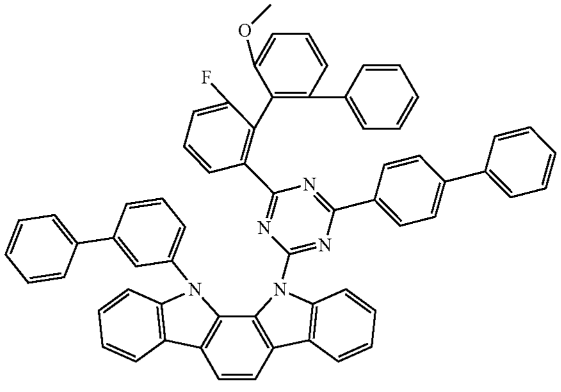

I-18

Intermediate I-18 (10.4 g, 39%) was obtained according to the same method as Synthesis Example 8 except that Intermediate I-17 (25 g, 29.1 mmol) and Intermediate I-3 (9.54 g, 43.6 mmol) were used.

HRMS (70 eV, EI+): m/z calcd for C64H42FN5O: 915.3373, found: 915.

Elemental Analysis: C, 84%; H, 5%

Synthesis Example 21: Synthesis of Intermediate I-19

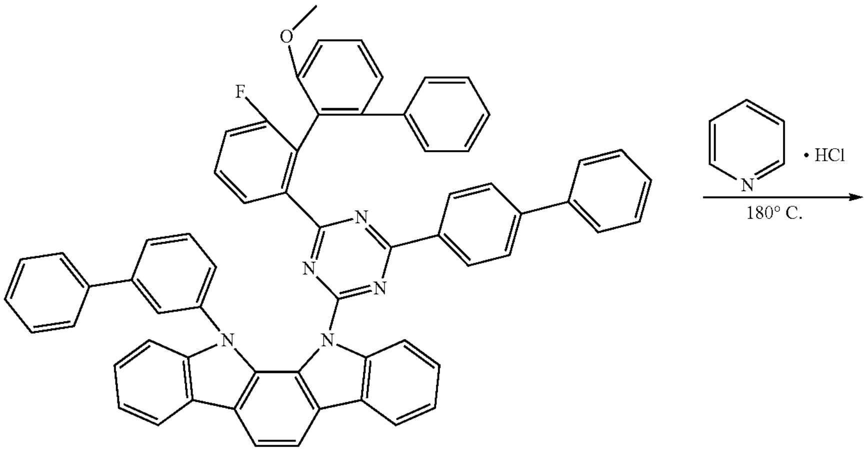

I-18

-continued

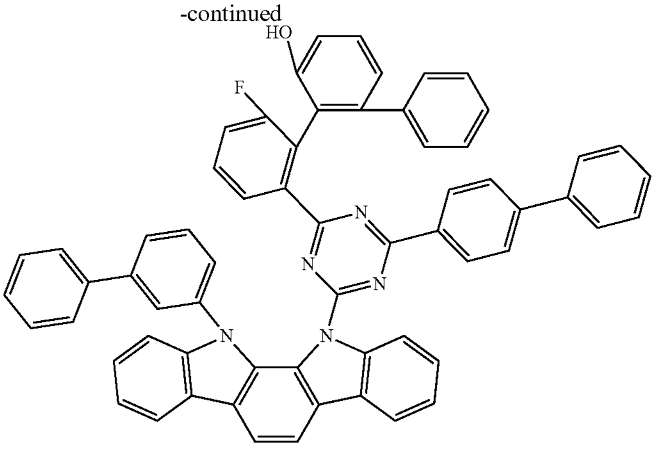

I-19

Intermediate I-19 (9.35 g, 95%) was obtained according to the same method as Synthesis Example 9 except that Intermediate I-18 (10 g, 10.9 mmol) was used.

HRMS (70 eV, EI+): m/z calcd for C63H40FN5O: 901.3217, found: 901.

Elemental Analysis: C, 84%; H, 4%

Synthesis Example 22: Synthesis of Compound 29

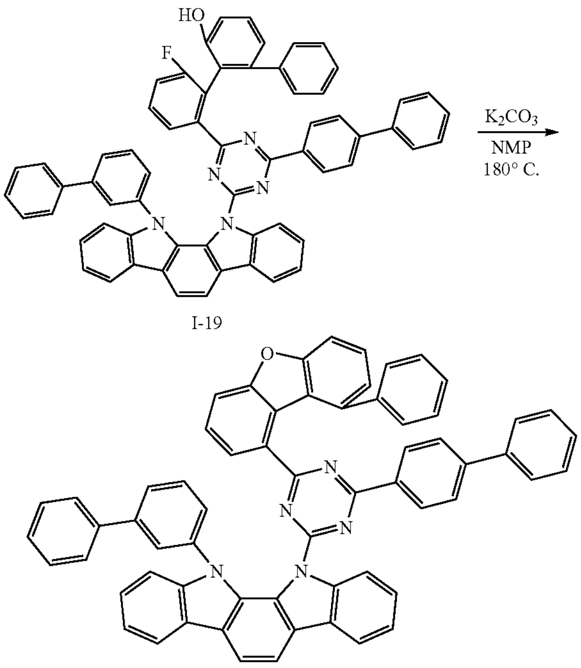

I-19

29

Compound 29 (6.86 g, 78%) was obtained according to the same method as Synthesis Example 10 except that Intermediate I-19 (9 g, 9.98 mmol) was used.

HRMS (70 eV, EI+): m/z calcd for C63H39N5O: 881.3155, found: 881.

Elemental Analysis: C, 86%; H, 4%

Synthesis Example 23: Synthesis of Intermediate I-20

I-20

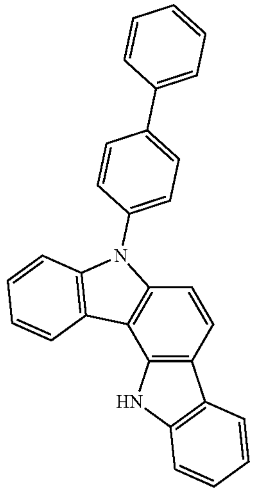

Intermediate I-20 was synthesized according to a method described in WO2018-095391.

HRMS (70 eV, EI+): m/z calcd for C30H20N2: 408.1626, found: 408.

Elemental Analysis: C, 88%; H, 5%

Synthesis Example 24: Synthesis of Intermediate I-21

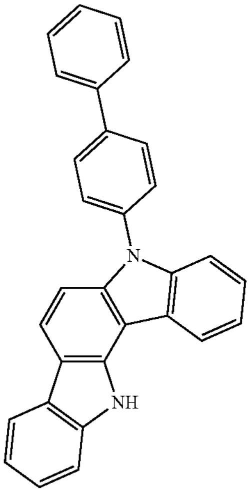

+

I-20

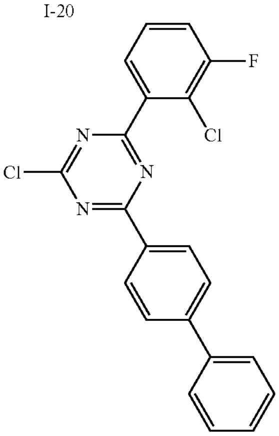

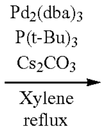

I-11

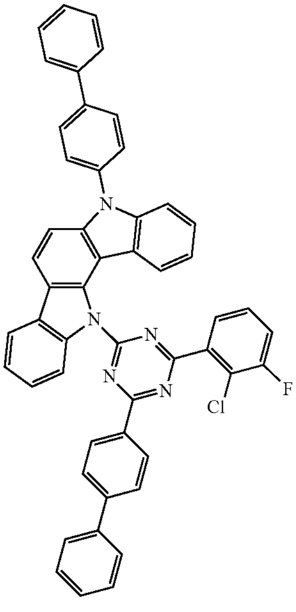

I-21

Under a nitrogen atmosphere, Intermediate I-20 (100 g, 245 mmol) was dissolved in 1 L of xylene, and Intermediate I-11 (116 g, 294 mmol), tris(dibenzylideneacetone)dipalladium (0) (6.73 g, 7.35 mmol), tris(tert butyl)phosphine (5.95 g, 29.4 mmol), and cesium carbonate (95.8 g, 294 mmol) were sequentially added thereto and then, heated under reflux at 130° C. for 14 hours. When a reaction was completed, water was added to the reaction solution and then, extracted with dichloromethane (DCM), treated with anhydrous magnesium sulfate to remove moisture, filtered, and concentrated under a reduced pressure. The obtained residue was separated and purified through flash column chromatography, obtaining Intermediate I-21 (122 g, 65%).

HRMS (70 eV, EI+): m/z calcd for C51H31ClFN5: 767.2252, found: 767.

Elemental Analysis: C, 80%; H, 4%

Synthesis Example 25: Synthesis of Intermediate I-22

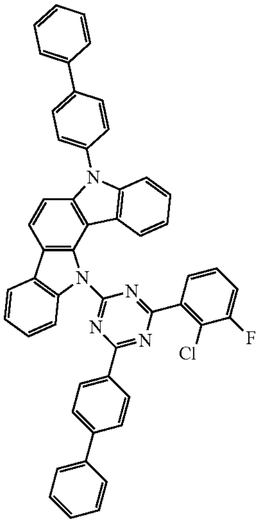

+

I-21

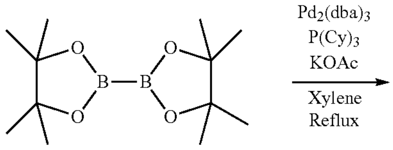

-continued

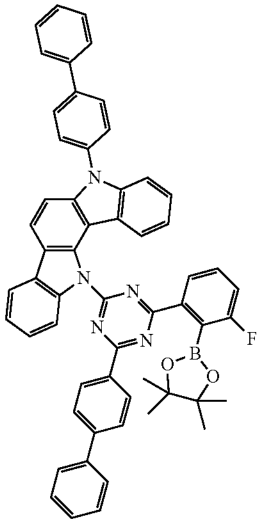

I-22

Intermediate I-22 (34.9 g, 26%) was obtained according to the same method as Synthesis Example 7 except that Intermediate I-21 (120 g, 156 mmol) was used.

HRMS (70 eV, EI+): m/z calcd for C57H43BFN5O2: 859.3494, found: 859.

Elemental Analysis: C, 80%; H, 5%

Synthesis Example 26: Synthesis of Intermediate I-23

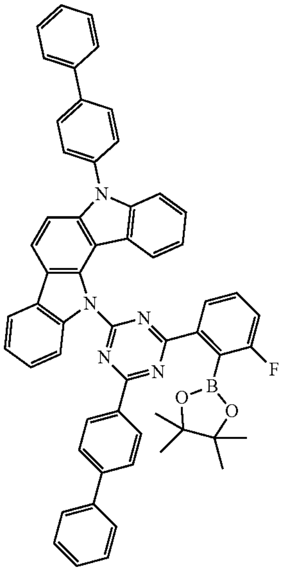

I-22

+

-continued

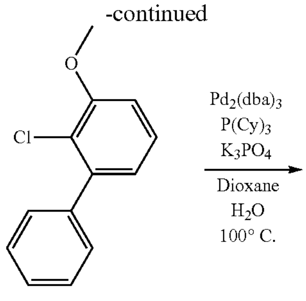

I-3

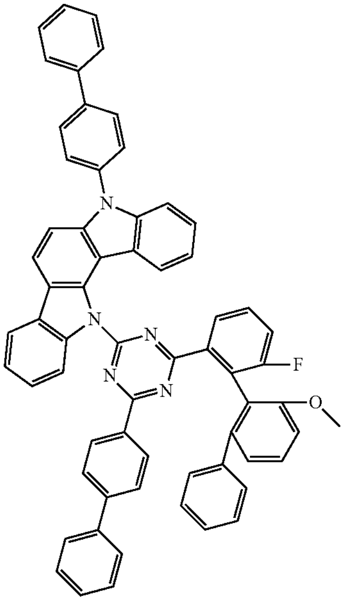

I-23

Intermediate I-23 (9.91 g, 31%) was obtained according to the same method as Synthesis Example 8 except that Intermediate I-22 (30 g, 34.9 mmol) and Intermediate I-3 (11.4 g, 52.3 mmol) were used.

HRMS (70 eV, EI+): m/z calcd for C64H42FN5O: 915.3373, found: 915.

Elemental Analysis: C, 84%; H, 5%

Synthesis Example 27: Synthesis of Intermediate I-24

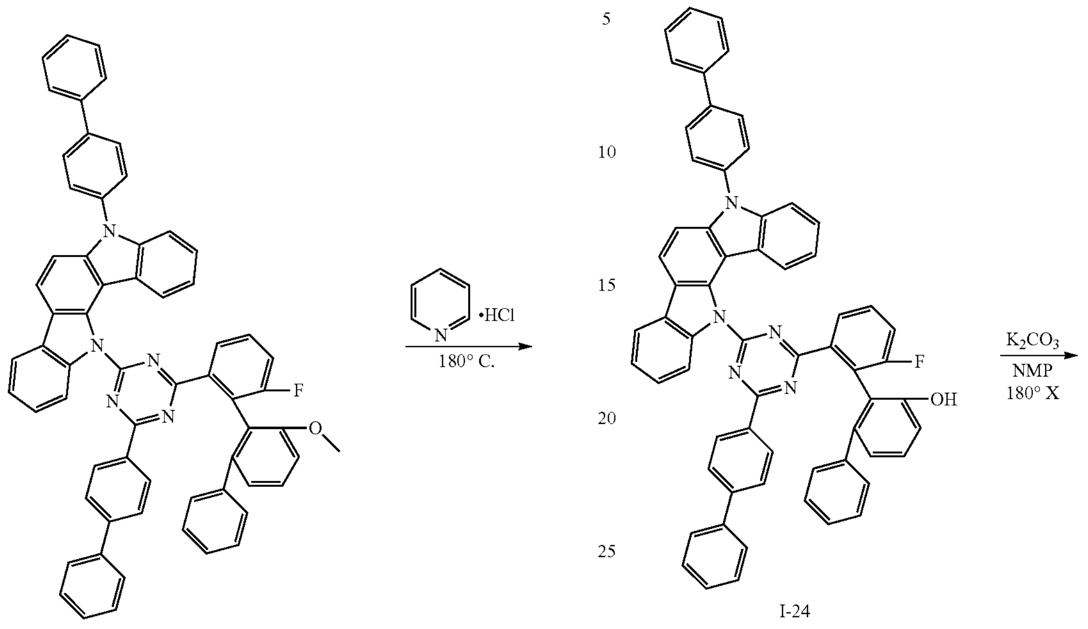

I-23 I-24

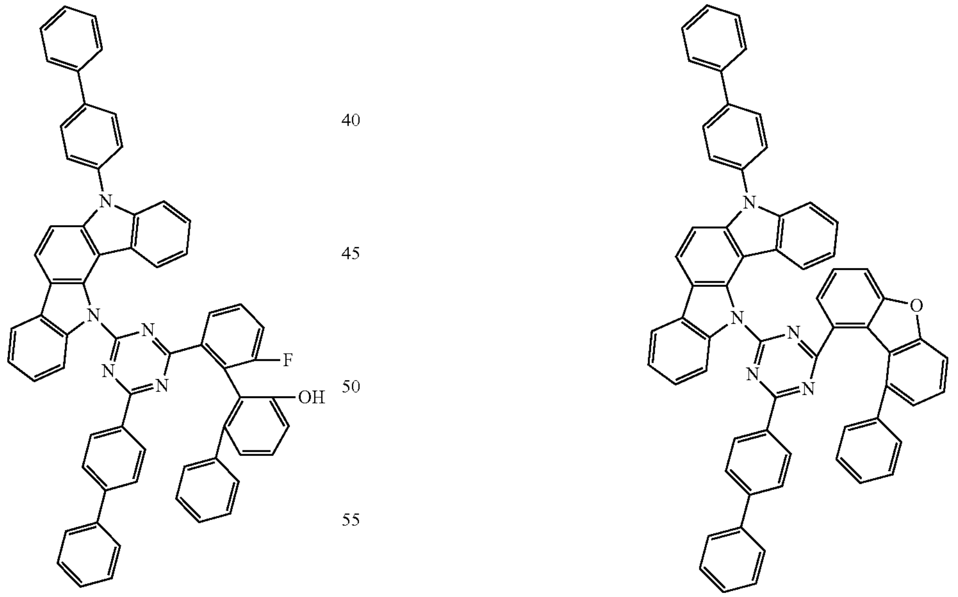

I-24 31

Intermediate I-24 (8.70 g, 93%) was obtained according to the same method as Synthesis Example 9 except that Intermediate I-23 (9.5 g, 10.4 mmol) was used.

HRMS (70 eV, EI+): m/z calcd for C63H40FN5O: 901.3217, found: 901.

Elemental Analysis: C, 84%; H, 4%

Synthesis Example 28: Synthesis of Compound 31

Compound 31 (5.95 g, 76%) was obtained according to the same method as Synthesis Example 10 except that Intermediate I-24 (8 g, 8.87 mmol) was used.

HRMS (70 eV, EI+): m/z calcd for C63H39N5O: 881.3155, found: 881.

Elemental Analysis: C, 86%; H, 4%

Synthesis Example 29: Synthesis of Intermediate I-25

I-25

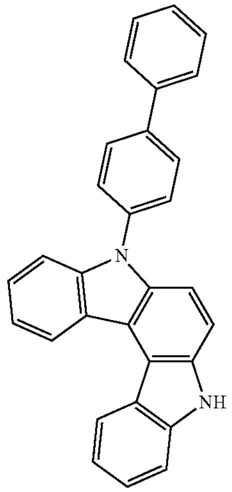

Intermediate I-25 was synthesized according to a method described in KR10-2031300.

HRMS (70 eV, EI+): m/z calcd for C30H20N2: 408.1626, found: 408.

Elemental Analysis: C, 88%; H, 5%

Synthesis Example 30: Synthesis of Intermediate I-26

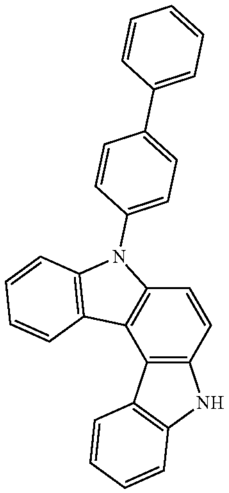

+

I-25

-continued

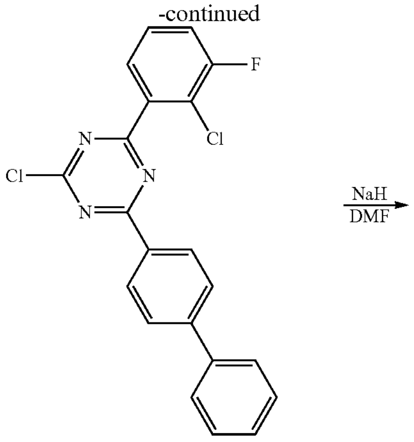

I-11

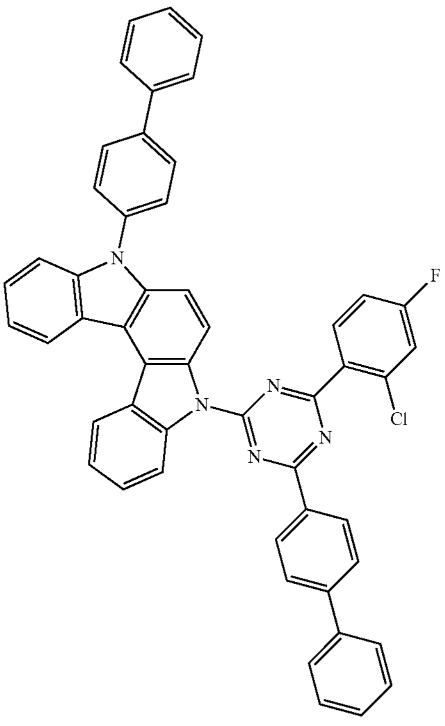

I-26

Intermediate I-26 (175 g, 93%) was obtained according to the same method as Synthesis Example 6 except that Intermediate I-25 (100 g, 245 mmol) and Intermediate I-11 (146 g, 367 mmol) were used.

HRMS (70 eV, EI+): m/z calcd for C51H31ClFN5: 767.2252, found: 767.

Elemental Analysis: C, 80%; H, 4%

Synthesis Example 31: Synthesis of Intermediate I-27

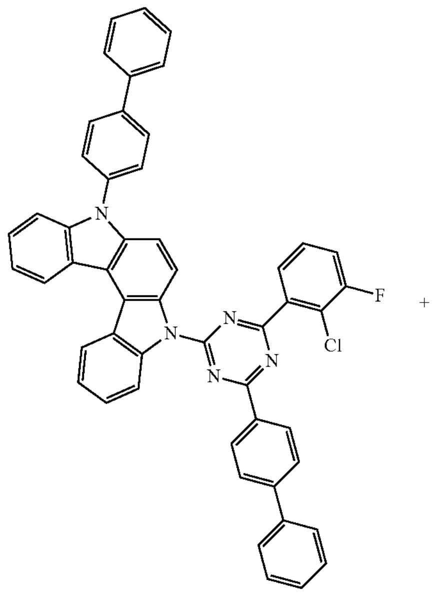

I-26

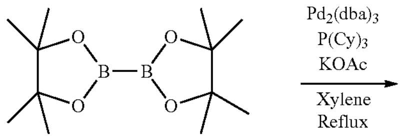

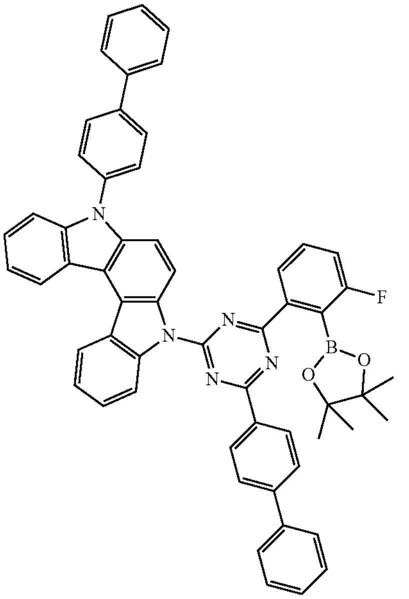

I-27

Intermediate I-27 (38.0 g, 20%) was obtained according to the same method as Synthesis Example 7 except that Intermediate I-26 (170 g, 221 mmol) was used.

HRMS (70 eV, EI+): m/z calcd for C57H43BFN5O2: 859.3494, found: 859.

Elemental Analysis: C, 80%; H, 5%

Synthesis Example 32: Synthesis of Intermediate I-28

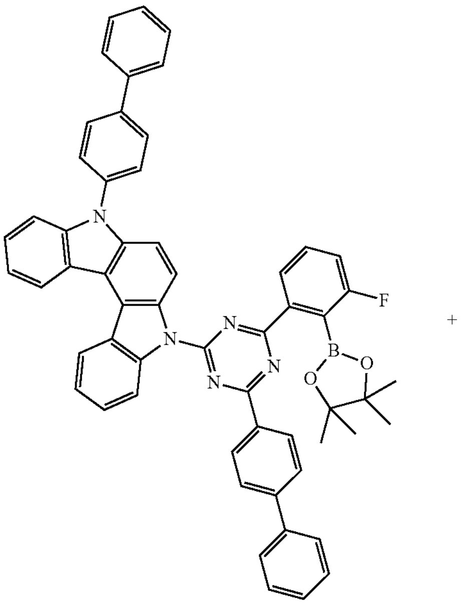

I-27

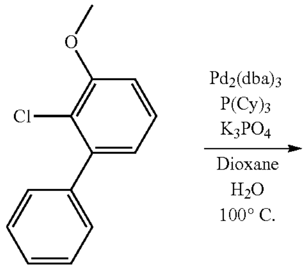

I-3

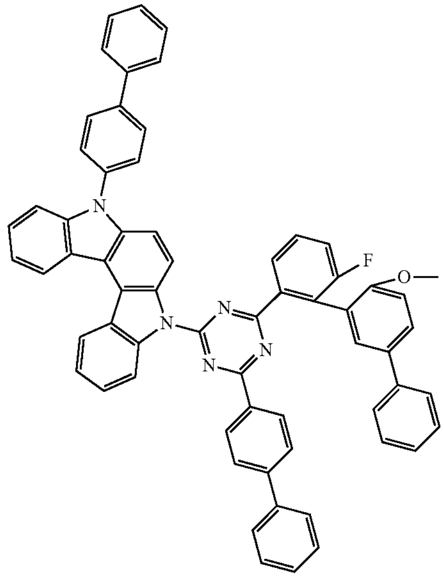

I-28

Intermediate I-28 (13.8 g, 37%) was obtained according to the same method as Synthesis Example 8 except that Intermediate I-27 (35 g, 40.7 mmol) and Intermediate I-3 (13.4 g, 61.1 mmol) were used.

HRMS (70 eV, EI+): m/z calcd for C64H42FN5O: 915.3373, found: 915.

Elemental Analysis: C, 84%; H, 5%

Synthesis Example 33: Synthesis of Intermediate I-29

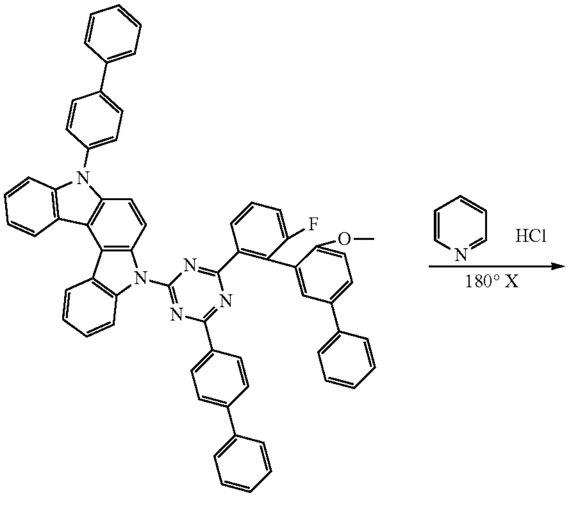

I-28

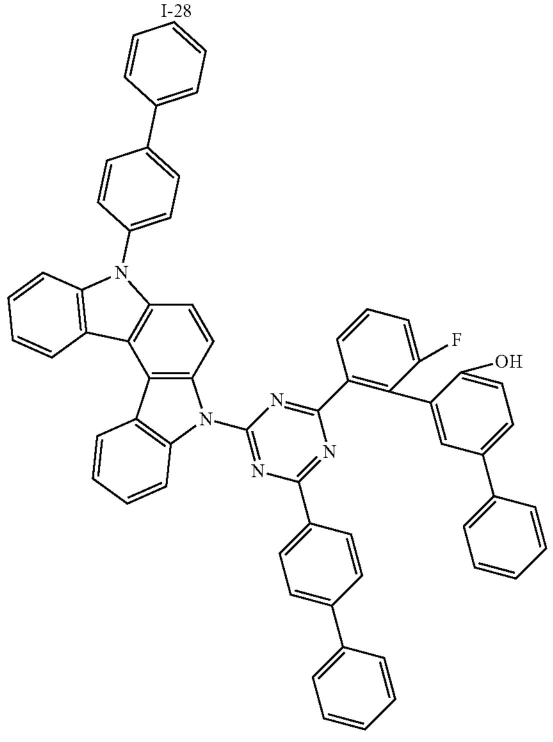

I-29

Intermediate I-29 (11.6 g, 91%) was obtained according to the same method as Synthesis Example 9 except that Intermediate I-28 (13 g, 14.2 mmol) was used.

HRMS (70 eV, EI+): m/z calcd for C63H40FN5O: 901.3217, found: 901.

Elemental Analysis: C, 84%; H, 4%

Synthesis Example 34: Synthesis of Compound 32

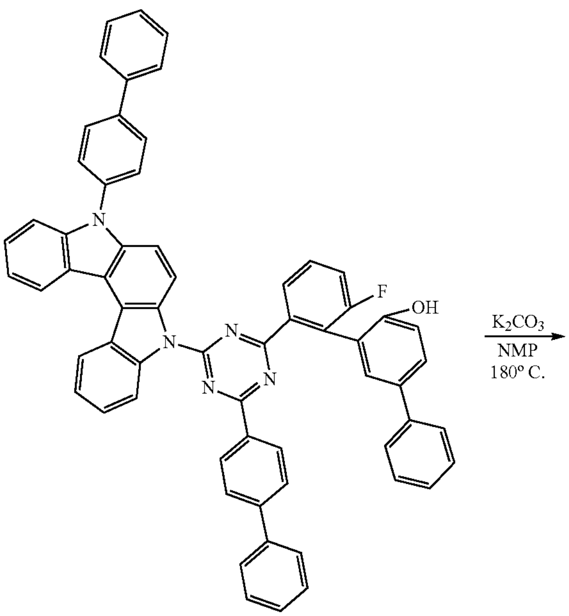

I-29

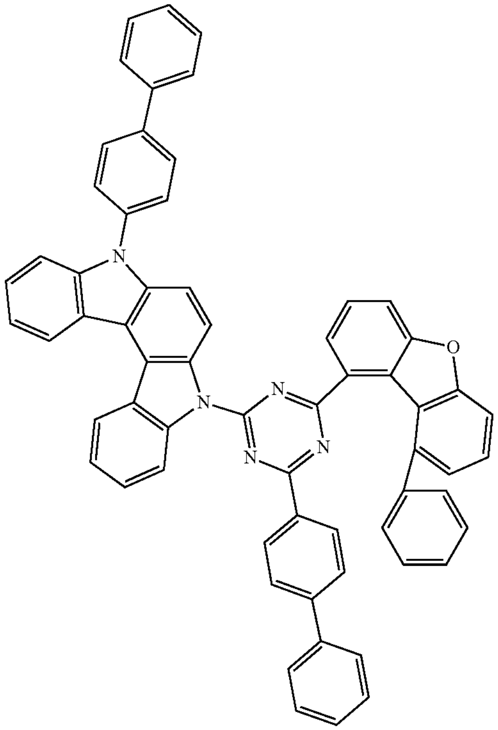

32

Compound 32 (7.14 g, 73%) was obtained according to the same method as Synthesis Example 10 except that Intermediate I-29 (10 g, 11.1 mmol) was used.

HRMS (70 eV, EI+): m/z calcd for C63H39N5O: 881.3155, found: 881.

Elemental Analysis: C, 86%; H, 4%

Synthesis Example 35: Synthesis of Compound Host 1

Host1

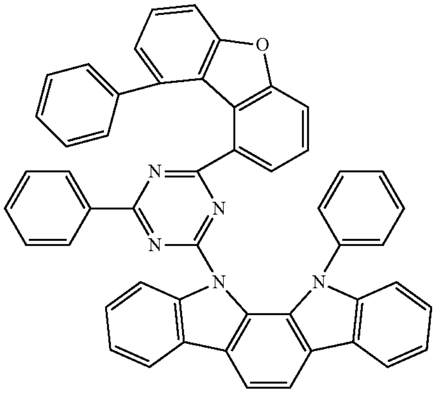

Compound Host 1 was synthesized according to a method described in KR10-2069310.

HRMS (70 eV, EI+): m/z calcd for C51H31N5O: 729.2529, found: 729.

Elemental Analysis: C, 84%; H, 4%

Synthesis Example 36: Synthesis of Compound Host 2

Host2

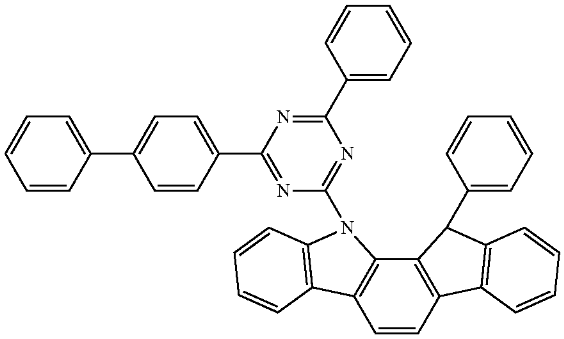

Compound Host 2 was synthesized according to a method described in WO2016-194604.

HRMS (70 eV, EI+): m/z calcd for C45H29N5: 639.2423, found: 639.

Elemental Analysis: C, 84%; H, 5%

Synthesis Example 37: Synthesis of Compound Host 3

Host3

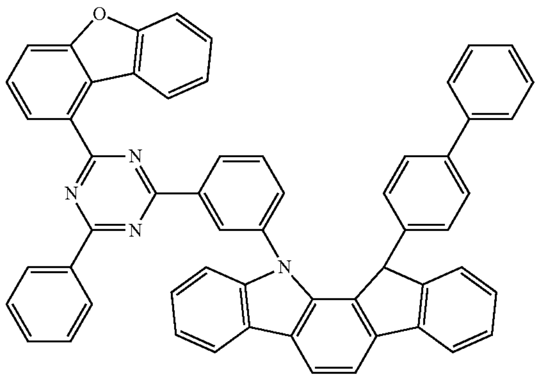

Compound Host 3 was synthesized according to a method described in KR2018-0137772.

HRMS (70 eV, EI+): m/z calcd for C57H35N5O: 805.2842, found: 805.

Elemental Analysis: C, 85%; H, 4%

Synthesis Example 38: Synthesis of Compound A-136

A-136

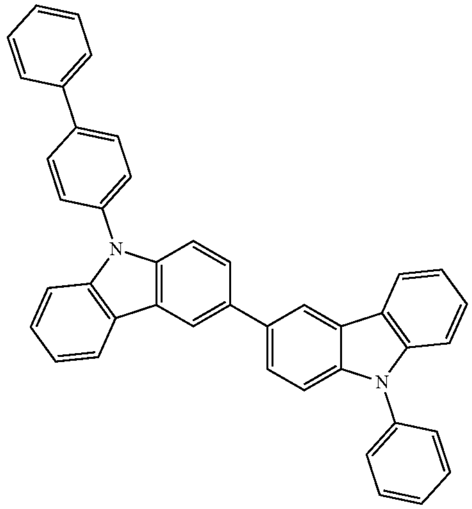

Compound A-136 was synthesized according to a method described in EP3034581.

HRMS (70 eV, EI+): m/z calcd for C42H28N2: 560.2252, found: 560.

Elemental Analysis: C, 90%; H, 5%

Synthesis Example 39: Synthesis of Compound A-99

A-99

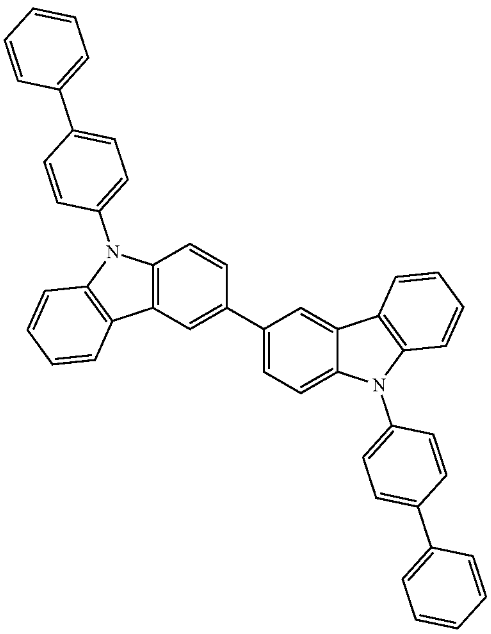

Compound A-99 was synthesized according to a method described in KR10-2019-0000597.

HRMS (70 eV, EI+): m/z calcd for C48H32N2: 636.2565, found: 636.

Elemental Analysis: C, 91%; H, 5%

Synthesis Example 40: Synthesis of Compound A-31

A-31

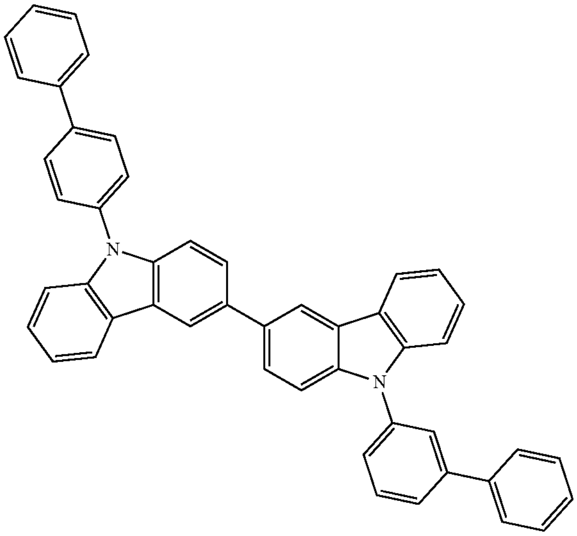

Compound HT5 was synthesized according to a method described in EP2947071.

HRMS (70 eV, EI+): m/z calcd for C48H32N2: 636.2565, found: 636.

Elemental Analysis: C, 91%; H, 5%

Synthesis Example 41: Synthesis of Compound B-4

B-4

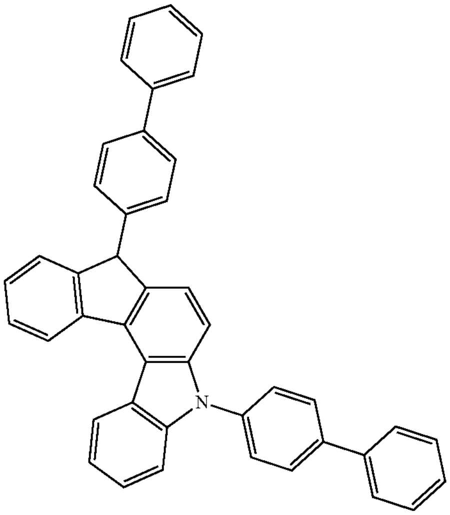

Compound B-4 was synthesized according to a method described in KR10-2031300.

HRMS (70 eV, EI+): m/z calcd for C42H28N2: 560.2252, found: 560.

Elemental Analysis: C, 90%; H, 5%

Synthesis Example 42: Synthesis of Compound B-57

B-57

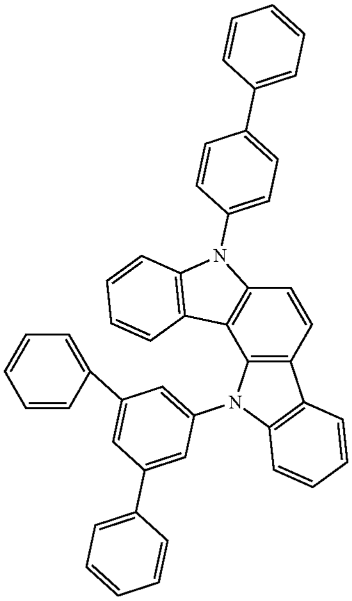

Compound B-57 was synthesized according to a method described in WO2018-095391.

HRMS (70 eV, EI+): m/z calcd for C48H32N2: 636.2565, found: 636.

Elemental Analysis: C, 91%; H, 5%

Synthesis Example 43: Synthesis of Intermediate I-30

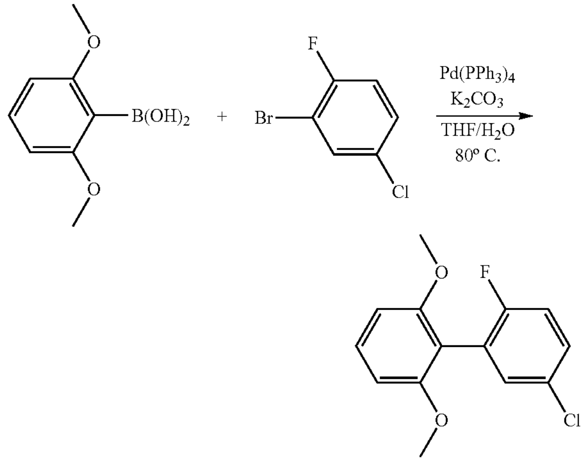

I-30

Under a nitrogen atmosphere, 2,6-dimethoxyphenylboronic acid (100 g, 550 mmol) purchased from Tokyo Chemical Industry Co., Ltd. (http://www.tcichemicals.com/) was dissolved in 1.1 L of tetrahydrofuran (THF) and then, 2-bromo-4-chloro-1-fluorobenzene (115 g, 550 mmol) and tetrakis(triphenylphosphine)palladium (12.7 g, 11.0 mmol) were added thereto, and then, stirred. Potassium carbonate (190 g, 1,375 mmol) saturated in water was added thereto and then, heated under reflux at 80° C. for 12 hours. When a reaction was completed, water was added to the reaction solution and then, extracted with dichloromethane (DCM), treated with anhydrous magnesium sulfate to remove moisture, filtered, and then, concentrated under a reduced pressure. The obtained residue was purified through flash column chromatography, obtaining Intermediate I-30 (95.3 g, 65%).

HRMS (70 eV, EI+): m/z calcd for C14H12ClFO2: 266.0510, found: 266.

Elemental Analysis: C, 63%; H, 5%

Synthesis Example 44: Synthesis of Intermediate I-31

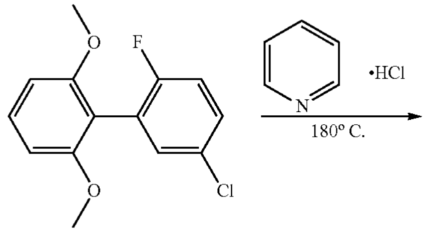

I-30

-continued

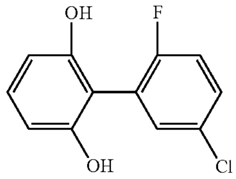

I-31

Intermediate I-30 (95 g, 356 mmol) was used to obtain Intermediate I-31 (77.3 g, 91%) according to the same method as Synthesis Example 9.

HRMS (70 eV, EI+): m/z calcd for C12H8ClFO2: 238.0197, found: 238.

Elemental Analysis: C, 60%; H, 3%

Synthesis Example 45: Synthesis of Intermediate I-32

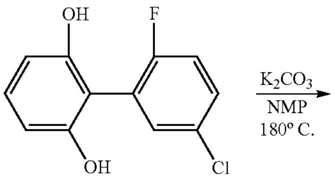

I-31

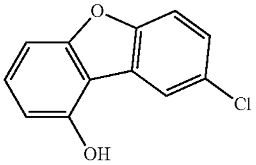

I-32

Intermediate I-31 (77 g, 323 mmol) was used to obtain Intermediate I-32 (37.4 g, 53%) according to the same method as Synthesis Example 10.

HRMS (70 eV, EI+): m/z calcd for C12H7ClO2: 218.0135, found: 218.

Elemental Analysis: C, 66%; H, 3%

Synthesis Example 46: Synthesis of Intermediate I-33

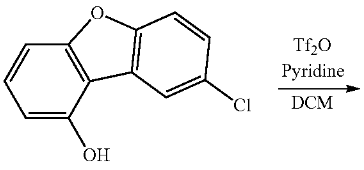

I-32

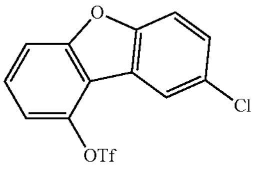

I-33

Under a nitrogen atmosphere, intermediate I-32 (37 g, 169 mmol) was dissolved in 1 L of dichloromethane (DCM), and then, the temperature was lowered to 0° C. Pyridine (57.3 g, 203 mmol) was added thereto, stirred for 30 minutes, trifluoromethanesulfonic anhydride (16.1 g, 203 mmol) was slowly added thereto, and then stirred. After 3 hours, reaction solution was cooled down at 0° C., water was slowly added thereto for 3 hours and then, extracted with dichloromethane (DCM), treated with anhydrous magnesium sulfate to remove moisture, filtered, and then, concentrated under a reduced pressure. The obtained residue was purified through flash column chromatography, obtaining Intermediate I-33 (46.2 g, 78%).

HRMS (70 eV, EI+): m/z calcd for C13H6C1F3O4S: 349.9627, found: 350.

Elemental Analysis: C, 45%; H, 2%

Synthesis Example 47: Synthesis of Intermediate I-34

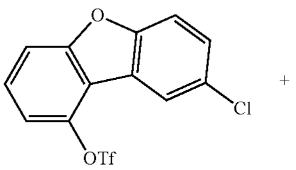

I-33

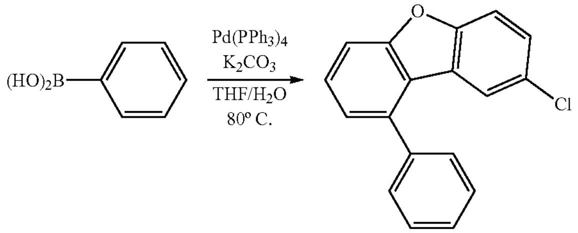

I-34

Intermediate I-33 (46 g, 131 mmol) and phenyl boronic acid (16.0 g, 131 mmol) were used to obtain Intermediate I-34 (34.7 g, 95%) according to the same method as Synthesis Example 43.

HRMS (70 eV, EI+): m/z calcd for C18H11ClO: 278.0498, found: 278.

Elemental Analysis: C, 78%; H, 4%

Synthesis Example 48: Synthesis of Intermediate I-35

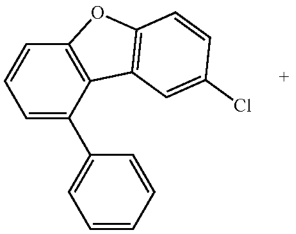

I-34

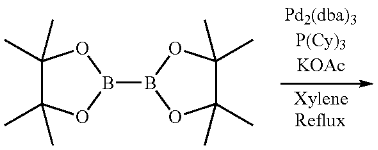

-continued

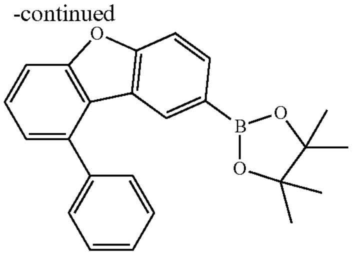

I-35

Intermediate I-34 (34.0 g, 122 mmol) was used to obtain Intermediate I-35 (33.0 g, 73%) according to the same method as Synthesis Example 7.

HRMS (70 eV, EI+): m/z calcd for C24H23BO3: 370.1740, found: 370.

Elemental Analysis: C, 78%; H, 6%

Synthesis Example 49: Synthesis of Intermediate I-36

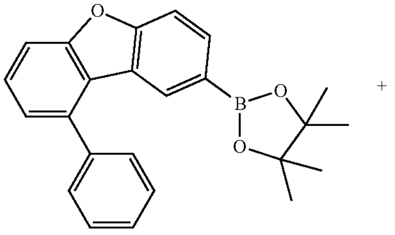

I-35

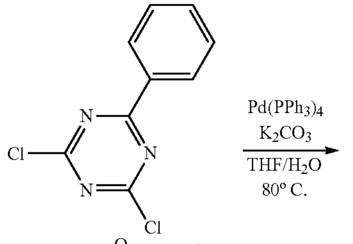

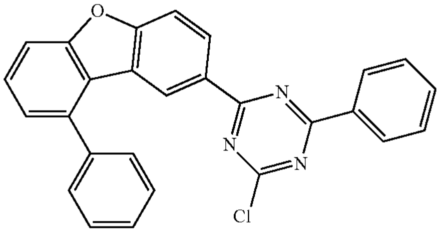

I-36

Intermediate I-35 (33.0 g, 89.1 mmol) and 2,4-dichloro-6-phenyl-1,3,5-triazine (30.2 g, 134 mmol) were used to obtain Intermediate I-36 (19.7 g, 51%) according to the same method as Synthesis Example 43.

HRMS (70 eV, EI+): m/z calcd for C27H16ClN3O: 433.0982, found: 433.

Elemental Analysis: C, 75%; H, 4%

Synthesis Example 50: Synthesis of Compound 33

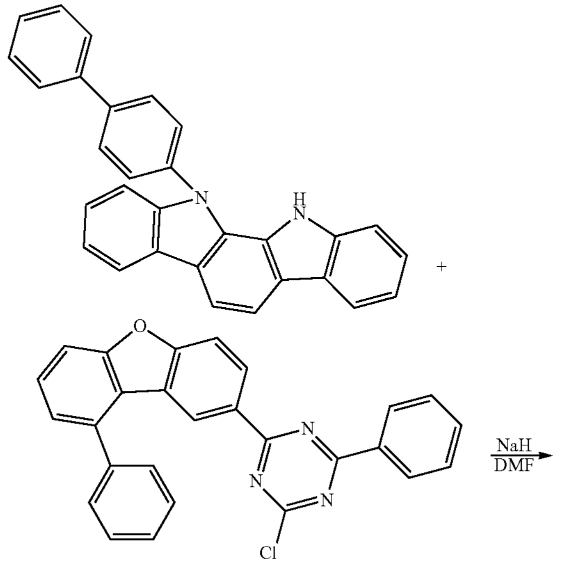

I-36

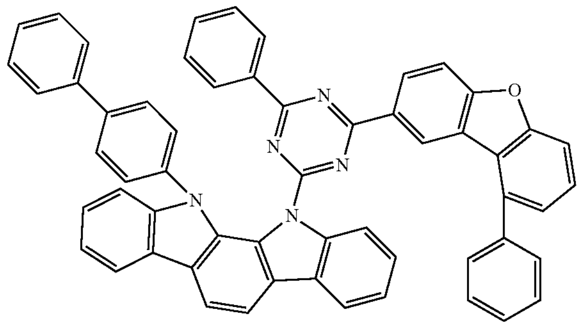

33

11-(biphenyl-4-yl)-11,12-dihydroindolo[2,3,a]carbazole (10 g, 24.5 mmol) purchased from Ukseung Chemical Co., Ltd. (http://www.ukseung.co.kr/) and Intermediate I-36 (12.8 g, 29.4 mmol) were used to obtain Compound 33 (15.8 g, 80%) according to the same method as Synthesis Example 6.

HRMS (70 eV, EI+): m/z calcd for C57H35N5O: 805.2842, found: 805.

Elemental Analysis: C, 85%; H, 4%

Synthesis Example 51: Synthesis of Intermediate I-37

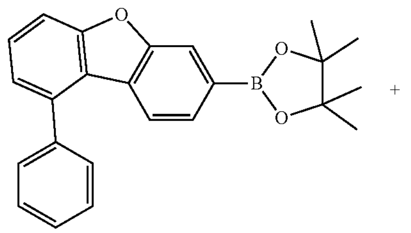

-continued

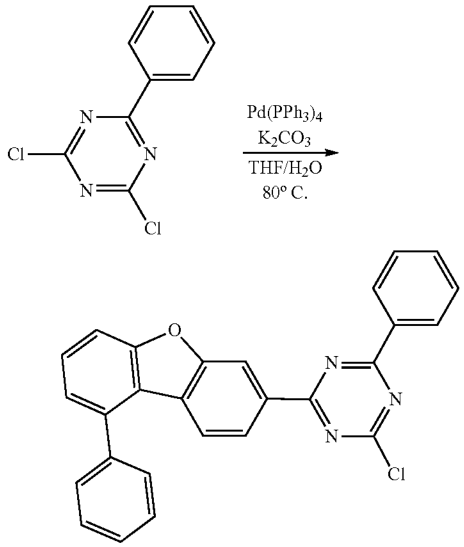

I-37

4,4,5,5-tetramethyl-2-(9-phenyldibenzofuran-3-yl)-1,3,2-dioxaborolane (30 g, 81 mmol) purchased from Gemchem (http://www.ytgemchem.com) and 2,4-dichloro-6-phenyl-1,3,5-triazine (27.5 g, 122 mmol) were used to obtain Intermediate I-37 (24.6 g, 70%) according to the same method as Synthesis Example 43.

HRMS (70 eV, EI+): m/z calcd for C27H16ClN3O: 433.0982, found: 433.

Elemental Analysis: C, 75%; H, 4%

Synthesis Example 52: Synthesis of Compound 34

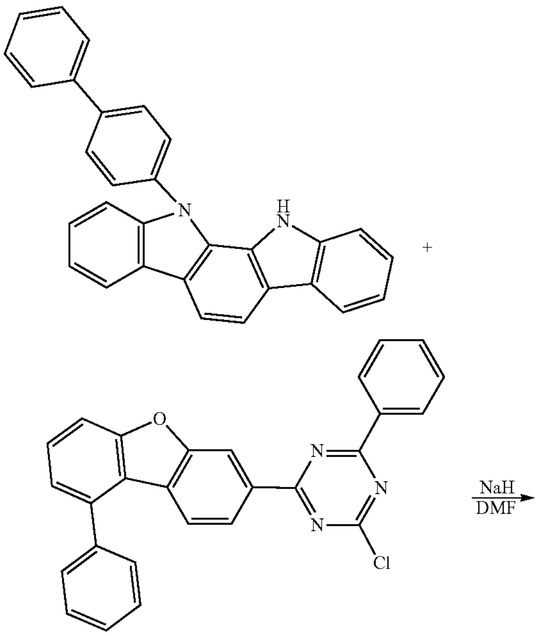

I-37

-continued

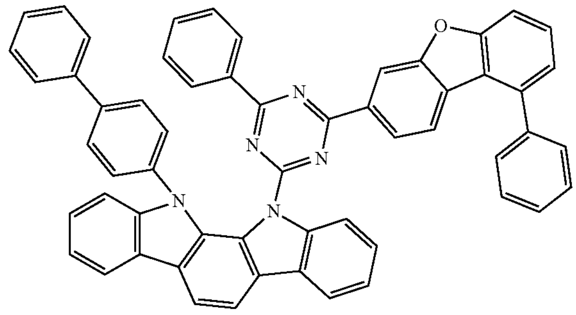

34

11-(biphenyl-4-yl)-11,12-dihydroindolo[2,3,a]carbazole (10 g, 24.5 mmol) purchased from Ukseung Chemical Co., Ltd. (http://www.ukseung.co.kr/) and Intermediate I-37 (12.8 g, 29.4 mmol) were used to obtain Compound 34 (16.8 g, 85%) according to the same method as Synthesis Example 6.

HRMS (70 eV, EI+): m/z calcd for C57H35N5O: 805.2842, found: 805.

Elemental Analysis: C, 85%; H, 4%

Synthesis Example 53: Synthesis of Intermediate I-38

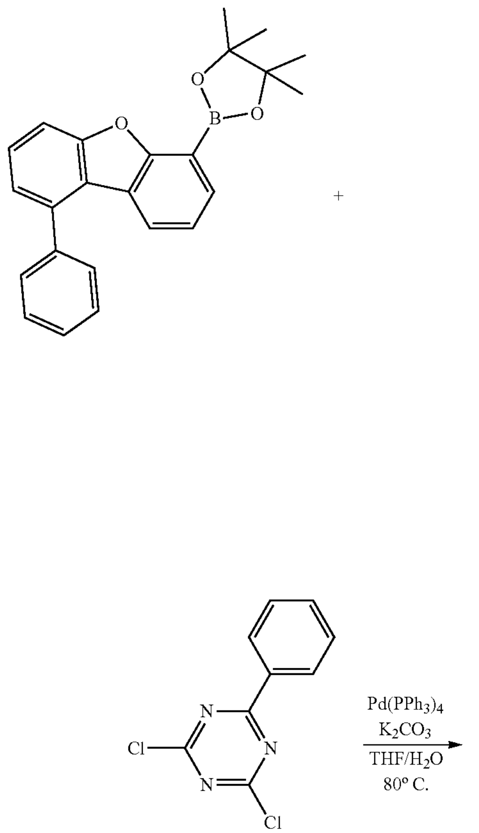

-continued

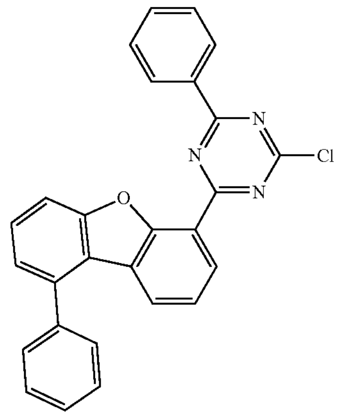

I-38

4,4,5,5-tetramethyl-2-(9-phenyldibenzofuran-4-yl)-1,3,2-dioxaborolane (30 g, 81 mmol) purchased from Gemchem (http://www.ytgemchem.com) and 2,4-dichloro-6-phenyl-1,3,5-triazine (27.5 g, 122 mmol) were used to obtain Intermediate I-38 (21.8 g, 62%) according to the same method as Synthesis Example 43.

HRMS (70 eV, EI+): m/z calcd for C27H16ClN3O: 433.0982, found: 433.

Elemental Analysis: C, 75%; H, 4%

Synthesis Example 54: Synthesis of Compound 35

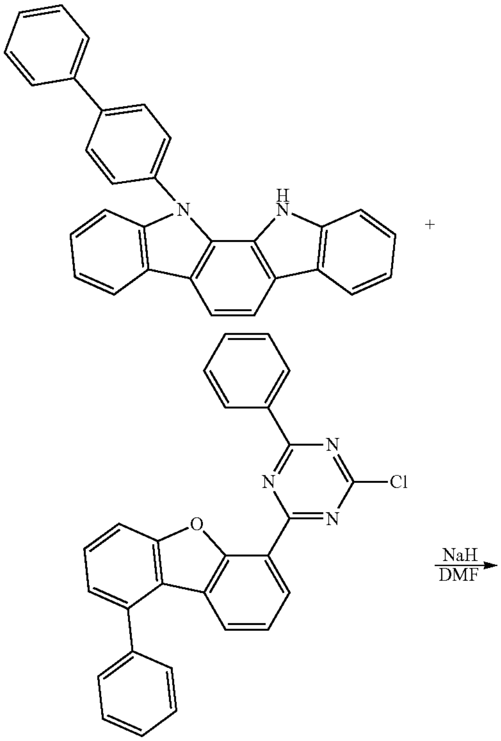

I-38

-continued

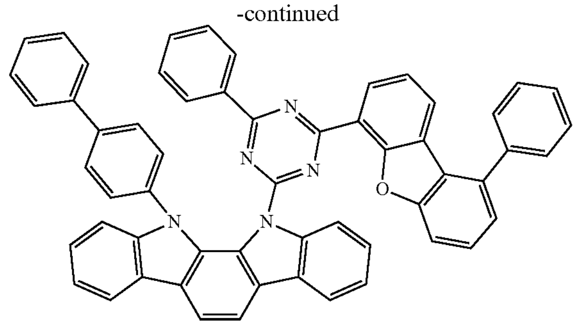

35

11-(biphenyl-4-yl)-11,12-dihydroindolo[2,3,a]carbazole (10 g, 24.5 mmol) purchased from Ukseung Chemical Co., Ltd. (http://www.ukseung.co.kr/) and Intermediate I-38 (12.8 g, 29.4 mmol) were used to obtain Compound 35 (15.1 g, 78%) according to the same method as Synthesis Example 6.

HRMS (70 eV, EI+): m/z calcd for C57H35N5O: 805.2842, found: 805.

Elemental Analysis: C, 85%; H, 4%

Synthesis Example 55: Synthesis of Intermediate I-39

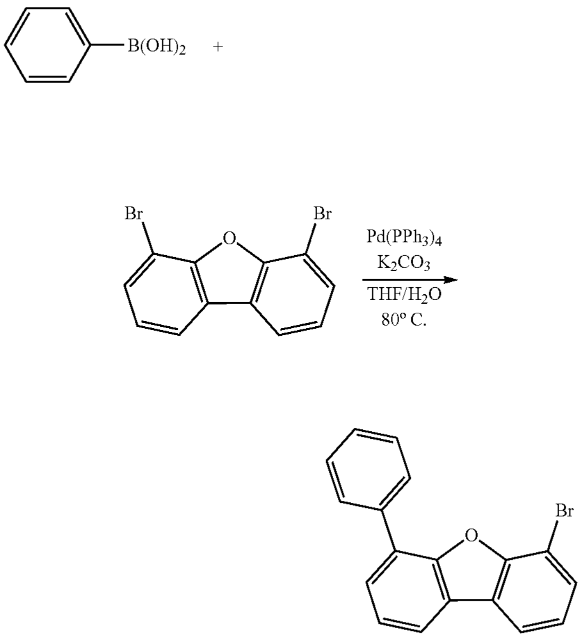

I-39

Phenyl boronic acid (50 g, 410 mmol) purchased from Tokyo chemical industry and 4,6-dibromobenzofuran (160 g, 492 mmol) were used to obtain Intermediate I-39 (45.1 g, 34%) according to the same method as Synthesis Example 43.

HRMS (70 eV, EI+): m/z calcd for C18H11BrO: 321.9993, found: 321.

Elemental Analysis: C, 67%; H, 3%

Synthesis Example 56: Synthesis of Intermediate I-40

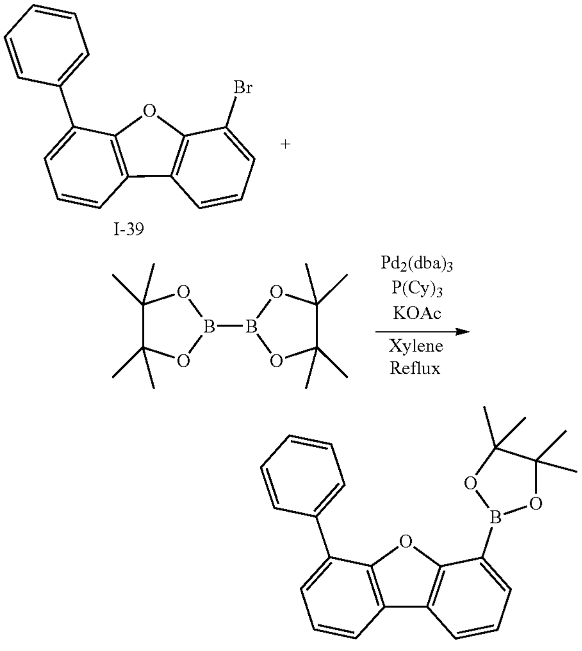

I-39

I-40

Intermediate I-39 (44 g, 136 mmol) was used to obtain Intermediate I-40 (35.3 g, 70%) according to the same method as Synthesis Example 7.

HRMS (70 eV, EI+): m/z calcd for C24H23BO3: 370.1740, found: 370.

Elemental Analysis: C, 78%; H, 6%

Synthesis Example 57: Synthesis of Intermediate I-41

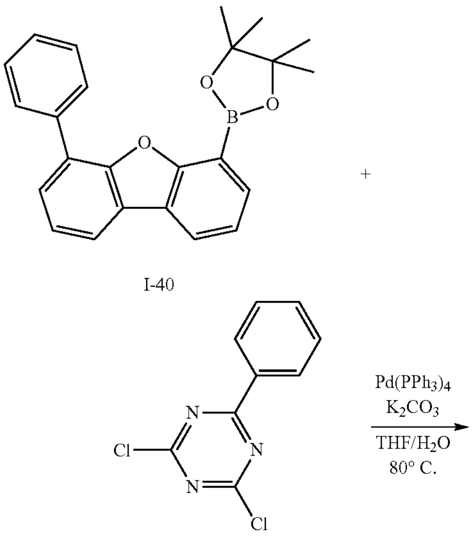

I-40

-continued

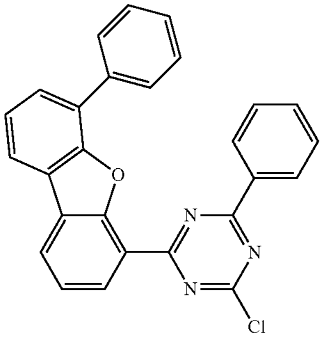

I-41

Intermediate I-40 (35 g, 94.5 mmol) and 2,4-dichloro-6-phenyl-1,3,5-triazine (25.6 g, 113 mmol) were used to obtain Intermediate I-41 (30.8 g, 75%) according to the same method as Synthesis Example 43.

HRMS (70 eV, EI+): m/z calcd for C27H16ClN3O: 433.0982, found: 433.

Elemental Analysis: C, 75%; H, 4%

Synthesis Example 58: Synthesis of Compound 73

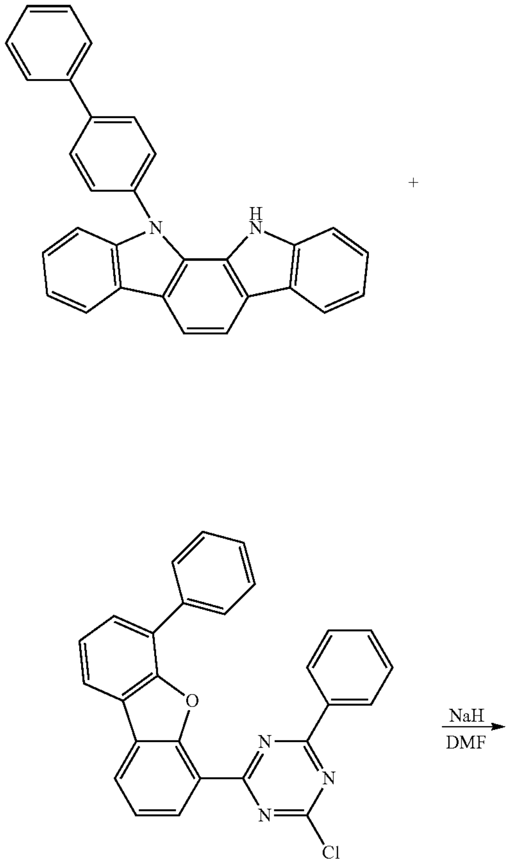

I-41

-continued

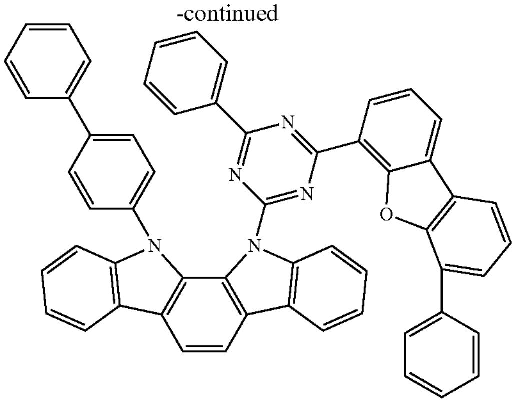

73

11-(biphenyl-4-yl)-11,12-dihydroindolo[2,3,a]carbazole (10 g, 24.5 mmol) purchased from Ukseung Chemical Co., Ltd. (http://www.ukseung.co.kr/) and Intermediate I-41 (12.8 g, 29.4 mmol) were used to obtain Compound 73 (12.8 g, 65%) according to the same method as Synthesis Example 6.

HRMS (70 eV, EI+): m/z calcd for C57H35N5O: 805.2842, found: 805.

Elemental Analysis: C, 85%; H, 4%

Synthesis Example 59: Synthesis of Intermediate I-42

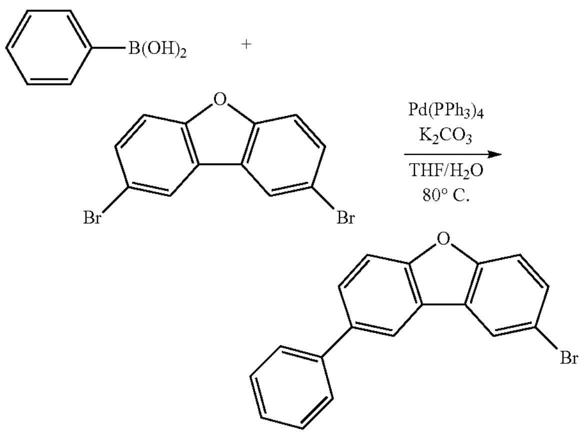

I-42

Phenyl boronic acid (50 g, 410 mmol) purchased from Tokyo chemical industry and 2,8-dibromobenzofuran (160 g, 492 mmol) were used to obtain Intermediate I-42 (39.8 g, 30%) according to the same method as Synthesis Example 43.

HRMS (70 eV, EI+): m/z calcd for C18H11BrO: 321.9993, found: 321.

Elemental Analysis: C, 67%; H, 3%

Synthesis Example 60: Synthesis of Intermediate I-43

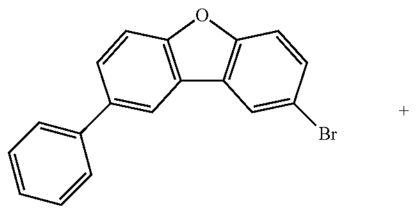

I-42

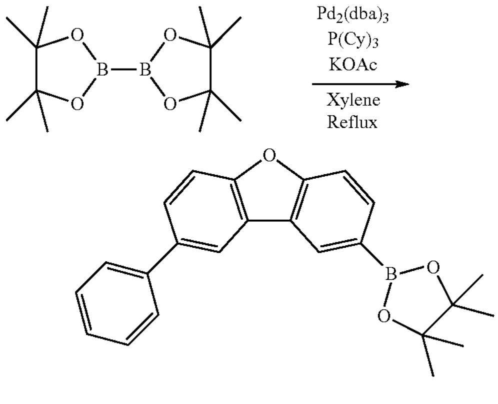

I-43

Intermediate I-42 (39 g, 121 mmol) was used to obtain Intermediate I-43 (37.1 g, 83%) according to the same method as Synthesis Example 7.

HRMS (70 eV, EI+): m/z calcd for C24H23BO3: 370.1740, found: 370.

Elemental Analysis: C, 78%; H, 6%

Synthesis Example 61: Synthesis of Intermediate I-44

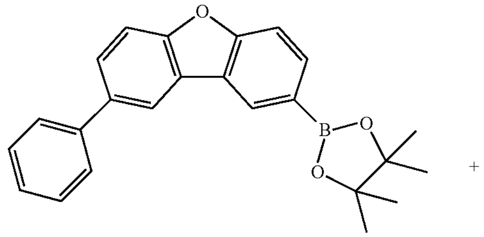

I-43

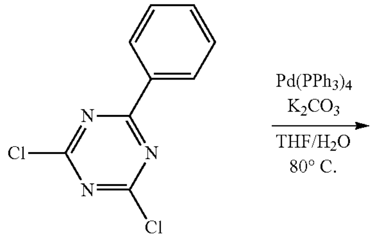

-continued

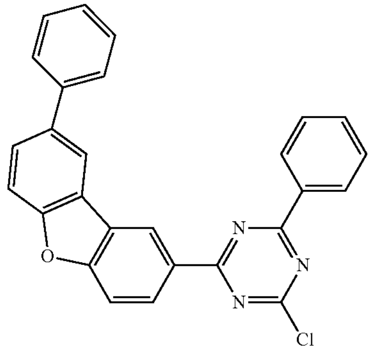

I-44

Intermediate I-43 (37 g, 100 mmol) and 2,4-dichloro-6-phenyl-1,3,5-triazine (27.2 g, 120 mmol) were used to obtain Intermediate I-44 (26.9 g, 62%) according to the same method as Synthesis Example 43.

HRMS (70 eV, EI+): m/z calcd for C27H16ClN3O: 433.0982, found: 433.

Elemental Analysis: C, 75%; H, 4%

Synthesis Example 62: Synthesis of Compound 74

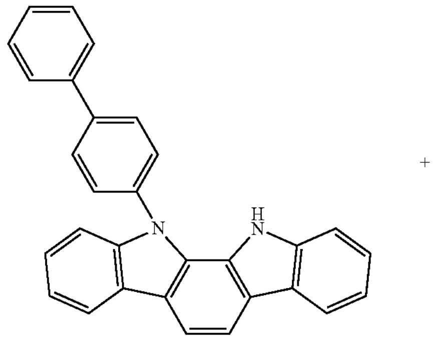

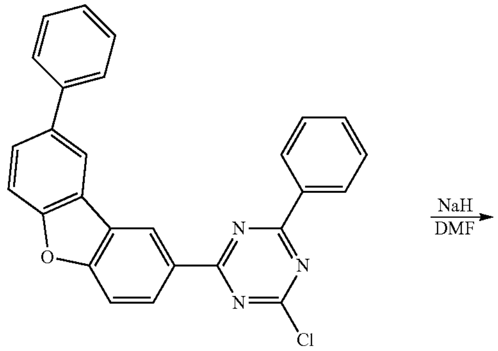

I-44

-continued

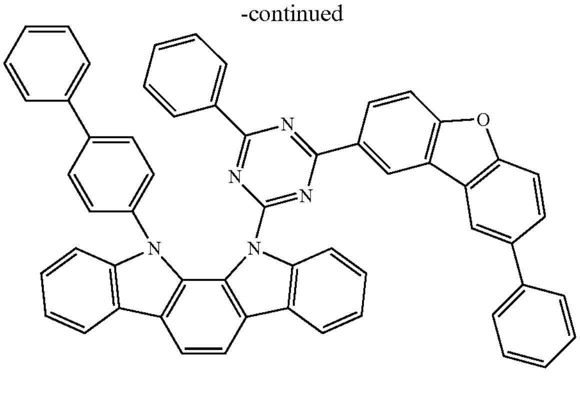

74

11-(biphenyl-4-yl)-11,12-dihydroindolo[2,3,a]carbazole (10 g, 24.5 mmol) purchased from Ukseung Chemical Co., Ltd. (http://www.ukseung.co.kr/) and Intermediate I-44 (12.8 g, 29.4 mmol) were used to obtain Compound 74 (14.0 g, 71%) according to the same method as Synthesis Example 6.

HRMS (70 eV, EI+): m/z calcd for C57H35N5O: 805.2842, found: 805.

Elemental Analysis: C, 85%; H, 4%

Synthesis Example 63: Synthesis of Intermediate I-46

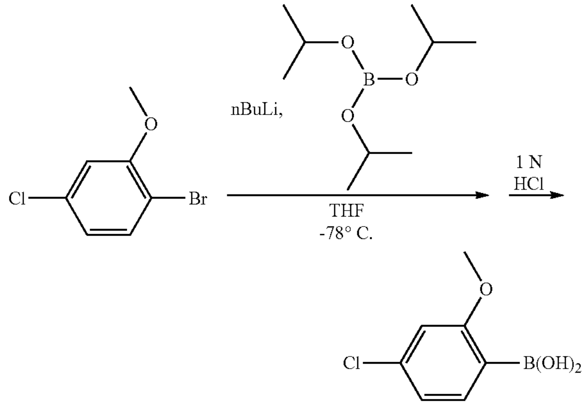

I-46

Under a nitrogen atmosphere, 1-boromo-4-chloro-2-methoxybenzene (50 g, 226 mmol) purchased from Tokyo Chemical Industry Co., Ltd. was dissolved in 500 mL of tetrahydrofuran, and then, the temperature was lowered to −78° C. 2.5 M of n-BuLi dissolved in hexane (108 mL, 271 mmol) was slowly added thereto in a dropwise fashion for 10 minutes, and after 30 minutes, triisopropyl borate (51.0 g, 271 mmol) was added. When a reaction was completed, the reaction solution was neutralized by adding 1N HCl (271 mL, 271 mmol). And then, extracted with ethylacetate (EA), treated with anhydrous magnesium sulfate to remove moisture. The obtained residue was washed with hexane and dichloromethane (DCM), obtaining Intermediate I-46 (35.8 g, 85%).

HRMS (70 eV, EI+): m/z calcd for C7H8BClO3: 186.0255, found: 186.

Elemental Analysis: C, 45%; H, 4%

Synthesis Example 64: Synthesis of Intermediate I-47

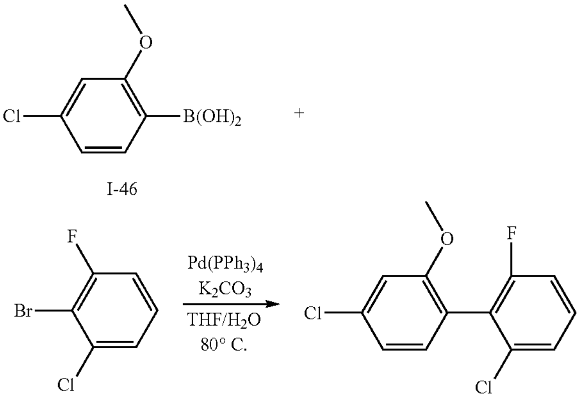

I-46

I-47

Intermediate I-46 (35 g, 188 mmol) and 2-bromo-3-chloro-1-fluorobenzene (39.3 g, 188 mmol) were used to obtain Intermediate I-47 (46.2 g, 91%) according to the same method as Synthesis Example 43.

HRMS (70 eV, EI+): m/z calcd for C13H9Cl2FO: 270.0014, found: 270.

Elemental Analysis: C, 58%; H, 3%

Synthesis Example 65: Synthesis of Intermediate I-48

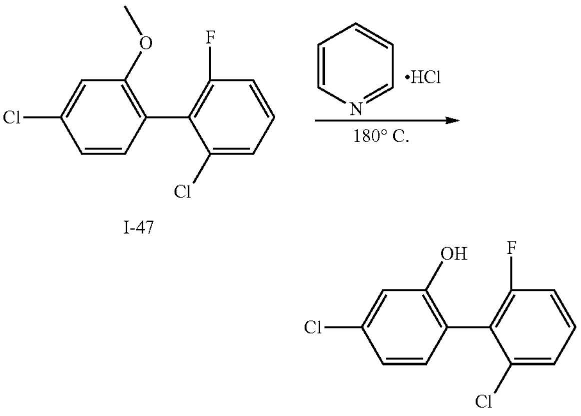

I-47

I-48

Intermediate I-47 (46 g, 170 mmol) was used to obtain Intermediate I-48 (38.4 g, 88%) according to the same method as Synthesis Example 9.

HRMS (70 eV, EI+): m/z calcd for C12H7Cl2FO: 255.9858, found: 256.

Elemental Analysis: C, 56%; H, 3%

Synthesis Example 66: Synthesis of Intermediate I-49

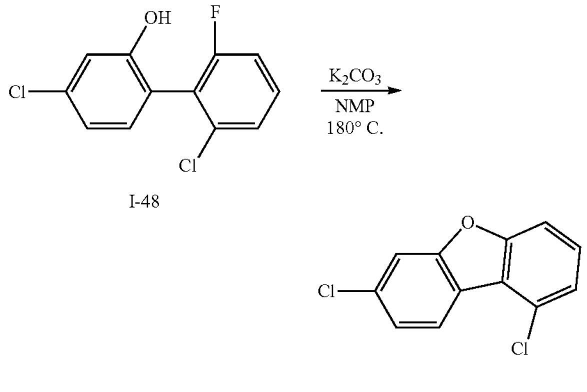

I-48

I-49

Intermediate I-48 (38 g, 148 mmol) was used to obtain Intermediate I-49 (26.3 g, 75%) according to the same method as Synthesis Example 10.

HRMS (70 eV, EI+): m/z calcd for C12H6Cl2O: 235.9796, found: 236.

Elemental Analysis: C, 61%; H, 3%

Synthesis Example 67: Synthesis of Intermediate I-50

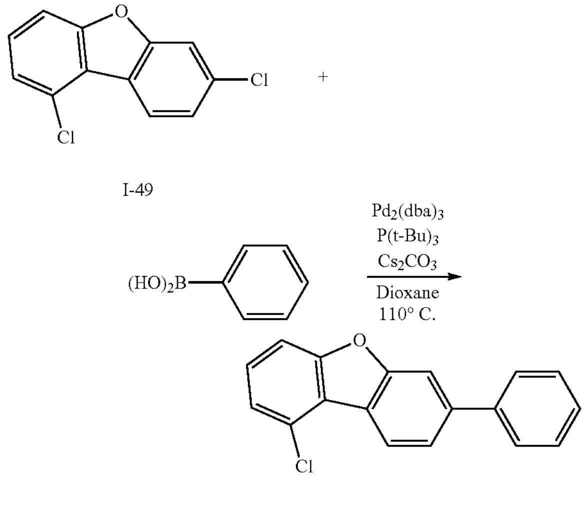

I-49

I-50

Under a nitrogen atmosphere, intermediate I-49 (26 g, 110 mmol) was dissolved in 0.3 L of dioxane, and then, phenyl boronic acid (13.4 g, 110 mmol), tris(diphenylideneacetone) dipalladium(0) (1.01 g, 1.1 mmol), tris-tert butylphosphine (1.11 g, 5.5 mmol) and cesium carbonate (89.6 g, 275 mmol) were added thereto sequentially, heated under reflux at 110° C. for 8 hour. When a reaction was completed, water was added to the reaction solution, extracted with dichloromethane (DCM), treated with anhydrous magnesium sulfate to remove moisture, filtered, and then, concentrated under a reduced pressure. The obtained residue was purified through flash column chromatography, obtaining Intermediate I-50 (16.9 g, 55%).

HRMS (70 eV, EI+): m/z calcd for C18H11ClO: 278.0498, found: 278.

Elemental Analysis: C, 78%; H, 4%

Synthesis Example 68: Synthesis of Intermediate I-51

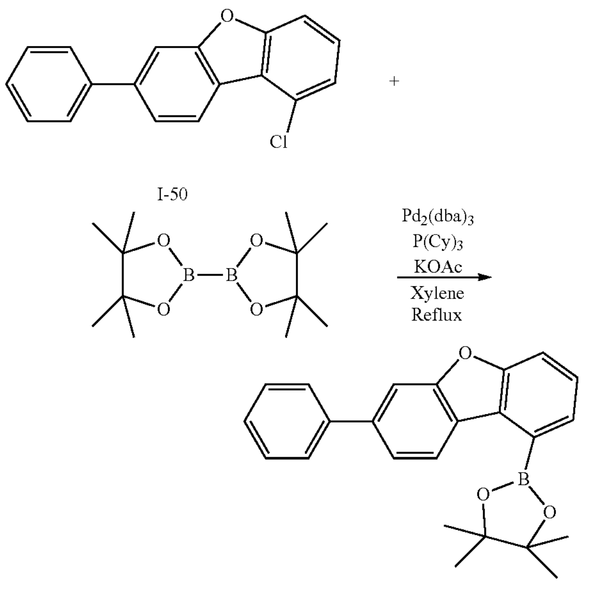

I-50

I-51

Intermediate I-50 (16.5 g, 59.2 mmol) was used to obtain Intermediate I-51 (17.5 g, 80%) according to the same method as Synthesis Example 7.

HRMS (70 eV, EI+): m/z calcd for C24H23BO3: 370.1740, found: 370.

Elemental Analysis: C, 78%; H, 6%

Synthesis Example 69: Synthesis of Intermediate I-52

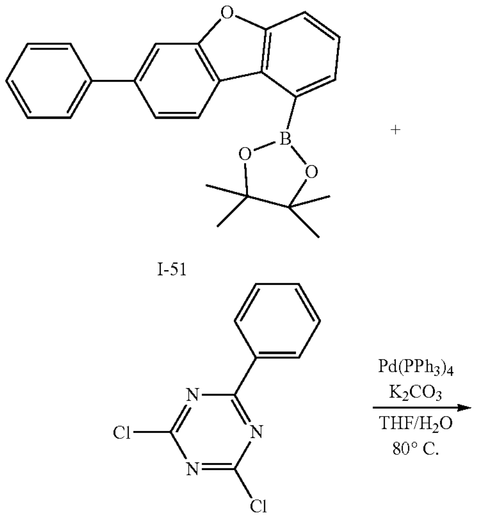

I-51

-continued

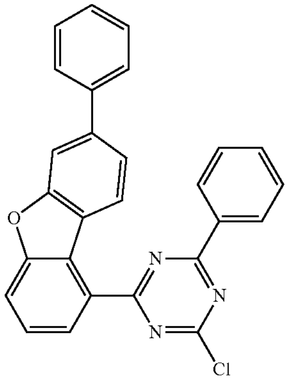

I-52

Intermediate I-51 (17.0 g, 45.9 mmol) and 2,4-dichloro-6-phenyl-1,3,5-triazine (12.5 g, 55.1 mmol) were used to obtain Intermediate I-52 (14.9 g, 75%) according to the same method as Synthesis Example 43.

HRMS (70 eV, EI+): m/z calcd for C27H16ClN3O: 433.0982, found: 433.

Elemental Analysis: C, 75%; H, 4%

Synthesis Example 70: Synthesis of Compound 75

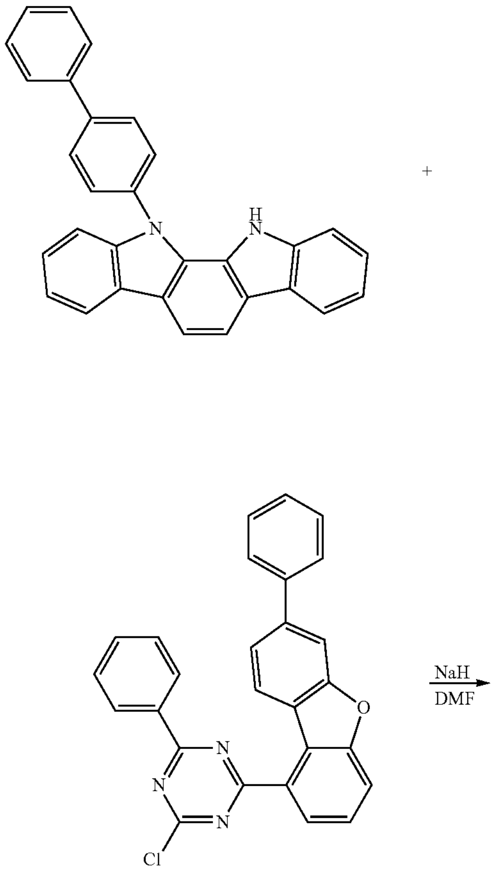

I-52

-continued

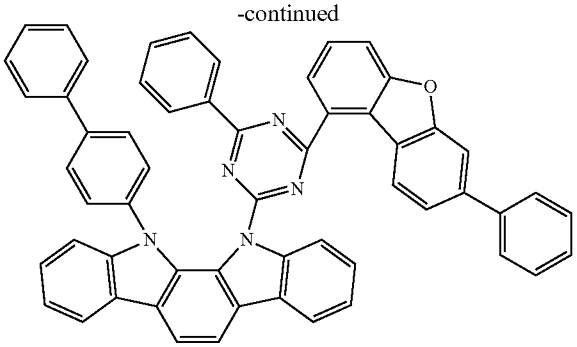

75

11-(biphenyl-4-yl)-11,12-dihydroindolo[2,3,a]carbazole (10 g, 24.5 mmol) purchased from Ukseung Chemical Co., Ltd. (http://www.ukseung.co.kr/) and Intermediate I-52 (12.8 g, 29.4 mmol) were used to obtain Compound 75 (17.0 g, 86%) according to the same method as Synthesis Example 6.

HRMS (70 eV, EI+): m/z calcd for C57H35N5O: 805.2842, found: 805.

Elemental Analysis: C, 85%; H, 4%

(Manufacture of Organic Light Emitting Diode)

Example 1

A glass substrate coated with a thin film of indium tin oxide (ITO) was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A doped with 1% NDP-9 (commercially available from Novaled) was vacuum-deposited on an ITO substrate to form a 1,400 Å-thick hole transport layer, and Compound B was deposited on the hole transport layer to form a 350 Å-thick hole transport auxiliary layer. On the hole transport auxiliary layer, Compound 1 and Compound A-136 of the Synthesis Examples were used as a host, and the host was doped with 10 wt % of PhGD as a dopant to form a 400 Å-thick light emitting layer by vacuum deposition. Herein, Compound 1 and Compound A-136 were used in a weight ratio of 3:7. Then, Compound C was deposited on the light emitting layer to form a 50 Å-thick electron transport auxiliary layer, and Compound D and Liq were simultaneously vacuum-deposited at a weight ratio of 1:1 to form a 300 Å-thick electron transport layer. 15 Å of LiQ and 1,200 Å of Al were sequentially vacuum-deposited on the electron transport layer to form a cathode to finish manufacturing an organic light emitting diode.

ITO/Compound A (1% NDP-9 doping, 1,400 Å)/Compound B (350 Å)/[Compound 1:Compound A-136:PhGD=3:7:10 wt %)] (400 Å)/Compound C (50 Å)/Compound D:LiQ (300 Å)/LiQ (15 Å)/Al (1,200 Å).

Compound A: N-(biphenyl-4-yl)-9,9-dimethyl-N-(4-(9-phenyl-9H-carbazol-3-yl)phenyl)-9H-fluoren-2-amine Compound B: N,N-bis(9,9-dimethyl-9H-fluoren-4-yl)-9,9-spirobi(fluorene)-2-amine Compound C: 2-(3-(3-(9,9-dimethyl-9H-fluoren-2-yl)phenyl)phenyl)-4,6-diphenyl-1,3,5-triazine Compound D: 8-(4-(4,6-di(naphthalen-2-yl)-1,3,5-triazin-2-yl)phenyl)quinolone

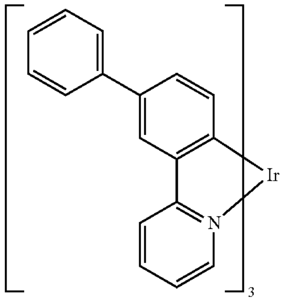

[PhGD]

Example 2

An organic light emitting diode was manufactured according to the same method as Example 1 except that Compound 5 was used instead of Compound 1.

Example 3

An organic light emitting diode was manufactured according to the same method as Example 1 except that Compound 29 was used instead of Compound 1.

Example 4

An organic light emitting diode was manufactured according to the same method as Example 1 except that Compound 31 was used instead of Compound 1.

Example 5

An organic light emitting diode was manufactured according to the same method as Example 1 except that Compound 32 was used instead of Compound 1.

Example 6

An organic light emitting diode was manufactured according to the same method as Example 1 except that Compound A-99 was used instead of Compound A-136.

Example 7

An organic light emitting diode was manufactured according to the same method as Example 1 except that Compound A-31 was used instead of Compound A-136.

Example 8

An organic light emitting diode was manufactured according to the same method as Example 1 except that Compound B-4 was used instead of Compound A-136.

Example 9

An organic light emitting diode was manufactured according to the same method as Example 1 except that Compound B-57 was used instead of Compound A-136.

Example 10

An organic light emitting diode was manufactured according to the same method as Example 1 except that Compound 1 and Compound A-136 were used in a weight ratio of 4:6 instead of 3:7.

Example 11

An organic light emitting diode was manufactured according to the same method as Example 1 except that Compound 1 and Compound A-136 were used in a weight ratio of 2:8 instead of 3:7.

Comparative Example 1

An organic light emitting diode was manufactured according to the same method as Example 1 except that Compound Host 1 was used instead of Compound 1.

Comparative Example 2

An organic light emitting diode was manufactured according to the same method as Example 1 except that Compound Host 2 was used instead of Compound 1.

Comparative Example 3

An organic light emitting diode was manufactured according to the same method as Example 1 except that Compound Host 3 was used instead of Compound 1.

Example 12

An organic light emitting diode was manufactured according to the same method as Example 1 except that Compound 33 was used instead of Compound 1.

Example 13

An organic light emitting diode was manufactured according to the same method as Example 1 except that Compound 34 was used instead of Compound 1.

Example 14

An organic light emitting diode was manufactured according to the same method as Example 1 except that Compound 35 was used instead of Compound 1.

Example 15

An organic light emitting diode was manufactured according to the same method as Example 1 except that Compound 73 was used instead of Compound 1.

Example 16

An organic light emitting diode was manufactured according to the same method as Example 1 except that Compound 74 was used instead of Compound 1.

Example 17

An organic light emitting diode was manufactured according to the same method as Example 1 except that Compound 75 was used instead of Compound 1.

Evaluation

The driving voltages, luminous efficiency, and lifespan characteristics of the organic light emitting diodes according to Examples 1 to 17 and Comparative Examples 1 to 3 were evaluated.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area of the device to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Luminous efficiency (cd/A) at the same current density (10 mA/$cm^2$) were calculated by using the luminance, current density, and a voltage from the items (1) and (2).

(4) Measurement of Life-Span

The luminance (cd/$m^2$) at 24,000 cd/$m^2$ was maintained and the time for the current efficiency (cd/A) to decrease to 97% was measured to obtain the results.

(5) Measurement of Driving Voltage

A driving voltage of each diode was measured using a current-voltage meter (Keithley 2400) at 15 mA/$cm^2$.

TABLE 1

| No. | Compounds | Driving voltage (V) | Color (EL color) | Efficiency (cd/A) | Life-span (T97@ 24K) (h) |
|---|---|---|---|---|---|
| Example 1 | 1/A-136 | 3.81 | Green | 70.1 | 60 |
| Example 2 | 5/A-136 | 3.75 | Green | 72.3 | 65 |
| Example 3 | 29/A-136 | 3.77 | Green | 71.0 | 68 |
| Example 4 | 31/A-136 | 3.85 | Green | 65.8 | 62 |
| Example 5 | 32/A-136 | 3.74 | Green | 69.5 | 66 |
| Example 6 | 1/A-99 | 3.78 | Green | 71.0 | 59 |
| Example 7 | 1/A-31 | 3.85 | Green | 70.0 | 61 |
| Example 8 | 1/B-4 | 3.70 | Green | 68.2 | 64 |
| Example 9 | 1/B-57 | 3.80 | Green | 64.2 | 65 |
| Example 10 | 1/A-136 | 3.75 | Green | 72.0 | 58 |
| Example 11 | 1/A-136 | 3.89 | Green | 68.0 | 64 |
| Example 12 | 33/A-136 | 3.85 | Green | 75.5 | 60 |
| Example 13 | 34/A-136 | 3.80 | Green | 68.0 | 62 |
| Example 14 | 35/A-136 | 3.88 | Green | 65.0 | 65 |
| Example 15 | 73/A-136 | 3.86 | Green | 63.8 | 58 |
| Example 16 | 74/A-136 | 3.85 | Green | 64.1 | 60 |
| Example 17 | 75/A-136 | 3.89 | Green | 63.6 | 59 |
| Comparative Example 1 | Host 1/ A-136 | 3.90 | Green | 63.0 | 58 |
| Comparative Example 2 | Host 2/ A-136 | 3.93 | Green | 59.0 | 57 |
| Comparative Example 3 | Host 3/ A-136 | 3.95 | Green | 55.0 | 30 |

Referring to Table 1, the organic light emitting diodes according to Examples 1 to 17 exhibited significantly improved driving voltage, luminous efficiency, and life-span characteristics, compared with the organic light emitting diodes according to Comparative Examples 1 to 3.

One or more embodiments may provide a compound for an organic optoelectronic device capable of implement an organic optoelectronic device having high efficiency and a long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic optoelectronic device, comprising:

an anode and a cathode facing each other, and at least one organic layer between the anode and the cathode, wherein:

the at least one organic layer includes a composition including a first compound and a second compound, the first compound is represented by a combination of Chemical Formula 1 and Chemical Formula 2-1-i or Chemical Formula 2-1-ii,

[Chemical Formula 1]

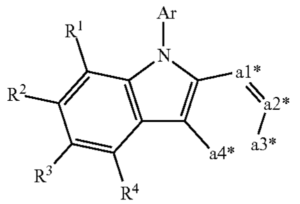

[Chemical Formula 2-1-i]

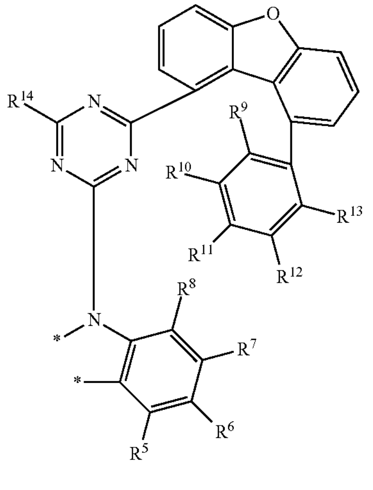

-continued

[Chemical Formula 2-1-ii]

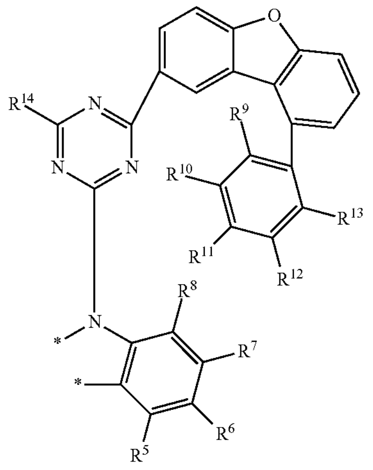

in Chemical Formulae 1, 2-1-i, and 2-1-ii,

Ar is a substituted or unsubstituted C12 to C30 aryl group, a1* and a2* are linking carbons, linked at * of Chemical Formula 2-1-i or at * of Chemical Formula 2-1-ii, a3* and a4* are each independently C—$R^a$, $R^a$ and $R^1$ to $R^{13}$ are each independently hydrogen, deuterium, a cyano group, a halogen, a substituted or unsubstituted C1 to C20 alkyl group, or a substituted or unsubstituted C6 to C20 aryl group, $R^{14}$ is a substituted or unsubstituted C6 to C20 aryl group, and the second compound is represented by Chemical Formula 3,

[Chemical Formula 3]

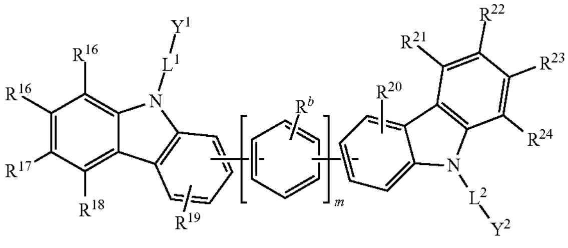

in Chemical Formula 3, $Y^1$ and $Y^2$ are each independently a substituted or unsubstituted C6 to C20 aryl group or a substituted or unsubstituted C2 to C30 heterocyclic group, $L^1$ and $L^2$ are each independently a single bond or a substituted or unsubstituted C6 to C20 arylene group, $R^b$ and $R^{15}$ to $R^{24}$ are each independently hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group, and m is an integer of 0 to 2, and a ratio of the first compound to the second compound is 3:7 to 6:4.

2. The organic optoelectronic device as claimed in claim 1, wherein Ar is a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylene group.

3. The organic optoelectronic device as claimed in claim 1, wherein:

Ar is a group of Group I:

[Group I]

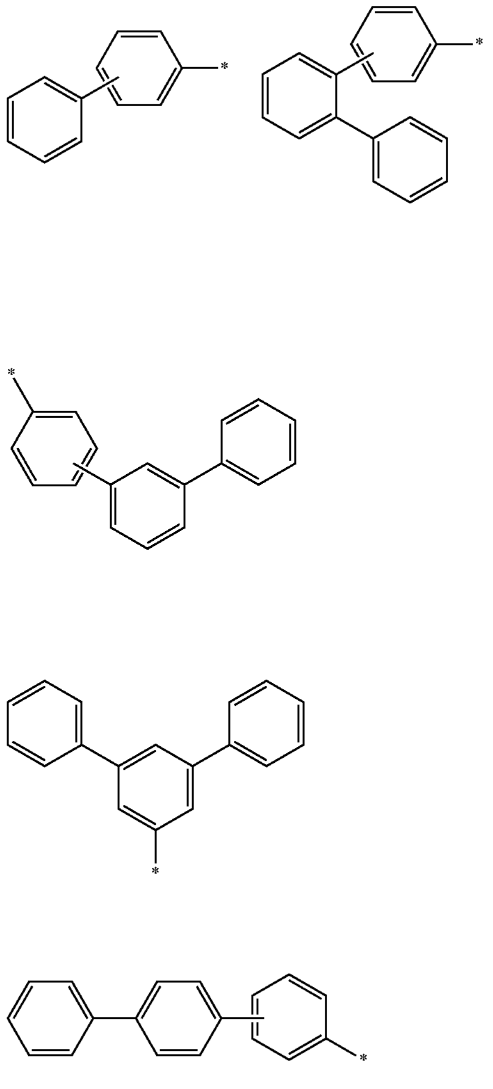

in Group I, * is a linking point.

4. The organic optoelectronic device as claimed in claim 1, wherein $R^{14}$ is a substituted or unsubstituted phenyl group, a substituted or unsubstituted biphenyl group, a substituted or unsubstituted terphenyl group, or a substituted or unsubstituted naphthyl group.

5. The organic optoelectronic device as claimed in claim 1, wherein $R^9$ to $R^{13}$ are each independently hydrogen, deuterium, a substituted or unsubstituted phenyl group, or a substituted or unsubstituted biphenyl group.

6. The organic optoelectronic device as claimed in claim 1, wherein the compound is a compound of Group 1:

[Group 1]
1
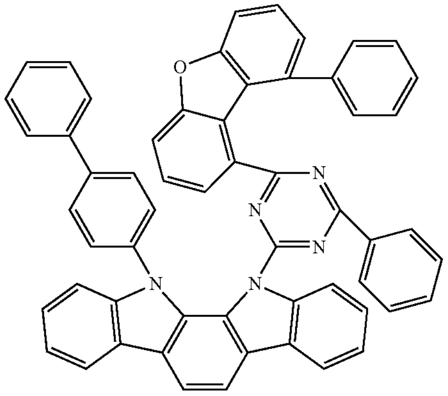
2
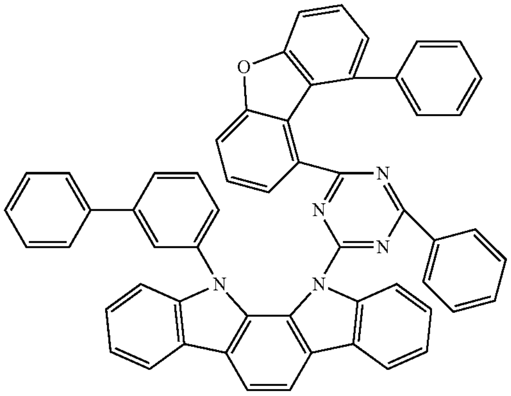
3
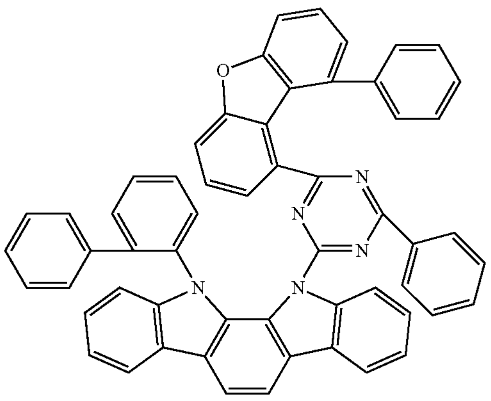
-continued
4
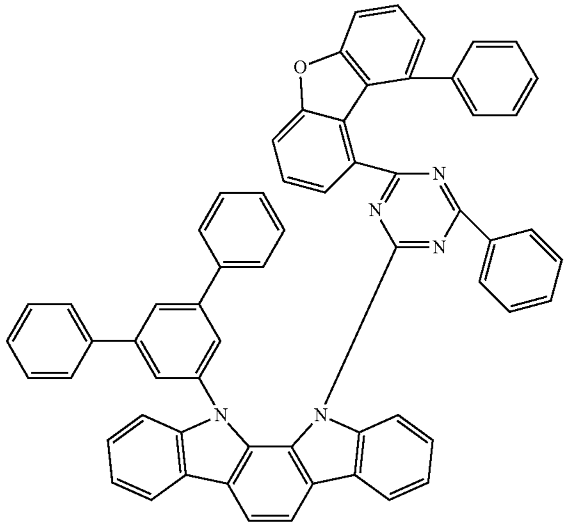
5
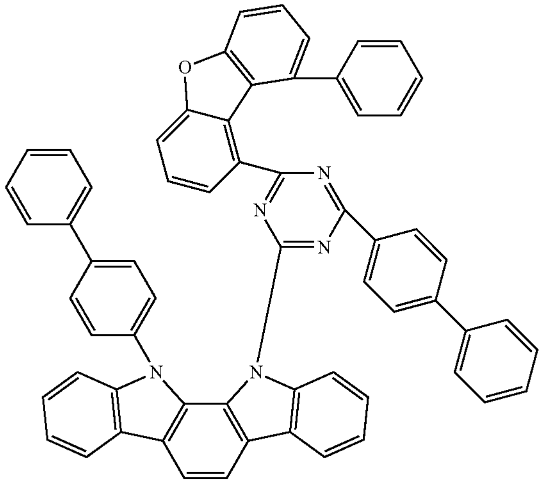
6
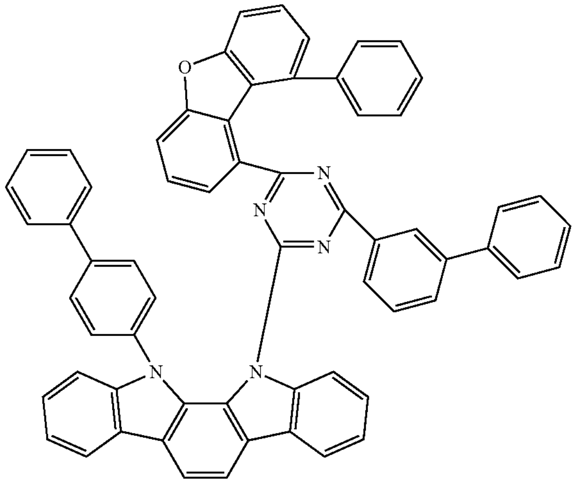

7
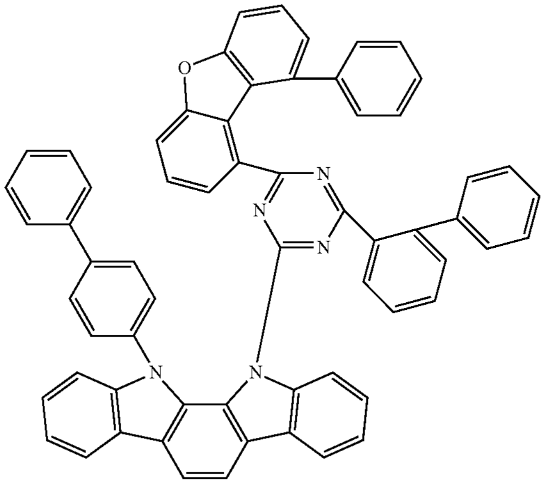
8
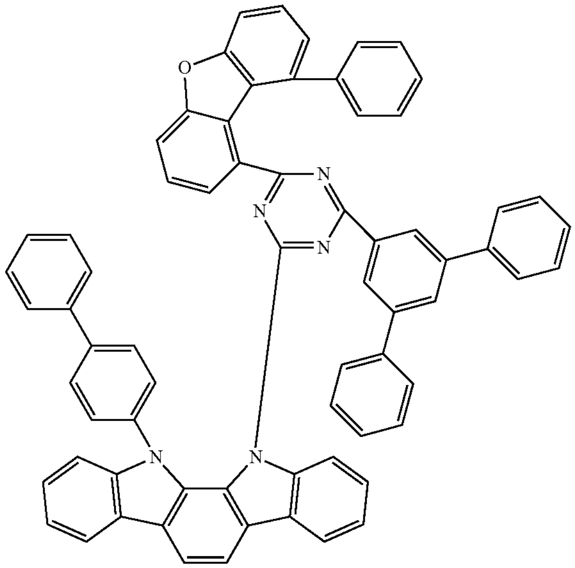
9
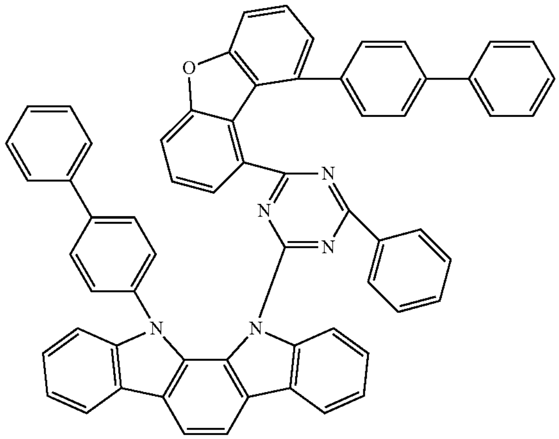
10
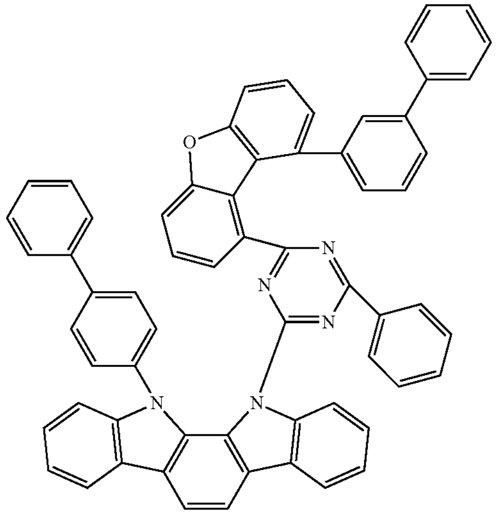
11
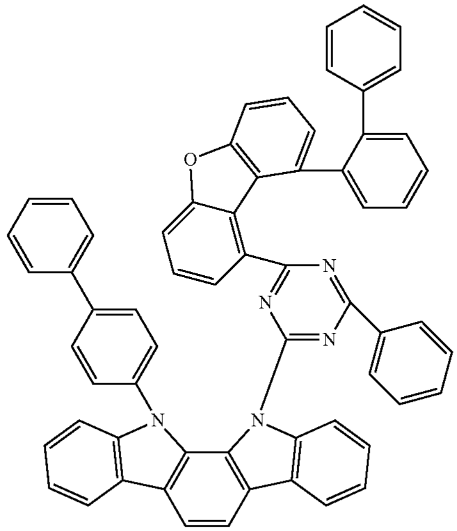
12
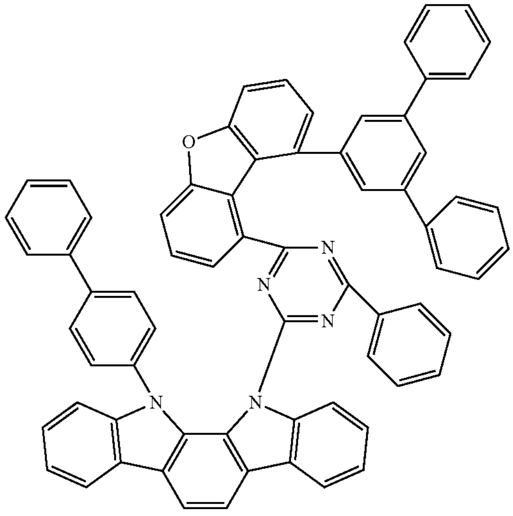

-continued
13
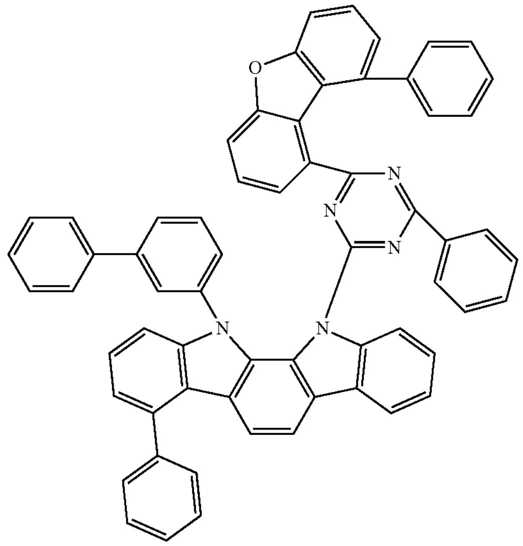
14
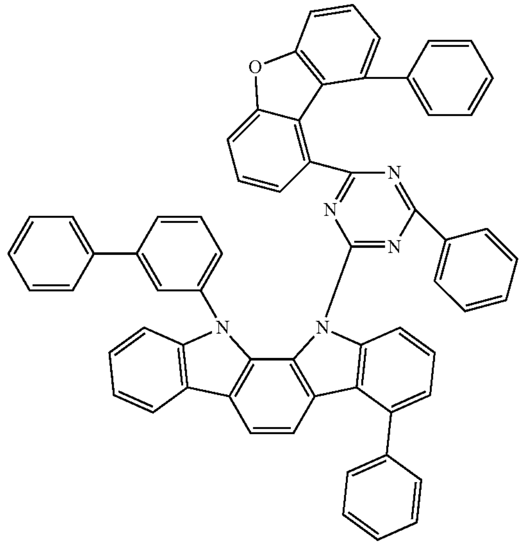
15
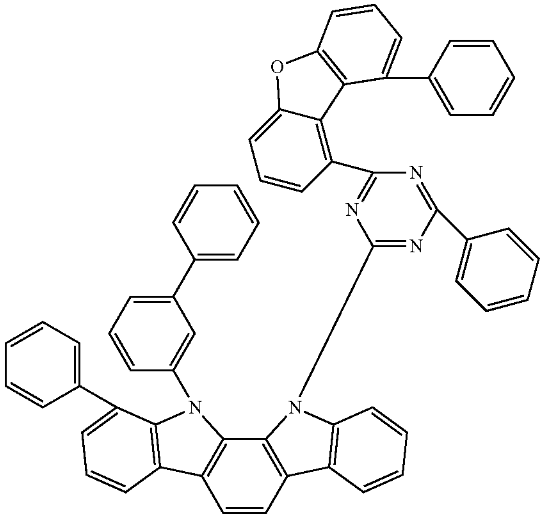
-continued
16
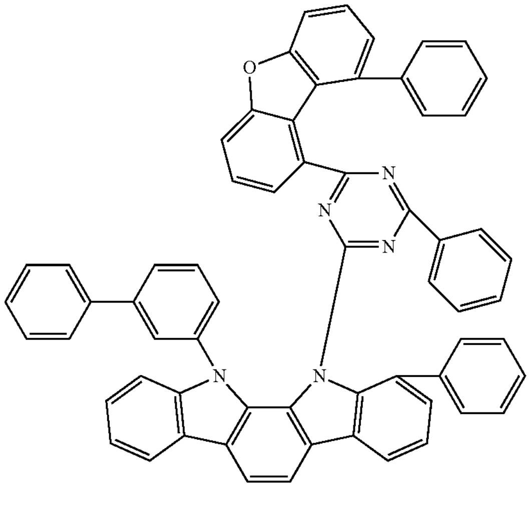
17
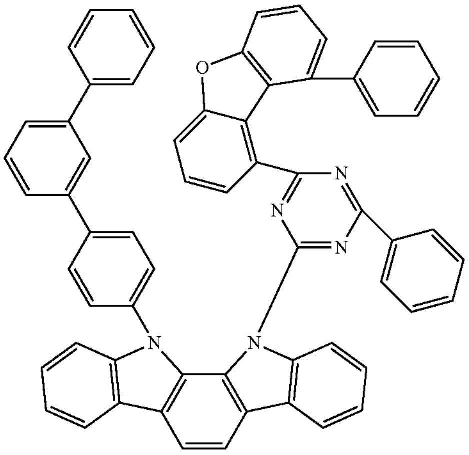
18
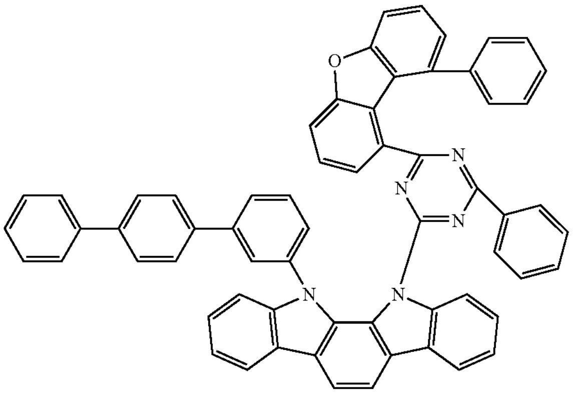

-continued
19
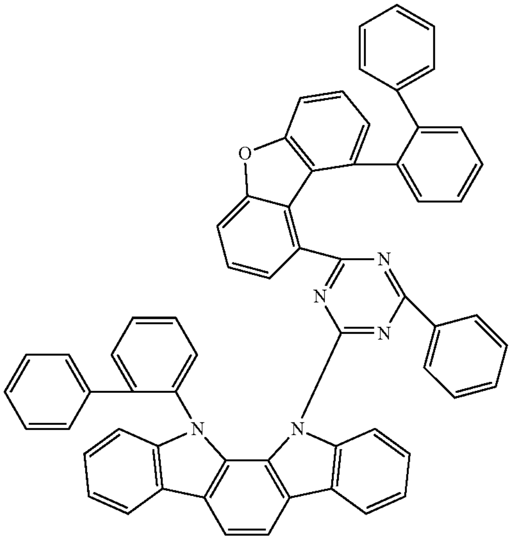
20
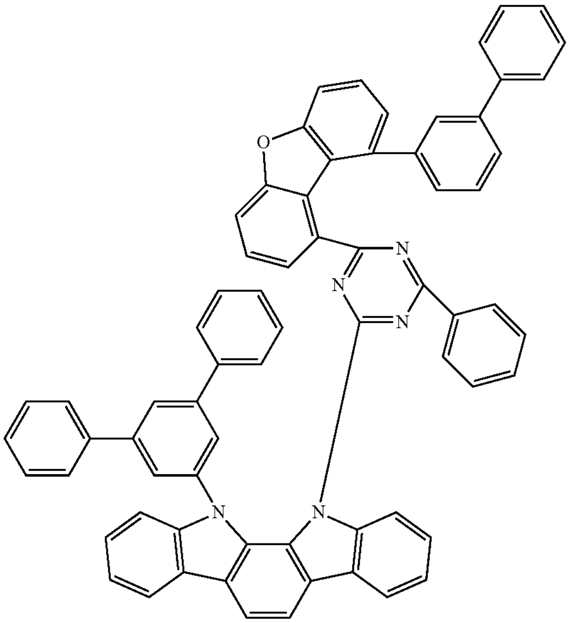
21
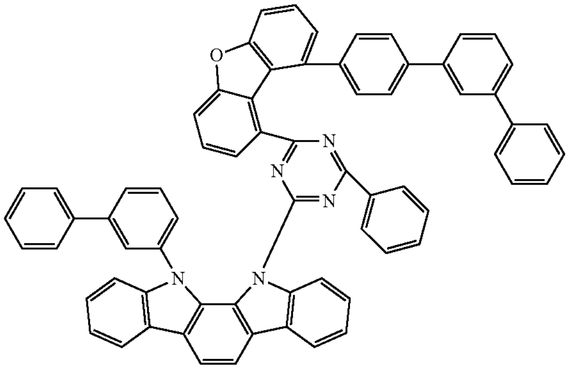
-continued
22
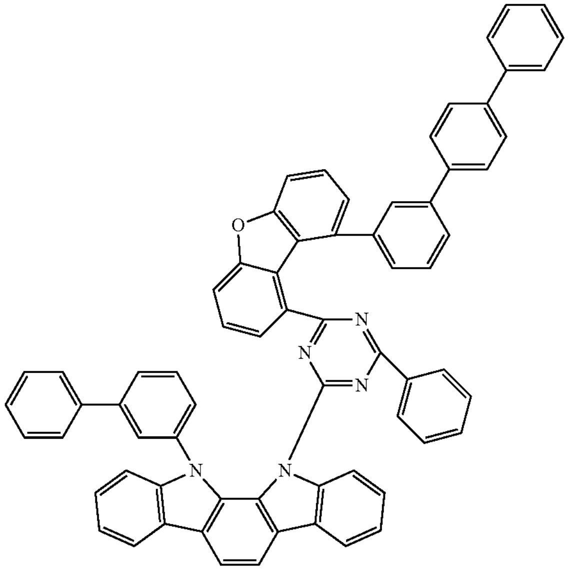
23
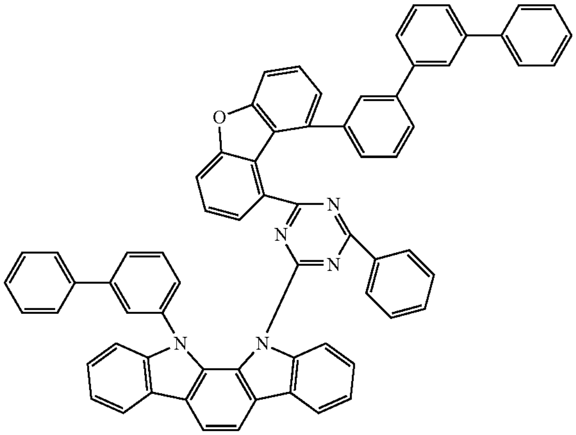
24
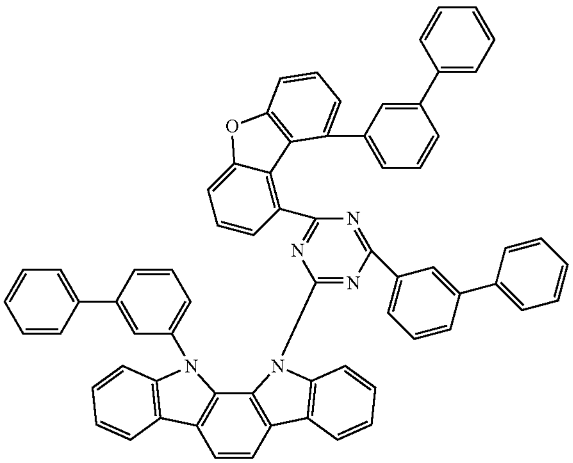

-continued
25
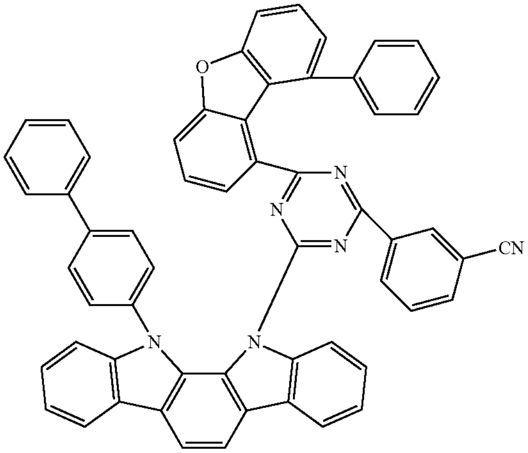
26
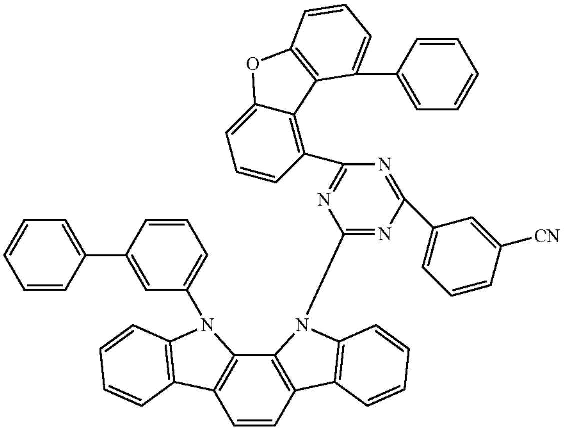
27
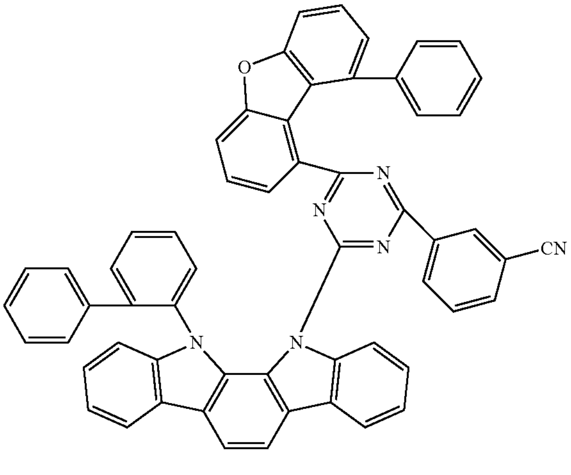
-continued
28
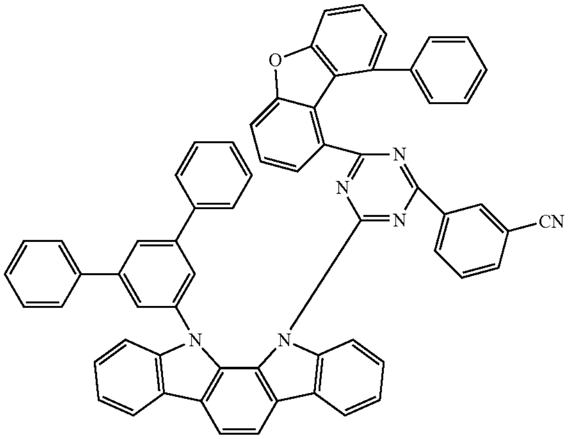
29
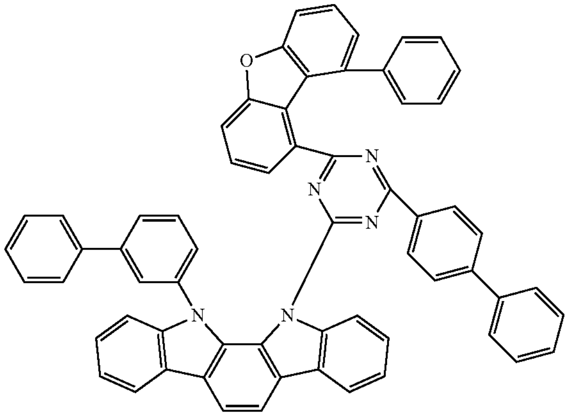
101
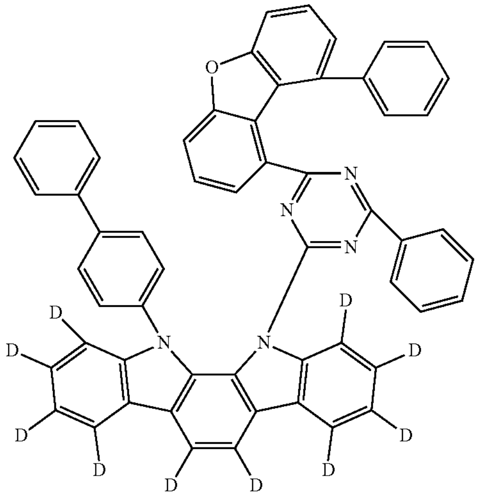

-continued
102
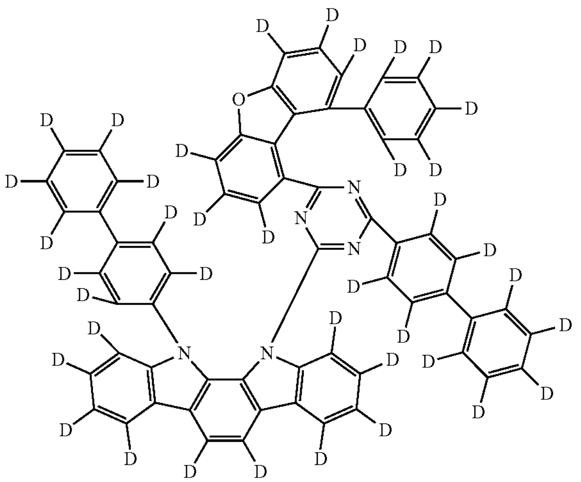
103
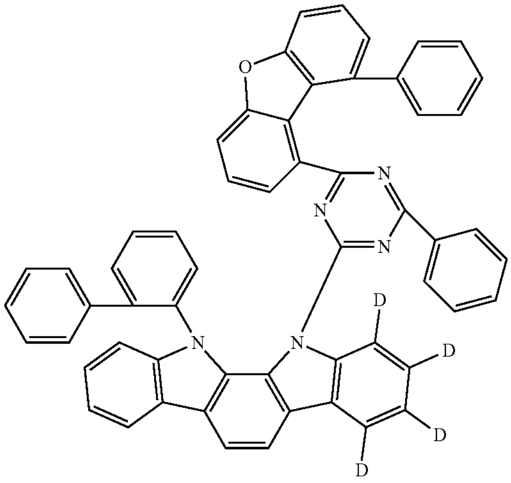
104
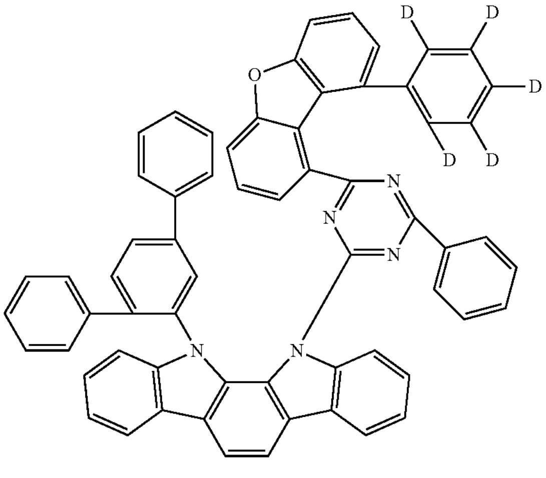
-continued
105
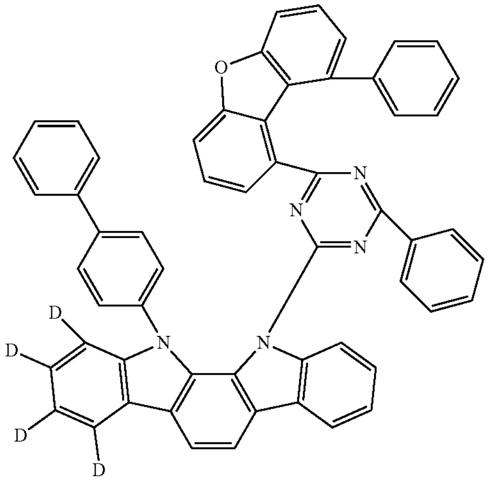
106
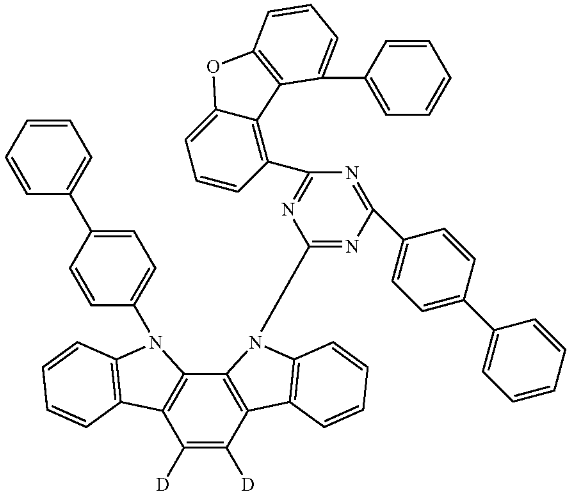
107
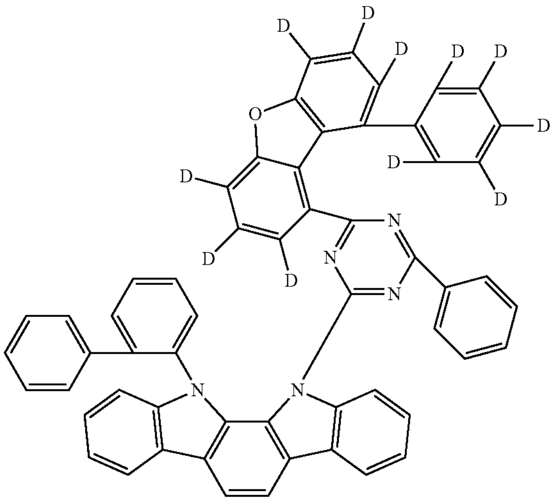

-continued

108

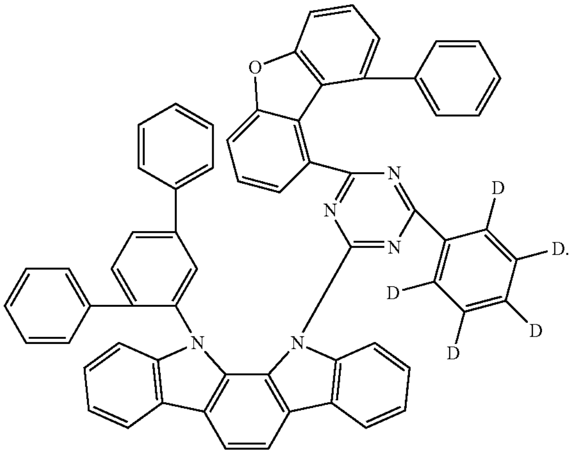

7. The organic optoelectronic device as claimed in claim 1, wherein:

Chemical Formula 3 is represented by Chemical Formula 3-8;

[Chemical Formula 3-8]

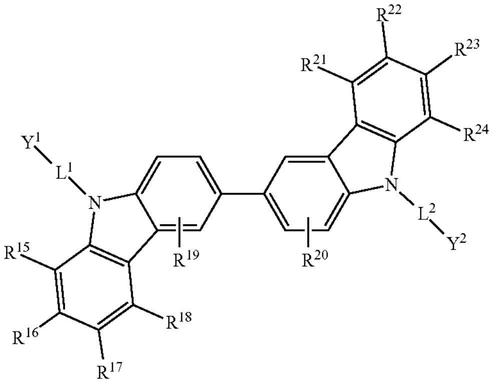

in Chemical Formula 3-8, $R^{15}$ to $R^{24}$ are each independently hydrogen or a substituted or unsubstituted C6 to C12 aryl group, and moieties $*-L^1-Y^1$ and $*-L^2-Y^2$ are each independently a moiety of Group II,

[Group II]

C-1

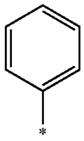

-continued

C-2

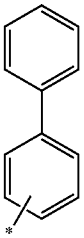

C-3

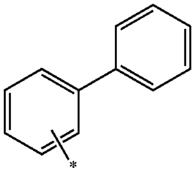

C-4

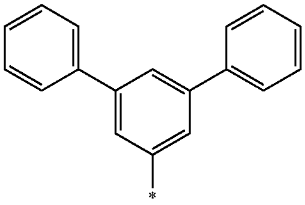

C-5

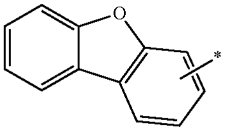

C-6

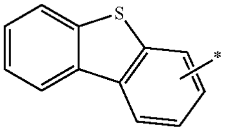

C-7

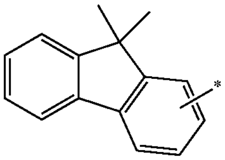

C-8

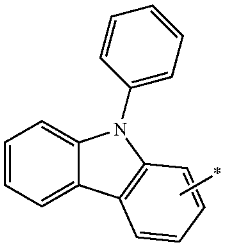

-continued
C-9
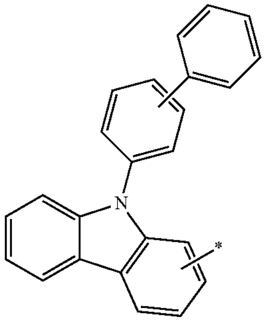
C-10
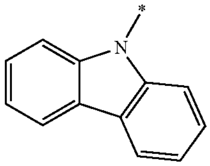
C-11
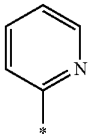
C-12
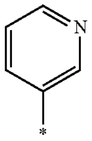
C-13
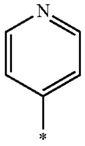
C-14
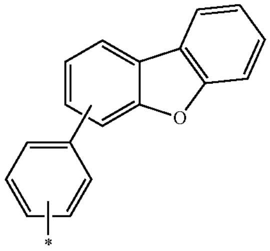
C-15
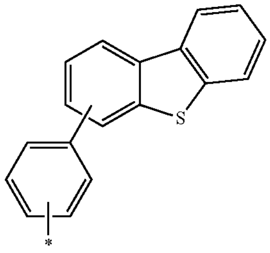
-continued
C-16
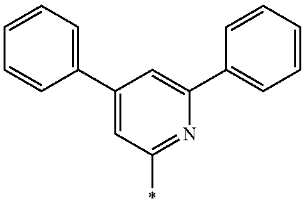
C-17
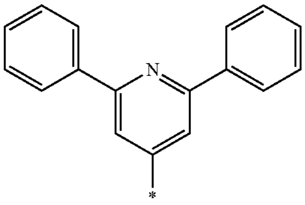
C-18
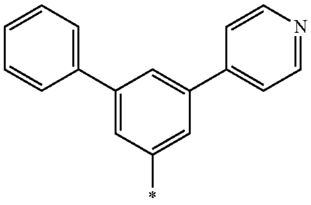
C-19
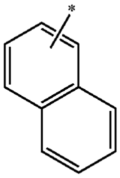
C-20
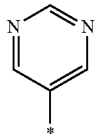
C-21
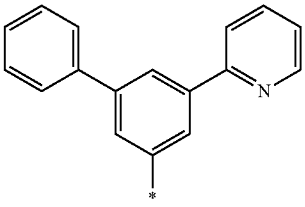
C-22
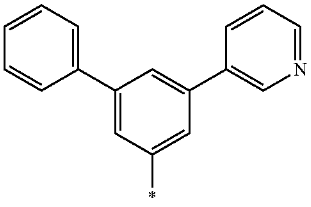
C-23
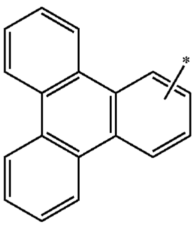

-continued
C-24
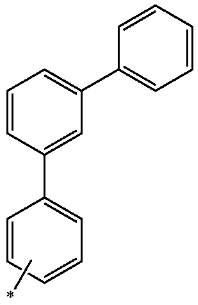
C-25
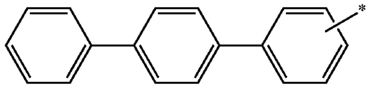
-continued
C-26
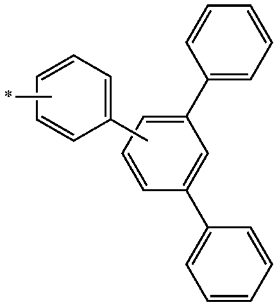
in Group II, * is a linking point.
8. A display device comprising the organic optoelectronic device as claimed in claim 1.
9. A display device comprising the organic optoelectronic device as claimed in claim 1.
* * * * *